(12) United States Patent
Fujimoto et al.

(10) Patent No.: US 10,696,651 B2
(45) Date of Patent: Jun. 30, 2020

(54) HETEROCYCLIC COMPOUND

(71) Applicant: Takeda Pharmaceutical Company Limited, Osaka (JP)

(72) Inventors: Jun Fujimoto, Kanagawa (JP); Xin Liu, Shanghai (CN); Osamu Kurasawa, Kanagawa (JP); Terufumi Takagi, Kanagawa (JP); Douglas Robert Cary, Tokyo (JP); Hiroshi Banno, Kanagawa (JP); Yasutomi Asano, Kanagawa (JP); Takuto Kojima, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/323,863

(22) PCT Filed: Aug. 9, 2017

(86) PCT No.: PCT/JP2017/028928
§ 371 (c)(1),
(2) Date: Feb. 7, 2019

(87) PCT Pub. No.: WO2018/030466
PCT Pub. Date: Feb. 15, 2018

(65) Prior Publication Data
US 2019/0169166 A1    Jun. 6, 2019

(30) Foreign Application Priority Data

Aug. 10, 2016 (JP) .................. 2016-158038
Jan. 31, 2017 (JP) .................. 2017-016275

(51) Int. Cl.
| | | |
|---|---|---|
| *C07D 401/12* | (2006.01) | |
| *C07D 403/12* | (2006.01) | |
| *C07D 401/14* | (2006.01) | |
| *C07D 213/75* | (2006.01) | |
| *C07D 405/12* | (2006.01) | |
| *C07D 239/42* | (2006.01) | |
| *C07D 241/12* | (2006.01) | |
| *C07D 471/04* | (2006.01) | |
| *C07D 498/04* | (2006.01) | |
| *C07D 213/65* | (2006.01) | |
| *A61P 35/00* | (2006.01) | |
| *C07D 241/20* | (2006.01) | |
| *C07D 213/73* | (2006.01) | |
| *A61K 31/53* | (2006.01) | |

(Continued)

(52) U.S. Cl.
CPC .......... *C07D 401/12* (2013.01); *A61K 31/437* (2013.01); *A61K 31/4375* (2013.01); *A61K 31/44* (2013.01); *A61K 31/444* (2013.01); *A61K 31/4406* (2013.01); *A61K 31/497* (2013.01); *A61K 31/4965* (2013.01); *A61K 31/505* (2013.01); *A61K 31/506* (2013.01); *A61K 31/53* (2013.01); *A61K 31/5383* (2013.01); *A61P 35/00* (2018.01); *A61P 43/00* (2018.01); *C07D 213/42* (2013.01); *C07D 213/65* (2013.01); *C07D 213/68* (2013.01); *C07D 213/73* (2013.01); *C07D 213/75* (2013.01); *C07D 239/20* (2013.01); *C07D 239/42* (2013.01); *C07D 241/12* (2013.01); *C07D 241/20* (2013.01); *C07D 253/06* (2013.01); *C07D 401/14* (2013.01); *C07D 403/12* (2013.01); *C07D 405/12* (2013.01); *C07D 471/04* (2013.01); *C07D 498/04* (2013.01); *C07D 231/12* (2013.01); *C07D 239/30* (2013.01); *C07D 239/34* (2013.01); *C07D 239/48* (2013.01); *C07D 253/07* (2013.01); *C07D 409/12* (2013.01); *C07D 487/04* (2013.01)

(58) Field of Classification Search
CPC .................................... C07D 401/12
USPC ............................................. 544/242
See application file for complete search history.

(56) References Cited

U.S. PATENT DOCUMENTS

2015/0051202 A1    2/2015  Schiemann et al.

FOREIGN PATENT DOCUMENTS

| CN | 104829613 A | * 8/2015 |
|---|---|---|
| CN | 105732614 | 7/2016 |

(Continued)

OTHER PUBLICATIONS

International Search Report dated Sep. 19, 2017 in International (PCT) Application No. PCT/JP2017/028928.

(Continued)

*Primary Examiner* — Taofiq A Solola
(74) *Attorney, Agent, or Firm* — Wenderoth, Lind & Ponack, L.L.P.

(57) ABSTRACT

Provided is a heterocyclic compound that may have a GCN2 inhibitory action, and is expected to be useful for the prophylaxis or treatment of GCN2 associated diseases including cancer and the like. A compound represented by the formula (I):

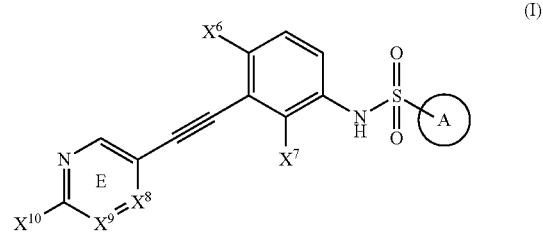

(I)

(Continued)

wherein each symbol is as described in the DESCRIPTION, or a salt thereof.

9 Claims, No Drawings

(51) Int. Cl.

| | |
|---|---|
| *A61K 31/505* | (2006.01) |
| *A61K 31/4406* | (2006.01) |
| *A61K 31/444* | (2006.01) |
| *A61K 31/4965* | (2006.01) |
| *C07D 213/68* | (2006.01) |
| *C07D 213/42* | (2006.01) |
| *A61K 31/506* | (2006.01) |
| *A61K 31/497* | (2006.01) |
| *A61K 31/4375* | (2006.01) |
| *C07D 239/20* | (2006.01) |
| *A61P 43/00* | (2006.01) |
| *A61K 31/5383* | (2006.01) |
| *A61K 31/437* | (2006.01) |
| *A61K 31/44* | (2006.01) |
| *C07D 253/06* | (2006.01) |
| *C07D 231/12* | (2006.01) |
| *C07D 239/30* | (2006.01) |
| *C07D 239/34* | (2006.01) |
| *C07D 239/48* | (2006.01) |
| *C07D 253/07* | (2006.01) |
| *C07D 409/12* | (2006.01) |
| *C07D 487/04* | (2006.01) |

(56) References Cited

FOREIGN PATENT DOCUMENTS

| | | | |
|---|---|---|---|
| CN | 105732614 A | * | 7/2016 |
| WO | 2006/082371 | | 8/2006 |
| WO | 2010/145998 | | 12/2010 |
| WO | 2013/110309 | | 8/2013 |
| WO | 2014/135244 | | 9/2014 |
| WO | 2014/135245 | | 9/2014 |

OTHER PUBLICATIONS

Li et al., "N-(3-Ethynyl-2,4-difluorophenyl)sulfonamide Derivatives as Selective Raf Inhibitors", ACS Medicinal Chemistry Letters, vol. 6, No. 5, pp. 543-547, 2015.

Chang et al., "Structure Based Design of N-(3-((1H-Pyrazolo[3,4-b]pyridiri-5yl)ethynyl) benzenesulfonamides as Selective Leucine-Zipper and Sterile-α Motif Kinase (ZAK) Inhibitors", Journal of Medicinal Chemistry, vol. 60, No. 13, pp. 5927-5932, 2017.

Wek et al., "Coping with stress: elF2 kinases and translational control", Biochemical Society Transactions, vol. 34 (Part1), pp. 7-11, 2006.

Wang et al., "Amino Acid Deprivation Promotes Tumor Angiogenesis through the GCN2/ATF4 Pathway", Neoplasia, vol. 15, No. 8, pp. 989-997, 2013.

Ye et al., "The GCN2-ATF4 pathway is critical for tumour cell survival and proliferation in response to nutrient deprivation", The EMBO Journal, vol. 29, No. 12, pp. 2082-2096, 2010.

Supplementary European Search Report dated Nov. 19, 2019 in corresponding European Patent Application No. 17 83 9533.

* cited by examiner

HETEROCYCLIC COMPOUND

TECHNICAL FIELD

The present invention relates to a heterocyclic compound that may have a general control nonderepressible 2(GCN2) inhibitory action, and is expected to be useful for the prophylaxis or treatment of GCN2 associated diseases including cancer and the like, a production method thereof and use thereof.

BACKGROUND OF THE INVENTION

Integrated stress response (ISR) plays an essential role when cells adapt to stress conditions such as hypoxia and malnutrition (non-patent document 1). ISR is regulated by 4 kinds of eIF2α kinase (EIF2AK); heme-regulated initiation factor 2 alpha kinase (HRI), double stranded RNA-activated protein kinase (PKR), PKR-like endoplasmic reticulum kinase (PERK), GCN2. These EIF2AKs are activated under a particular stress and phosphorylate a protein translation initiation regulatory factor, eIF2α. It is known that GCN2 is activated by amino acid starvation, ultraviolet irradiation and the like. Phosphorylation of eIF2α by GCN2 is considered to cause expression of the activating transcription factor 4 (ATF4) at the downstream thereof and involvement in amino acid synthesis, metabolism, cell death and the like.

In the intratumoral microenvironment, angiogenesis may become locally insufficient along with abnormal proliferation of cancer cells and the like. When the hematological supply is stagnant, a state of oxygen or nutrient deficiency is induced. Cancer cells support tumor growth by having the ability to survive by overcoming these harsh environments.

It is suggested that the GCN2/eIF2α/ATF4 pathway has the possibility of playing an important role in the survival and proliferation of cells in the amino acid starved state and is involved in angiogenesis in tumor (non-patent documents 2, 3). In addition, GCN2 has been reported to show high expression in certain tumors as compared to normal tissues (non-patent document 3).

As a compound inhibiting GCN2, the compounds described in patent documents 1-3 and the like are known. However, specific disclosure of anti-cancer action and preventive and therapeutic effects on other diseases which are caused by GCN2 inhibition is absent. Non-patent document 4 discloses Raf inhibitors and patent documents 4, 5 and 6 disclose pyrimidine derivatives and compounds which are pyrimidylpyrrolopyridinone derivatives and having a sulfonamide structure for the treatment of cancer and autoimmune diseases. To date, there is no compound launched as a therapeutic agent for cancer and other diseases based on a GCN2 inhibitory action.

DOCUMENT LIST

Patent Documents patent document 1: WO 2013/110309
patent document 2: WO 2014/135244
patent document 3: WO 2014/135245
patent document 4: WO 2006/082371
patent document 5: WO 2010/145998
patent document 6: CN105732614

Non-Patent Documents non-patent document 1: Wek et al., Biochem. Soc. Trans. (2006), 34(Pt1):7-11
non-patent document 2: Wang et al., Neoplasia, August 2013, Vol. 15, No. 8, pp. 989-997
non-patent document 3: Ye et al., The EMBO Journal (2010), 29, No. 12, 2082-2096
non-patent document 4: Li et al., ACS Med. Chem. Lett. (2015), 6, 543-547

SUMMARY OF THE INVENTION

Problems to be Solved by the Invention

An object of the present invention is to provide a heterocyclic compound that may have a GCN2 inhibitory action, and is expected to be useful for the prophylaxis or treatment of GCN2 associated diseases including cancer and the like, and a medicament containing same.

Means of Solving the Problems

The present inventors have conducted intensive studies in an attempt to solve the above-mentioned problems and found that a compound represented by the following formula (I) may have a superior GCN2 inhibitory action, which resulted in the completion of the present invention.

Therefore, the present invention provides the following.

[1] A compound represented by the formula (I):

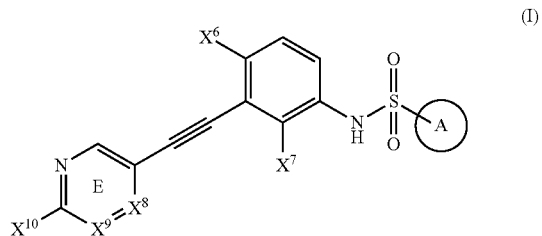

wherein
ring A is the formula:

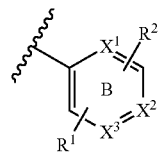

wherein ring B is an optionally further substituted 6-membered aromatic ring;
two of $X^1$, $X^2$ and $X^3$ are carbon atoms and the remaining one is a carbon atom or a nitrogen atom;
$R^1$ is a halogen atom, optionally halogenated methyl, or a hydroxy group optionally substituted by optionally halogenated methyl;
$R^2$ is a substituent, or the formula:

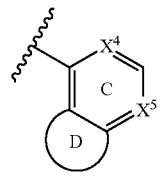

wherein ring C is an optionally further substituted 6-membered aromatic ring;
ring D is an optionally further substituted 5- to 7-membered ring;
one of $X^4$ and $X^5$ is a carbon atom, and the other one is a carbon atom or a nitrogen atom;
$X^6$ is a hydrogen atom or a halogen atom;
$X^7$ is a halogen atom;
ring E is an optionally further substituted nitrogen-containing 6-membered aromatic ring;
$X^8$ is a carbon atom or a nitrogen atom;
$X^9$ is a carbon atom or a nitrogen atom; and
$X^{10}$ is a hydrogen atom or an optionally substituted amino group, or
$X^9$ and $X^{10}$ are bonded to each other to form an optionally substituted ring,
or a salt thereof (sometimes to be abbreviated as "compound (I)" in the present specification).

[2] The compound of [1], wherein ring A is

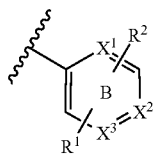

wherein ring B is an optionally further substituted 6-membered aromatic ring;
two of $X^1$, $X^2$ and $X^3$ are carbon atoms and the remaining one is a carbon atom or a nitrogen atom;
$R^1$ is a halogen atom, optionally halogenated methyl, or a hydroxy group optionally substituted by optionally halogenated methyl;
$R^2$ is a substituent;
$X^6$ is a hydrogen atom or a halogen atom;
$X^7$ is a halogen atom;
ring E is an optionally further substituted nitrogen-containing 6-membered aromatic ring;
$X^8$ is a carbon atom or a nitrogen atom;
$X^9$ is a carbon atom or a nitrogen atom; and
$X^{10}$ is a hydrogen atom or an optionally substituted amino group,
or a salt thereof.

[3] The compound of [1], wherein ring A is (1) the formula:

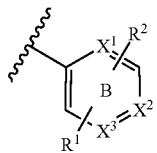

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a fluorine atom, a chlorine atom, a bromine atom, (2) methyl, trifluoromethyl, or (3) a hydroxy group optionally substituted by methyl, difluoromethyl or trifluoromethyl;
$R^2$ is (1) a halogen atom, (2) a cyano group, (3) a $C_{1-6}$ alkyl group optionally substituted by 1 to 3 substituents selected from a halogen atom and a hydroxy group, (4) a $C_{1-6}$ alkoxy group optionally substituted by 1 to 3 halogen atoms or (5) a mono- or di-$C_{1-6}$ alkylamino group; and
ring B is optionally further substituted by 1 to 3 substituents selected from (1) a halogen atom, (2) a $C_{1-6}$ alkyl group optionally substituted by 1 to 3 hydroxy groups and (3) a $C_{1-6}$ alkoxy group, or (2) the formula:

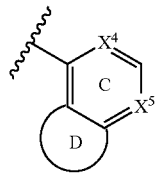

wherein the combination of $X^4$ and $X^5$ ($X^4$, $X^5$) is (carbon atom, carbon atom);
ring C is optionally further substituted by 1 to 3 halogen atoms;
ring D is a 5- to 7-membered aromatic heterocycle or a 5- to 7-membered non-aromatic heterocycle;
ring D is optionally further substituted by 1 to 3 substituents selected from (1) a halogen atom and (2) a hydroxy group;
$X^6$ is a hydrogen atom, a fluorine atom or a chlorine atom;
$X^7$ is a fluorine atom or a chlorine atom;
the combination of $X^8$ and $X^9$ ($X^8$, $X^9$) is (carbon atom, nitrogen atom), (nitrogen atom, carbon atom) or (nitrogen atom, nitrogen atom);
ring E is optionally further substituted by 1 to 3 substituents selected from (1) a $C_{1-6}$ alkyl group and (2) an amino group; and
$X^{10}$ is an amino group optionally substituted by 1-2 substituents selected from (1) a $C_{1-6}$ alkyl group optionally substituted by 1 to 3 substituents selected from a hydroxy group and a 3- to 14-membered non-aromatic heterocyclic group, (2) a $C_{3-10}$ cycloalkyl group optionally substituted by 1 to 3 hydroxy groups, (3) a 3- to 14-membered non-aromatic heterocyclic group and (4) a 5- to 14-membered aromatic heterocyclic group optionally substituted by 1 to 3 $C_{1-6}$ alkyl groups; or
$X^9$ and $X^{10}$ are bonded to each other to form a 5- to 14-membered aromatic heterocycle,
or a salt thereof.

[4] The compound of [1], wherein ring A is (1) the formula:

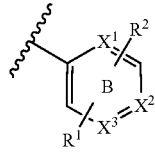

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a chlorine atom, a bromine atom, (2) methyl, trifluoromethyl, or (3) a hydroxy group substituted by methyl or trifluoromethyl;
$R^2$ is (1) a halogen atom, (2) a $C_{1-6}$ alkyl group optionally substituted by 1 to 3 substituents selected from a halogen atom and a hydroxy group or (3) a $C_{1-6}$ alkoxy group optionally substituted by 1 to 3 halogen atoms;

ring B is optionally further substituted by 1 to 3 substituents selected from (1) a halogen atom and (2) a $C_{1-6}$ alkyl group optionally substituted by 1 to 3 hydroxy groups, or (2) the formula:

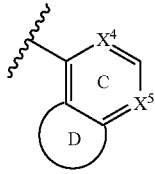

wherein the combination of $X^4$ and $X^5$ ($X^4$, $X^5$) is (carbon atom, carbon atom);
ring C is optionally further substituted by 1 to 3 halogen atoms;
ring D is a 5- to 7-membered non-aromatic heterocycle;
$X^6$ is a hydrogen atom, a fluorine atom or a chlorine atom;
$X^7$ is a fluorine atom or a chlorine atom;
the combination of $X^8$ and $X^9$ ($X^8$, $X^9$) is (carbon atom, nitrogen atom), (nitrogen atom, carbon atom) or (nitrogen atom, nitrogen atom);
ring E is optionally further substituted by 1 to 3 $C_{1-6}$ alkyl groups; and
$X^{10}$ is an amino group optionally substituted by 1-2 substituents selected from (1) a $C_{1-6}$ alkyl group optionally substituted by 1 to 3 hydroxy groups, (2) a $C_{3-10}$ cycloalkyl group optionally substituted by 1 to 3 hydroxy groups and (3) a 3- to 14-membered non-aromatic heterocyclic group; or
$X^9$ and $X^{10}$ are bonded to each other to form a 5- to 14-membered aromatic heterocycle,
or a salt thereof.
[5] The compound of [1], wherein ring A is the formula

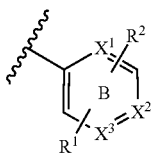

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a chlorine atom, a bromine atom, (2) methyl, trifluoromethyl, or (3) a hydroxy group substituted by methyl or trifluoromethyl;
$R^2$ is (1) a halogen atom, (2) a $C_{1-6}$ alkyl group optionally substituted by 1 to 3 substituents selected from a halogen atom and a hydroxy group or (3) a $C_{1-6}$ alkoxy group optionally substituted by 1 to 3 halogen atoms;
ring B is optionally further substituted by 1 to 3 substituents selected from (1) a halogen atom and (2) a $C_{1-6}$ alkyl group optionally substituted by 1 to 3 hydroxy groups;
$X^6$ is a hydrogen atom, a fluorine atom or a chlorine atom;
$X^7$ is a fluorine atom or a chlorine atom;
the combination of $X^8$ and $X^9$ ($X^8$, $X^9$) is (carbon atom, nitrogen atom);
ring E is optionally further substituted by 1 to 3 $C_{1-6}$ alkyl groups; and
$X^{10}$ is an amino group optionally substituted by 1-2 substituents selected from (1) a $C_{1-6}$ alkyl group optionally substituted by 1 to 3 hydroxy groups, (2) a $C_{3-10}$ cycloalkyl group optionally substituted by 1 to 3 hydroxy groups and (3) a 3- to 14-membered non-aromatic heterocyclic group, or a salt thereof.
[6] N-(3-((2-Aminopyrimidin-5-yl)ethynyl)-2,4-difluorophenyl)-5-chloro-2-methoxypyridine-3-sulfonamide or a salt thereof.
[7] 5-Chloro-N-(2,4-difluoro-3-((2-((trans-4-hydroxycyclohexyl)amino)pyrimidin-5-yl)ethynyl)phenyl)-2-methoxypyridine-3-sulfonamide or a salt thereof.
[8] 2,5-Dichloro-N-(2,4-difluoro-3-((2-(((2R)-1-hydroxypropan-2-yl)amino)pyrimidin-5-yl)ethynyl)phenyl)-3-(hydroxymethyl)benzenesulfonamide or a salt thereof.
[9] A medicament comprising the compound of [1] or a salt thereof.
[10] The medicament of [9] which is a prophylactic or therapeutic agent for cancer.
[11] The medicament of [9] which is a GCN2 inhibitor.
[12] A method for inhibiting GCN2 in a mammal, comprising administering an effective amount of the compound of [1] or a salt thereof to the mammal.
[13] A method for the prophylaxis or treatment of cancer in a mammal, comprising administering an effective amount of the compound of [1] or a salt thereof to the mammal.
[14] Use of the compound of [1] or a salt thereof for producing a prophylactic or therapeutic agent for cancer.
[15] The compound of [1] or a salt thereof which is used for the prophylaxis or treatment of cancer.

Effect of the Invention

According to the present invention, a heterocyclic compound that may have a GCN2 inhibitory action, and is expected to be useful for the prophylaxis or treatment of GCN2 associated diseases including cancer and the like, and a medicament containing same are provided.

DETAILED DESCRIPTION OF THE INVENTION

The definition of each substituent used in the present specification is described in detail in the following. Unless particularly indicated, each substituent is as defined below.
In the present specification, examples of the "halogen atom" include fluorine, chlorine, bromine and iodine.
In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.
In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.
In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.
In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),

(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) an amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, R-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-3-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl) an amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) an amino group (e.g., methylcarbamoylamino), a (mono- or di-$C_{7-16}$ aralkyl-carbamoyl) an amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) an amino group (e.g., N-acetyl-N-methylamino) and a ($C_{1-6}$ alkyl) ($C_{6-14}$ aryl-carbonyl) an amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{16}$ alkyl-carbamoyl group and a mono- or di-$C_{716}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbocycle" include a $C_{6-14}$ aromatic hydrocarbocycle, $C_{3-10}$ cycloalkane and $C_{3-10}$ cycloalkene.

In the present specification, examples of the "$C_{6-14}$ aromatic hydrocarbocycle" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "6-membered aromatic ring" of the "optionally further substituted 6-membered aromatic ring" include "benzene ring" and the above-mentioned "aromatic heterocycle" having 6 members, and as the substituent thereof, the above-mentioned "substituent" can be mentioned.

In the present specification, examples of the "5- to 7-membered ring" of the "optionally further substituted 5- to 7-membered ring" include the above-mentioned "hydrocarbon ring" and "heterocycle" having 5 to 7 members, and as the substituent thereof, the above-mentioned "substituent" can be mentioned.

In the present specification, examples of the "nitrogen-containing 6-membered aromatic ring" of the "optionally further substituted nitrogen-containing 6-membered aromatic ring" include the above-mentioned "aromatic heterocycle" containing at least one nitrogen atom as the ring-constituting atom and having 6 members, and as the substituent thereof, the above-mentioned "substituent" can be mentioned.

In the present specification, examples of the "ring" of the "optionally substituted ring" include the above-mentioned "hydrocarbon ring" and "heterocycle", and as the substituent thereof, the above-mentioned "substituent" can be mentioned.

The definition of each symbol in the formula (I) is described in detail in the following.

Ring A is (1) the formula:

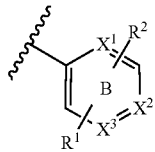

wherein ring B is an optionally further substituted 6-membered aromatic ring;
two of $X^1$, $X^2$ and $X^3$ are carbon atoms and the remaining one is a carbon atom or a nitrogen atom;
$R^1$ is a halogen atom, optionally halogenated methyl, or a hydroxy group optionally substituted by optionally halogenated methyl; and
$R^2$ is a substituent, or (2) the formula:

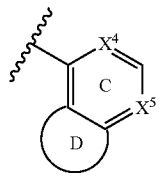

wherein ring C is an optionally further substituted 6-membered aromatic ring;
ring D is an optionally further substituted 5- to 7-membered ring; and
one of $X^4$ and $X^5$ is a carbon atom, and the other one is a carbon atom or a nitrogen atom.

(1) Two of $X^1$, $X^2$ and $X^3$ constituting ring B are carbon atoms and the remaining one is a carbon atom or a nitrogen atom. That is, the "6-membered aromatic ring" of the "optionally further substituted 6-membered aromatic ring" for ring B is a benzene ring or a pyridine ring.

The combination of $X^1$, $X^2$ and $X^3$ ($X^1$, $X^2$, $X^3$) is preferably (carbon atom, carbon atom, carbon atom) or (carbon atom, carbon atom, nitrogen atom)

The "6-membered aromatic ring" of the "optionally further substituted 6-membered aromatic ring" for ring B is optionally further substituted, at substitutable position(s), by 1-3 (preferably 1-2, more preferably 1) substituents other than $R^1$, $R^2$ and —NH—S(=O)$_2$— group. Examples of such substituent include the above-mentioned "substituent", preferably, (1) a halogen atom (e.g., chlorine atom), (2) an optionally substituted $C_{1-6}$ alkyl group (e.g., methyl, isopropyl), (3) an optionally substituted $C_{1-6}$ alkoxy group (e.g., methoxy), (4) a carboxy group, (5) an optionally substituted $C_{1-6}$ alkoxy-carbonyl group (e.g., ethoxycarbonyl) or (6) a carbamoyl group, more preferably, (1) a halogen atom (e.g., chlorine atom), (2) a $C_{1-6}$ alkyl group (e.g., methyl, isopropyl) optionally substituted by 1 to 3 substituents selected from a hydroxy group and a $C_{1-6}$ alkoxy-carbonyl group (e.g., methoxycarbonyl), (3) a $C_{1-6}$ alkoxy group (e.g., methoxy), (4) a carboxy group, (5) a $C_{1-6}$ alkoxy-carbonyl group (e.g., ethoxycarbonyl) or (6) a carbamoyl group, further preferably, (1) a halogen atom (e.g., chlorine atom), (2) a $C_{1-6}$ alkyl group (e.g., methyl) optionally substituted by 1 to 3 hydroxy groups or (3) a $C_{1-6}$ alkoxy group (e.g., methoxy), particularly preferably, (1) a halogen atom (e.g., chlorine atom) or (2) a $C_{1-6}$ alkyl group (e.g., methyl) optionally substituted by 1 to 3 hydroxy groups. When plural substituents are present, each substituent may be the same or different.

$R^1$ is preferably (1) a halogen atom (e.g., fluorine atom, chlorine atom, bromine atom), (2) optionally halogenated methyl (e.g., methyl, trifluoromethyl), or (3) a hydroxy group optionally substituted by optionally halogenated methyl (e.g., methyl, difluoromethyl, trifluoromethyl), more preferably, (1) a fluorine atom, a chlorine atom, a bromine atom, (2) methyl, trifluoromethyl, or (3) a hydroxy group substituted by methyl, difluoromethyl or trifluoromethyl, further preferably, (1) a chlorine atom, a bromine atom, (2) methyl, trifluoromethyl, or (3) a hydroxy group substituted by methyl or trifluoromethyl.

Examples of the "substituent" for $R^2$ include the above-mentioned "substituent", preferably, (1) a halogen atom (e.g., fluorine atom, chlorine atom, bromine atom), (2) a hydroxy group, (3) a cyano group, (4) an optionally substituted $C_{1-6}$ alkyl group (e.g., methyl, isopropyl), (5) an optionally substituted $C_{1-6}$ alkoxy group (e.g., methoxy, ethoxy), (6) a carboxy group, (7) an optionally substituted $C_{1-6}$ alkoxy-carbonyl group (e.g., methoxycarbonyl, ethoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl), more preferably, (1) a halogen atom (e.g., fluorine atom, chlorine atom, bromine atom), (2) a hydroxy group, (3) a cyano group, (4) a $C_{1-6}$ alkyl group (e.g., methyl, isopropyl) optionally substituted by 1 to 3 substituents selected from a halogen atom (e.g., fluorine atom) and a hydroxy group, (5) a $C_{1-6}$ alkoxy group (e.g., methoxy, ethoxy) optionally substituted by 1 to 3 halogen atoms (e.g., fluorine atom), (6) a carboxy group, (7) a $C_{1-6}$ alkoxy-carbonyl group (e.g., methoxycarbonyl, ethoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl), further preferably, (1) a halogen atom (e.g., fluorine atom, chlorine atom, bromine atom), (2) a cyano group, (3) a $C_{1-6}$ alkyl group (e.g., methyl) optionally substituted by 1 to 3 substituents selected from a halogen atom (e.g., fluorine atom) and a hydroxy group, (4) a $C_{1-6}$ alkoxy group (e.g., methoxy) optionally substituted by 1 to 3 halogen atoms (e.g., fluorine atom) or (5) a mono- or di-$C_{1-6}$ alkylamino group (e.g., methylamino), particularly preferably, (1) a halogen atom (e.g., chlorine atom, bromine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom).

(2) One of $X^4$ and $X^5$ constituting ring C is a carbon atom, and the other one is a carbon atom or a nitrogen atom. That is, the "6-membered aromatic ring" of the "optionally further substituted 6-membered aromatic ring" for ring C is a benzene ring or a pyridine ring.

The combination of $X^4$ and $X^5$ ($X^4$, $X^5$) is preferably (carbon atom, carbon atom).

The "6-membered aromatic ring" of the "optionally further substituted 6-membered aromatic ring" for ring C is optionally further substituted, at substitutable position(s), by 1-3 (preferably 1-2, more preferably 1) substituents other than —NH—S(=O)$_2$— group. Examples of such substituent include the above-mentioned "substituent", preferably, a halogen atom (e.g., chlorine atom). When plural substituents are present, each substituent may be the same or different.

The "5- to 7-membered ring" of the "optionally further substituted 5- to 7-membered ring" for ring D is preferably a benzene ring, a 5- to 7-membered aromatic heterocycle (e.g., imidazole ring, pyrazole ring, furan ring, pyridine ring) or a 5- to 7-membered non-aromatic heterocycle (e.g., dihydrofuran ring), more preferably, a benzene ring, an imidazole ring, a pyrazole ring, a furan ring, a pyridine ring or a dihydrofuran ring, further preferably, an imidazole ring, a furan ring or a dihydrofuran ring, particularly preferably, a dihydrofuran ring.

The "5- to 7-membered ring" of the "optionally further substituted 5- to 7-membered ring" for ring D is optionally further substituted by 1-3 (preferably 1-2, more preferably 1) substituents at substitutable position(s). Examples of such substituent include the above-mentioned "substituent", preferably, (1) a halogen atom (e.g., chlorine atom), (2) a hydroxy group or (3) a $C_{1-6}$ alkyl group (e.g., methyl), more preferably, (1) a halogen atom (e.g., chlorine atom) or (2) a hydroxy group. When plural substituents are present, each substituent may be the same or different.

In one embodiment of the present invention, ring A is preferably the formula:

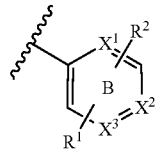

wherein each symbol is as defined above.

In one embodiment of the present invention, ring A is further preferably the formula:

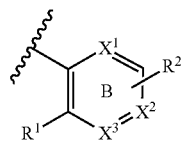

wherein each symbol is as defined above.

$X^6$ is a hydrogen atom or a halogen atom.

$X^6$ is preferably a hydrogen atom, a fluorine atom or a chlorine atom $X^7$ is a halogen atom.

$X^7$ is preferably a fluorine atom or a chlorine atom

Ring E is an optionally further substituted nitrogen-containing 6-membered aromatic ring, $X^8$ is a carbon atom or a nitrogen atom, $X^9$ is a carbon atom or a nitrogen atom, $X^{10}$ is a hydrogen atom or an optionally substituted amino group, or $X^9$ and $X^{10}$ are bonded to each other to form an optionally substituted ring.

$X^8$ and $X^9$ constituting ring E is each a carbon atom or a nitrogen atom. That is, the "nitrogen-containing 6-membered aromatic ring" of the "optionally further substituted nitrogen-containing 6-membered aromatic ring" for ring E is a pyridine ring, a pyrimidine ring, a pyrazine ring or a 1,2,4-triazine ring.

The combination of $X^8$ and $X^9$ ($X^8$, $X^9$) is preferably (carbon atom, carbon atom), (carbon atom, nitrogen atom), (nitrogen atom, carbon atom) or (nitrogen atom, nitrogen atom), more preferably, (carbon atom, nitrogen atom), (nitrogen atom, carbon atom) or (nitrogen atom, nitrogen atom).

The "nitrogen-containing 6-membered aromatic ring" of the "optionally further substituted nitrogen-containing 6-membered aromatic ring" for ring E is optionally further substituted, at substitutable position(s), by 1-3 (preferably 1-2, more preferably 1) substituents other than $X^{10}$ and —C≡C— group. Examples of such substituent include the above-mentioned "substituent", preferably, (1) a halogen atom (e.g., fluorine atom, bromine atom), (2) an optionally substituted $C_{1-6}$ alkyl group (e.g., methyl), (3) an optionally substituted $C_{1-6}$ alkoxy group (e.g., methoxy) or (4) an optionally substituted amino group, more preferably, (1) a halogen atom (e.g., fluorine atom, bromine atom), (2) a $C_{1-6}$ alkyl group (e.g., methyl), (3) a $C_{1-6}$ alkoxy group (e.g., methoxy) or (4) an amino group, further preferably, (1) a $C_{1-6}$ alkyl group (e.g., methyl) or (2) an amino group, particularly preferably, a $C_{1-6}$ alkyl group (e.g., methyl). When plural substituents are present, each substituent may be the same or different.

Examples of the substituent of the "optionally substituted amino group" for $X^{10}$ include the above-mentioned "substituent", preferably, (1) an optionally substituted $C_{1-6}$ alkyl group (e.g., methyl, ethyl, propyl, isopropyl, isobutyl, tert-butyl, 1,1-dimethylpropyl, isopentyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., oxetanyl, tetrahydrofuranyl, tetrahydropyranyl, pyrrolidinyl), (4) an optionally substituted 5- to 14-membered aromatic heterocyclic group (e.g., pyrazolyl), (5) an optionally substituted $C_{1-6}$ alkyl-carbonyl group (e.g., methylcarbonyl) or (6) an optionally substituted $C_{3-10}$ cycloalkyl-carbonyl group (e.g., cyclopropylcarbonyl), more preferably, (1) a $C_{1-6}$ alkyl group (e.g., methyl, ethyl, propyl, isopropyl, isobutyl, tert-butyl, 1,1-dimethylpropyl, isopentyl) optionally substituted by 1 to 3 substituents selected from (i) a halogen atom (e.g., fluorine atom), (ii) a hydroxy group, (iii) a $C_{3-10}$ cycloalkyl group (e.g., cyclopropyl, cyclobutyl, cyclopentyl) optionally substituted by 1 to 3 hydroxy groups, (iv) a 3- to 14-membered non-aromatic heterocyclic group (e.g., tetrahydrofuranyl, tetrahydropyranyl) optionally substituted 1 to 3 $C_{1-6}$ alkyl groups (e.g., methyl) and (v) a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., oxetanyl, tetrahydrofuranyl, tetrahydropyranyl, pyrrolidinyl) optionally substituted by 1 to 3 hydroxy groups, (4) a 5- to 14-membered aromatic heterocyclic group (e.g., pyrazolyl) optionally substituted by 1 to 3 $C_{1-6}$ alkyl groups (e.g., methyl), (5) a $C_{1-6}$ alkyl-carbonyl group (e.g., methylcarbonyl) or (6) a $C_{3-10}$ cycloalkyl-carbonyl group (e.g., cyclopropylcarbonyl), further preferably, (1) a $C_{1-6}$ alkyl group (e.g., methyl, ethyl, propyl, isopropyl, isobutyl, tert-butyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopropyl, cyclohexyl) optionally substituted by 1 to 3 hydroxy groups, (3) a 3- to 14-membered non-aromatic heterocyclic group (e.g., oxetanyl, tetrahydrofuranyl) or (4) a 5- to 14-membered aromatic heterocyclic group (e.g., pyrazolyl) optionally substituted by 1 to 3 $C_{1-6}$ alkyl groups (e.g., methyl), particularly preferably, (1) a $C_{1-6}$ alkyl group (e.g., isopropyl) optionally substituted by 1 to 3 hydroxy groups, (2) a $C_{3-10}$ cycloalkyl group (e.g., cyclopropyl, cyclohexyl) optionally substituted by 1 to 3 hydroxy groups or (3) a 3- to 14-membered non-aromatic heterocyclic group (e.g., tetrahydrofuranyl). When plural substituents are present, each substituent may be the same or different.

$X^{10}$ is preferably a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl, isopentyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., oxetanyl, tetrahydrofuranyl, tetrahydropyranyl, pyrrolidinyl), (4) an optionally substituted 5- to 14-membered aromatic heterocyclic group (e.g., pyrazolyl), (5) an optionally substituted $C_{1-6}$ alkyl-carbonyl group (e.g., methylcarbonyl) and (6) an optionally substituted $C_{3-10}$ cycloalkyl-carbonyl group (e.g., cyclopropylcarbonyl), more preferably, a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl, isopentyl) optionally substituted by 1 to 3 substituents selected from (i) a halogen atom (e.g., fluorine atom), (ii) a hydroxy group, (iii) a $C_{3-10}$ cycloalkyl group (e.g., cyclopropyl, cyclobutyl, cyclopentyl) optionally substituted by 1 to 3 hydroxy groups, (iv) a 3- to 14-membered non-aromatic heterocyclic group (e.g., tetrahydrofuranyl, tetrahydropyranyl) optionally substituted by 1 to 3 $C_{1-6}$ alkyl groups (e.g., methyl) and (v) a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., oxetanyl, tetrahydrofuranyl, tetrahydropyranyl, pyrrolidinyl) optionally substituted by 1 to 3 hydroxy groups, (4) a 5- to 14-membered aromatic heterocyclic group (e.g., pyrazolyl) optionally substituted by 1 to 3 $C_{1-6}$ alkyl groups (e.g., methyl), (5) a $C_{1-6}$ alkyl-carbonyl group (e.g., methylcarbonyl) and (6) a $C_{3-10}$ cycloalkyl-carbonyl group (e.g., cyclopropylcarbonyl), further preferably, an amino group optionally substituted by 1-2 substituents selected from (1) a $C_{1-6}$ alkyl group (e.g., methyl, ethyl, propyl, isopropyl, isobutyl, tert-butyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopropyl, cyclohexyl) optionally substituted by 1 to 3 hydroxy groups, (3) a 3- to 14-membered non-aromatic heterocyclic group (e.g., oxetanyl, tetrahydrofuranyl) and (4) a 5- to 14-membered aromatic heterocyclic group (e.g., pyrazolyl) optionally substituted by 1 to 3 $C_{1-6}$ alkyl groups (e.g., methyl), particularly preferably, an amino group optionally substituted by 1-2 substituents selected from (1) a $C_{1-6}$ alkyl group (e.g., isopropyl) optionally substituted by 1 to 3 hydroxy groups, (2) a $C_{3-10}$ cycloalkyl group (e.g., cyclopropyl, cyclohexyl) optionally substituted by 1 to 3 hydroxy groups and (3) a 3- to 14-membered non-aromatic heterocyclic group (e.g., tetrahydrofuranyl).

Examples of the "ring" of the "optionally substituted ring" formed by $X^9$ and $X^{10}$ bonded to each other include the above-mentioned "hydrocarbon ring" and "heterocycle", preferably, a 5- to 14-membered aromatic heterocycle (e.g., pyrazole ring, pyridine ring) or a 3- to 14-membered non-aromatic heterocycle (e.g., dihydropyrrole ring, tetrahydropyridine ring, dihydrooxazine ring), more preferably, a 5- or 6-membered monocyclic aromatic heterocycle (e.g., pyrazole ring, pyridine ring) or a 3- to 8-membered monocyclic non-aromatic heterocycle (e.g., dihydropyrrole ring, tetrahydropyridine ring, dihydrooxazine ring), further preferably, a pyrazole ring, a pyridine ring, a dihydropyrrole ring, a tetrahydropyridine ring (particularly, 1,2,3,4-tetrahydropyridine ring) or a dihydrooxazine ring (particularly, 3,4-dihydro-2H-1,4-oxazine ring), particularly preferably, a pyrazole ring.

The "ring" of the "optionally substituted ring" formed by $X^9$ and $X^{10}$ bonded to each other is optionally substituted by 1-3 (preferably 1-2, more preferably 1) substituents at substitutable position(s). Examples of such substituent include the above-mentioned "substituent", preferably, an oxo group. When plural substituents are present, each substituent may be the same or different.

In one embodiment of the present invention, preferably, ring E is an optionally further substituted nitrogen-containing 6-membered aromatic ring, $X^8$ is a carbon atom or a nitrogen atom, $X^9$ is a carbon atom or a nitrogen atom, and $X^{10}$ is a hydrogen atom or an optionally substituted amino group. That is, an embodiment in which $X^9$ and $X^{10}$ are bonded to each other to form an optionally substituted ring is excluded.

In another embodiment of the present invention, preferably, ring E is an optionally further substituted nitrogen-containing 6-membered aromatic ring, $X^8$ is a carbon atom, $X^9$ is a nitrogen atom, and $X^{10}$ is a hydrogen atom or an optionally substituted amino group. That is, an embodiment in which $X^9$ and $X^{10}$ are bonded to each other to form an optionally substituted ring is excluded. Such compound is superior in the GCN2 inhibitory activity, and is particularly preferable from the aspects of pharmacokinetics and toxicity.

Preferable examples of compound (I) include the following compounds.

[Compound A]

Compound (I) wherein ring A is (1) the formula:

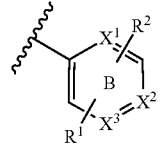

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group substituted by optionally halogenated methyl (e.g., methyl, difluoromethyl, trifluoromethyl);

$R^2$ is (1) a halogen atom (e.g., fluorine atom, chlorine atom, bromine atom), (2) a cyano group, (3) an optionally substituted $C_{1-6}$ alkyl group (e.g., methyl, isopropyl), (4) an optionally substituted $C_{1-6}$ alkoxy group (e.g., methoxy, ethoxy), (5) a carboxy group, (6) an optionally substituted $C_{1-6}$ alkoxy-carbonyl group (e.g., methoxycarbonyl, ethoxycarbonyl), (7) a carbamoyl group or (8) a mono- or di-$C_{1-6}$ alkyl-carbamoyl group (e.g., methylcarbamoyl); and ring B is optionally further substituted by 1-3 (preferably 1-2, more preferably 1) substituents selected from (1) a halogen atom (e.g., chlorine atom), (2) an optionally substituted $C_{1-6}$ alkyl group (e.g., methyl), (3) an optionally substituted $C_{1-6}$ alkoxy group (e.g., methoxy), (4) a carboxy group, (5) an optionally substituted $C_{1-6}$ alkoxy-carbonyl group (e.g., ethoxycarbonyl) and (6) a carbamoyl group, or (2) the formula:

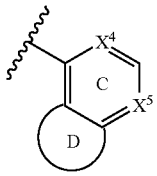

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., pyridine ring) or a 5- to 7-membered non-aromatic heterocycle (e.g., dihydrofuran ring));

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) an optionally substituted $C_{1-6}$ alkyl group (e.g., methyl), (3) an optionally substituted $C_{1-6}$ alkoxy group (e.g., methoxy) and (4) an optionally substituted amino group; and $X^{10}$ is a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., tetrahydrofuranyl, tetrahydropyranyl, pyrrolidinyl), (4) an optionally substituted $C_{1-6}$ alkyl-carbonyl group (e.g., methylcarbonyl) and (5) an optionally substituted $C_{3-10}$ cycloalkyl-carbonyl group (e.g., cyclopropylcarbonyl); or $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., tetrahydropyridine ring, dihydrooxazine ring), each of which is optionally substituted.

[Compound B]

Compound (I) wherein ring A is (1) the formula:

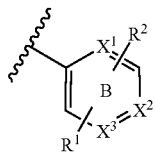

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group substituted by optionally halogenated methyl (e.g., methyl, difluoromethyl, trifluoromethyl);

$R^2$ is (1) a halogen atom (e.g., fluorine atom, chlorine atom, bromine atom), (2) a cyano group, (3) a $C_{1-6}$ alkyl group (e.g., methyl, isopropyl) optionally substituted by 1 to 3 substituents selected from a halogen atom (e.g., fluorine atom) and a hydroxy group, (4) a $C_{1-6}$ alkoxy group (e.g., methoxy, ethoxy) optionally substituted by 1 to 3 halogen atoms (e.g., fluorine atom), (5) a carboxy group, (6) a $C_{1-6}$ alkoxy-carbonyl group (e.g., methoxycarbonyl, ethoxycarbonyl), (7) a carbamoyl group or (8) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups, (3) a $C_{1-6}$ alkoxy group (e.g., methoxy), (4) a carboxy group, (5) a $C_{1-6}$ alkoxy-carbonyl group (e.g., ethoxycarbonyl) and (6) a carbamoyl group, or (2) the formula:

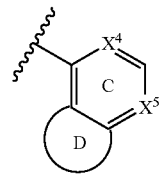

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., pyridine ring) or a 5- to 7-membered non-aromatic heterocycle (e.g., dihydrofuran ring);

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) a $C_{1-6}$ alkyl group (e.g., methyl), (3) a $C_{1-6}$ alkoxy group (e.g., methoxy) and (4) an amino group; and $X^{10}$ is a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl) optionally substituted by 1 to 3 substituents selected from a hydroxy group, a $C_{3-10}$ cycloalkyl group (e.g., cyclopropyl, cyclopentyl) optionally substituted by a hydroxy group and a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., tetrahydrofuranyl, tetrahydropyranyl, pyrrolidinyl) optionally substituted by a hydroxy group, (4) a $C_{1-6}$ alkyl-carbonyl group (e.g., methylcarbonyl) and (5) a $C_{3-10}$ cycloalkyl-carbonyl group (e.g., cyclopropylcarbonyl); or $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., tetrahydropyridine ring, dihydrooxazine ring), each of which is optionally substituted by an oxo group.

[Compound C]

Compound (I) wherein ring A is (1) the formula:

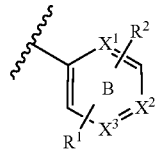

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a fluorine atom, a chlorine atom, a bromine atom, (2) methyl, trifluoromethyl, or (3) a hydroxy group substituted by methyl, difluoromethyl or trifluoromethyl;

$R^2$ is (1) a halogen atom (e.g., fluorine atom, chlorine atom, bromine atom), (2) a cyano group, (3) a $C_{1-6}$ alkyl group (e.g., methyl) optionally substituted by 1 to 3 substituents selected from a halogen atom (e.g., fluorine atom) and a hydroxy group or (4) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups and (3) a $C_{1-6}$ alkoxy group (e.g., methoxy), or (2) the formula:

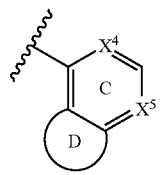

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a $C_{1-6}$ alkyl group (e.g., methyl) and (2) an amino group; and $X^{10}$ is an amino group optionally substituted by 1-2 substituents selected from (1) a $C_{1-6}$ alkyl group (e.g., methyl, ethyl, propyl, isopropyl, isobutyl, tert-butyl) optionally substituted by a hydroxy group, (2) a $C_{3-10}$ cycloalkyl group (e.g., cyclopropyl, cyclohexyl) optionally substituted by a hydroxy group and (3) a 3- to 14-membered non-aromatic heterocyclic group (e.g., tetrahydrofuranyl); or $X^9$ and $X^{10}$ are bonded to each other to form a 5- to 14-membered aromatic heterocycle (e.g., a pyrazole ring).

[Compound D]

Compound (I) wherein ring A is (1) the formula:

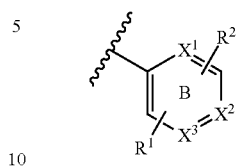

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, a bromine atom, (2) methyl, trifluoromethyl, or (3) a hydroxy group substituted by methyl or trifluoromethyl;

$R^2$ is (1) a halogen atom (e.g., chlorine atom, bromine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups, or (2) the formula:

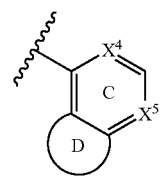

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) $C_{1-6}$ alkyl groups (e.g., methyl); and $X^{10}$ is an amino group optionally substituted by 1-2 substituents selected from (1) a $C_{1-6}$ alkyl group (e.g., isopropyl), (2) a $C_{3-10}$ cycloalkyl group (e.g., cyclopropyl) and (3) a 3- to 14-membered non-aromatic heterocyclic group (e.g., tetrahydrofuranyl); or $X^9$ and $X^{10}$ are bonded to each other to form a 5- to 14-membered aromatic heterocycle (e.g., a pyrazole ring).

[Compound A-1]

Compound (I) wherein ring A is the formula:

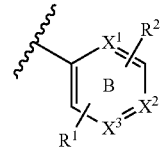

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group substituted by optionally halogenated methyl (e.g., methyl, difluoromethyl, trifluoromethyl);

$R^2$ is (1) a halogen atom (e.g., fluorine atom, chlorine atom, bromine atom), (2) a cyano group, (3) an optionally substituted $C_{1-6}$ alkyl group (e.g., methyl, isopropyl), (4) an optionally substituted $C_{1-6}$ alkoxy group (e.g., methoxy, ethoxy), (5) a carboxy group, (6) an optionally substituted $C_{1-6}$ alkoxy-carbonyl group (e.g., methoxycarbonyl, ethoxycarbonyl), (7) a carbamoyl group or (8) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) an optionally substituted $C_{1-6}$ alkyl group (e.g., methyl), (3) an optionally substituted $C_{1-6}$ alkoxy group (e.g., methoxy), (4) a carboxy group, (5) an optionally substituted $C_{1-6}$ alkoxy-carbonyl group (e.g., ethoxycarbonyl) and (6) a carbamoyl group;

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) an optionally substituted $C_{1-6}$ alkyl group (e.g., methyl), (3) an optionally substituted $C_{1-6}$ alkoxy group (e.g., methoxy) and (4) an optionally substituted amino group; and $X^{10}$ is a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., tetrahydrofuranyl, tetrahydropyranyl, pyrrolidinyl), (4) an optionally substituted $C_{1-6}$ alkyl-carbonyl group (e.g., methylcarbonyl) and (5) an optionally substituted $C_{3-10}$ cycloalkyl-carbonyl group (e.g., cyclopropylcarbonyl); or $X^9$ and $X^{10}$ are bonded to each other to form a 5- to 14-membered aromatic heterocycle (e.g., a pyrazole ring, a pyridine ring) or a 3- to 14-membered non-aromatic heterocycle (e.g., tetrahydropyridine ring, dihydrooxazine ring), each of which is optionally substituted.

[Compound B-1]

Compound (I) wherein ring A is the formula:

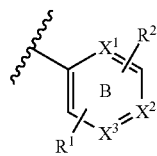

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group substituted by optionally halogenated methyl (e.g., methyl, difluoromethyl, trifluoromethyl);

$R^2$ is (1) a halogen atom (e.g., fluorine atom, chlorine atom, bromine atom), (2) a cyano group, (3) a $C_{1-6}$ alkyl group (e.g., methyl, isopropyl) optionally substituted by 1 to 3 substituents selected from a halogen atom (e.g., fluorine atom) and a hydroxy group, (4) a $C_{1-6}$ alkoxy group (e.g., methoxy, ethoxy) optionally substituted by 1 to 3 halogen atoms (e.g., fluorine atom), (5) a carboxy group, (6) a $C_{1-6}$ alkoxy-carbonyl group (e.g., methoxycarbonyl, ethoxycarbonyl), (7) a carbamoyl group or (8) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups, (3) a $C_{1-6}$ alkoxy group (e.g., methoxy), (4) a carboxy group, (5) a $C_{1-6}$ alkoxy-carbonyl group (e.g., ethoxycarbonyl) and (6) a carbamoyl group;

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) a $C_{1-6}$ alkyl group (e.g., methyl), (3) a $C_{1-6}$ alkoxy group (e.g., methoxy) and (4) an amino group; and $X^{10}$ is a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl) optionally substituted by 1 to 3 substituents selected from a hydroxy group, a $C_{3-10}$ cycloalkyl group (e.g., cyclopropyl, cyclopentyl) optionally substituted by a hydroxy group and a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., tetrahydrofuranyl, tetrahydropyranyl, pyrrolidinyl) optionally substituted by a hydroxy group, (4) a $C_{1-6}$ alkyl-carbonyl group (e.g., methylcarbonyl) and (5) a $C_{3-10}$ cycloalkyl-carbonyl group (e.g., cyclopropylcarbonyl); or $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., tetrahydropyridine ring, dihydrooxazine ring), each of which is optionally substituted by an oxo group.

[Compound C-1]

Compound (I) wherein ring A is the formula:

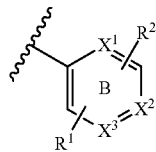

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a fluorine atom, a chlorine atom, a bromine atom, (2) methyl, trifluoromethyl, or (3) a hydroxy group substituted by methyl, difluoromethyl or trifluoromethyl;

$R^2$ is (1) a halogen atom (e.g., fluorine atom, chlorine atom, bromine atom), (2) a cyano group, (3) a $C_{1-6}$ alkyl group (e.g., methyl) optionally substituted by 1 to 3 substituents selected from a halogen atom (e.g., fluorine atom) and a hydroxy group or (4) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups and (3) a $C_{1-6}$ alkoxy group (e.g., methoxy);

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a $C_{1-6}$ alkyl group (e.g., methyl) and (2) an amino group; and $X^{10}$ is an amino group optionally substituted by 1-2 substituents selected from (1) a $C_{1-6}$ alkyl group (e.g., methyl, ethyl, propyl, isopropyl, isobutyl, tert-butyl) optionally substituted by a hydroxy group, (2) a $C_{3-10}$ cycloalkyl group (e.g., cyclopropyl, cyclohexyl) optionally substituted by a hydroxy group and (3) a 3- to 14-membered non-aromatic heterocyclic group (e.g., tetrahydrofuranyl); or $X^9$ and $X^{10}$ are bonded to each other to form a 5- to 14-membered aromatic heterocycle (e.g., a pyrazole ring).

[Compound D-1]

Compound (I) wherein ring A is the formula:

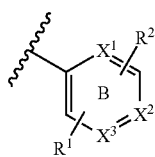

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, a bromine atom, (2) methyl, trifluoromethyl, or (3) a hydroxy group substituted by methyl or trifluoromethyl;

$R^2$ is (1) a halogen atom (e.g., chlorine atom, bromine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups;

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) $C_{1-6}$ alkyl groups (e.g., methyl); and $X^{10}$ is an amino group optionally substituted by 1-2 substituents selected from (1) a $C_{1-6}$ alkyl group (e.g., isopropyl), (2) a $C_{3-10}$ cycloalkyl group (e.g., cyclopropyl) and (3) a 3- to 14-membered non-aromatic heterocyclic group (e.g., tetrahydrofuranyl); or $X^9$ and $X^{10}$ are bonded to each other to form a 5- to 14-membered aromatic heterocycle (e.g., a pyrazole ring).

[Compound A-2]

Compound (I) wherein ring A is the formula:

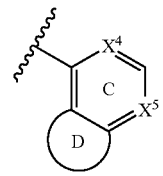

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., pyridine ring) or a 5- to 7-membered non-aromatic heterocycle (e.g., dihydrofuran ring);

$X^6$ is a halogen atom (e.g., fluorine atom);

$X^7$ is a halogen atom (e.g., fluorine atom);

the combination of $X^8$ and $X^9$ ($X^8$, $X^9$) is (carbon atom, nitrogen atom); and $X^{10}$ is an optionally substituted amino group; or $X^9$ and $X^{10}$ are bonded to each other to form an optionally substituted 5- to 14-membered aromatic heterocycle (e.g., a pyrazole ring).

[Compound B-2]

Compound (I) wherein ring A is the formula:

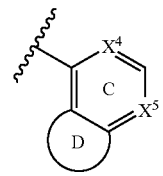

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., pyridine ring) or a 5- to 7-membered non-aromatic heterocycle (e.g., dihydrofuran ring);

$X^6$ is a halogen atom (e.g., fluorine atom);

$X^7$ is a halogen atom (e.g., fluorine atom);

the combination of $X^8$ and $X^9$ ($X^8$, $X^9$) is (carbon atom, nitrogen atom); and $X^{10}$ is an amino group; or $X^9$ and $X^{10}$ are bonded to each other to form a 5- to 14-membered aromatic heterocycle (e.g., a pyrazole ring).

[Compound C-2]
Compound (I) wherein ring A is the formula:

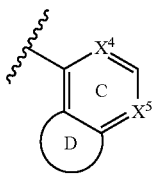

wherein the combination of $X^4$ and $X^5$ ($X^4$, $X^5$) is (carbon atom, carbon atom);
ring C is optionally further substituted by 1-3 (preferably 1-2, more preferably 1) halogen atoms (e.g., chlorine atom);
ring D is a 5- to 7-membered non-aromatic heterocycle (e.g., dihydrofuran ring);
$X^6$ is a fluorine atom;
$X^7$ is a fluorine atom;
the combination of $X^8$ and $X^9$ ($X^8$, $X^9$) is (carbon atom, nitrogen atom); and
$X^{10}$ is an amino group; or
$X^9$ and $X^{10}$ are bonded to each other to form a 5- to 14-membered aromatic heterocycle (e.g., a pyrazole ring).

[Compound A-3]
Compound (I) wherein ring A is (1) the formula:

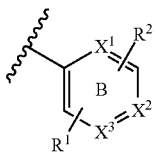

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a halogen atom (e.g., chlorine atom), (2) optionally halogenated methyl (e.g., methyl, trifluoromethyl), or (3) a hydroxy group substituted by optionally halogenated methyl (e.g., methyl, difluoromethyl, trifluoromethyl);
$R^2$ is (1) a halogen atom (e.g., chlorine atom), (2) a cyano group, (3) an optionally substituted $C_{1-6}$ alkyl group (e.g., methyl, isopropyl), (4) an optionally substituted $C_{1-6}$ alkoxy group (e.g., methoxy, ethoxy), (5) a carboxy group, (6) an optionally substituted $C_{1-6}$ alkoxy-carbonyl group (e.g., methoxycarbonyl), (7) a carbamoyl group or (8) a mono- or di-$C_{1-6}$ alkyl-carbamoyl group (e.g., methylcarbamoyl);
ring B is optionally further substituted by 1-3 (preferably 1-2, more preferably 1) substituents selected from (1) a halogen atom (e.g., chlorine atom) and (2) an optionally substituted $C_{1-6}$ alkyl group (e.g., methyl), or (2) the formula:

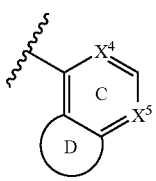

wherein the combination of $X^4$ and $X^5$ ($X^4$, $X^5$) is (carbon atom, carbon atom);
ring C is optionally further substituted by 1-3 (preferably 1-2, more preferably 1) halogen atoms (e.g., chlorine atom);
ring D is a 5- to 7-membered non-aromatic heterocycle (e.g., dihydrofuran ring);
$X^6$ is a hydrogen atom or a halogen atom (e.g., fluorine atom, chlorine atom);
$X^7$ is a halogen atom (e.g., fluorine atom, chlorine atom);
the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);
ring E is optionally further substituted by 1-3 (preferably 1-2, more preferably 1) substituents selected from (1) a halogen atom (e.g., fluorine atom, bromine atom), (2) an optionally substituted $C_{1-6}$ alkyl group (e.g., methyl), (3) an optionally substituted $C_{1-6}$ alkoxy group (e.g., methoxy) and (4) an optionally substituted amino group; and
$X^{10}$ is a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., tetrahydrofuranyl, tetrahydropyranyl, pyrrolidinyl), (4) an optionally substituted $C_{1-6}$ alkyl-carbonyl group (e.g., methylcarbonyl) and (5) an optionally substituted $C_{3-10}$ cycloalkyl-carbonyl group (e.g., cyclopropylcarbonyl).

[Compound B-3]
Compound (I) wherein ring A is (1) the formula:

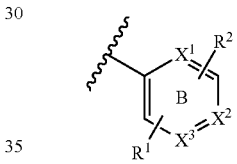

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a halogen atom (e.g., chlorine atom), (2) optionally halogenated methyl (e.g., methyl, trifluoromethyl), or (3) a hydroxy group substituted by optionally halogenated methyl (e.g., methyl, difluoromethyl, trifluoromethyl);
$R^2$ is (1) a halogen atom (e.g., chlorine atom), (2) a cyano group, (3) a $C_{1-6}$ alkyl group (e.g., methyl, isopropyl) optionally substituted by 1 to 3 substituents selected from a halogen atom (e.g., fluorine atom) and a hydroxy group, (4) a $C_{1-6}$ alkoxy group (e.g., methoxy, ethoxy) optionally substituted by 1 to 3 halogen atoms (e.g., fluorine atom), (5) a carboxy group, (6) a $C_{1-6}$ alkoxy-carbonyl group (e.g., methoxycarbonyl), (7) a carbamoyl group or (8) a mono- or di-$C_{1-6}$ alkyl-carbamoyl group (e.g., methylcarbamoyl);
ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups, or (2) the formula:

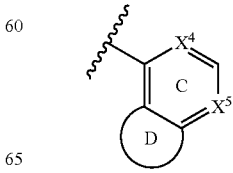

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^6$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) a $C_{1-6}$ alkyl group (e.g., methyl), (3) a $C_{1-6}$ alkoxy group (e.g., methoxy) and (4) an amino group; and $X^{10}$ is a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl) optionally substituted by 1 to 3 substituents selected from a hydroxy group, a $C_{3-10}$ cycloalkyl group (e.g., cyclopropyl, cyclopentyl) optionally substituted by a hydroxy group and a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., tetrahydrofuranyl, tetrahydropyranyl, pyrrolidinyl) optionally substituted by a hydroxy group, (4) a $C_{1-6}$ alkyl-carbonyl group (e.g., methylcarbonyl) and (5) a $C_{3-10}$ cycloalkyl-carbonyl group (e.g., cyclopropylcarbonyl).

[Compound C-3]

Compound (I) wherein ring A is (1) the formula:

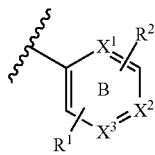

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, (2) methyl, trifluoromethyl, or (3) a hydroxy group substituted by methyl, difluoromethyl or trifluoromethyl;

$R^2$ is (1) a halogen atom (e.g., chlorine atom), (2) a cyano group, (3) a $C_{1-6}$ alkyl group (e.g., methyl) optionally substituted by 1 to 3 substituents selected from a halogen atom (e.g., fluorine atom) and a hydroxy group or (4) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups, or (2) the formula:

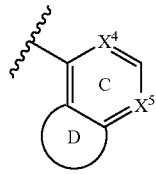

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a $C_{1-6}$ alkyl group (e.g., methyl) and (2) an amino group; and $X^{10}$ is an amino group optionally substituted by 1-2 substituents selected from (1) a $C_{1-6}$ alkyl group (e.g., methyl, ethyl, propyl, isopropyl, isobutyl, tert-butyl) optionally substituted by a hydroxy group, (2) a $C_{3-10}$ cycloalkyl group (e.g., cyclopropyl, cyclohexyl) optionally substituted by a hydroxy group and (3) a 3- to 14-membered non-aromatic heterocyclic group (e.g., tetrahydrofuranyl).

[Compound D-3]

Compound (I) wherein ring A is (1) the formula:

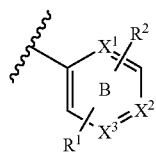

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, (2) methyl, trifluoromethyl, or (3) a hydroxy group substituted by methyl or trifluoromethyl;

$R^2$ is (1) a halogen atom (e.g., chlorine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups, or (2) the formula:

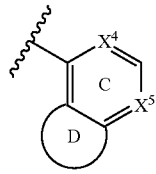

wherein the combination of $X^4$ and $X^5$ ($X^4$, $X^5$) is (carbon atom, carbon atom);
ring C is optionally further substituted by 1-3 (preferably 1-2, more preferably 1) halogen atoms (e.g., chlorine atom);
ring D is a 5- to 7-membered non-aromatic heterocycle (e.g., dihydrofuran ring);
$X^6$ is a hydrogen atom, a fluorine atom or a chlorine atom;
$X^7$ is a fluorine atom or a chlorine atom;
the combination of $X^8$ and $X^9$ ($X^8$, $X^9$) is (carbon atom, nitrogen atom), (nitrogen atom, carbon atom) or (nitrogen atom, nitrogen atom);
ring E is optionally further substituted by 1-3 (preferably 1-2, more preferably 1) $C_{1-6}$ alkyl groups (e.g., methyl); and
$X^{10}$ is an amino group optionally substituted by 1-2 substituents selected from (1) a $C_{1-6}$ alkyl group (e.g., isopropyl), (2) a $C_{3-10}$ cycloalkyl group (e.g., cyclopropyl) and (3) a 3- to 14-membered non-aromatic heterocyclic group (e.g., tetrahydrofuranyl).

[Compound A-4]
Compound (I) wherein ring A is (1) the formula:

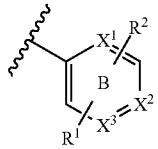

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a halogen atom (e.g., fluorine atom, chlorine atom, bromine atom), (2) optionally halogenated methyl (e.g., methyl, trifluoromethyl), or (3) a hydroxy group substituted by optionally halogenated methyl (e.g., methyl);
$R^2$ is (1) a halogen atom (e.g., fluorine atom, chlorine atom, bromine atom), (2) a cyano group, (3) an optionally substituted $C_{1-6}$ alkyl group (e.g., methyl), (4) an optionally substituted $C_{1-6}$ alkoxy group (e.g., methoxy), (5) a carboxy group, (6) an optionally substituted $C_{1-6}$ alkoxy-carbonyl group (e.g., methoxycarbonyl, ethoxycarbonyl) or (7) a carbamoyl group;
ring B is optionally further substituted by 1-3 (preferably 1-2, more preferably 1) substituents selected from (1) a halogen atom (e.g., chlorine atom), (2) an optionally substituted $C_{1-6}$ alkyl group (e.g., methyl), (3) an optionally substituted $C_{1-6}$ alkoxy group (e.g., methoxy), (4) a carboxy group, (5) an optionally substituted $C_{1-6}$ alkoxy-carbonyl group (e.g., ethoxycarbonyl) and (6) a carbamoyl group, or (2) the formula:

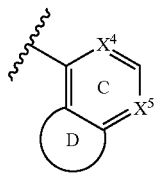

wherein the combination of $X^4$ and $X^5$ ($X^4$, $X^5$) is (carbon atom, carbon atom);
ring C is optionally further substituted by 1-3 (preferably 1-2, more preferably 1) halogen atoms (e.g., chlorine atom);
ring D is a benzene ring, a 5- to 7-membered aromatic heterocycle (e.g., pyridine ring) or a 5- to 7-membered non-aromatic heterocycle (e.g., dihydrofuran ring);
$X^6$ is a halogen atom (e.g., fluorine atom);
$X^7$ is a halogen atom (e.g., fluorine atom);
the combination of $X^8$ and $X^9$ ($X^8$, $X^9$) is (carbon atom, carbon atom); and
$X^9$ and $X^{10}$ are bonded to each other to form a 5- to 14-membered aromatic heterocycle (e.g., a pyrazole ring, a pyridine ring) or a 3- to 14-membered non-aromatic heterocycle (e.g., tetrahydropyridine ring, dihydrooxazine ring), each of which is optionally substituted.

[Compound B-4]
Compound (I) wherein ring A is (1) the formula:

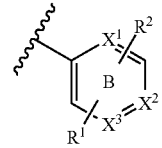

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a halogen atom (e.g., fluorine atom, chlorine atom, bromine atom), (2) optionally halogenated methyl (e.g., methyl, trifluoromethyl), or (3) a hydroxy group substituted by optionally halogenated methyl (e.g., methyl);
$R^2$ is (1) a halogen atom (e.g., fluorine atom, chlorine atom, bromine atom), (2) a cyano group, (3) a $C_{1-6}$ alkyl group (e.g., methyl) optionally substituted by 1 to 3 substituents selected from a halogen atom (e.g., fluorine atom) and a hydroxy group, (4) a $C_{1-6}$ alkoxy group (e.g., methoxy), (5) a carboxy group, (6) a $C_{1-6}$ alkoxy-carbonyl group (e.g., methoxycarbonyl, ethoxycarbonyl) or (7) a carbamoyl group;
ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups, (3) a $C_{1-6}$ alkoxy group (e.g., methoxy), (4) a carboxy group, (5) a $C_{1-6}$ alkoxy-carbonyl group (e.g., ethoxycarbonyl) and (6) a carbamoyl group, or (2) the formula:

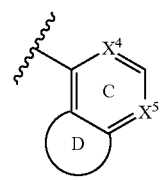

wherein the combination of $X^4$ and $X^5$ ($X^4$, $X^5$) is (carbon atom, carbon atom);
ring C is optionally further substituted by 1-3 (preferably 1-2, more preferably 1) halogen atoms (e.g., chlorine atom);
ring D is a benzene ring, a 5- to 7-membered aromatic heterocycle (e.g., pyridine ring) or a 5- to 7-membered non-aromatic heterocycle (e.g., dihydrofuran ring);
$X^6$ is a halogen atom (e.g., fluorine atom);
$X^7$ is a halogen atom (e.g., fluorine atom);
the combination of $X^8$ and $X^9$ ($X^8$, $X^9$) is (carbon atom, carbon atom); and X⁹ and X¹⁰ are bonded to each other to form a 5- to 14-membered aromatic heterocycle (e.g., pyrazole ring, pyridine ring) or a 3- to 14-membered non-aromatic heterocycle (e.g., tetrahydropyridine ring, dihydrooxazine ring), each of which is optionally substituted by an oxo group.

[Compound C-4]

Compound (I) wherein ring A is (1) the formula:

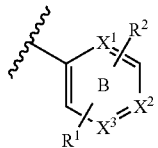

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a fluorine atom, a chlorine atom, a bromine atom, (2) methyl, or (3) a hydroxy group substituted by methyl;

$R^2$ is (1) a halogen atom (e.g., fluorine atom, chlorine atom, bromine atom), (2) a $C_{1-6}$ alkyl group (e.g., methyl) optionally substituted by 1 to 3 hydroxy groups or (3) a $C_{1-6}$ alkoxy group (e.g., methoxy);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups and (3) a $C_{1-6}$ alkoxy group (e.g., methoxy), or (2) the formula:

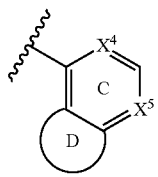

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a fluorine atom;

$X^7$ is a fluorine atom;

the combination of $X^8$ and $X^9$ ($X^8$, $X^9$) is (carbon atom, carbon atom); and $X^9$ and $X^{10}$ are bonded to each other to form a 5- to 14-membered aromatic heterocycle (e.g., a pyrazole ring).

[Compound D-4]

Compound (I) wherein ring A is (1) the formula:

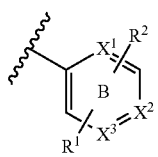

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, a bromine atom, (2) methyl, or (3) a hydroxy group substituted by methyl;

$R^2$ is (1) a halogen atom (e.g., chlorine atom, bromine atom), (2) a $C_{1-6}$ alkyl group (e.g., methyl) optionally substituted by 1 to 3 hydroxy groups or (3) a $C_{1-6}$ alkoxy group (e.g., methoxy);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups, or (2) the formula:

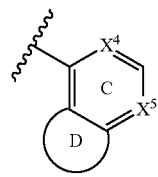

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a fluorine atom;

$X^7$ is a fluorine atom;

the combination of $X^8$ and $X^9$ ($X^8$, $X^9$) is (carbon atom, carbon atom); and $X^9$ and $X^{10}$ are bonded to each other to form a 5- to 14-membered aromatic heterocycle (e.g., a pyrazole ring).

[Compound A-5]

Compound (I) wherein ring A is the formula:

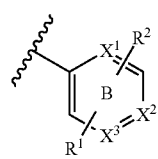

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., chlorine atom), (2) optionally halogenated methyl (e.g., methyl, trifluoromethyl), or (3) a hydroxy group substituted by optionally halogenated methyl (e.g., methyl, difluoromethyl, trifluoromethyl);

$R^2$ is (1) a halogen atom (e.g., chlorine atom), (2) a cyano group, (3) an optionally substituted $C_{1-6}$ alkyl group (e.g., methyl, isopropyl), (4) an optionally substituted $C_{1-6}$ alkoxy group (e.g., methoxy, ethoxy), (5) a carboxy group, (6) an optionally substituted $C_{1-6}$ alkoxy-carbonyl group (e.g., methoxycarbonyl), (7) a carbamoyl group or (8) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom) and (2) an optionally substituted $C_{1-6}$ alkyl group (e.g., methyl);

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) an optionally substituted $C_{1-6}$ alkyl group (e.g., methyl), (3) an optionally substituted $C_{1-6}$ alkoxy group (e.g., methoxy) and (4) an optionally substituted amino group; and $X^{10}$ is a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., tetrahydrofuranyl, tetrahydropyranyl, pyrrolidinyl), (4) an optionally substituted $C_{1-6}$ alkyl-carbonyl group (e.g., methylcarbonyl) and (5) an optionally substituted $C_{3-10}$ cycloalkyl-carbonyl group (e.g., cyclopropylcarbonyl).

[Compound B-5]

Compound (I) wherein ring A is the formula:

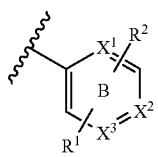

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., chlorine atom), (2) optionally halogenated methyl (e.g., methyl, trifluoromethyl), or (3) a hydroxy group substituted by optionally halogenated methyl (e.g., methyl, difluoromethyl, trifluoromethyl);

$R^2$ is (1) a halogen atom (e.g., chlorine atom), (2) a cyano group, (3) a $C_{1-6}$ alkyl group (e.g., methyl, isopropyl) optionally substituted by 1 to 3 substituents selected from a halogen atom (e.g., fluorine atom) and a hydroxy group, (4) a $C_{1-6}$ alkoxy group (e.g., methoxy, ethoxy) optionally substituted by 1 to 3 halogen atoms (e.g., fluorine atom), (5) a carboxy group, (6) a $C_{1-6}$ alkoxy-carbonyl group (e.g., methoxycarbonyl), (7) a carbamoyl group or (8) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups;

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) a $C_{1-6}$ alkyl group (e.g., methyl), (3) a $C_{1-6}$ alkoxy group (e.g., methoxy) and (4) an amino group; and $X^{10}$ is a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl) optionally substituted by 1 to 3 substituents selected from a hydroxy group, a $C_{3-10}$ cycloalkyl group (e.g., cyclopropyl, cyclopentyl) optionally substituted by a hydroxy group and a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., tetrahydrofuranyl, tetrahydropyranyl, pyrrolidinyl) optionally substituted by a hydroxy group, (4) a $C_{1-6}$ alkyl-carbonyl group (e.g., methylcarbonyl) and (5) a $C_{3-10}$ cycloalkyl-carbonyl group (e.g., cyclopropylcarbonyl).

[Compound C-5]

Compound (I) wherein ring A is the formula:

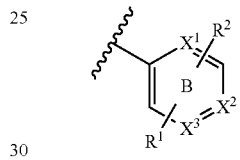

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, (2) methyl, trifluoromethyl, or (3) a hydroxy group substituted by methyl, difluoromethyl or trifluoromethyl;

$R^2$ is (1) a halogen atom (e.g., chlorine atom), (2) a cyano group, (3) a $C_{1-6}$ alkyl group (e.g., methyl) optionally substituted by 1 to 3 substituents selected from a halogen atom (e.g., fluorine atom) and a hydroxy group or (4) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups;

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a $C_{1-6}$ alkyl group (e.g., methyl) and (2) an amino group; and $X^{10}$ is an amino group optionally substituted by 1-2 substituents selected from (1) a $C_{1-6}$ alkyl group (e.g., methyl, ethyl, propyl, isopropyl, isobutyl, tert-butyl) optionally substituted by a hydroxy group, (2) a $C_{3-10}$ cycloalkyl group (e.g., cyclopropyl, cyclohexyl) optionally substituted by a hydroxy group and (3) a 3- to 14-membered non-aromatic heterocyclic group (e.g., tetrahydrofuranyl).

[Compound D-5]

Compound (I) wherein ring A is the formula:

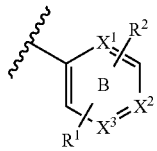

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, (2) methyl, trifluoromethyl, or (3) a hydroxy group substituted by methyl or trifluoromethyl;

$R^2$ is (1) a halogen atom (e.g., chlorine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups;

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) $C_{1-6}$ alkyl groups (e.g., methyl); and $X^{10}$ is an amino group optionally substituted by 1-2 substituents selected from (1) a $C_{1-6}$ alkyl group (e.g., isopropyl), (2) a $C_{3-10}$ cycloalkyl group (e.g., cyclopropyl) and (3) a 3- to 14-membered non-aromatic heterocyclic group (e.g., tetrahydrofuranyl).

[Compound A-I]

Compound (I) wherein ring A is (1) the formula:

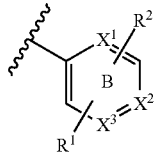

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group optionally substituted by optionally halogenated methyl (e.g., methyl, difluoromethyl, trifluoromethyl);

$R^2$ is (1) a halogen atom (e.g., fluorine atom, chlorine atom, bromine atom), (2) a hydroxy group, (3) a cyano group, (4) an optionally substituted $C_{1-6}$ alkyl group (e.g., methyl, isopropyl), (5) an optionally substituted $C_{1-6}$ alkoxy group (e.g., methoxy, ethoxy), (6) a carboxy group, (7) an optionally substituted $C_{1-6}$ alkoxy-carbonyl group (e.g., methoxycarbonyl, ethoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) an optionally substituted $C_{1-6}$ alkyl group (e.g., methyl, isopropyl), (3) an optionally substituted $C_{1-6}$ alkoxy group (e.g., methoxy), (4) a carboxy group, (5) an optionally substituted $C_{1-6}$ alkoxycarbonyl group (e.g., ethoxycarbonyl) and (6) a carbamoyl group, or (2) the formula:

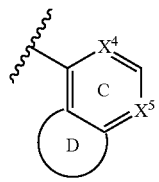

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., imidazole ring, pyrazole ring, furan ring, pyridine ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom), (2) a hydroxy group and (3) a $C_{1-6}$ alkyl group (e.g., methyl);

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) an optionally substituted $C_{1-6}$ alkyl group (e.g., methyl), (3) an optionally substituted $C_1$ alkoxy group (e.g., methoxy) and (4) an optionally substituted amino group; and $X^{10}$ is a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl, isopentyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., oxetanyl, tetrahydrofuranyl, tetrahydropyranyl, pyrrolidinyl), (4) an optionally substituted 5- to 14-membered aromatic heterocyclic group (e.g., pyrazolyl), (5) an optionally substituted $C_{1-6}$ alkyl-carbonyl group (e.g., methylcarbonyl) and (6) an optionally substituted $C_{3-10}$ cycloalkyl-carbonyl group (e.g., cyclopropylcarbonyl); or $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., dihydropyrrole ring, tetrahydropyridine ring, dihydrooxazine ring), each of which is optionally substituted.

[Compound B-I]
Compound (I) wherein ring A is (1) the formula:

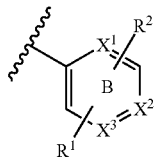

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group optionally substituted by optionally halogenated methyl (e.g., methyl, difluoromethyl, trifluoromethyl);

$R^2$ is (1) a halogen atom (e.g., fluorine atom, chlorine atom, bromine atom), (2) a hydroxy group, (3) a cyano group, (4) a $C_{1-6}$ alkyl group (e.g., methyl, isopropyl) optionally substituted by 1 to 3 substituents selected from a halogen atom (e.g., fluorine atom), a hydroxy group and a $C_{1-6}$ alkoxy-carbonyl group (e.g., methoxycarbonyl) group, (5) a $C_{1-6}$ alkoxy group (e.g., methoxy, ethoxy) optionally substituted by 1 to 3 halogen atoms (e.g., fluorine atom), (6) a carboxy group, (7) a $C_{1-6}$ alkoxy-carbonyl group (e.g., methoxycarbonyl, ethoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) a $C_{1-6}$ alkyl group (e.g., methyl, isopropyl) optionally substituted by 1 to 3 substituents selected from a hydroxy group and a $C_{1-6}$ alkoxy-carbonyl group (e.g., methoxycarbonyl), (3) a $C_{1-6}$ alkoxy group (e.g., methoxy), (4) a carboxy group, (5) a $C_{1-6}$ alkoxy-carbonyl group (e.g., ethoxycarbonyl) and (6) a carbamoyl group, or (2) the formula:

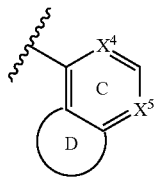

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., imidazole ring, pyrazole ring, furan ring, pyridine ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom), (2) a hydroxy group and (3) a $C_{1-6}$ alkyl group (e.g., methyl);

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) a $C_{1-6}$ alkyl group (e.g., methyl), (3) a $C_{1-6}$ alkoxy group (e.g., methoxy) and (4) an amino group; and $X^{10}$ is a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl, isopentyl) optionally substituted by 1 to 3 substituents selected from (i) a halogen atom (e.g., fluorine atom), (ii) a hydroxy group, (iii) a $C_{3-10}$ cycloalkyl group (e.g., cyclopropyl, cyclobutyl, cyclopentyl) optionally substituted by 1 to 3 hydroxy groups, (iv) a 3- to 14-membered non-aromatic heterocyclic group (e.g., tetrahydrofuranyl, tetrahydropyranyl) optionally substituted by 1 to 3 $C_{1-6}$ alkyl groups (e.g., methyl) and (v) a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., oxetanyl, tetrahydrofuranyl, tetrahydropyranyl, pyrrolidinyl) optionally substituted by 1 to 3 hydroxy groups, (4) a 5- to 14-membered aromatic heterocyclic group (e.g., pyrazolyl) optionally substituted by 1 to 3 $C_{1-6}$ alkyl groups (e.g., methyl), (5) a $C_{1-6}$ alkyl-carbonyl group (e.g., methylcarbonyl) and (6) a $C_{3-10}$ cycloalkyl-carbonyl group (e.g., cyclopropylcarbonyl); or $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., dihydropyrrole ring, tetrahydropyridine ring, dihydrooxazine ring), each of which is optionally substituted by an oxo group.

[Compound C-I]
Compound (I) wherein ring A is (1) the formula:

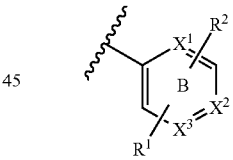

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a fluorine atom, a chlorine atom, a bromine atom, (2) methyl, trifluoromethyl, or (3) a hydroxy group optionally substituted by methyl, difluoromethyl or trifluoromethyl;

$R^2$ is (1) a halogen atom (e.g., fluorine atom, chlorine atom, bromine atom), (2) a cyano group, (3) a $C_{1-6}$ alkyl group (e.g., methyl) optionally substituted by 1 to 3 substituents selected from a halogen atom (e.g., fluorine atom) and a hydroxy group, (4) a $C_{1-6}$ alkoxy group (e.g., methoxy) optionally substituted by 1 to 3 halogen atoms (e.g., fluorine atom) or (5) a mono- or di-$C_{1-6}$ alkylamino group (e.g., methylamino);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups and (3) a $C_{1-6}$ alkoxy group (e.g., methoxy), or (2) the formula:

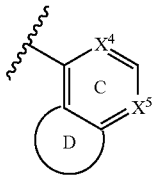

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered aromatic heterocycle (e.g., imidazole ring, furan ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom) and (2) a hydroxy group;

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a $C_{1-6}$ alkyl group (e.g., methyl) and (2) an amino group; and $X^{10}$ is an amino group optionally substituted by 1-2 substituents selected from (1) a $C_{1-6}$ alkyl group (e.g., methyl, ethyl, propyl, isopropyl, isobutyl, tert-butyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopropyl, cyclohexyl) optionally substituted by 1 to 3 hydroxy groups, (3) a 3- to 14-membered non-aromatic heterocyclic group (e.g., oxetanyl, tetrahydrofuranyl) and (4) a 5- to 14-membered aromatic heterocyclic group (e.g., pyrazolyl) optionally substituted by 1 to 3 $C_{1-6}$ alkyl groups (e.g., methyl); or $X^9$ and $X^{10}$ are bonded to each other to form a 5- to 14-membered aromatic heterocycle (e.g., a pyrazole ring).

[Compound D-I]

Compound (I) wherein ring A is (1) the formula:

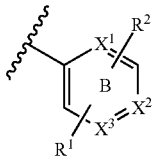

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, a bromine atom, (2) methyl, trifluoromethyl, or (3) a hydroxy group substituted by methyl or trifluoromethyl;

$R^2$ is (1) a halogen atom (e.g., chlorine atom, bromine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups, or (2) the formula:

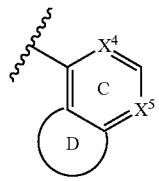

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) $C_{1-6}$ alkyl groups (e.g., methyl); and $X^{10}$ is an amino group optionally substituted by 1-2 substituents selected from (1) a $C_{1-6}$ alkyl group (e.g., isopropyl) optionally substituted by 1 to 3 hydroxy groups, (2) a $C_{3-10}$ cycloalkyl group (e.g., cyclopropyl, cyclohexyl) optionally substituted by 1 to 3 hydroxy groups and (3) a 3- to 14-membered non-aromatic heterocyclic group (e.g., tetrahydrofuranyl); or $X^9$ and $X^{10}$ are bonded to each other to form a 5- to 14-membered aromatic heterocycle (e.g., a pyrazole ring).

[Compound A-1-I]

Compound (I) wherein ring A is the formula:

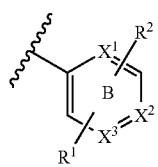

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group optionally substituted by optionally halogenated methyl (e.g., methyl, difluoromethyl, trifluoromethyl);

$R^2$ is (1) a halogen atom (e.g., fluorine atom, chlorine atom, bromine atom), (2) a hydroxy group, (3) a cyano group, (4) an optionally substituted $C_{1-6}$ alkyl group (e.g., methyl, isopropyl), (5) an optionally substituted $C_{1-6}$ alkoxy group (e.g., methoxy, ethoxy), (6) a carboxy group, (7) an optionally substituted $C_{1-6}$ alkoxy-carbonyl group (e.g., methoxycarbonyl, ethoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) an optionally substituted $C_{1-6}$ alkyl group (e.g., methyl), (3) an optionally substituted $C_{1-6}$ alkoxy group (e.g., methoxy), (4) a carboxy group, (5) an optionally substituted $C_{1-6}$ alkoxy-carbonyl group (e.g., ethoxycarbonyl) and (6) a carbamoyl group;

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) an optionally substituted $C_{1-6}$ alkyl group (e.g., methyl), (3) an optionally substituted $C_{1-6}$ alkoxy group (e.g., methoxy) and (4) an optionally substituted amino group; and $X^{10}$ is a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl, isopentyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., oxetanyl, tetrahydrofuranyl, tetrahydropyranyl, pyrrolidinyl), (4) an optionally substituted 5- to 14-membered aromatic heterocyclic group (e.g., pyrazolyl), (5) an optionally substituted $C_{1-6}$ alkyl-carbonyl group (e.g., methylcarbonyl) and (6) an optionally substituted $C_{3-10}$ cycloalkyl-carbonyl group (e.g., cyclopropylcarbonyl); or $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., dihydropyrrole ring, tetrahydropyridine ring, dihydrooxazine ring), each of which is optionally substituted.

[Compound B-1-I]

Compound (I) wherein ring A is the formula:

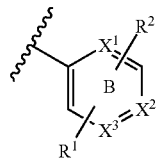

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group optionally substituted by optionally halogenated methyl (e.g., methyl, difluoromethyl, trifluoromethyl);

$R^2$ is (1) a halogen atom (e.g., fluorine atom, chlorine atom, bromine atom), (2) a hydroxy group, (3) a cyano group, (4) a $C_{1-6}$ alkyl group (e.g., methyl, isopropyl) optionally substituted by 1 to 3 substituents selected from a halogen atom (e.g., fluorine atom), a hydroxy group and a $C_{1-6}$ alkoxy-carbonyl group (e.g., methoxycarbonyl) group, (5) a $C_{1-6}$ alkoxy group (e.g., methoxy, ethoxy) optionally substituted by 1 to 3 halogen atoms (e.g., fluorine atom), (6) a carboxy group, (7) a $C_{1-6}$ alkoxy-carbonyl group (e.g., methoxycarbonyl, ethoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) a $C_{1-6}$ alkyl group (e.g., methyl, isopropyl) optionally substituted by 1 to 3 substituents selected from a hydroxy group and a $C_{1-6}$ alkoxy-carbonyl group (e.g., methoxycarbonyl), (3) a $C_{1-6}$ alkoxy group (e.g., methoxy), (4) a carboxy group, (5) a $C_{1-6}$ alkoxy-carbonyl group (e.g., ethoxycarbonyl) and (6) a carbamoyl group;

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) a $C_{1-6}$ alkyl group (e.g., methyl), (3) a $C_{1-6}$ alkoxy group (e.g., methoxy) and (4) an amino group; and $X^{10}$ is a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl, isopentyl) optionally substituted by 1 to 3 substituents selected from (i) a halogen atom (e.g., fluorine atom), (ii) a hydroxy group, (iii) a $C_{3-10}$ cycloalkyl group (e.g., cyclopropyl, cyclobutyl, cyclopentyl) optionally substituted by 1 to 3 hydroxy groups, (iv) a 3- to 14-membered non-aromatic heterocyclic group (e.g., tetrahydrofuranyl, tetrahydropyranyl) optionally substituted by 1 to 3 $C_{1-6}$ alkyl groups (e.g., methyl) and (v) a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., oxetanyl, tetrahydrofuranyl, tetrahydropyranyl, pyrrolidinyl) optionally substituted by 1 to 3 hydroxy groups, (4) a 5- to 14-membered aromatic heterocyclic group (e.g., pyrazolyl) optionally substituted by 1 to 3 $C_{1-6}$ alkyl groups (e.g., methyl), (5) a $C_{1-6}$ alkyl-carbonyl group (e.g., methylcarbonyl) and (6) a $C_{3-10}$ cycloalkyl-carbonyl group (e.g., cyclopropylcarbonyl); or $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., dihydropyrrole ring, tetrahydropyridine ring, dihydrooxazine ring), each of which is optionally substituted by an oxo group.

[Compound C-1-I]

Compound (I) wherein ring A is the formula:

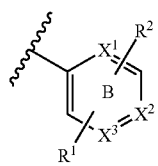

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a fluorine atom, a chlorine atom, a bromine atom, (2) methyl, trifluoromethyl, or (3) a hydroxy group optionally substituted by methyl, difluoromethyl or trifluoromethyl;

$R^2$ is (1) a halogen atom (e.g., fluorine atom, chlorine atom, bromine atom), (2) a cyano group, (3) a $C_{1-6}$ alkyl group (e.g., methyl) optionally substituted by 1 to 3 substituents selected from a halogen atom (e.g., fluorine atom) and a hydroxy group, (4) a $C_{1-6}$ alkoxy group (e.g., methoxy) optionally substituted by 1 to 3 halogen atoms (e.g., fluorine atom) or (5) a mono- or di-$C_{1-6}$ alkylamino group (e.g., methylamino);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups and (3) a $C_{1-6}$ alkoxy group (e.g., methoxy);

$X^6$ is a hydrogen atom, a fluorine atom or a chlorine atom;
$X^7$ is a fluorine atom or a chlorine atom;
the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a $C_{1-6}$ alkyl group (e.g., methyl) and (2) an amino group; and $X^{10}$ is (1) a $C_{1-6}$ alkyl group (e.g., methyl, ethyl, propyl, isopropyl, isobutyl, tert-butyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopropyl, cyclohexyl) optionally substituted by 1 to 3 hydroxy groups, (3) a 3- to 14-membered non-aromatic heterocyclic group (e.g., oxetanyl, tetrahydrofuranyl) or (4) a 5- to 14-membered aromatic heterocyclic group (e.g., pyrazolyl) optionally substituted by 1 to 3 $C_{1-6}$ alkyl groups (e.g., methyl); or $X^9$ and $X^{10}$ are bonded to each other to form a 5- to 14-membered aromatic heterocycle (e.g., a pyrazole ring).

[Compound D-1-I]
Compound (I) wherein ring A is the formula:

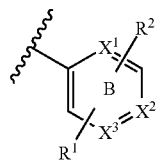

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, a bromine atom, (2) methyl, trifluoromethyl, or (3) a hydroxy group substituted by methyl or trifluoromethyl;

$R^2$ is (1) a halogen atom (e.g., chlorine atom, bromine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups;

$X^6$ is a hydrogen atom, a fluorine atom or a chlorine atom;
$X^7$ is a fluorine atom or a chlorine atom;
the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) $C_{1-6}$ alkyl groups (e.g., methyl); and $X^{10}$ is an amino group optionally substituted by 1-2 substituents selected from (1) a $C_{1-6}$ alkyl group (e.g., isopropyl) optionally substituted by 1 to 3 hydroxy groups, (2) a $C_{3-10}$ cycloalkyl group (e.g., cyclopropyl, cyclohexyl) optionally substituted by 1 to 3 hydroxy groups and (3) a 3- to 14-membered non-aromatic heterocyclic group (e.g., tetrahydrofuranyl); or $X^9$ and $X^{10}$ are bonded to each other to form a 5- to 14-membered aromatic heterocycle (e.g., a pyrazole ring).

[Compound A-2-I]
Compound (I) wherein ring A is the formula:

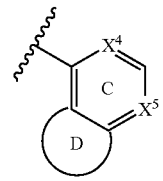

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., imidazole ring, pyrazole ring, furan ring, pyridine ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom), (2) a hydroxy group and (3) a $C_{1-6}$ alkyl group (e.g., methyl);

$X^6$ is a halogen atom (e.g., fluorine atom);
$X^7$ is a halogen atom (e.g., fluorine atom);
the combination of $X^8$ and $X^9$ ($X^8$, $X^9$) is (carbon atom, nitrogen atom); and $X^{10}$ is an optionally substituted amino group; or
$X^9$ and $X^{10}$ are bonded to each other to form an optionally substituted 5- to 14-membered aromatic heterocycle (e.g., a pyrazole ring).

[Compound B-2-I]
Compound (I) wherein ring A is the formula:

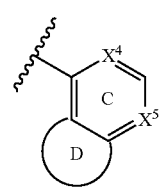

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., imidazole ring, pyrazole ring, furan ring, pyridine ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom), (2) a hydroxy group and (3) a $C_{1-6}$ alkyl group (e.g., methyl);

$X^6$ is a halogen atom (e.g., fluorine atom);

$X^7$ is a halogen atom (e.g., fluorine atom);

the combination of $X^8$ and $X^9$ ($X^8$, $X^9$) is (carbon atom, nitrogen atom); and $X^{10}$ is an amino group optionally substituted by 1-2 substituents selected from (1) a $C_{1-6}$ alkyl group (e.g., isopropyl) optionally substituted by 1 to 3 hydroxy groups and (2) a $C_{3-10}$ cycloalkyl group (e.g., cyclohexyl) optionally substituted by 1 to 3 hydroxy groups; or $X^9$ and $X^{10}$ are bonded to each other to form a 5- to 14-membered aromatic heterocycle (e.g., a pyrazole ring).

[Compound C-2-I]

Compound (I) wherein ring A is the formula:

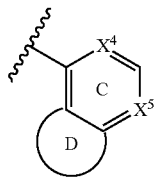

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered aromatic heterocycle (e.g., imidazole ring, furan ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom) and (2) a hydroxy group;

$X^6$ is a fluorine atom;

$X^7$ is a fluorine atom;

the combination of $X^8$ and $X^9$ ($X^8$, $X^9$) is (carbon atom, nitrogen atom); and $X^{10}$ is an amino group optionally substituted by 1-2 substituents selected from (1) a $C_{1-6}$ alkyl group (e.g., isopropyl) optionally substituted by 1 to 3 hydroxy groups and (2) a $C_{3-10}$ cycloalkyl group (e.g., cyclohexyl) optionally substituted by 1 to 3 hydroxy groups; or $X^9$ and $X^{10}$ are bonded to each other to form a 5- to 14-membered aromatic heterocycle (e.g., a pyrazole ring).

[Compound D-2-I]

Compound (I) wherein ring A is the formula:

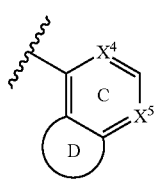

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a fluorine atom;

$X^7$ is a fluorine atom;

the combination of $X^8$ and $X^9$ ($X^8$, $X^9$) is (carbon atom, nitrogen atom); and $X^{10}$ is an amino group; or $X^9$ and $X^{10}$ are bonded to each other to form a 5- to 14-membered aromatic heterocycle (e.g., a pyrazole ring).

[Compound A-3-I]

Compound (I) wherein ring A is (1) the formula:

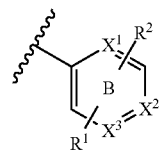

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., chlorine atom), (2) optionally halogenated methyl (e.g., methyl, trifluoromethyl), or (3) a hydroxy group optionally substituted by optionally halogenated methyl (e.g., methyl, difluoromethyl, trifluoromethyl);

$R^2$ is (1) a halogen atom (e.g., chlorine atom), (2) a hydroxy group, (3) a cyano group, (4) an optionally substituted $C_{1-6}$ alkyl group (e.g., methyl, isopropyl), (5) an optionally substituted $C_{1-6}$ alkoxy group (e.g., methoxy, ethoxy), (6) a carboxy group, (7) an optionally substituted $C_{1-6}$ alkoxy-carbonyl group (e.g., methoxycarbonyl), (8) a mono- or di-$C_{1-6}$ alkylamino group (e.g., methylamino), (8) a carbamoyl group or (10) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) an optionally substituted $C_{1-6}$ alkyl group (e.g., methyl, isopropyl) and optionally substituted $C_{1-6}$ alkoxy group (e.g., methoxy), or (2) the formula:

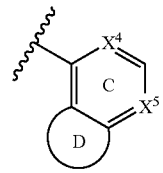

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered aromatic heterocycle (e.g., imidazole ring, a pyrazole ring, furan ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom), (2) a hydroxy group and (3) a $C_{1-6}$alkyl group (e.g., methyl);

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 Jo (preferably 1-2, more preferably 1) substituents selected from (1) a halogen atom (e.g., fluorine atom, bromine atom), (2) an optionally substituted $C_{1-6}$ alkyl group (e.g., methyl), (3) an optionally substituted $C_{1-6}$ alkoxy group (e.g., methoxy) and (4) an optionally substituted amino group; and $X^{10}$ is a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl, isopentyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., oxetanyl, tetrahydrofuranyl, tetrahydropyranyl, pyrrolidinyl), (4) an optionally substituted 5- to 14-membered aromatic heterocyclic group (e.g., pyrazolyl), (5) an optionally substituted $C_{1-6}$ alkyl-carbonyl group (e.g., methylcarbonyl) and (6) an optionally substituted $C_{3-10}$ cycloalkyl-carbonyl group (e.g., cyclopropylcarbonyl).

[Compound B-3-I]

Compound (I) wherein ring A is (1) the formula:

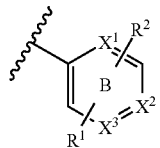

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., chlorine atom), (2) optionally halogenated methyl (e.g., methyl, trifluoromethyl), or (3) a hydroxy group optionally substituted by optionally halogenated methyl (e.g., methyl, difluoromethyl, trifluoromethyl);

$R^2$ is (1) a halogen atom (e.g., chlorine atom), (2) a hydroxy group, (3) a cyano group, (4) a $C_{1-6}$ alkyl group (e.g., methyl, isopropyl) optionally substituted by 1 to 3 substituents selected from a halogen atom (e.g., fluorine atom), a hydroxy group and a $C_{1-6}$ alkoxy-carbonyl group (e.g., methoxycarbonyl) group, (5) a $C_{1-6}$ alkoxy group (e.g., methoxy, ethoxy) optionally substituted by 1 to 3 halogen atoms (e.g., fluorine atom), (6) a carboxy group, (7) a $C_{1-6}$ alkoxy-carbonyl group (e.g., methoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 substituents selected from a hydroxy group and $C_{1-6}$ alkoxy-carbonyl group (e.g., methoxycarbonyl) group and (3) a $C_{1-6}$ alkoxy group (e.g., methoxy), or (2) the formula:

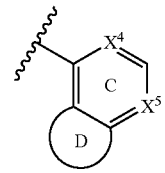

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered aromatic heterocycle (e.g., imidazole ring, a pyrazole ring, furan ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom), (2) a hydroxy group and (3) a $C_{1-6}$ alkyl group (e.g., methyl);

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) a $C_{1-6}$ alkyl group (e.g., methyl), (3) a $C_{1-6}$ alkoxy group (e.g., methoxy) and (4) an amino group; and $X^{10}$ is a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl, isopentyl) optionally substituted by 1 to 3 substituents selected from (i) a halogen atom (e.g., fluorine atom), (ii) a hydroxy group, (iii) a $C_{3-10}$ cycloalkyl group (e.g., cyclopropyl, cyclobutyl, cyclopentyl) optionally substituted by 1 to 3 hydroxy groups, (iv) a 3- to 14-membered non-aromatic heterocyclic group (e.g., tetrahydrofuranyl, tetrahydropyranyl) optionally substituted by 1 to 3 $C_{1-6}$ alkyl groups (e.g., methyl) and (v) a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., oxetanyl, tetrahydrofuranyl, tetrahydropyranyl, pyrrolidinyl) optionally substituted by 1 to 3 hydroxy groups, (4) a 5- to 14-membered aromatic heterocyclic group (e.g., pyrazolyl) optionally substituted by 1 to 3 $C_{1-6}$ alkyl groups (e.g., methyl), (5) a $C_{1-6}$ alkyl-carbonyl group (e.g., methylcarbonyl) and (6) a $C_{3-10}$ cycloalkyl-carbonyl group (e.g., cyclopropylcarbonyl).

[Compound C-3-I]

Compound (I) wherein ring A is (1) the formula:

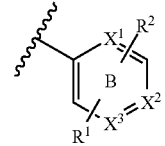

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, (2) methyl, trifluoromethyl, or (3) a hydroxy group substituted by methyl, difluoromethyl, difluoromethyl or trifluoromethyl;

$R^2$ is (1) a halogen atom (e.g., chlorine atom), (2) a cyano group, (3) a $C_{1-6}$ alkyl group (e.g., methyl) optionally substituted by 1 to 3 substituents selected from a halogen atom (e.g., fluorine atom) and a hydroxy group, (4) a $C_{1-6}$ alkoxy group (e.g., methoxy) optionally substituted by 1 to 3 halogen atoms (e.g., fluorine atom) or (5) a mono- or di-$C_{1-6}$ alkylamino group (e.g., methylamino);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups and (3) a $C_{1-6}$ alkoxy group (e.g., methoxy), or (2) the formula:

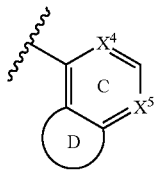

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered aromatic heterocycle (e.g., imidazole ring, furan ring) or a 5- to 7-membered non-aromatic heterocycle (e.g., dihydrofuran ring);

ring D is optionally further substituted by 1-3 (preferably 1-2, more preferably 1) substituents selected from (1) a halogen atom (e.g., chlorine atom), (2) a hydroxy group and (3) a $C_{1-6}$ alkyl group (e.g., methyl);

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a $C_{1-6}$ alkyl group (e.g., methyl) and (2) an amino group; and $X^{10}$ is (1) a $C_{1-6}$ alkyl group (e.g., methyl, ethyl, propyl, isopropyl, isobutyl, tert-butyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopropyl, cyclohexyl) optionally substituted by 1 to 3 hydroxy groups, (3) a 3- to 14-membered non-aromatic heterocyclic group (e.g., oxetanyl, tetrahydrofuranyl) or (4) a 5- to 14-membered aromatic heterocyclic group (e.g., pyrazolyl) optionally substituted by 1 to 3 $C_{1-6}$ alkyl groups (e.g., methyl).

[Compound D-3-I]
Compound (I) wherein ring A is (1) the formula:

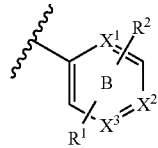

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, (2) methyl, trifluoromethyl, or (3) a hydroxy group substituted by methyl or trifluoromethyl;

$R^2$ is (1) a halogen atom (e.g., chlorine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups, or (2) the formula:

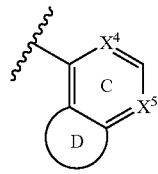

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a 5- to 7-membered non-aromatic heterocycle (e.g., dihydrofuran ring);

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) $C_{1-6}$ alkyl groups (e.g., methyl); and $X^{10}$ is an amino group optionally substituted by 1-2 substituents selected from (1) a $C_{1-6}$ alkyl group (e.g., isopropyl) optionally substituted by 1 to 3 hydroxy groups, (2) a $C_{3-10}$ cycloalkyl group (e.g., cyclopropyl, cyclohexyl) optionally substituted by 1 to 3 hydroxy groups and (3) a 3- to 14-membered non-aromatic heterocyclic group (e.g., tetrahydrofuranyl).

[Compound A-4-I]
Compound (I) wherein ring A is (1) the formula:

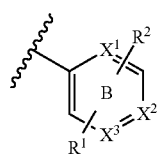

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group substituted by optionally halogenated methyl (e.g., methyl);

$R^2$ is (1) a halogen atom (e.g., fluorine atom, chlorine atom, bromine atom), (2) a cyano group, (3) an optionally substituted $C_{1-6}$ alkyl group (e.g., methyl), (4) an optionally substituted $C_{1-6}$ alkoxy group (e.g., methoxy), (5) a carboxy group, (6) an optionally substituted $C_{1-6}$ alkoxy-carbonyl group (e.g., methoxycarbonyl, ethoxycarbonyl) or (7) a carbamoyl group;

ring B is optionally further substituted by 1-3 (preferably 1-2, more preferably 1) substituents selected from (1) a halogen atom (e.g., chlorine atom), (2) an optionally substituted $C_{1-6}$ alkyl group (e.g., methyl), (3) an optionally substituted $C_{1-6}$ alkoxy group (e.g., methoxy), (4) a carboxy group, (5) an optionally substituted $C_{1-6}$ alkoxy-carbonyl group (e.g., ethoxycarbonyl) and (6) a carbamoyl group, or (2) the formula:

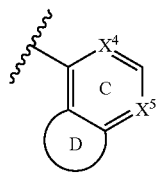

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., pyridine ring) or a 5- to 7-membered non-aromatic heterocycle (e.g., dihydrofuran ring);

$X^6$ is a halogen atom (e.g., fluorine atom);

$X^7$ is a halogen atom (e.g., fluorine atom);

the combination of $X^8$ and $X^9$ ($X^8$, $X^9$) is (carbon atom, carbon atom); and $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., dihydropyrrole ring, tetrahydropyridine ring, dihydrooxazine ring), each of which is optionally substituted.

[Compound B-4-I]
Compound (I) wherein ring A is (1) the formula:

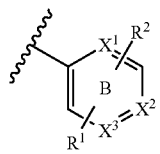

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group substituted by optionally halogenated methyl (e.g., methyl);

$R^2$ is (1) a halogen atom (e.g., fluorine atom, chlorine atom, bromine atom), (2) a cyano group, (3) a $C_{1-6}$ alkyl group (e.g., methyl) optionally substituted by 1 to 3 substituents selected from a halogen atom (e.g., fluorine atom) and a hydroxy group, (4) a $C_{1-6}$ alkoxy group (e.g., methoxy), (5) a carboxy group, (6) a $C_{1-6}$ alkoxy-carbonyl group (e.g., methoxycarbonyl, ethoxycarbonyl) or (7) a carbamoyl group;

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups, (3) a $C_{1-6}$ alkoxy group (e.g., methoxy), (4) a carboxy group, (5) a $C_{1-6}$ alkoxy-carbonyl group (e.g., ethoxycarbonyl) and (6) a carbamoyl group, or (2) the formula:

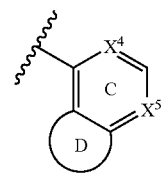

wherein the combination of $X^4$ and $X^5$ ($X^4$, $X^5$) is (carbon atom, carbon atom);

ring C is optionally further substituted by 1-3 (preferably 1-2, more preferably 1) halogen atoms (e.g., chlorine atom);

ring D is a benzene ring, a 5- to 7-membered aromatic heterocycle (e.g., pyridine ring) or a 5- to 7-membered non-aromatic heterocycle (e.g., dihydrofuran ring);

$X^6$ is a halogen atom (e.g., fluorine atom);

$X^7$ is a halogen atom (e.g., fluorine atom);

the combination of $X^8$ and $X^9$ ($X^8$, $X^9$) is (carbon atom, carbon atom); and $X^9$ and $X^{10}$ are bonded to each other to form a 5- to 14-membered aromatic heterocycle (e.g., pyrazole ring, pyridine ring) or a 3- to 14-membered non-aromatic heterocycle (e.g., dihydropyrrole ring, tetrahydropyridine ring, dihydrooxazine ring), each of which is optionally substituted by an oxo group.

[Compound C-4-I]
Compound (I) wherein ring A is (1) the formula:

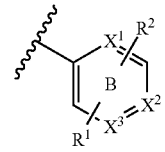

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a fluorine atom, a chlorine atom, a bromine atom, (2) methyl, or (3) a hydroxy group substituted by methyl;

$R^2$ is (1) a halogen atom (e.g., fluorine atom, chlorine atom, bromine atom), (2) a $C_{1-6}$ alkyl group (e.g., methyl) optionally substituted by 1 to 3 hydroxy groups or (3) a $C_{1-6}$ alkoxy group (e.g., methoxy);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups and (3) a $C_{1-6}$ alkoxy group (e.g., methoxy), or (2) the formula:

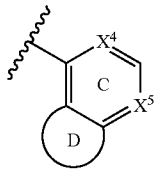

wherein the combination of $X^4$ and $X^5$ ($X^4$, $X^5$) is (carbon atom, carbon atom);
ring C is optionally further substituted by 1-3 (preferably 1-2, more preferably 1) halogen atoms (e.g., chlorine atom);
ring D is a 5- to 7-membered non-aromatic heterocycle (e.g., dihydrofuran ring);
$X^6$ is a fluorine atom;
$X^7$ is a fluorine atom;
the combination of $X^8$ and $X^9$ ($X^8$, $X^9$) is (carbon atom, carbon atom); and
$X^9$ and $X^{10}$ are bonded to each other to form a 5- to 14-membered aromatic heterocycle (e.g., a pyrazole ring).
[Compound D-4-I]
Compound (I) wherein ring A is (1) the formula:

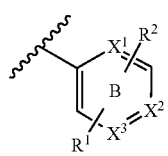

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a chlorine atom, a bromine atom, (2) methyl, or (3) a hydroxy group substituted by methyl;
$R^2$ is (1) a halogen atom (e.g., chlorine atom, bromine atom), (2) a $C_{1-6}$ alkyl group (e.g., methyl) optionally substituted by 1 to 3 hydroxy groups or (3) a $C_{1-6}$ alkoxy group (e.g., methoxy);
ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups, or (2) the formula:

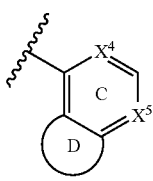

wherein the combination of $X^4$ and $X^5$ ($X^4$, $X^5$) is (carbon atom, carbon atom);
ring C is optionally further substituted by 1-3 (preferably 1-2, more preferably 1) halogen atoms (e.g., chlorine atom);
ring D is a 5- to 7-membered non-aromatic heterocycle (e.g., dihydrofuran ring);
$X^6$ is a fluorine atom;
$X^7$ is a fluorine atom;
the combination of $X^8$ and $X^9$ ($X^8$, $X^9$) is (carbon atom, carbon atom); and
$X^9$ and $X^{10}$ are bonded to each other to form a 5- to 14-membered aromatic heterocycle (e.g., a pyrazole ring).
[Compound A-5-I]
Compound (I) wherein ring A is the formula:

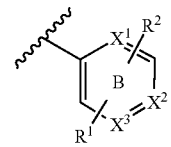

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a halogen atom (e.g., fluorine atom, chlorine atom, bromine atom), (2) optionally halogenated methyl (e.g., methyl, trifluoromethyl), or (3) a hydroxy group optionally substituted by optionally halogenated methyl (e.g., methyl, difluoromethyl, trifluoromethyl);
$R^2$ is (1) a halogen atom (e.g., fluorine atom, chlorine atom, bromine atom), (2) a hydroxy group, (3) a cyano group, (4) an optionally substituted $C_{1-6}$ alkyl group (e.g., methyl, isopropyl), (5) an optionally substituted $C_{1-6}$ alkoxy group (e.g., methoxy, ethoxy), (6) a carboxy group, (7) an optionally substituted $C_{1-6}$ alkoxy-carbonyl group (e.g., methoxycarbonyl, ethoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl);
ring B is optionally further substituted by 1-3 (preferably 1-2, more preferably 1) substituents selected from (1) a halogen atom (e.g., chlorine atom), (2) an optionally substituted $C_{1-6}$ alkyl group (e.g., methyl, isopropyl), (3) an optionally substituted $C_{1-6}$ alkoxy group (e.g., methoxy), (4) a carboxy group, (5) an optionally substituted $C_{1-6}$ alkoxycarbonyl group (e.g., ethoxycarbonyl) and (6) a carbamoyl group;
$X^6$ is a hydrogen atom or a halogen atom (e.g., fluorine atom, chlorine atom);
$X^7$ is a halogen atom (e.g., fluorine atom, chlorine atom);
the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);
ring E is optionally further substituted by 1-3 (preferably 1-2, more preferably 1) substituents selected from (1) a halogen atom (e.g., fluorine atom, bromine atom), (2) an optionally substituted $C_{1-6}$ alkyl group (e.g., methyl), (3) an optionally substituted $C_{1-6}$ alkoxy group (e.g., methoxy) and (4) an optionally substituted amino group; and
$X^{10}$ is a hydrogen atom or an amino group optionally substituted by 1-2 substituents selected from (1) an optionally substituted $C_{1-6}$ alkyl group (e.g., methyl, ethyl, propyl, isopropyl, isobutyl, tert-butyl, 1,1-dimethylpropyl, isopentyl), (2) an optionally substituted $C_{3-10}$ cycloalkyl group (e.g., cyclopropyl, cyclopentyl, cyclohexyl), (3) an optionally substituted 3- to 14-membered non-aromatic heterocyclic group (e.g., oxetanyl, tetrahydrofuranyl, tetrahydropyranyl, pyrrolidinyl), (4) an optionally substituted 5- to 14-membered aromatic heterocyclic group (e.g., pyrazolyl), (5) an optionally substituted $C_{1-6}$ alkyl-carbonyl group (e.g., methylcarbonyl) and (6) an optionally substituted $C_{3-10}$ cycloalkyl-carbonyl group (e.g., cyclopropylcarbonyl).

[Compound B-5-I]
Compound (I) wherein ring A is the formula:

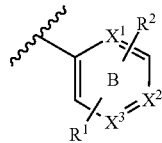

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a halogen atom (e.g., fluorine atom, chlorine atom, bromine atom), (2) optionally halogenated methyl (e.g., methyl, trifluoromethyl), or (3) a hydroxy group optionally substituted by optionally halogenated methyl (e.g., methyl, difluoromethyl, trifluoromethyl);

$R^2$ is (1) a halogen atom (e.g., fluorine atom, chlorine atom, bromine atom), (2) a hydroxy group, (3) a cyano group, (4) a $C_{1-6}$ alkyl group (e.g., methyl, isopropyl) optionally substituted by 1 to 3 substituents selected from a halogen atom (e.g., fluorine atom), a hydroxy group and a $C_{1-6}$ alkoxy-carbonyl group (e.g., methoxycarbonyl) group, (5) a $C_{1-6}$ alkoxy group (e.g., methoxy, ethoxy) optionally substituted by 1 to 3 halogen atoms (e.g., fluorine atom), (6) a carboxy group, (7) a $C_{1-6}$ alkoxy-carbonyl group (e.g., methoxycarbonyl, ethoxycarbonyl), (8) a mono- or di-$C_{1-6}$ alkylamino group (e.g., methylamino), (9) a carbamoyl group or (10) a mono- or di-$C_{1-6}$ alkyl-carbamoyl group (e.g., methylcarbamoyl);

ring B is optionally further substituted by 1-3 (preferably 1-2, more preferably 1) substituents selected from (1) a halogen atom (e.g., chlorine atom), (2) a $C_{1-6}$ alkyl group (e.g., methyl, isopropyl) optionally substituted by 1 to 3 substituents selected from a hydroxy group and a $C_{1-6}$ alkoxy-carbonyl group (e.g., methoxycarbonyl), (3) a $C_{1-6}$ alkoxy group (e.g., methoxy), (4) a carboxy group, (5) a $C_{1-6}$ alkoxy-carbonyl group (e.g., ethoxycarbonyl) and (6) a carbamoyl group;

$X^6$ is a hydrogen atom or a halogen atom (e.g., fluorine atom, chlorine atom);

$X^7$ is a halogen atom (e.g., fluorine atom, chlorine atom);

the combination of $X^8$ and $X^9$ ($X^8$, $X^9$) is (carbon atom, carbon atom), (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a halogen atom (e.g., fluorine atom, bromine atom), (2) a $C_{1-6}$ alkyl group (e.g., methyl), (3) a $C_{1-6}$ alkoxy group (e.g., methoxy) and (4) an amino group; and $X^{10}$ is a hydrogen atom or an amino group optionally substituted by 1-2 substituents selected from (1) a $C_{1-6}$ alkyl group (e.g., methyl, ethyl, propyl, isopropyl, isobutyl, tert-butyl, 1,1-dimethylpropyl, isopentyl) optionally substituted by 1 to 3 substituents selected from (i) a halogen atom (e.g., fluorine atom), (ii) a hydroxy group, (iii) a $C_{3-10}$ cycloalkyl group (e.g., cyclopropyl, cyclobutyl, cyclopentyl) optionally substituted by 1 to 3 hydroxy groups, (iv) a 3- to 14-membered non-aromatic heterocyclic group (e.g., tetrahydrofuranyl, tetrahydropyranyl) optionally substituted by 1 to 3 $C_{1-6}$ alkyl groups (e.g., methyl) and (v) a $C_{1-6}$ alkoxy group (e.g., methoxy), (2) a $C_{3-10}$ cycloalkyl group (e.g., cyclopropyl, cyclopentyl, cyclohexyl) optionally substituted by 1 to 3 substituents selected from a hydroxy group and a $C_{1-6}$ alkyl group (e.g., methyl) optionally substituted by a hydroxy group, (3) a 3- to 14-membered non-aromatic heterocyclic group (e.g., oxetanyl, tetrahydrofuranyl, tetrahydropyranyl, pyrrolidinyl) optionally substituted by 1 to 3 hydroxy groups, (4) a 5- to 14-membered aromatic heterocyclic group (e.g., pyrazolyl) optionally substituted by 1 to 3 $C_{1-6}$ alkyl groups (e.g., methyl), (5) a $C_{1-6}$ alkyl-carbonyl group (e.g., methylcarbonyl) and (6) a $C_{3-10}$ cycloalkyl-carbonyl group (e.g., cyclopropylcarbonyl).

[Compound C-5-I]
Compound (I) wherein ring A is the formula:

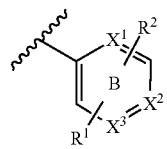

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a fluorine atom, a chlorine atom, a bromine atom, (2) methyl, trifluoromethyl, or (3) a hydroxy group optionally substituted by methyl, difluoromethyl or trifluoromethyl;

$R^2$ is (1) a halogen atom (e.g., fluorine atom, chlorine atom, bromine atom), (2) a cyano group, (3) a $C_{1-6}$ alkyl group (e.g., methyl) optionally substituted by 1 to 3 substituents selected from a halogen atom (e.g., fluorine atom) and a hydroxy group, (4) a $C_{1-6}$ alkoxy group (e.g., methoxy) optionally substituted by 1 to 3 halogen atoms (e.g., fluorine atom) or (5) a mono- or di-$C_{1-6}$ alkylamino group (e.g., methylamino);

ring B is optionally further substituted by 1-3 (preferably 1-2, more preferably 1) substituents selected from (1) a halogen atom (e.g., chlorine atom), (2) a $C_{1-6}$ alkyl group (e.g., methyl) optionally substituted by 1 to 3 hydroxy groups and (3) a $C_{1-6}$ alkoxy group (e.g., methoxy);

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) substituents selected from (1) a $C_{1-6}$ alkyl group (e.g., methyl) and (2) an amino group; and $X^{10}$ is an amino group optionally substituted by 1-2 substituents selected from (1) a $C_{1-6}$ alkyl group (e.g., methyl, ethyl, propyl, isopropyl, isobutyl, tert-butyl) optionally substituted by 1 to 3 substituents selected from a hydroxy group and a 3- to 14-membered non-aromatic heterocyclic group (e.g., tetrahydrofuranyl), (2) a $C_{3-10}$ cycloalkyl group (e.g., cyclopropyl, cyclohexyl) optionally substituted by 1 to 3 hydroxy groups, (3) a 3- to 14-membered non-aromatic heterocyclic group (e.g., oxetanyl, tetrahydrofuranyl) and (4) a 5- to 14-membered aromatic heterocyclic group (e.g., pyrazolyl) optionally substituted by 1 to 3 $C_{1-6}$ alkyl groups (e.g., methyl).

[Compound D-5-I]

Compound (I) wherein ring A is the formula:

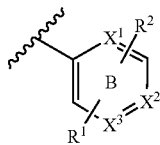

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, a bromine atom, (2) methyl, trifluoromethyl, or (3) a hydroxy group substituted by methyl or trifluoromethyl;

$R^2$ is (1) a halogen atom (e.g., chlorine atom, bromine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups;

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom), (nitrogen atom, carbon atom) or (nitrogen atom, nitrogen atom);

ring E is optionally further substituted by 1-3 (preferably 1-2, more preferably 1) $C_{1-6}$ alkyl groups (e.g., methyl); and $X^{10}$ is an amino group optionally substituted by 1-2 substituents selected from (1) a $C_{1-6}$ alkyl group (e.g., isopropyl) optionally substituted by 1 to 3 hydroxy groups, (2) a $C_{3-10}$ cycloalkyl group (e.g., cyclopropyl, cyclohexyl) optionally substituted by 1 to 3 hydroxy groups and (3) a 3- to 14-membered non-aromatic heterocyclic group (e.g., tetrahydrofuranyl).

[Compound D-6-I]

Compound (I) wherein ring A is (1) the formula:

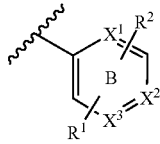

wherein the combination of $X^1$, $X^2$ and $X^3$ ($X^1$, $X^2$, $X^3$) is (carbon atom, carbon atom, carbon atom) or (carbon atom, carbon atom, nitrogen atom);

$R^1$ is (1) a chlorine atom, a bromine atom, (2) methyl, trifluoromethyl, or (3) a hydroxy group substituted by methyl or trifluoromethyl;

$R^2$ is (1) a halogen atom (e.g., chlorine atom, bromine atom), (2) a $C_{1-6}$ alkyl group (e.g., methyl) optionally substituted by 1 to 3 substituents selected from a halogen atom (e.g., fluorine atom) and a hydroxy group or (3) a $C_{1-6}$ alkoxy group (e.g., methoxy) optionally substituted by 1 to 3 halogen atoms (e.g., fluorine atom);

ring B is optionally further substituted by 1-3 (preferably 1-2, more preferably 1) substituents selected from (1) a halogen atom (e.g., chlorine atom) and (2) a $C_{1-6}$ alkyl group (e.g., methyl) optionally substituted by 1 to 3 hydroxy groups;

$X^6$ is a hydrogen atom, a fluorine atom or a chlorine atom;

$X^7$ is a fluorine atom or a chlorine atom;

the combination of $X^8$ and $X^9$ ($X^8$, $X^9$) is (carbon atom, nitrogen atom);

ring E is optionally further substituted by 1-3 (preferably 1-2, more preferably 1) $C_{1-6}$ alkyl groups (e.g., methyl); and $X^{10}$ is an amino group optionally substituted by 1-2 substituents selected from (1) a $C_{1-6}$ alkyl group (e.g., isopropyl) optionally substituted by 1 to 3 hydroxy groups, (2) a $C_{3-10}$ cycloalkyl group (e.g., cyclopropyl, cyclohexyl) optionally substituted by 1 to 3 hydroxy groups and (3) a 3- to 14-membered non-aromatic heterocyclic group (e.g., tetrahydrofuranyl).

Specific examples of compound (I) include the below-mentioned compounds of Examples 1-196, particularly, N-(3-((2-aminopyrimidin-5-yl)ethynyl)-2,4-difluorophenyl)-5-chloro-2-methoxypyridine-3-sulfonamide (Example 7), 5-chloro-N-(2,4-difluoro-3-((2-((trans-4-hydroxycyclohexyl)amino)pyrimidin-5-yl)ethynyl)phenyl)-2-methoxypyridine-3-sulfonamide (Example 174), or 2,5-dichloro-N-(2,4-difluoro-3-((2-(((2R)-1-hydroxypropan-2-yl)amino)pyrimidin-5-yl)ethynyl)phenyl)-3-(hydroxymethyl)benzenesulfonamide (Example 180) is preferable.

As a salt of a compound represented by the formula (I), a pharmacologically acceptable salt is preferable. Examples of such salt include salts with inorganic bases, salts with organic bases, salts with inorganic acids, salts with organic acids, and salts with basic or acidic amino acid.

Preferable examples of the salts with inorganic bases include alkali metal salts such as sodium salt, potassium salt and the like; alkaline earth metal salts such as calcium salt, magnesium salt and the like; aluminum salt; and ammonium salt.

Preferable examples of the salts with organic bases include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzylethylenediamine.

Preferable examples of the salts with inorganic acids include salts with hydrogen chloride, hydrogen bromide, nitric acid, sulfuric acid, phosphoric acid.

Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, malonic acid, methanesulfonic acid, benzenesulfonic acid, p-toluenesulfonic acid.

Preferable examples of the salts with basic amino acids include salts with arginine, lysine, ornithine.

Preferable examples of the salts with acidic amino acid include salts with aspartic acid, glutamic acid.

When compound (I) is a salt, a salt with acetic acid, fumaric acid, maleic acid, succinic acid, malic acid, tartaric acid, citric acid, malonic acid or trifluoroacetic acid is preferable.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature-300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbon s: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropyl amide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in *Jikken Kagaku Kouza* 5th edition, vol. 13-vol. 19 (The Chemical Society of Japan ed.); *Shinjikken Kagaku Kouza* (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine, 4-methoxybenzylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used. Also, a method using both boranes and salts such as calcium chloride and the like is available.

When an oxidation reaction is performed in each step, examples of an oxidant to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid is esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride or a combination of Lewis acid and an alkylating agent (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5.4.0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, dichlorobis(tricyclohexylphosphine)palladium(II), bis(di-tert-butyl(4-dimethylaminophenyl)phosphine)dichloropalladium(II) and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases, organic salts and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a alkyl halide form from alcohol by reacting with triphenylphosphine and carbon tetrachloride or carbon tetrabromide, and the like may be used. Alternatively, a method of synthesizing a alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of tert-butyl ester is performed, formic acid, triethylsilane and the like are sometimes added to reductively trap the by-produced tert-butyl cation.

When a dehydration reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

When a detrimethylsilylation reaction is performed in each step, examples of the reagent to be used include fluorides such as TBAF and the like, acids such as hydrochloric acid and the like and bases such as potassium hydroxide and the like.

When a sulfonamidation reaction is performed in each step, examples of the reagent to be used include sulfonyl halides such as sulfonyl chloride and the like.

When a sulfonyl chloride synthesis reaction from anilines by the Sandmeyer reaction is performed in each step, examples of the reagent to be used for a diazotization step include nitrite salts such as sodium nitrite and the like. Also, an acid such as hydrochloric acid and the like is used. As the reagent to be used in a step for converting a diazonio group to a sulfonyl chloride group, a sulfur dioxide-containing solution, copper(I) chloride and the like can be mentioned. The solution containing sulfur dioxide is obtained by a reaction using thionyl chloride and water and the like. The reaction is preferably performed at 0° C. or below.

When a synthesis reaction of a benzylsulfide compound from anilines or a heterocyclic compound having amino group is performed in each step, examples of the reagent to be used include alkyl nitrites such as amyl nitrite and the like, 1,2-dibenzyl disulfide and the like.

When a nucleophilic substitution reaction from an aromatic ring having halogen and a heterocyclic compound to a benzylsulfide compound is performed in each step, examples of the reagent to be used include thiols such as benzylmercaptan and the like, transition metal catalysts such as tris(dibenzylideneacetone)dipalladium(0) and the like, ligands such as 4,5-bis(diphenylphosphino)-9,9-dimethylxanthene, 1,1'-bis(diphenylphosphino)ferrocene and the like, bases such as DIPEA and the like.

When a synthesis reaction of a heterocyclic compound having halogen from a heterocyclic compound having an amino group by the Sandmeyer reaction is performed in each step, examples of the reagent to be used for a diazotization step include alkyl nitrites such as amyl nitrite and the like, copper(II) chloride and the like.

When a synthesis reaction of a sulfonyl chloride compound from a benzylsulfide compound is performed in each step, examples of the solvent and the reagent to be used include solvents such as acetic acid, water and the like, halogens such as N-chlorosuccinimide and the like, and the like.

When a chlorosulfonylation reaction of aromatics is performed in each step, examples of the reagent to be used include chlorosulfonic acid can be mentioned.

When a methylation reaction of a hydroxy group of sulfonyl chloride is performed in each step, examples of the reagent to be used include trifluoroborane hydrofluoride, (diazomethyl)trimethylsilane and the like.

When a Curtius metastasis reaction is performed in each step, examples of the reagent to be used include bases such as diisopropylethylamine (DIPEA) and the like, diphenylphosphoryl azide, tert-butanol and the like.

When a synthesis reaction from sulfonic acids to sulfonyl chlorides is performed in each step, examples of the reagent to be used include thionyl chloride, a catalytic amount of DMF and the like.

In the following, the production method of compound (I) is more specifically explained including the reaction schemes.

Unless otherwise specified, each symbol in the following reaction schemes is as defined above.

[Production Method A-1]

Compound (I) can be produced by the following method.

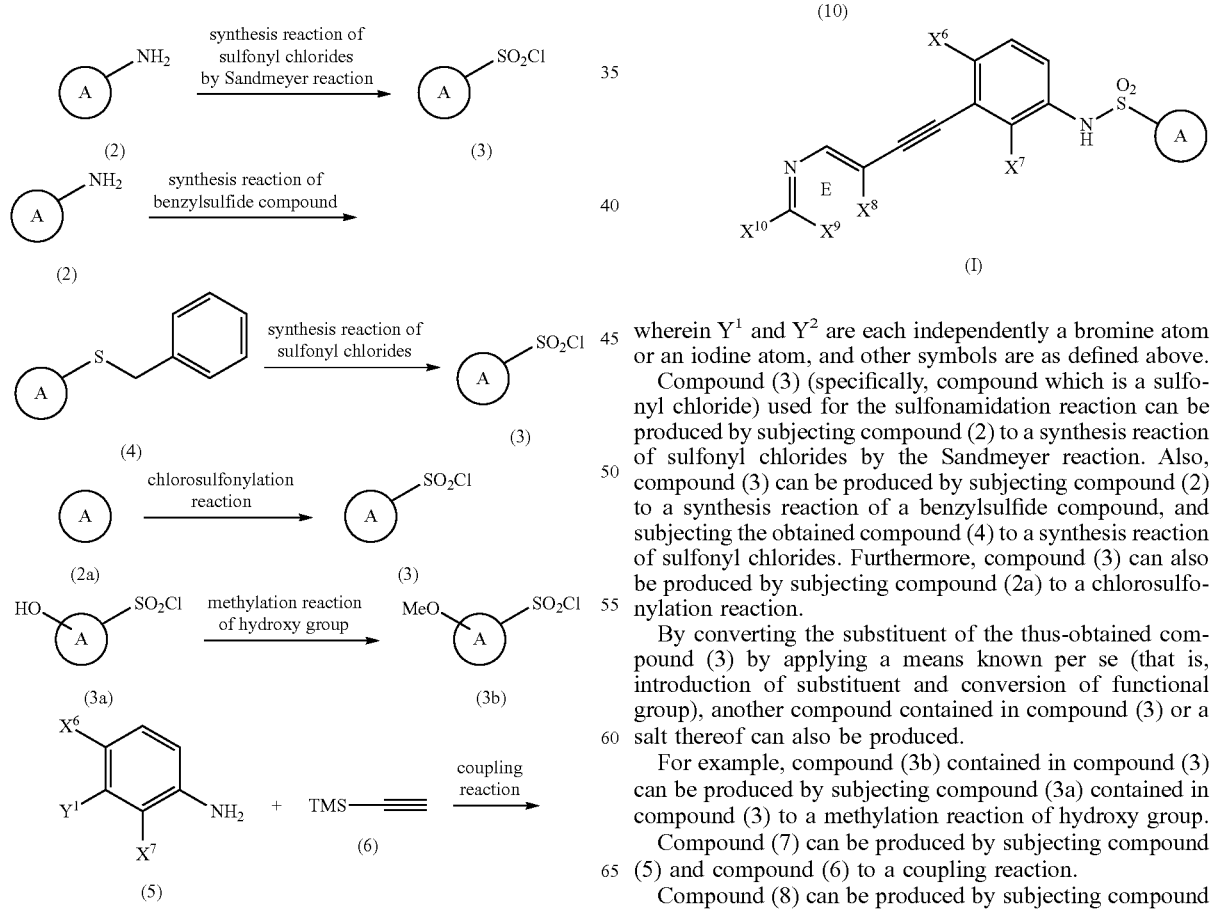

wherein $Y^1$ and $Y^2$ are each independently a bromine atom or an iodine atom, and other symbols are as defined above.

Compound (3) (specifically, compound which is a sulfonyl chloride) used for the sulfonamidation reaction can be produced by subjecting compound (2) to a synthesis reaction of sulfonyl chlorides by the Sandmeyer reaction. Also, compound (3) can be produced by subjecting compound (2) to a synthesis reaction of a benzylsulfide compound, and subjecting the obtained compound (4) to a synthesis reaction of sulfonyl chlorides. Furthermore, compound (3) can also be produced by subjecting compound (2a) to a chlorosulfonylation reaction.

By converting the substituent of the thus-obtained compound (3) by applying a means known per se (that is, introduction of substituent and conversion of functional group), another compound contained in compound (3) or a salt thereof can also be produced.

For example, compound (3b) contained in compound (3) can be produced by subjecting compound (3a) contained in compound (3) to a methylation reaction of hydroxy group.

Compound (7) can be produced by subjecting compound (5) and compound (6) to a coupling reaction.

Compound (8) can be produced by subjecting compound (7) to detrimethylsilylation reaction.

Compound (10) can be produced by subjecting compound (8) and compound (9) to a coupling reaction.

Compound (I) can be produced by subjecting compound (10) to a sulfonamidation reaction.

[Production Method A-2]

Compound (I) can also be produced from compound (8) by the following method.

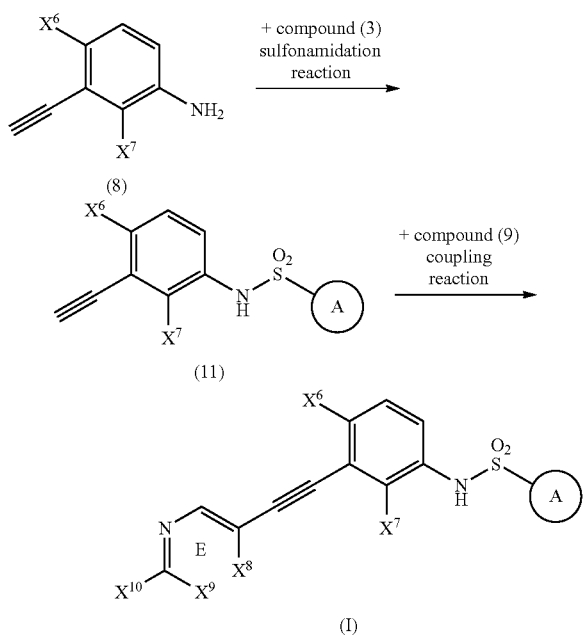

Compound (11) can be produced by subjecting compound (8) to sulfonamidation reaction.

Compound (I) can be produced by subjecting compound (11) and compound (9) to a coupling reaction.

[Production Method A-3]

Compound (1a) contained in compound (I) can also be produced by the following method.

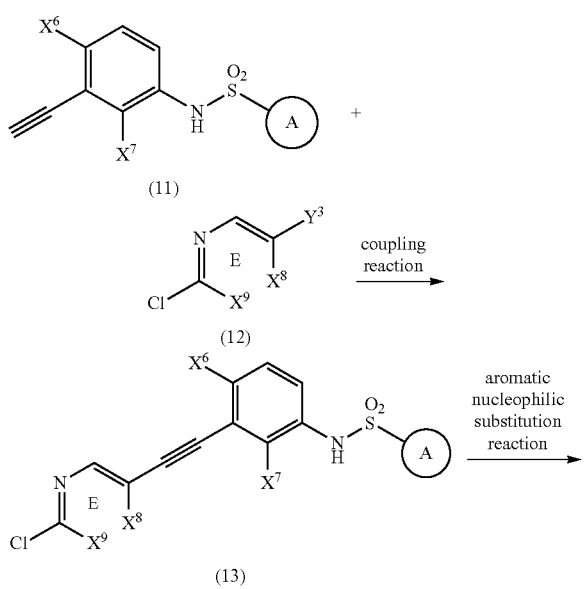

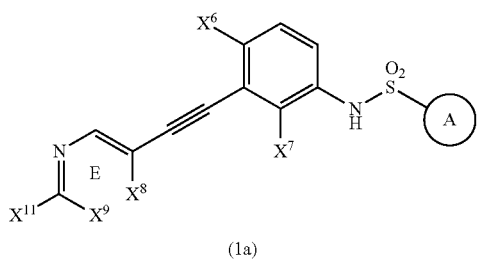

wherein $X^{11}$ is an optionally substituted amino group, $Y^3$ is a bromine atom or an iodine atom, and other symbols are as defined above.

Compound (13) can be produced by subjecting compound (11) and compound (12) to a coupling reaction.

Compound (1a) can be produced by subjecting compound (13) to an aromatic nucleophilic substitution reaction.

[Production Method A-4]

Compound (1c) contained in compound (I) can be produced from compound (1b) contained in compound (I) by the following method. Compound (1b) can be produced by production methods A-1 to A-3 shown above.

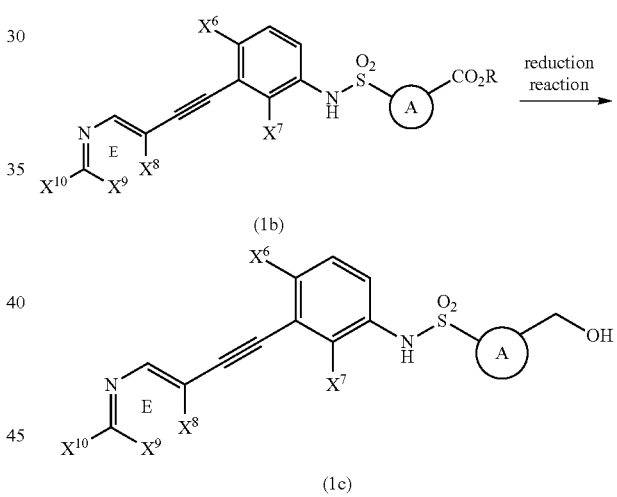

wherein R is an alkyl group, and other symbols are as defined above.

Compound (1c) can be produced by subjecting compound (1b) to a reduction reaction.

[Production Method A-5]

Compound (1c) can also be produced from compound (14) contained in compound (11) by the following method.

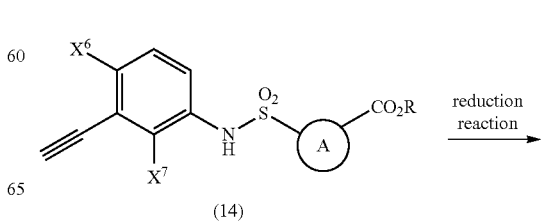

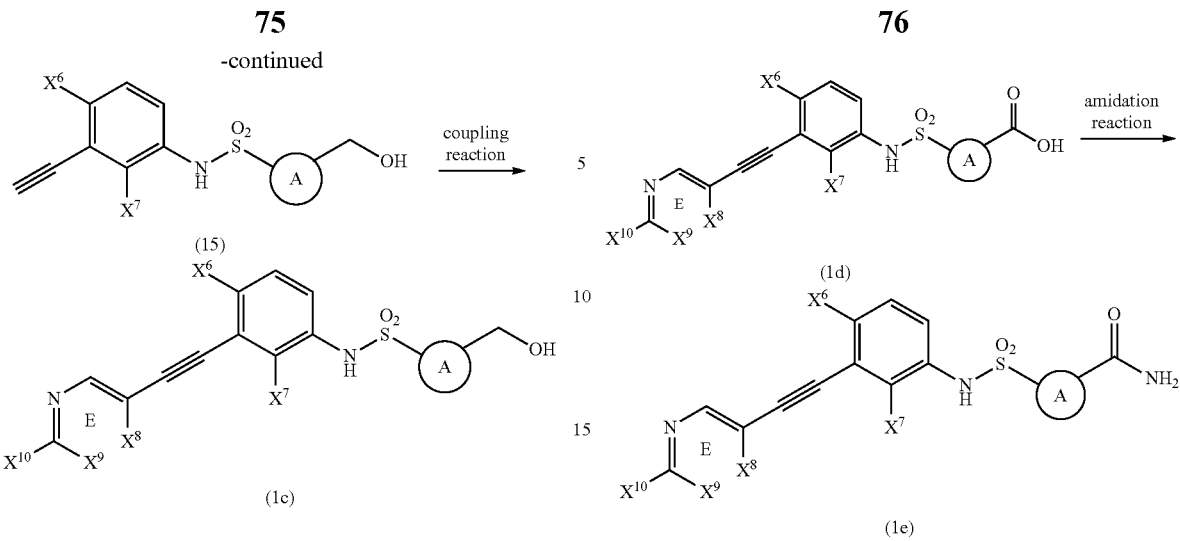

Compound (15) can be produced by subjecting compound (14) to reduction reaction. Compound (1c) can be produced by subjecting compound (15) to a coupling reaction.

[Production Method A-6]

Compound (1d) contained in compound (I) can be produced from compound (1b) contained in compound (I) by the following method.

Compound (1e) can be synthesized by subjecting compound (1d) to an amidation reaction.

[Production Method A-8]

Compound (1f) contained in compound (I) can be produced from compound (1b) contained in compound (I) by the following method.

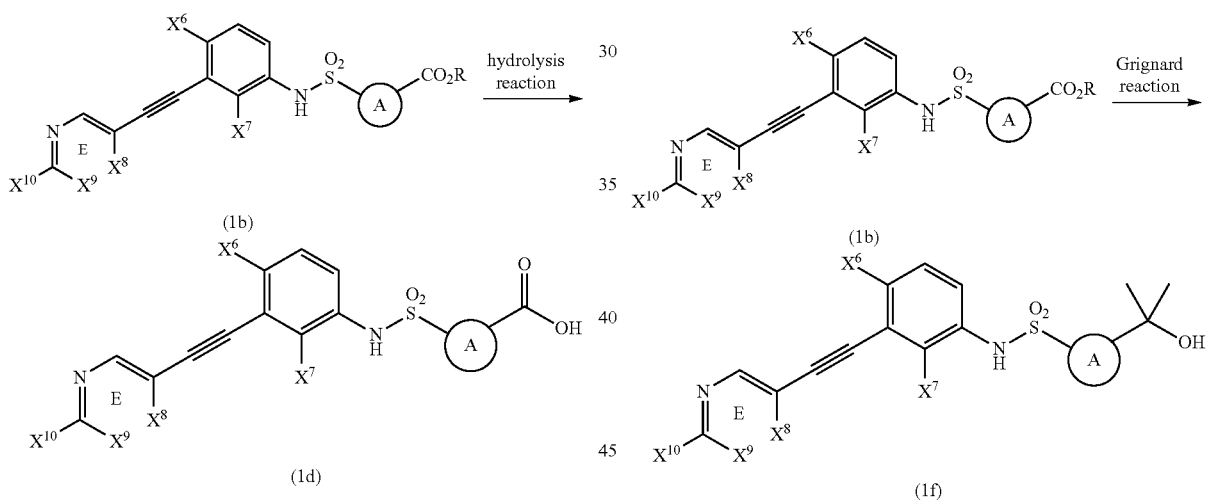

Compound (1d) can be synthesized by subjecting compound (1b) to hydrolysis reaction.

[Production Method A-7]

Compound (1e) contained in compound (I) can be produced from compound (1d) contained in compound (I) by the following method.

Compound (1f) can be produced by subjecting compound (1b) to Grignard reaction.

[Production Method A-9]

Compound (1g) and compound (1h) contained in compound (I) can be produced by the following method.

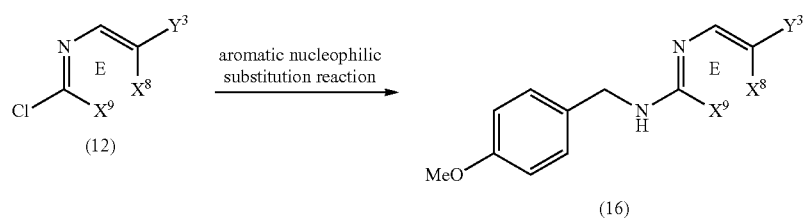

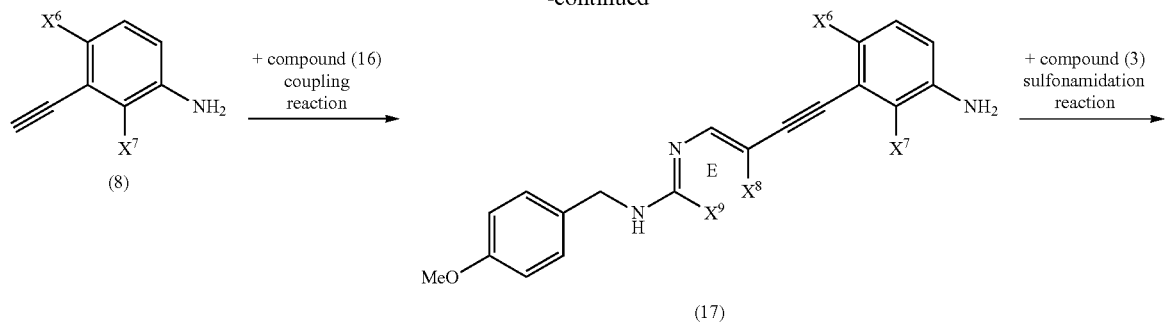

(17)

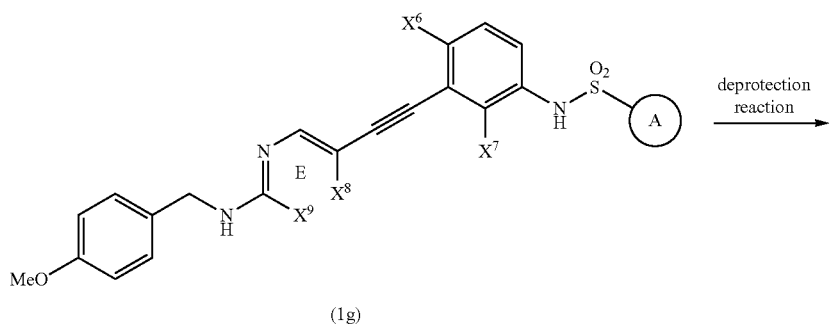

(1g)

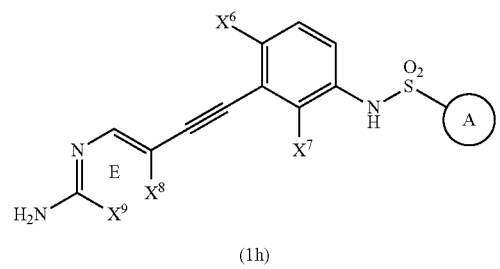

(1h)

Compound (16) can be produced by subjecting compound (12) to an aromatic nucleophilic substitution reaction using 4-methoxybenzylamine.

Compound (17) can be produced by subjecting compound (8) and compound (16) to a coupling reaction.

Compound (1g) can be produced by subjecting compound (17) and compound (3) to a sulfonamidation reaction.

Compound (1h) can be produced by subjecting compound (1g) to deprotection reaction of 4-methoxybenzyl group using acids such as trifluoroacetic acid and the like.

[Production Method A-10]

Compound (8) can also be produced by the following method.

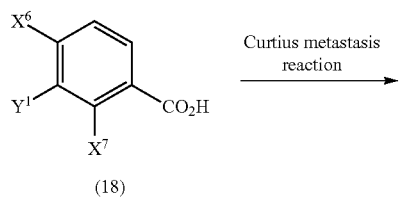

(18)

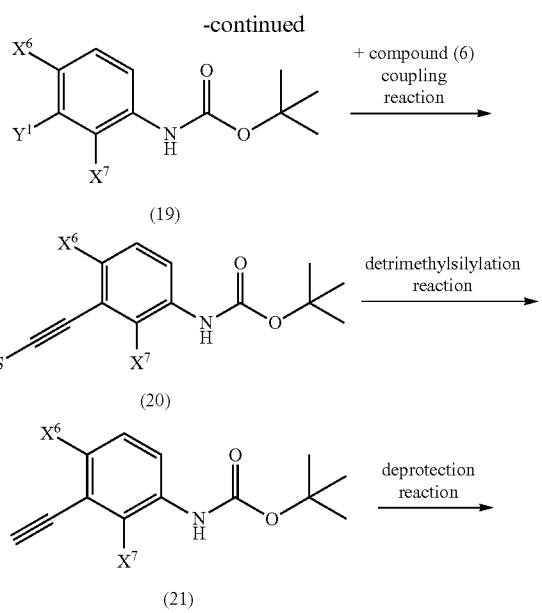

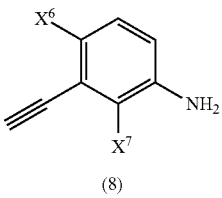

(8)

Compound (19) can be produced by subjecting compound (18) to a Curtius metastasis reaction.

Compound (20) can be produced by subjecting compound (19) and compound (6) to a coupling reaction.

Compound (21) can be produced by subjecting compound (20) to a detrimethylsilylation reaction.

Compound (8) can be produced by subjecting compound (21) to deprotection reaction of tert-butoxycarbonyl group using acids such as hydrochloric acid/dioxane and the like.

Compound (2), compound (2a), compound (5), compound (6), compound (9), compound (12), and compound (18) are available as commercially available products or produced by a method known per se.

By converting the substituent of the thus-obtained compound (I) by applying a means known per se (that is, introduction of substituent and conversion of functional group), another compound contained in compound (I) or a salt thereof can also be produced.

As a method for the introduction of substituent and conversion of functional group, a known general method is used. For example, conversion of a halogen atom (e.g., fluorine, chlorine, bromine, iodine) and an optionally halogenated $C_{1-6}$ alkylsulfonyl-oxy group [e.g., methanesulfonyloxy, ethanesulfonyloxy, trichloromethanesulfonyloxy, trifluoromethanesulfonyloxy(triflate)] to a methyl group, a cyclopropyl group, a vinyl group, a cyano group, a formyl group, a carbonyl group, a carboxyl group, a hydroxyl group, an amino group, a boryl group and the like, conversion of a formyl group to an ethynyl group by a Seyferth-Gilbert homologation reaction, conversion of an ester to a carboxy group by hydrolysis, conversion of a carboxy group to a carbamoyl group by amidation, conversion of a carboxy group to a hydroxymethyl group by reduction, conversion of a carbonyl group to an alcohol form by reduction and alkylation, reductive amination of a carbonyl group, oximation of a carbonyl group, acylation of an amino group, ureation of an amino group, sulfonylation of an amino group, alkylation of an amino group, substitution or amination of active halogen by amine, alkylation of a hydroxy group, and substitution or amination of a hydroxy group can be mentioned.

In performing the introduction of substituent and conversion of functional group, when a reactive site where a reaction other than the intended reaction occurs is present, a protecting group may be previously introduced as necessary into the reactive site by a means known per se and, after carrying out the intended reaction, the protecting group is removed also by a means known per se to produce a compound within the scope of the present invention.

For example, when a starting compound and an intermediate have an amino group, a carboxyl group or a hydroxyl group as a substituent, these groups may be protected by a protecting group generally used in the peptide chemistry and the like. In this case, the object compound can be obtained by removing the protecting group as necessary after the reaction.

Compound (I) obtained by the above-mentioned production method can be isolated and purified by a known means, such as solvent extraction, pH change of solution, phase transfer, crystallization, recrystallization, chromatography and the like.

When compound (I) has an optical isomer, a stereoisomer, a regioisomer or a rotamer, these are also encompassed in compound (I), and can be obtained as a single product according to a synthesis method and separation method known per se. For example, when compound (I) has an optical isomer, the optical isomer resolved from the compound is also encompassed in compound (I).

The optical isomer can be produced according to a method known per se.

Compound (I) may be a crystal.

A crystal of compound (I) (hereinafter sometimes to be abbreviated as the crystal of the present invention) can be produced by crystallization, by applying a crystallization method known per se.

The crystal of the present invention is superior in the physicochemical properties (e.g., melting point, solubility, stability) and biological properties (e.g., pharmacokinetics (absorbability, distribution, metabolism, excretion), efficacy), and is expected to be useful as a medicament.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity and stability). The cocrystal and cocrystal salt may be produced by cocrystallization method known per se.

Compound (I) may be a hydrate or a non-hydrate, or a solvate, or a non-solvate, each of which is encompassed in compound (I).

Compounds labeled with an isotope (e.g., $^{2}H$, $^{3}H$, $^{11}C$, $^{14}C$, $^{1}F$, $^{35}S$, $^{125}I$) and the like are also encompassed in compound (I). Compound (I) labeled with or substituted by an isotope can be used, for example, as a tracer used for Positron Emission Tomography (PET) (PET tracer), and may be useful in the field of medical diagnosis and the like.

Compound (I) may be a prodrug.

The prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include
(1) a compound obtained by subjecting amino in compound (I) to acylation, alkylation or phosphorylation (e.g., a compound obtained by subjecting amino in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation, acetylation, cyclopropylcarbonylation and the like);
(2) a compound obtained by subjecting hydroxy in compound (I) to acylation, alkylation, phosphorylation or boration (e.g., a compound obtained by subjecting hydroxy in compound (I) to acetylation, palmitoylation, propanoylation, pivaloylation, succinylation, fumarylation, alanylation or dimethylaminomethylcarbonylation and the like);

(3) a compound obtained by subjecting carboxy in compound (I) to esterification or amidation (e.g., a compound obtained by subjecting carboxy in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl) methyl esterification, cyclohexyloxycarbonylethyl esterification or methylamidation, and the like) and the like. These compounds can be produced from compound (I) according to a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

Compound (I) or a prodrug thereof (hereinafter sometimes to be simply abbreviated as the compound of the present invention) has a GCN2 inhibitory activity and may be useful as a prophylactic or therapeutic agent for cancer, a cancer growth inhibitor, or a cancer metastasis inhibitor.

The compound of the present invention has a selective inhibitory activity against GCN2 and is also superior in the efficacy expression, pharmacokinetics (e.g., absorbability, distribution, metabolism, excretion), solubility (e.g., water-solubility), interaction with other pharmaceutical products (e.g., drug-metabolizing enzyme inhibitory action), safety (e.g., acute toxicity, chronic toxicity, genetic toxicity, reproductive toxicity, cardiotoxicity, carcinogenicity, central nervous system toxicity), and stability (e.g., chemical stability, stability to enzyme). Therefore, the compound of the present invention may be useful as a medicament.

Therefore, the compound of the present invention can be used for inhibiting excessive (abnormal) GCN2 action on mammals (e.g., mouse, rat, hamster, rabbit, cat, dog, bovine, sheep, monkey, human).

The compound of the present invention is expected to be useful as a prophylactic or therapeutic agent for diseases possibly influenced by GCN2 (sometimes to be abbreviated as "GCN2 associated disease" in the present specification), for example, cancer [e.g., colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), renal cancer (e.g., renal cell carcinoma (e.g., clear cell renal cell carcinoma), transitional cell carcinoma of renal pelvis and ureter), uterine cancer (e.g., cervixcancer, uterine body cancer, uterus sarcoma), gestational choriocarcinoma, brain tumor (e.g., medulloblastoma, glioma, pineal astrocytoma, pilocytic astrocytoma, diffuse astrocytoma, anaplastic astrocytoma, hypophyseal adenoma), retina blastoma, skin cancer (e.g., basal cell carcinoma, malignant melanoma (melanoma)), sarcoma (e.g., rhabdomyosarcoma, leiomyosarcoma, soft tissue sarcoma, spindle cell sarcoma, osteosarcoma), malignant bone tumor, urinary bladder cancer, hematologic cancer (e.g., multiple myeloma, leukemia (e.g., acute myeloid leukemia, acute lymphocytic leukemia (including blast crisis of chronic leukemia)), malignant lymphoma, Hodgkin's disease, chronic myeloproliferative disease), cancer of unknown primary nucleus], cancer growth inhibitor, cancer metastasis inhibitor, apoptosis promoter, and for the prophylaxis or treatment of precancerous lesion (e.g., bone marrow myelodysplastic syndrome).

Particularly, the compound of the present invention can be used as a medicament for osteosarcoma, acute myeloid leukemia, acute lymphocytic leukemia, pancreatic cancer, colorectal cancer, melanoma, and malignant lymphoma.

The compound of the present invention may be administered orally or parenterally as it is or as a medicament by adding a pharmacologically acceptable carrier to a mammal (preferably, human).

In the following, a medicament containing the compound of the present invention (sometimes to be abbreviated as "the medicament of the present invention") is described in detail. Examples of the dosage form of the medicament of the present invention include oral preparations such as tablet (e.g., sugar-coated tablet, film-coated tablet, sublingual tablet, buccal tablet, orally quick-integrating tablet), pill, granule, powder, capsule (e.g., soft capsule, microcapsule), syrup, emulsion, suspension, film (e.g., orally disintegrable film, mouth cavity mucosa patch film) and the like. In addition, examples of the dosage form of the medicament of the present invention include parenteral agents such as injection, drip infusion, transdermal agent (e.g., iontophoresis transdermal agent), suppository, ointment, nasal preparation, pulmonary preparation, eye drop and the like. The medicament of the present invention may also be a controlled-release preparation such as immediate-release preparation, sustained-release preparation (e.g., sustained-release microcapsule) and the like.

The medicament of the present invention may be produced by a known production method generally used in the technical field of preparations (e.g., the method described in the Japanese Pharmacopoeia). In addition, the medicament of the present invention may appropriately contain, where necessary, an appropriate amount of additive such as excipient, binder, disintegrant, lubricant, sweetening agent, surfactant, suspending agent, emulsifier, colorant, preservative, aromatic, corrigent, stabilizer, thickener and the like generally used in the pharmaceutical field.

As the aforementioned pharmacologically acceptable carrier, these additives can be mentioned.

For example, a tablet may be produced using excipient, binder, disintegrant, lubricant and the like, and pill and granule may be produced using excipient, binder and disintegrant. In addition, powder and capsule may be produced using excipient and the like, syrup may be produced using sweetening agent and the like, and emulsion and suspension may be produced using suspending agent, surfactant, emulsifier and the like.

Examples of the excipient include lactose, sucrose, glucose, starch, saccharose, microcrystalline cellulose, *Glycyr-*

*rhiza uralensis*, mannitol, sodium hydrogen carbonate, calcium phosphate, calcium sulfate.

Examples of the binder include 5 to 10 wt % starch solution, 10 to 20 wt % gum arabic solution or gelatin solution, 1 to 5 wt % tragacanth solution, carboxymethylcellulose solution, sodium alginate solution, glycerol.

Examples of the disintegrant include starch, calcium carbonate.

Examples of the lubricant include magnesium stearate, stearic acid, calcium stearate, purified talc.

Examples of the sweetening agent include glucose, fructose, invert sugar, sorbitol, xylitol, glycerol, simple syrup.

Examples of the surfactant include sodium lauryl sulfate, polysorbate 80, sorbitan monofatty acid ester, polyoxyl stearate 40.

Examples of the suspending agent include gum arabic, sodium alginate, sodium carboxymethylcellulose, methylcellulose, bentonite.

Examples of the emulsifier include gum arabic, tragacanth, gelatin, polysorbate 80.

For example, when the medicament of the present invention is a tablet, the tablet may be produced according to a method known per se, by adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose) or lubricant (e.g., talc, magnesium stearate, polyethylene glycol 6000) to the compound of the present invention, compression molding the mixture and, where necessary, coating same by a method known per se for masking of the taste, enteric coating or sustainability. Examples of the coating agent to be used for coating include hydroxypropylmethylcellulose, ethylcellulose, hydroxymethylcellulose, hydroxypropylcellulose, polyoxyethyleneglycol, Tween 80, pluronic F68, cellulose acetate phthalate, hydroxypropylmethylcellulose phthalate, hydroxymethylcellulose acetate succinate, Eudragit (manufactured by Rohm, Germany, methacrylic acid-acrylic acid copolymer) and dye (e.g., red iron oxide, titanium dioxide).

The aforementioned injection includes intravenous injection, as well as subcutaneous injection, intradermal injection, muscle injection, intraperitoneal injection, drip injection and the like.

Such injection may be prepared by a method known per se, that is, by dissolving, suspending or emulsifying the compound of the present invention in an aseptic aqueous solution or oily solution. Examples of the aqueous solution include isotonic solution (e.g., D-sorbitol, D-mannitol, sodium chloride) containing saline, glucose and other auxiliary agents and the like. The aqueous solution may contain suitable solubilizing agents, for example, alcohol (e.g., ethanol), polyalcohol (e.g., propylene glycol, polyethylene glycol), non-ionic surfactant (e.g., polysorbate 80, HCO-50). Examples of the oily solution include sesame oil, soybean oil and the like. The oily solution may contain suitable solubilizing agents. Examples of the solubilizing agent include benzyl benzoate, benzyl alcohol and the like. The injection may contain buffering agent (e.g., phosphate buffer, sodium acetate buffer), soothing agent (e.g., benzalkonium chloride, procaine hydrochloride), stabilizer (e.g., human serum albumin, polyethylene glycol), preservative (e.g., benzyl alcohol, phenol) and the like. The prepared injection may be generally filled in an ampoule.

The content of the compound of the present invention in the medicament of the present invention varies according to the preparation form. It is generally about 0.01 to about 100 wt %, preferably about 2 to about 85 wt %, further preferably about 5 to about 70 wt %, relative to the whole preparation.

The content of the additive in the medicament of the present invention varies according to the preparation form. Generally, it is about 1 to about 99.9 wt %, preferably about 10 to about 90 wt %, relative to the whole preparation.

The compound of the present invention is stable and low toxic and can be used safely. The daily dose of the compound of the present invention varies depending on the condition and body weight of the patient, the kind of the compound, administration route and the like. For example, for oral administration to patients for the purpose of cancer treatment, the daily dose to an adult (body weight about 60 kg) is about 1 to about 1000 mg, preferably about 3 to about 300 mg, further preferably about 10 to about 200 mg, of the compound of the present invention, and this may be administered at once or in 2 or 3 portions.

When the compound of the present invention is administered parenterally, it is generally administered in the form of a liquid (e.g., injection). A dose of the compound of the present invention varies depending on the subject of administration, target organ, symptom, administration method and the like. For example, generally about 0.01 to about 100 mg, preferably about 0.01 to about 50 mg, more preferably about 0.01 to about 20 mg, of the compound of the present invention is preferably administered per 1 kg body weight by intravenous injection.

The compound of the present invention may be used in combination with other drugs. Specifically, the compound of the present invention may be used in combination with drugs such as hormonal therapeutic agent, chemotherapeutic agent, immunotherapeutic agent or medicament inhibiting actions of cell growth factor and receptor thereof and the like. In the following, a drug that may be used in combination with the compound of the present invention is to be abbreviated as a "concomitant drug".

As the "hormonal therapeutic agent", for example, fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), pill preparation, mepitiostane, testrolactone, aminoglutethimide, LH-RH agonist (e.g., goserelin acetate, buserelin, leuprorelin acetate), droloxifene, epitiostanol, ethinylestradiol sulfonate, aromatase inhibitor (e.g., fadrozole hydrochloride, anastrozole, retrozole, exemestane, vorozole, formestane), anti-androgen (e.g., flutamide, bicartamide, nilutamide, enzalutamide), 5α-reductase inhibitor (e.g., finasteride, epristeride, dutasteride), adrenocortical hormone drug (e.g., dexamethasone, predonisolone, betamethasone, triamcinolone), androgen synthesis inhibitor (e.g., abiraterone), retinoid and drugs that retard retinoid metabolism (e.g., liarozole), thyroid gland hormone, and DDS (Drug Delivery System) preparations thereof may be used.

As the "chemotherapeutic agent", for example, alkylating agents, metabolic antagonists, antitumor antibiotics, and plant-derived antitumor drugs may be used.

As the "alkylating agent", for example, nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof may be used.

As the "metabolic antagonist", for example, mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterin, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, tiazofurin, ambamustine, bendamustine, and DDS preparations thereof may be used.

As the "antitumor antibiotic", for example, actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and DDS preparations thereof (e.g., Doxorubicin encapsulated PEG ribosome) may be used.

As the "plant-derived antitumor agent", for example, etoposide, etoposide phosphate, vinblastine sulfate, vincristine sulfate, vindesine sulfate, teniposide, paclitaxel, docetaxel, vinorelbine, and DDS preparations thereof may be used.

As the "immunotherapeutic agent", picibanil, krestin, schizophyllan, lentinan, ubenimex, interferon, interleukin, chloroquine, hydroxychloroquine, macrophagecolony stimulating factor, granulocyte colony stimulating factor, erythropoietin, lymphotoxin, BCG vaccine, *Corynebacterium parvum*, levamisole, polysaccharide K, procodazole, anti-CTLA4 antibody (e.g., ipilimumab, tremelimumab), anti-PD-1 antibody (e.g., nivolumab, pembrolizumab), anti-PD-L1 antibody may be used.

The "cell growth factors" in the "medicament inhibiting actions of cell growth factor and receptor thereof" may be any substance that promotes cell proliferation, which is normally peptide having not more than 20,000 molecular weight, and capable of exhibiting the activity at low concentrations by binding to a receptor, and specifically, (1) EGF (epidermal growth factor) or substances possessing substantially the same activity as EGF [e.g., TGFα], (2) insulin or substances possessing substantially the same activity as insulin [e.g., insulin, IGF (insulin-like growth factor)-1, IGF-2], (3) FGF (fibroblast growth factor) or substances possessing substantially the same activity as FGF [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGF (transforming growth factor β), HGF (hepatocyte growth factor), VEGF (vascular endothelial growth factor), heregulin, angiopoietin]; and the like may be used.

The "cell growth factor receptor" may be any receptor capable of binding to the aforementioned cell growth factors, and specifically, EGF receptor, heregulin receptor (e.g., HER3), insulin receptor, IGF receptor-1, IGF receptor-2, FGF receptor-1 or FGF receptor-2, VEGF receptor, angiopoietin receptor (e.g., Tie2), PDGF receptor, and the like may be used.

As the "medicament inhibiting actions of cell growth factor and receptor thereof", EGF inhibitor, TGF inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Smo inhibitor, ALK inhibitor, ROR1 inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor, PI3K inhibitor and the like may be used. More specifically, anti-VEGF antibody (e.g., Bevacizumab, Ramucurumab), anti-HER2 antibody (e.g., Trastuzumab, Pertuzumab), anti-EGFR antibody (e.g., Cetuximab, Panitumumab, Matuzumab, Nimotuzumab), anti-HGF antibody, Imatinib, Erlotinib, Gefitinib, Sorafenib, Sunitinib, Dasatinib, Lapatinib, Vatalanib, Ibrutinib, Bosutinib, Cabozantinib, Crizotinib, Alectinib, Vismodegib, Axitinib, Motesanib, Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, Tozasertib, phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), Volasertib, Selumetinib, Trametinib, N-[2(R),3-dihydroxypropoxy]-3,4-difluoro-2-(2-fluoro-4-iodophenylamino)benzamide (PD-0325901), Bosutinib, Regorafenib, Afatinib, Idelalisib, Ceritinib, Dabrafenib and the like may be used.

Besides the above-mentioned medicaments, asparaginase (irrespective of derivation such as *E. coli*-derived asparaginase, *Erwinia*-derived asparaginase and the like, may be added with modification such as PEGylation and the like, or may be capsulated using erythrocytic cell and the like), arginase (e.g., human-derived arginase), arginine deiminase (e.g., derived from *Mycoplasma*), cysteinase, methioninase, glutaminase inhibitor (e.g., CB839), amino acid transporter inhibitor (e.g., LAT1 inhibitor) aceglatone, procarbazine hydrochloride, protoporphyrin-cobalt complex salt, mercuric hematoporphyrin-sodium, topoisomerase I inhibitor (e.g., irinotecan, topotecan, Indotecan, Indimitecan), topoisomerase II inhibitor (e.g., sobuzoxane), differentiation-inducing factor (e.g., retinoid, vitamins D), other angiogenesis inhibitors (e.g., fumagillin, shark extract, COX-2 inhibitor), α-blocker (e.g., tamsulosin hydrochloride), bisphosphonic acid (e.g., pamidronate, zoledronate), thalidomide, Lenalidomide, pomalidomide, 5 azacytidine, decitabine, proteasome inhibitor (e.g., bortezomib, carfizomib, Ixazomib), NEDD8 inhibitor (e.g., Pevonedistat), UAE inhibitor, PARP inhibitor (e.g., Olaparib, Niraparib, Veliparib), antitumor antibodies such as anti-CD20 antibody (e.g., Rituximab, Obinutuzumab), anti-CCR4 antibody (e.g., Mogamulizumab) and the like, antibody drug complex (e.g., Trastuzumab emtansine, Brentuximab vedotin) and the like may also be used as a concomitant drug.

As the concomitant drug, asparaginase, arginine deiminase, LAT1 inhibitor are preferable, and asparaginase is particularly preferable.

By combining the compound of the present invention and a concomitant drug, superior effects, for example, (1) the dose, administration frequency or both thereof may be reduced as compared to single administration of the compound of the present invention or a concomitant drug, (2) the drug to be combined with the compound of the present invention may be selected according to the condition of patients (mild case, severe case and the like), (3) the period of treatment may be set longer, (4) sustention of treatment effect may be designed, (5) a synergistic effect may be afforded, (6) an unpreferable action of side effects and the like of a concomitant drug can be reduced, and the like may be obtained.

Particularly, a high antitumor effect may be obtained by using the compound of the present invention and asparaginase (e.g., L-asparaginase) in combination to a tumor resistant or tolerant to asparaginase.

Hereinafter use of the compound of the present invention and a concomitant drug in combination is referred to as the "combination agent of the present invention".

For use of the combination agent of the present invention, the administration period of the compound of the present invention and the concomitant drug is not limited, and the compound of the present invention and a concomitant drug can be administered simultaneously, or may be administered in a staggered manner. When administered at a time interval, the interval varies depending on the effective ingredient to be administered, dosage form and administration method, and, for example, when the concomitant drug is administered first, the compound of the present invention may be administered within time range of from 1 minute to 3 days, preferably from 10 minutes to 1 day, more preferably from 15 minutes to 1 hour, after administration of the concomitant drug. When the compound of the present invention is administered first, the concomitant drug may be administered within time range of from 1 minute to 1 day, preferably from 10 minutes to 6 hours, more preferably from 15 minutes to 1 hour after administration of the compound of the present invention. The dosage of the concomitant drug may be determined according to the dose clinically used, and can be appropriately selected depending on an administration subject, administration route, disease, combination and the like.

As the administration mode of the combined use of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (e.g., the compound of the present invention→the concomitant drug are administered in this order, or in the reverse order).

The dose of the concomitant drug may be appropriately determined based on the dose employed in clinical situations. The mixing ratio of the compound of the present invention and a concomitant drug may be appropriately determined depending on the administration subject, administration route, target disease, symptom, combination and the like. For example, when the subject of administration is a human, 0.01 to 100 parts by weight of a concomitant drug may be used relative to 1 part by weight of the compound of the present invention.

Furthermore, the compound of the present invention or the combination agent of the present invention can be used in combination with a non-drug therapy. Specifically, the compound of the present invention or the combination agent of the present invention can be used in combination with, for example, a non-drug therapy such as (1) operation, (2) hypertensive chemical therapy using angiotensin II and the like, (3) gene therapy, (4) hyperthermic therapy, (5) cryotherapy; (6) laser ablation method; (7) radiation therapy; (8) diet therapy (e.g., amino acid restriction diet) and the like.

For example, using the compound of the present invention or the combination agent of the present invention before or after the aforementioned surgery and the like, or before or after the treatment of two or three kinds of these in combination, effects such as inhibition of expression of resistance, prolongation of disease-free survival, suppression of cancer metastasis or recurrence, prolongation of life and the like can be achieved.

In addition, the treatment with the compound of the present invention or the combination agent of the present invention can be combined with a supporting therapy [(i) administration of antibiotics (for example, β-lactam system such as pansporin and the like, macrolide system such as clarithromycin and the like) for complications of various infectious diseases, (ii) administration of intravenous hyperalimentation, amino acid preparation, multiple vitamin preparation for improving malnutrition, (iii) morphine administration for pain relief, (iv) administration of medicament for improving side effects such as nausea, vomiting, anorexia, diarrhea, leucopenia, thrombocytopenia, hemoglobin concentration reduction, hair loss, hepatopathy, renopathy, DIC, fever and the like and (v) administration of medicament for suppressing multiple drug resistance of cancer and the like].

EXAMPLE

The present invention is explained in detail in the following by referring to Examples, preparation Examples and Experimental Examples, which are not to be construed as limitative, and the invention may be changed within the scope of the present invention.

In the following Examples, the "room temperature" generally means about 10° C. to about 35° C. The ratios indicated for mixed solvents are volume ratios, unless otherwise specified. % means wt %, unless otherwise specified.

In silica gel column chromatography, when NH is indicated, aminopropylsilane-bonded silica gel was used, and when C18 is indicated in HPLC (high performance liquid chromatography), octadecyl-bonded silica gel was used. Unless otherwise specified, the ratio of elution solvents is a volume ratio.

In Examples, the following abbreviations are used.
MS: mass spectrum
$[M+H]^+$, $[M-H]^-$: molecular ion peak
M: mol concentration
N: normal
$CDCl_3$: deuterochloroform
DMSO-$d_6$: deuterodimethyl sulfoxide ¹H NMR: proton nuclear magnetic resonance
LC/MS: liquid chromatograph mass spectrometer
ESI: Electron Spray Ionization
APCI: atmospheric pressure chemical ionization
THF: tetrahydrofuran
DCM: dichloromethane
DMAP: 4-dimethylaminopyridine
DMF: N,N-dimethylformamide
DMSO: dimethyl sulfoxide
IPE: diisopropyl ether
DIPEA: N,N'-diisopropylethylamine
NBS: N-bromosuccinimide
NIS: N-iodosuccinimide
TBAF: tetrabutylammonium fluoride
TFA: trifluoroacetic acid
TLC: thin layer chromatography ¹H NMR was measured by Fourier-transform NMR. For the analysis, ACD/SpecManager (trade name) and the like were used. Very mild peaks for protons of a hydroxy group, an amino group and the like are not described.

MS was measured by LC/MS. As Ionization, ESI method or APCI method was used. The data indicates those found. Generally, a molecular ion peak is observed. In the case of a compound having a tert-butoxycarbonyl group, a peak after elimination of a tert-butoxycarbonyl group or tert-butyl group may be observed as a fragment ion. In the case of a compound having a hydroxyl group, a peak after elimination of $H_2O$ may be observed as a fragment ion. In the case of a salt, a molecular ion peak or fragment ion peak of free form is generally observed.

Example 1

2,5-dichloro-N-(2,4-difluoro-3-(1H-pyrazolo[3,4-b]pyridin-5-ylethynyl)phenyl)-3-(hydroxymethyl)benzenesulfonamide a) 1,3-difluoro-2-iodo-6-nitrobenzene 1,3-Difluoro-2-iodobenzene (125 g) was added to sulfuric acid (500 mL) little by little at 0° C. Potassium nitrate (79 g) was added at 0° C. little by little, and the mixture was stirred at 0° C. for 30 min and at 15° C. for 3.5 hr. The same reaction using the same amounts was performed 4 times in total. The reaction mixtures were combined and added to ice water (1 L) at 0° C. A saturated aqueous sodium hydroxide solution was added to adjust the pH to 9. The mixture was filtered, and the filtrate was extracted twice with DCM (3 L). The obtained organic layer was washed with saturated brine (5 L), dried over sodium sulfate and concentrated to give the title compound (410 g).
¹H NMR (400 MHz, DMSO-$d_6$) δ 7.37-7.41 (1H, m), 8.28-8.32 (1H, m).

b) 2,4-difluoro-3-iodoaniline

Concentrated hydrochloric acid (321 mL) was added to a solution of 1,3-difluoro-2-iodo-6-nitrobenzene (300 g) in ethanol (1 L) at 15° C. Tin chloride dihydrate (948 g) was added at 15° C. little by little, and the mixture was stirred at 100° C. for 2 hr. The reaction mixture was added to ice water (1 L) at 0° C., and a saturated aqueous sodium hydroxide solution was added to adjust the pH to 9. The mixture was filtered, and the filtrate was extracted twice with ethyl acetate (600 mL). The obtained organic layer was dried over sodium sulfate and concentrated to give the title compound (165 g).
¹H NMR (400 MHz, DMSO-$d_6$) δ 5.17 (2H, s), 6.76-6.81 (2H, m).

c) 2,4-difluoro-3-((trimethylsilyl)ethynyl)aniline

Ethynyl(trimethyl)silane (39 g), triethylamine (110 g), bis(triphenylphosphine)palladium(II) dichloride (6.9 g) and copper(I) chloride (3.7 g) were added to a solution of 2,4-difluoro-3-iodoaniline (50 g) in DMF (150 mL)/THF (350 mL) at 15° C. The mixture was stirred under a nitrogen atmosphere at 50° C. for 5 hr. The same reaction using the same amounts was performed 4 times in total. The reaction mixtures were combined at 15° C., added to water (1 L) and the mixture was extracted 3 times with ethyl acetate (500 mL). The obtained organic layer was washed with saturated brine, dried over sodium sulfate and concentrated to give the title compound as a crude purified product (170 g). This was used for the next reaction.

d) 3-ethynyl-2,4-difluoroaniline

TBAF (130 g) was added to a solution of 2,4-difluoro-3-((trimethylsilyl)ethynyl)aniline (56 g) in THF (500 mL) at 15° C. The mixture was stirred at 15° C. for 30 min. The same reaction using the same amounts was performed 3 times in total. The reaction mixtures were combined and concentrated to give a residue. The residue was purified by silica gel column chromatography (ethyl acetate/petroleum ether) to give the title compound (47 g).
¹H NMR (400 MHz, DMSO-$d_6$) δ 4.64 (1H, s), 5.17 (2H, s), 6.78-6.89 (2H, m).

e) 3-((1H-pyrazolo[3,4-b]pyridin-5-yl)ethynyl)-2,4-difluoroaniline

A mixture of 3-ethynyl-2,4-difluoroaniline (1.00 g), 5-bromo-1H-pyrazolo[3,4-b]pyridine (1.29 g), triethylamine (2.74 mL), bis(di-tert-butyl(4-dimethylaminophenyl)phosphine)dichloropalladium(II) (0.088 g), copper(I) iodide (0.044 g) and DMSO (15 mL) was stirred under microwave irradiation at 120° C. for 1 hr. The same reaction using the same amounts was performed 2 times in total. The reaction mixtures were combined, and saturated aqueous sodium hydrogen carbonate solution (50 mL) and ethyl acetate (50 mL) were added. Insoluble material was filtered, and insoluble material was washed with ethyl acetate/THF (3/1). The organic layer was collected from the filtrate and the aqueous layer was extracted 3 times with ethyl acetate/THF (5/1, 30 mL). The combined organic layer was washed with saturated brine, dried over magnesium sulfate and concentrated to give a residue. The residue was purified by silica gel column chromatography (NH, ethyl acetate/hexane) and subjected to ethyl acetate/IPE/hexane, and the precipitate was collected by filtration to give the title compound (2.15 g).
¹H NMR (300 MHz, DMSO-$d_6$) δ 5.22 (2H, s), 6.77-7.00 (2H, m), 8.21 (1H, s), 8.51 (1H, d, J=2.1 Hz), 8.67 (1H, d, J=2.1 Hz), 13.97 (1H, brs).

f) ethyl 3-amino-2,5-dichlorobenzoate

Sulfuric acid (5.17 mL) was added to a solution of 3-amino-2,5-dichlorobenzoic acid (10 g) in ethanol (100 mL) at room temperature. The mixture was stirred at 70° C. for 2 hr and at 80° C. overnight. The reaction mixture was neutralized with 8N aqueous sodium hydroxide solution at 0° C., and concentrated to an about half amount. Water (50 mL) was added and the precipitate was collected by filtration and washed with water to give the title compound (9.75 g).
$^1$H NMR (300 MHz, DMSO-d$_6$) δ 1.29 (3H, t, J=7.1 Hz), 4.28 (2H, q, J=7.0 Hz), 5.97 (2H, s), 6.85 (1H, d, J=2.4 Hz), 6.96 (1H, d, J=2.4 Hz).

g) ethyl 2,5-dichloro-3-(chlorosulfonyl)benzoate

Thionyl chloride (18.7 mL) was added dropwise to water (108 mL) at 0° C. over 30 min. The mixture was stirred for 16 hr while allowing to warm to room temperature. Copper (I) chloride (0.211 g) was added and the mixture was cooled to 0° C. to give solution A. A solution of sodium nitrite (1.62 g) in water (6.54 mL) was added dropwise to a mixture of ethyl 3-amino-2,5-dichlorobenzoate (5.00 g) and concentrated hydrochloric acid (21.4 mL) at 0° C. over 30 min. The mixture was stirred at 0° C. for 10 min to give mixture B. The supernatant of mixture B was added to solution A at 0° C. over 30 min. The mixture was stirred at 0° C. for 30 min, and the precipitate was collected by filtration, washed with water and dried under reduced pressure to give the title compound (6.01 g).
$^1$H NMR (300 MHz, DMSO-d$_6$) δ 1.31 (3H, t, J=7.2 Hz), 4.33 (2H, q, J=7.2 Hz), 7.71 (1H, d, J=2.6 Hz), 7.97 (1H, d, J=2.6 Hz).

h) ethyl 3-(N-(3-((1H-pyrazolo[3,4-b]pyridin-5-yl)ethynyl)-2,4-difluorophenyl)sulfamoyl)-2,5-dichlorobenzoate 3-((1H-pyrazolo[3,4-b]pyridin-5-yl)ethynyl)-2,4-difluoroaniline (161 mg) was added to a solution of ethyl 2,5-dichloro-3-(chlorosulfonyl)benzoate (530 mg) in pyridine (2 mL) at 0° C. The mixture was stirred at 0° C. for 2 hr. To the reaction mixture was added methanol, and the mixture was concentrated. The residue was purified by silica gel column chromatography (ethyl acetate/hexane) and subjected to ethanol/water, and the precipitate was collected by filtration to give the title compound (87 mg).
$^1$H NMR (300 MHz, DMSO-d$_6$) δ 1.33 (3H, t, J=7.1 Hz), 4.37 (2H, q, J=7.2 Hz), 7.14-7.30 (1H, m), 7.36 (1H, td, J=8.9, 5.8 Hz), 8.04 (1H, d, J=2.6 Hz), 8.14 (1H, d, J=2.6 Hz), 8.22 (1H, d, J=1.3 Hz), 8.54 (1H, d, J=2.0 Hz), 8.67 (1H, d, J=2.0 Hz), 10.93 (1H, s), 13.98 (1H, s).

i) 2,5-dichloro-N-(2,4-difluoro-3-(1H-pyrazolo[3,4-b]pyridin-5-ylethynyl)phenyl)-3-(hydroxymethyl)benzenesulfonamide Lithium aluminum hydride (15.9 mg) was added to a solution of ethyl 3-(N-(3-((1H-pyrazolo[3,4-b]pyridin-5-yl)ethynyl)-2,4-difluorophenyl)sulfamoyl)-2,5-dichlorobenzoate (77 mg) in THF (2 mL) at 0° C. The mixture was stirred at room temperature for 16 hr. The reaction mixture was neutralized with saturated aqueous ammonium chloride solution at 0° C. and extracted with ethyl acetate. The obtained organic layer was washed with saturated brine, dried over magnesium sulfate and concentrated to give a residue. The residue was purified by silica gel column chromatography (ethyl acetate/hexane) and further purified by HPLC (C18, mobile phase: water/acetonitrile (0.1% TFA-containing system)). Fractions containing the object product were collected, neutralized with saturated aqueous sodium hydrogen carbonate solution, and extracted with ethyl acetate. The obtained organic layer was dried over magnesium sulfate and concentrated to give the title compound (34 mg).
$^1$H NMR (300 MHz, DMSO-d$_6$) δ 4.63 (2H, d, J=5.7 Hz), 5.74 (1H, t, J=5.8 Hz), 7.02-7.24 (1H, m), 7.24-7.47 (1H, m), 7.80 (2H, s), 8.22 (1H, d, J=1.3 Hz), 8.53 (1H, d, J=1.3 Hz), 8.67 (1H, d, J=2.0 Hz), 10.78 (1H, brs), 13.98 (1H, brs).

Example 2

5-chloro-N-(2,4-difluoro-3-(1H-pyrazolo[3,4-b]pyridin-5-ylethynyl)phenyl)-2-methylpyridine-3-sulfonamide a) 3-(benzylthio)-5-chloro-2-methylpyridine Isoamyl nitrite (5.32 mL) was added dropwise to a solution of 5-chloro-2-methylpyridin-3-amine (2.56 g) and 1,2-dibenzyl disulfide (5.32 g) in acetonitrile (37.8 mL) at 80° C. over 5 min. The mixture was stirred at 80° C. for 2 hr. The reaction mixture was concentrated under reduced pressure. The residue was purified by silica gel column chromatography (ethyl acetate/hexane) to give the title compound (744 mg).
MS: [M+H]$^+$ 250.0.

b) 5-chloro-2-methylpyridine-3-sulfonyl chloride

NCS (2.38 g) was added to a mixed solution of 3-(benzylthio)-5-chloro-2-methylpyridine (744 mg) in acetic acid (8.53 mL) and water (2.69 mL) at room temperature. The mixture was stirred at room temperature for 45 min. The mixture was diluted with water (40 mL) and extracted 2 times with ethyl acetate (60 mL). The organic layer was washed with saturated brine, dried over magnesium sulfate and concentrated to give a residue. The residue was purified by silica gel column chromatography (ethyl acetate/hexane) to give the title compound as a crude purified product (396 mg). The product was used without further purification for the next reaction.

c) 5-chloro-N-(2,4-difluoro-3-(1H-pyrazolo[3,4-b]pyridin-5-ylethynyl)phenyl)-2-methylpyridine-3-sulfonamide A mixture of 5-chloro-2-methylpyridine-3-sulfonyl chloride (147 mg), 3-((1H-pyrazolo[3,4-b]pyridin-5-yl)ethynyl)-2,4-difluoroaniline (176 mg) and pyridine (2.62 mL) was stirred at room temperature overnight. The same reaction was performed at 2.70-fold amount and 2.37-fold amount. The reaction mixtures were combined, and methanol (5 mL) was added. The mixture was concentrated under reduced pressure and the residue was purified by silica gel column chromatography (ethyl acetate/hexane) to give the title compound as a crude purified product (1 g). The obtained crude purified product of the title compound was dissolved in DMF/toluene and subjected to silica gel column chromatography (NH, methanol/ethyl acetate) to elute a byproduct. Silica gel supporting the title compound was added to ethyl acetate (50 mL), acetic acid (10 mL) and water (50 mL), and the mixture was stirred at room temperature for 10 min. The mixture was filtered, and silica gel on the filter was treated 4 times with ethyl acetate/acetic acid/water (50 mL/10 mL/20 mL) and 2 times with ethyl acetate/acetic acid (50 mL/10 mL) to elute the object product. The organic layer was collected from the filtrate and washed with water and saturated brine, dried over magnesium sulfate and concentrated to give a residue. The residue was dissolved by heating in DMSO (3 mL) at 50° C. A trace amount of solid in the solution was removed by filtration and ethanol (4 mL)

was added. The obtained solution was heated to 50° C. and water (8 mL) was added dropwise over 10 min. The mixture was stirred at room temperature for 30 min and the precipitate was collected by filtration, washed with ethanol/water (1 mL/10 mL) and dried under reduced pressure to give the title compound (653 mg).

$^1$H NMR (300 MHz, DMSO-$d_6$) δ 2.78 (3H, s), 7.18-7.28 (1H, m), 7.30-7.40 (1H, m), 8.07 (1H, d, J=2.3 Hz), 8.22 (1H, d, J=1.3 Hz), 8.53 (1H, d, J=1.9 Hz), 8.66 (1H, d, J=2.1 Hz), 8.78 (1H, d, J=2.4 Hz), 10.75-10.94 (1H, m), 13.98 (1H, brs).

Example 3

N-(3-((2-aminopyrimidin-5-yl)ethynyl)-2,4-difluorophenyl)-5-chloro-2-methylpyridine-3-sulfonamide a) 5-iodo-N-(4-methoxybenzyl)pyrimidin-2-amine 4-methoxybenzylamine (1.40 mL) was added to a solution of 2-chloro-5-iodopyrimidine (2.0 g) and triethylamine (1.75 mL) in ethanol (20 mL) at room temperature. The mixture was stirred under microwave irradiation at 120° C. for 10 min. The reaction mixture was subjected to water and the precipitate was collected by filtration to give the title compound (2.20 g).

MS: [M+H]$^+$ 341.9.

b) 5-((3-amino-2,6-difluorophenyl)ethynyl)-N-(4-methoxybenzyl)pyrimidin-2-amine bis(Di-tert-butyl(4-dimethylaminophenyl)phosphine)dichloropalladium(II) (0.039 g) was added to a solution of 3-ethynyl-2,4-difluoroaniline (0.45 g), 5-iodo-N-(4-methoxybenzyl)pyrimidin-2-amine (1.0 g), triethylamine (1.2 mL) and copper(I) iodide (0.022 g) in DMSO (18 mL) at room temperature. The mixture was stirred under microwave irradiation at 120° C. for 1 hr. The same reaction using the same amounts was performed 2 times in total. The reaction mixture was filtered through celite, and the filtrate was diluted with water, and extracted with ethyl acetate/ THF. The obtained organic layer was washed with saturated brine, dried over magnesium sulfate and concentrated to give a residue. The residue was washed with methanol to give the title compound (1.58 g).

MS: [M+H]$^+$ 367.1.

c) N-(3-((2-aminopyrimidin-5-yl)ethynyl)-2,4-difluorophenyl)-5-chloro-2-methylpyridine-3-sulfonamide A mixture of 5-((3-amino-2,6-difluorophenyl)ethynyl)-N-(4-methoxybenzyl)pyrimidin-2-amine (0.15 g), 5-chloro-2-methylpyridine-3-sulfonyl chloride (0.16 g) and pyridine (1.58 g) was stirred at room temperature for 2 hr. To the reaction mixture were added methanol (1.62 mL) and 2M aqueous sodium hydroxide solution (2 mL), and the mixture was stirred at room temperature for 30 min. The reaction mixture was diluted with saturated aqueous sodium hydrogen carbonate solution, and the mixture was extracted with ethyl acetate. The obtained organic layer was washed with saturated brine, dried over magnesium sulfate and concentrated to give a residue. To the residue was added TFA (2.28 g), and the mixture was stirred at 50° C. overnight. The reaction mixture was diluted with saturated aqueous sodium hydrogen carbonate solution, and extracted with ethyl acetate. The obtained organic layer was washed with saturated brine, dried over magnesium sulfate and concentrated to give a residue. The residue was purified by silica gel column chromatography (ethyl acetate/hexane) to give the title compound as a crude purified product. The obtained crude purified product of the title compound was subjected to silica gel column chromatography (NH, methanol/ethyl acetate) to elute a byproduct. Silica gel supporting the title compound was added to ethyl acetate (20 mL), acetic acid (5 mL) and water (20 mL), and the mixture was stirred at room temperature for 10 min. The mixture was filtered and silica gel on the filter was treated 4 times with ethyl acetate/acetic acid (5 mL/1 mL) to elute the object product. The organic layer was collected from the filtrate, washed with water and saturated aqueous sodium hydrogen carbonate solution and saturated brine, dried over magnesium sulfate and concentrated to give a residue. The residue was subjected to ethyl acetate/hexane, and the precipitate was collected by filtration to give the title compound (88 mg).

$^1$H NMR (300 MHz, DMSO-$d_6$) δ 2.76 (3H, s), 7.17-7.24 (1H, m), 7.27-7.36 (3H, m), 8.05 (1H, d, J=2.4 Hz), 8.43 (2H, s), 8.78 (1H, d, J=2.4 Hz), 10.81 (1H, s).

Example 4

N-(3-((2-aminopyrimidin-5-yl)ethynyl)-2,4-difluorophenyl)-2,5-dichloro-3-(hydroxymethyl)benzenesulfonamide a) ethyl 2,5-dichloro-3-(N-(3-ethynyl-2,4-difluorophenyl)sulfamoyl)benzoate Ethyl 2,5-dichloro-3-(chlorosulfonyl)benzoate (6.00 g) was added to a solution of 3-ethynyl-2,4-difluoroaniline (2.41 g) in pyridine (31.8 mL) at 0° C. The mixture was stirred overnight while allowing to warm to room temperature. The reaction mixture was concentrated to give a residue. The residue was purified by silica gel column chromatography (ethyl acetate/hexane) and washed with ethyl acetate/hexane to give the title compound (3.97 g).

$^1$H NMR (300 MHz, DMSO-$d_6$) δ 1.33 (3H, t, J=7.2 Hz), 4.37 (2H, q, J=7.1 Hz), 4.87 (1H, s), 7.15-7.23 (1H, m), 7.34 (1H, td, J=8.9, 6.0 Hz), 8.00 (1H, d, J=2.6 Hz), 8.13 (1H, d, J=2.6 Hz), 10.87 (1H, s).

b) 2,5-dichloro-N-(3-ethynyl-2,4-difluorophenyl)-3-(hydroxymethyl)benzenesulfonamide A solution of ethyl 2,5-dichloro-3-(N-(3-ethynyl-2,4-difluorophenyl)sulfamoyl)benzoate (1.09 g) in THF (24 mL) was added dropwise to a suspension of lithium aluminum hydride (190 mg) in THF (15.2 mL) at 0° C. for 20 min. The mixture was stirred at 0° C. for 10 min and water (5 mL) was added dropwise. The mixture was stirred at 0° C. for 10 min, a saturated aqueous ammonium chloride solution (5 mL) was added, and the mixture was stirred at room temperature for 10 min. The reaction mixture was filtered, an insoluble material on the filter paper was washed with ethyl acetate and saturated aqueous ammonium chloride solution. The organic layer obtained from the filtrate was washed with saturated brine, dried over magnesium sulfate and concentrated to give a residue. The residue was purified by silica gel column chromatography (ethyl acetate/hexane) to give the title compound (858 mg).

MS: [M−H]⁻ 390.1.

c) N-(3-((2-aminopyrimidin-5-yl)ethynyl)-2,4-difluorophenyl)-2,5-dichloro-3-(hydroxymethyl)benzenesulfonamide A mixture of 2,5-dichloro-N-(3-ethynyl-2,4-difluorophenyl)-3-(hydroxymethyl)benzenesulfonamide (900 mg), 5-iodopyrimidin-2-amine (761 mg), dichlorobis(tricyclohexylphosphine)palladium(II) (113 mg), cesium carbonate (2.99 g) and DMSO (14.5 mL) was stirred under microwave irradiation at 120° C. for 1.5 hr. The same reaction was performed two more times at 1.3-fold amount. After cooling to room temperature, the reaction mixtures were combined, diluted with water/saturated aqueous ammonium chloride solution, and extracted 3 times with ethyl acetate. The obtained organic layer was washed with saturated brine, dried over magnesium sulfate and concentrated to give a residue. The residue was purified by silica gel column chromatography (ethyl acetate/hexane) and subjected to ethyl acetate/hexane, and the precipitate was collected by filtration to give the title compound as a crude purified product. The filtrate was concentrated to give a residue. The crude purified product of the title compound and the obtained residue were combined, and further purified by HPLC (C18, mobile phase: water/acetonitrile (0.1% TFA-containing system)). Fractions containing the object product were collected, neutralized with a saturated aqueous sodium hydrogen carbonate solution, and extracted with ethyl acetate. The obtained organic layer was washed with saturated brine, dried over magnesium sulfate and concentrated to give a residue. The residue was dissolved in ethanol/water (90 mL/9 mL) at 60° C., and the mixture was filtered, and a trace amount of insoluble material was washed with ethanol (10 mL). The filtrate was heated to 60° C., and water (191 mL) was added dropwise over 15 min. The mixture was cooled to room temperature over 2 hr. The precipitate was collected by filtration, washed 3 times with ethanol/water (1/1, 5 mL) and dried at 50° C. under reduced pressure to give the title compound (1.25 g).

¹H NMR (300 MHz, DMSO-d₆) δ 4.63 (2H, d, J=5.7 Hz), 5.75 (1H, t, J=5.7 Hz), 7.12-7.36 (4H, m), 7.76-7.86 (2H, m), 8.43 (2H, s), 10.73 (1H, s).

Example 5

5-chloro-N-(2,4-difluoro-3-(1H-pyrazolo[3,4-b]pyridin-5-ylethynyl)phenyl)-2-methoxypyridine-3-sulfonamide a) 3-(benzylthio)-5-chloro-2-methoxypyridine

Pentyl nitrite (17.6 mL) was added dropwise to a solution of 5-chloro-2-methoxypyridin-3-amine (9.52 g) and 1,2-dibenzyl disulfide (17.7 g) in acetonitrile (126 mL) at 80° C. over 20 min. The mixture was stirred at 80° C. for 30 min. The reaction mixture was concentrated under reduced pressure. The residue was purified by silica gel column chromatography (ethyl acetate/hexane) to give the title compound (9.22 g).

MS: [M+H]⁺ 266.0.

b) 5-chloro-2-methoxypyridine-3-sulfonyl chloride

NCS (16.3 g) was added to a mixed solution of 3-(benzylthio)-5-chloro-2-methoxypyridine (5.40 g) in acetic acid (34.9 mL) and water (11.0 mL) at room temperature. The mixture was stirred at room temperature overnight. The mixture was diluted with water and extracted 2 times with ethyl acetate.

The organic layer was washed with saturated brine, dried over magnesium sulfate and concentrated to give a residue. The residue was purified by silica gel column chromatography (ethyl acetate/hexane) to give the title compound (4.40 g).

¹H NMR (300 MHz, DMSO-d₆) δ 3.86 (3H, s), 7.91 (1H, d, J=2.6 Hz), 8.17 (1H, d, J=2.6 Hz).

c) 5-chloro-N-(2,4-difluoro-3-(1H-pyrazolo[3,4-b]pyridin-5-ylethynyl)phenyl)-2-methoxypyridine-3-sulfonamide 5-Chloro-2-methoxypyridine-3-sulfonyl chloride (90 mg) was added to a solution of 3-((1H-pyrazolo[3,4-b]pyridin-5-yl)ethynyl)-2,4-difluoroaniline (54 mg) in pyridine (0.81 mL) at room temperature. The mixture was stirred at room temperature for 1 hr. Methanol (1 mL) was added and the mixture was stirred at room temperature for 10 min. The reaction mixture was concentrated under reduced pressure, and the residue was purified by silica gel column chromatography (ethyl acetate/hexane) to give the title compound as a crude purified product. The obtained crude purified product of the title compound was subjected to silica gel (NH, 6 g) and methanol/ethyl acetate (2/8, v/v) was flown until completion of the elution of a byproduct. Silica gel supporting the title compound was added to ethyl acetate (50 mL), acetic acid (10 mL) and water (50 mL), and the mixture was stirred at room temperature for 10 min. The mixture was filtered, and the organic layer was collected from the filtrate, washed with water and saturated brine, dried over magnesium sulfate and concentrated to give the title compound (45 mg).

¹H NMR (300 MHz, DMSO-d₆) δ 3.94 (3H, s), 7.15-7.41 (2H, m), 8.07 (1H, d, J=2.4 Hz), 8.22 (1H, d, J=1.1 Hz), 8.48-8.55 (2H, m), 8.67 (1H, d, J=1.9 Hz), 10.50 (1H, s), 13.98 (1H, s).

Example 6

N-(3-((2-aminopyrimidin-5-yl)ethynyl)-2,4-difluorophenyl)-5-chloro-2-(trifluoromethyl)benzenesulfonamide a) 5-chloro-2-(trifluoromethyl)benzene-1-sulfonyl Chloride

Thionyl chloride (2 mL) was added dropwise to ice-cooled water (12 mL), and the mixture was stirred at 0° C. for 3 hr. To this solution was added copper(I) chloride (28 mg) to give solution A. To the ice-cooled concentrated hydrochloric acid (3 mL) was added 5-chloro-2-(trifluoromethyl)aniline (500 mg), and the mixture was stirred at 0° C. for 10 min. To the obtained mixture was added dropwise a solution of sodium nitrite (210 mg) in water (0.8 mL) at 0° C., and the mixture was stirred at 0° C. for 10 min. The obtained mixture was added dropwise to solution A at 0° C., and the mixture was stirred at 0° C. for 1 hr. To the reaction mixture was added water, and the mixture was extracted with ethyl acetate. The obtained organic layer was washed with water and saturated brine, dried over magnesium sulfate and concentrated to give the title compound (663 mg).

¹H NMR (300 MHz, DMSO-d₆) δ 7.56-7.64 (1H, m), 7.68-7.76 (1H, m), 8.04 (1H, d, J=2.4 Hz).

b) 5-chloro-N-(3-ethynyl-2,4-difluorophenyl)-2-(trifluoromethyl)benzenesulfonamide To a solution of 3-ethynyl-2,4-difluoroaniline (247 mg) in pyridine (5 mL) was added 5-chloro-2-(trifluoromethyl)benzene-1-sulfonyl chloride (660 mg) at 0° C. The mixture was stirred at room temperature for 1 hr. The reaction mixture was concentrated, and the residue was purified by silica gel column chromatography (ethyl acetate/hexane) to give the title compound (378 mg).
$^1$H NMR (300 MHz, DMSO-$d_6$) δ 4.85 (1H, s), 7.15-7.27 (1H, m), 7.35 (1H, td, J=8.9, 5.9 Hz), 7.95-8.09 (3H, m), 10.69 (1H, brs).

c) N-(3-((2-aminopyrimidin-5-yl)ethynyl)-2,4-difluorophenyl)-5-chloro-2-(trifluoromethyl)benzenesulfonamide A mixture of 2-amino-5-iodopyrimidine (172 mg), 5-chloro-N-(3-ethynyl-2,4-difluorophenyl)-2-(trifluoromethyl)benzenesulfonamide (212 mg), dichlorobis(tricyclohexylphosphine)palladium(II) (30 mg), cesium carbonate (656 mg) and DMSO (4 mL) was stirred under microwave irradiation at 120° C. for 1.5 hr. The reaction mixture was purified by silica gel column chromatography (ethyl acetate/hexane) and further separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The obtained organic layer was dried over magnesium sulfate and concentrated. The residue was washed with ethyl acetate/IPE to give the title compound (142 mg).
$^1$H NMR (300 MHz, DMSO-$d_6$) δ 7.05-7.36 (4H, m), 7.87-7.95 (1H, m), 7.95-8.02 (1H, m), 8.03 (1H, d, J=2.1 Hz), 8.43 (2H, s), 10.72 (1H, brs).

Example 7

N-(3-((2-aminopyrimidin-5-yl)ethynyl)-2,4-difluorophenyl)-5-chloro-2-methoxypyridine-3-sulfonamide Acetate a) 5-chloro-N-(3-ethynyl-2,4-difluorophenyl)-2-methoxypyridine-3-sulfonamide A mixture of 3-ethynyl-2,4-difluoroaniline (2.78 g), 5-chloro-2-methoxypyridine-3-sulfonyl chloride (4.40 g) and pyridine (43.1 g) was stirred at room temperature overnight. To the reaction mixture was added methanol (10 mL), and the mixture was stirred at room temperature for 10 min. The reaction mixture was concentrated under reduced pressure. The residue was purified by silica gel column chromatography (ethyl acetate/hexane) to give the title compound (5.02 g).
MS: [M+H]$^+$ 359.0.

b) N-(3-((2-aminopyrimidin-5-yl)ethynyl)-2,4-difluorophenyl)-5-chloro-2-methoxypyridine-3-sulfonamide acetate A mixture of 5-chloro-N-(3-ethynyl-2,4-difluorophenyl)-2-methoxypyridine-3-sulfonamide (1.24 g), 5-iodopyrimidin-2-amine (1.15 g), dichlorobis(tricyclohexylphosphine)palladium(II) (170 mg), cesium carbonate (4.51 g) and DMSO (16.5 mL) was stirred under a nitrogen atmosphere at 120° C. for 3 hr. After cooling to room temperature, the mixture was diluted with water/saturated brine and extracted three times with ethyl acetate. The obtained organic layer was washed with saturated brine, dried over magnesium sulfate and concentrated to give a residue. The residue was purified by silica gel column chromatography (ethyl acetate/hexane) to give the title compound as a crude purified product in a free form. The obtained title compound as a crude purified product in a free form was dissolved in DMF/toluene and subjected to silica gel column chromatography (NH, methanol/ethyl acetate) to elute a byproduct. Silica gel supporting a free form of the title compound was added to ethyl acetate (100 mL), acetic acid (18 mL) and water (100 mL), and the mixture was stirred at room temperature for 10 min. The mixture was filtered and silica gel on the filter was treated 4 times with ethyl acetate/acetic acid (30 mL/6 mL) to elute the object product. The organic layer was collected from the filtrate, and the organic layer was washed with water and saturated brine, dried over magnesium sulfate and concentrated to give a residue. The residue was dissolved in an ethyl acetate/THF/saturated aqueous sodium hydrogen carbonate solution, and the obtained organic layer was washed with a saturated aqueous sodium hydrogen carbonate solution and saturated brine, dried over magnesium sulfate and concentrated to give a residue. The residue was purified by silica gel column chromatography (ethyl acetate/hexane) and washed with ethyl acetate to give the title compound as a crude purified product in a free form. The same reaction was performed at 4.05-fold amount and 4.12-fold amount. The obtained title compounds as crude purified products in a free form were collected, acetic acid (24.8 mL) was added and the mixture was heated to 50° C. To the mixture was added DMSO (66 mL) at 50° C. and dissolved therein. The mixture was filtered, and a trace amount of an insoluble material on the filter was washed with acetic acid (24.8 mL). The filtrate was heated to 50° C. and water (50 mL) was added dropwise. The mixture was cooled to room temperature over 30 min. The precipitate was collected by filtration, washed three times with ethanol/water (1/10, 33 mL) and dried at 50° C. under reduced pressure to give the title compound (5.53 g).
$^1$H NMR (300 MHz, DMSO-$d_6$) δ 1.91 (3H, s), 3.94 (3H, s), 7.14-7.37 (4H, m), 8.07 (1H, d, J=2.6 Hz), 8.43 (2H, s), 8.52 (1H, d, J=2.6 Hz), 10.46 (1H, s), 11.94 (1H, s).

Example 7a

N-(3-((2-aminopyrimidin-5-yl)ethynyl)-2,4-difluorophenyl)-5-chloro-2-methoxypyridine-3-sulfonamide The compound (500 mg) of Example 7 was dissolved in a 1:1 mixed solvent (about 50 mL) of ethyl acetate and THF and a saturated aqueous sodium hydrogen carbonate solution (30 mL). The organic layer was collected, washed with a saturated aqueous sodium hydrogen carbonate solution, saturated brine, dried over magnesium sulfate and concentrated. The residue was dissolved in DMSO (2 mL) and the mixture was heated to 50° C. To the obtained solution was added dropwise water (5 mL) and the mixture was cooled to room temperature. The precipitated solid was collected by filtration, washed with water and dried at 80° C. under reduced pressure to give a solid. The obtained solid was dissolved in acetone (20 mL) by heating and water (20 mL) was added dropwise to the obtained solution and the mixture was cooled to room temperature. The precipitated solid was collected by filtration, washed with water, and dried under reduced pressure at 80° C. to give the title compound (338 mg).

$^1$H NMR (300 MHz, DMSO-d$_6$) δ 3.83-4.04 (3H, m), 7.15-7.23 (1H, m), 7.27-7.36 (3H, m), 8.07 (1H, d, J=2.5 Hz), 8.43 (2H, s), 8.52 (1H, d, J=2.5 Hz), 10.46 (1H, s).

Example 8

5-chloro-N-(2,4-difluoro-3-(1H-pyrazolo[3,4-b]pyridin-5-ylethynyl)phenyl)-2,3-dihydro-1-benzofuran-7-sulfonamide 5-Chloro-2,3-dihydrobenzofuran-7-sulfonyl chloride (47 mg) was added to a solution of 3-((1H-pyrazolo[3,4-b]pyridin-5-yl)ethynyl)-2,4-difluoroaniline (50 mg) in pyridine (2 mL) at 0° C. The mixture was stirred at 0° C. for 2 hr. To the reaction mixture was added methanol and the mixture was concentrated under reduced pressure. The residue was purified by silica gel column chromatography (ethyl acetate/hexane) to give the title compound as a crude purified product. The obtained crude purified product of the title compound was solidified with methanol and collected by filtration to give the title compound (3 mg). The filtrate was concentrated under reduced pressure, and the residue was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The extract was dried over anhydrous magnesium sulfate and concentrated under reduced pressure to give the title compound (36 mg).

$^1$H NMR (300 MHz, DMSO-d$_6$) δ 3.27 (2H, t, J=9.0 Hz), 4.65 (2H, t, J=8.8 Hz), 7.16-7.37 (3H, m), 7.60 (1H, d, J=2.2 Hz), 8.22 (1H, d, J=1.3 Hz), 8.54 (1H, d, J=1.3 Hz), 8.68 (1H, d, J=2.0 Hz), 10.35 (1H, s), 13.99 (1H, s).

Example 9

N-(3-((2-aminopyrimidin-5-yl)ethynyl)-2,4-difluorophenyl)-5-chloro-2,3-dihydro-1-benzofuran-7-sulfonamide To a solution of 5-((3-amino-2,6-difluorophenyl)ethynyl)-N-(4-methoxybenzyl)pyrimidin-2-amine (50 mg) in pyridine (1 mL) was added 5-chloro-2,3-dihydrobenzofuran-7-sulfonyl chloride (70 mg) at 0° C. The mixture was stirred at room temperature overnight. The reaction mixture was diluted with toluene and concentrated. The residue was dissolved in TFA (2 mL) at room temperature, and the mixture was stirred at 70° C. for 2 hr. To the reaction mixture was added a saturated aqueous sodium hydrogen carbonate solution, and the mixture was extracted with ethyl acetate. The obtained organic layer was washed with saturated brine, dried over magnesium sulfate, and concentrated. The residue was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The obtained organic layer was washed with saturated brine, dried over magnesium sulfate and concentrated. The obtained residue was washed with ethyl acetate/IPE to give the title compound (39 mg).

$^1$H NMR (300 MHz, DMSO-d$_6$) δ 3.26 (2H, t, J=8.7 Hz), 4.64 (2H, t, J=8.8 Hz), 7.11-7.36 (5H, m), 7.55-7.62 (1H, m), 8.44 (2H, s), 10.30 (1H, s).

Example 10

2,5-dichloro-N-(2,4-difluoro-3-(1H-pyrazolo[3,4-b]pyridin-5-ylethynyl)phenyl)benzenesulfonamide TFA Salt To a solution of 2,5-dichlorobenzenesulfonyl chloride (22 mg) in THF (0.2 mL) was added a solution of 3-((1H-pyrazolo[3,4-b]pyridin-5-yl)ethynyl)-2,4-difluoroaniline (22 mg) in pyridine (0.6 mL) at −15° C. The mixture was stirred at −15° C. to 0° C. for 1 hr. The reaction mixture was diluted with ethyl acetate, water was added, and the mixture was stirred for 2 min. The organic layer was collected, and further extracted with ethyl acetate from the aqueous layer. The combined organic layers were concentrated by blowing air at 60° C. to give a residue. The residue was purified by HPLC (C18, mobile phase: water/acetonitrile (0.1% TFA-containing system)). Fractions containing the object product were collected and concentrated by blowing air at 60° C. to give the title compound (11.4 mg).

Example 11

2,5-dichloro-N-(3-((2-(cyclopropylamino)pyrimidin-5-yl)ethynyl)-2,4-difluorophenyl)benzenesulfonamide TFA Salt a) 2,5-dichloro-N-(3-ethynyl-2,4-difluorophenyl)benzenesulfonamide 2,5-Dichlorobenzenesulfonyl chloride (1.6 g) was added to a solution of 3-ethynyl-2,4-difluoroaniline (1.0 g) in pyridine (15 mL) at 0° C. The mixture was stirred at 0° C. for 10 min and at room temperature for 2 hr. The reaction mixture was concentrated to give a residue. The residue was purified by silica gel column chromatography (ethyl acetate/hexane). The obtained crude purified product of the title compound was washed with IPE/hexane to give the title compound (1.67 g).

$^1$H NMR (300 MHz, DMSO-d$_6$) δ 4.85 (1H, s), 7.12-7.23 (1H, m), 7.32 (1H, td, J=9.0, 5.9 Hz), 7.73-7.78 (2H, m), 7.84 (1H, dd, J=2.0, 0.9 Hz), 10.73 (1H, s).

b) 2,5-dichloro-N-(3-((2-chloropyrimidin-5-yl)ethynyl)-2,4-difluorophenyl)benzenesulfonamide Bis(di-tert-butyl(4-dimethylaminophenyl)phosphine)dichloropalladium(II) (0.56 g) was added to a solution of 2,5-dichloro-N-(3-ethynyl-2,4-difluorophenyl)benzenesulfonamide (3.0 g), 2-chloro-5-iodopyrimidine (2.6 g), DIPEA (3.0 mL) and copper(I) iodide (79 mg) in THF (50 mL) at room temperature. The mixture was stirred under a nitrogen atmosphere at room temperature for 16 hr. The reaction mixture was filtered through celite, and the filtrate was diluted with water and the mixture was extracted with ethyl acetate. The obtained organic layer was washed with saturated brine, dried over magnesium sulfate and concentrated to give a residue. The residue was purified by silica gel column chromatography (ethyl acetate/hexane) to give the title compound (761 mg).

$^1$H NMR (300 MHz, DMSO-d$_6$) δ 7.22-7.32 (1H, m), 7.42 (1H, td, J=8.9, 5.9 Hz), 7.71-7.81 (2H, m), 7.87 (1H, dd, J=2.0, 0.8 Hz), 9.03 (2H, s), 10.83 (1H, s).

c) 2,5-dichloro-N-(3-((2-(cyclopropylamino)pyrimidin-5-yl)ethynyl)-2,4-difluorophenyl)benzenesulfonamide TFA Salt A mixture of 2,5-dichloro-N-(3-((2-chloropyrimidin-5-yl)ethynyl)-2,4-difluorophenyl)benzenesulfonamide (28 mg), aminocyclopropane (6.7 mg), DIPEA (0.031 mL) and DMSO (0.5 mL) was stirred at room temperature overnight. The reaction mixture was purified by HPLC (C18, mobile phase: water/acetonitrile (0.1% TFA-containing system)).

Fractions containing the object product were collected and concentrated by blowing air at 60° C. to give the title compound (14.7 mg).

Example 12

N-(3-((2-aminopyrimidin-5-yl)ethynyl)-2,4-difluorophenyl)-5-chloro-2-(trifluoromethoxy)benzenesulfonamide a) 5-chloro-2-(trifluoromethoxy)benzene-1-sulfonyl Chloride Thionyl chloride (2.2 mL) was added dropwise to water (2.2 mL) at 0° C. The mixture was stirred for 16 hr at room temperature. Copper(I) chloride (23 mg) was added and the mixture was cooled to 0° C. to give solution A. A solution of sodium nitrite (179 mg) in water (2.2 mL) was added dropwise to a mixture of 5-chloro-2-(trifluoromethoxy)aniline (500 mg) and concentrated hydrochloric acid (2.2 mL) at 0° C. The mixture was stirred at 0° C. for 30 min to give mixture B. Mixture B was added to solution A at 0° C. The mixture was stirred at 0° C. for min, diluted with water, and the mixture was extracted with ethyl acetate. The obtained organic layer was washed with saturated brine, dried over magnesium sulfate and concentrated to give a residue. The residue was purified by silica gel column chromatography (ethyl acetate/hexane) to give a crude purified product of the title compound (233 mg).
MS, found: [M−H]⁻275.0.

b) N-(3-((2-aminopyrimidin-5-yl)ethynyl)-2,4-difluorophenyl)-5-chloro-2-(trifluoromethoxy)benzenesulfonamide 5-Chloro-2-(trifluoromethoxy)benzene-1-sulfonyl chloride (233 mg) was added to a solution of 5-((3-amino-2,6-difluorophenyl) ethynyl)-N-(4-methoxybenzyl)pyrimidin-2-amine (120 mg) in pyridine (5 mL) at 0° C. The mixture was stirred at room temperature for 5 hr. The reaction mixture was concentrated to give a residue. To the residue was added TFA (2 ml) at 0° C. and the mixture was stirred at 50° C. for 16 hr. A part of TFA in the reaction mixture was evaporated under reduced pressure, to the residue was added a saturated aqueous sodium hydrogen carbonate solution at 0° C., and the mixture was extracted with ethyl acetate. The obtained organic layer was washed with saturated brine, dried over magnesium sulfate and concentrated to give a residue. The residue was purified by silica gel column chromatography (ethyl acetate/hexane) to give the title compound as a crude purified product. The crude purified product of the title compound was solidified with DMSO/water to give the title compound (34 mg).
$^1$H NMR (300 MHz, DMSO-$d_6$) δ 7.17-7.37 (4H, m), 7.60-7.69 (1H, m), 7.82-7.94 (2H, m), 8.43 (2H, s), 10.71 (1H, s).

Example 13

N-(3-((2-aminopyrimidin-5-yl)ethynyl)-2,4-difluorophenyl)-2,5-dichlorobenzenesulfonamide TFA Salt A mixture of 2,5-dichloro-N-(3-ethynyl-2,4-difluorophenyl)benzenesulfonamide (29 mg), 5-iodopyrimidin-2-amine (35 mg), cesium carbonate (104 mg), bis(tricyclohexylphosphine)palladium(II) dichloride (5.6 mg) and DMSO (0.5 mL) was stirred under microwave irradiation at 120° C. for 2 hr. After cooling to room temperature, the precipitate was removed by filtration, and the filtrate was purified by HPLC (C18, mobile phase: water/acetonitrile (0.1% TFA-containing system)). Fractions containing the object product were collected and concentrated by blowing air at 60° C. to give the title compound (10.5 mg).

Example 14

2,5-dichloro-N-(2,4-difluoro-3-(1H-pyrazolo[3,4-b]pyridin-5-ylethynyl)phenyl)benzenesulfonamide 2,5-Dichlorobenzene-1-sulfonyl chloride (4.47 g) was added to a solution of 3-((1H-pyrazolo[3,4-b]pyridin-5-yl) ethynyl)-2,4-difluoroaniline (4.47 g) in pyridine (60 mL) at 0° C. over 15 min. The mixture was stirred at 0° C. for 2 hr. To the reaction mixture was added methanol and the mixture was concentrated under reduced pressure. To the residue was added methanol, and the precipitated solid was collected by filtration. The obtained solid was dissolved in ethanol and purified by silica gel column chromatography (ethyl acetate/ hexane and methanol/ethyl acetate) to give the title compound as a crude purified product. The filtrate was purified by silica gel column chromatography (ethyl acetate/hexane and methanol/ethyl acetate) to give the title compound as a crude purified product. The crude purified products of the title compound obtained by the above-mentioned operation were combined, and crystallized from ethanol (300 mL) and water (200 mL) at 50° C. to give the title compound as a crude purified product. The obtained crude purified product of the title compound was dissolved in ethanol (300 mL), and a 4N aqueous lithium hydroxide solution (20 mL) was added. The reaction mixture was stirred at 50° C. for 30 min. To the reaction mixture was added 6N hydrochloric acid at room temperature to adjust to pH6 and water (200 mL) was added. The reaction mixture was stirred at room temperature for 2 days and the precipitated solid was collected by filtration to give the title compound (4.34 g).
$^1$H NMR (300 MHz, DMSO-$d_6$) δ 7.18-7.28 (1H, m), 7.35 (1H, td, J=8.9, 5.9 Hz), 7.76-7.80 (2H, m), 7.88 (1H, dd, J=1.9, 1.0 Hz), 8.22 (1H, d, J=1.3 Hz), 8.54 (1H, d, J=1.4 Hz), 8.68 (1H, d, J=2.0 Hz), 10.80 (1H, s), 13.99 (1H, brs).

Example 15

5-chloro-N-(2,4-difluoro-3-(1H-pyrazolo[3,4-b]pyridin-5-ylethynyl)phenyl)-2-methylbenzenesulfonamide 5-Chloro-2-methylbenzene-1-sulfonyl chloride (55 mg) was added to a solution of 3-((1H-pyrazolo[3,4-b]pyridin-5-yl)ethynyl)-2,4-difluoroaniline (65 mg) in pyridine (2 mL) at 0° C. The mixture was stirred at 0° C. for 2 hr. To the reaction mixture were added methanol at room temperature and the mixture was concentrated under reduced pressure. The residue was purified by silica gel column chromatography (ethyl acetate/hexane) to give the title compound as a crude purified product. The obtained crude purified product of the title compound was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The extract was dried over anhydrous magnesium sulfate, concentrated under reduced pressure, and the residue was solidified with ethyl acetate/ hexane/diisopropyl ether and collected by filtration to give the title compound (30 mg).

¹H NMR (300 MHz, DMSO-d₆) δ 2.58 (3H, s), 7.18-7.37 (2H, m), 7.48 (1H, d, J=8.3 Hz), 7.60-7.66 (1H, m), 7.68 (1H, d, J=2.4 Hz), 8.22 (1H, d, J=1.3 Hz), 8.53 (1H, d, J=1.3 Hz), 8.66 (1H, d, J=2.0 Hz), 10.58 (1H, s), 13.97 (1H, brs).

Example 16

2,5-dichloro-N-(2,4-difluoro-3-((2-(tetrahydrofuran-3-ylamino)pyrimidin-5-yl)ethynyl)phenyl)benzenesulfonamide TFA Salt A mixture of 2,5-dichloro-N-(3-((2-chloropyrimidin-5-yl)ethynyl)-2,4-difluorophenyl)benzenesulfonamide (28 mg), 3-aminotetrahydrofuran (10 mg), DIPEA (0.031 mL) and DMSO (0.5 mL) was stirred at room temperature overnight. The reaction mixture was purified by HPLC (C18, mobile phase: water/acetonitrile (0.1% TFA-containing system)). Fractions containing the object product were collected and concentrated by blowing air at 60° C. to give the title compound (21.2 mg).

Example 17

N-(3-((2-aminopyrimidin-5-yl)ethynyl)-2,4-difluorophenyl)-2,5-dichlorobenzenesulfonamide A mixture of 2,5-dichloro-N-(3-ethynyl-2,4-difluorophenyl)benzenesulfonamide (0.65 g), 5-iodopyrimidin-2-amine (0.60 g), cesium carbonate (2.34 g), bis(tricyclohexylphosphine)palladium(II) dichloride (0.088 g) and DMSO (20 mL) was stirred under microwave irradiation at 120° C. for 2 hr. The same reaction using the same amounts was performed 2 times in total. The reaction mixtures were combined, an insoluble material was filtered off, water was added and the mixture was extracted with ethyl acetate. The organic layer was washed with saturated brine, dried over magnesium sulfate and concentrated to give a residue. The residue was purified by silica gel column chromatography (ethyl acetate/hexane). The obtained crude purified product of the title compound was subjected to a recrystallization operation with ethanol/water at 60° C. to give the title compound (0.52 g).
¹H NMR (300 MHz, DMSO-d₆) δ 7.10-7.23 (1H, m), 7.24-7.41 (3H, m), 7.76 (2H, s), 7.83-7.94 (1H, m), 8.43 (2H, s), 10.76 (1H, s).

Example 18

3-bromo-N-(2,4-difluoro-3-(1H-pyrazolo[3,4-b]pyridin-5-ylethynyl)phenyl)-5-methylbenzenesulfonamide 3-Bromo-5-methylbenzene-1-sulfonyl chloride (83 mg) was added to a solution of 3-((1H-pyrazolo[3,4-b]pyridin-5-yl)ethynyl)-2,4-difluoroaniline (83 mg) in pyridine (2 mL) at room temperature. The mixture was stirred at 0° C. for 30 min. To the reaction mixture was added methanol at 0° C. and the mixture was concentrated under reduced pressure. The residue was purified by silica gel column chromatography (ethyl acetate/hexane) to give the title compound as a crude purified product. The obtained crude purified product of the title compound was solidified with ethyl acetate and collected by filtration to give the title compound (36 mg).
¹H NMR (300 MHz, DMSO-d₆) δ 2.37 (3H, s), 7.13-7.37 (2H, m), 7.53 (1H, s), 7.67 (1H, s), 7.76 (1H, s), 8.22 (1H, d, J=1.3 Hz), 8.53 (1H, d, J=1.3 Hz), 8.67 (1H, d, J=1.9 Hz), 10.44 (1H, s), 13.98 (1H, s).

Example 19

N-(3-((2-aminopyrimidin-5-yl)ethynyl)-2,4-difluorophenyl)-5-chloro-2-methylbenzenesulfonamide a) 5-chloro-N-(3-ethynyl-2,4-difluorophenyl)-2-methylbenzenesulfonamide 5-Chloro-2-methylbenzenesulfonyl chloride (920 mg) was added to a solution of 3-ethynyl-2,4-difluoroaniline (596 mg) in pyridine (12 mL) at 0° C. The mixture was stirred at 0° C. for 3 hr. The reaction mixture was concentrated to give a residue. The residue was purified by silica gel column chromatography (ethyl acetate/hexane) and washed with IPE/hexane to give the title compound (340 mg). The precipitate resulting from the mother liquor was collected by filtration to further give the title compound (178 mg).
¹H NMR (300 MHz, DMSO-d₆) δ 2.55 (3H, s), 4.84 (1H, s), 7.12-7.23 (1H, m), 7.31 (1H, td, J=8.9, 6.0 Hz), 7.43-7.52 (1H, m), 7.62-7.71 (2H, m), 10.08-10.82 (1H, m).

b) N-(3-((2-aminopyrimidin-5-yl) ethynyl)-2,4-difluorophenyl)-5-chloro-2-methylbenzenesulfonamide A mixture of 5-chloro-N-(3-ethynyl-2,4-difluorophenyl)-2-methylbenzenesulfonamide (100 mg), 5-iodopyrimidin-2-amine (78 mg), dichlorobis(tricyclohexylphosphine)palladium(II) (14 mg), cesium carbonate (381 mg) and DMSO (2 mL) was stirred under microwave irradiation at 120° C. for 2 hr. After cooling to room temperature, the reaction mixture was filtered through celite, and the filtrate was diluted with water, and the mixture was extracted with ethyl acetate. The obtained organic layer was washed with saturated brine, dried over magnesium sulfate and concentrated to give a residue. The residue was purified by silica gel column chromatography (ethyl acetate/hexane) and washed with ethyl acetate/hexane to give the title compound (40 mg).
¹H NMR (300 MHz, DMSO-d₆) δ 2.57 (3H, s), 7.15-7.23 (1H, m), 7.23-7.34 (3H, m), 7.48 (1H, d, J=8.0 Hz), 7.60-7.70 (2H, m), 8.43 (2H, s), 10.55 (1H, s).

Example 20

2,3,5-trichloro-N-(2,4-difluoro-3-(1H-pyrazolo[3,4-b]pyridin-5-ylethynyl)phenyl)benzenesulfonamide a) 2,3,5-trichlorobenzene-1-sulfonyl Chloride Thionyl chloride (1 mL) was added dropwise to water (5 mL) at 0° C. The mixture was stirred overnight while allowing to warm to room temperature. Copper(I) chloride (9.9 mg) was added and the mixture was cooled to 0° C. to give solution A. A solution of sodium nitrite (76 mg) in water (1 mL) was added dropwise to a mixture of 2,3,5-trichloroaniline (196 mg) and concentrated hydrochloric acid (2 mL) at 0° C. The mixture was stirred at 0° C. for 30 min to give mixture B. The supernatant of mixture B was added to solution A at 0° C. The mixture was stirred at 0° C. for 1 hr and the precipitate was collected by filtration, washed with water, and dried under reduced pressure to give a crude purified product of the title compound (141 mg). The product was used for the reaction of the next step without further purification.

b) 2,3,5-trichloro-N-(2,4-difluoro-3-(1H-pyrazolo[3,4-b]pyridin-5-ylethynyl)phenyl)benzenesulfonamide To a solution of 3-((1H-pyrazolo[3,4-b]pyridin-5-yl)ethynyl)-2,4-difluoroaniline (108 mg) in pyridine (1.62 mL) was added 2,3,5-trichlorobenzene-1-sulfonyl chloride (140 mg) at room temperature. The mixture was stirred at room temperature for 1 hr. To the reaction mixture was added methanol (1 mL), and the mixture was stirred at room temperature for 10 min and concentrated to give a residue. The residue was purified by silica gel column chromatography (ethyl acetate/hexane) and washed with ethyl acetate/hexane to give the title compound (102 mg).

$^1$H NMR (300 MHz, DMSO-$d_6$) δ 7.17-7.40 (2H, m), 7.87 (1H, d, J=2.6 Hz), 8.21-8.26 (2H, m), 8.54 (1H, d, J=2.1 Hz), 8.68 (1H, d, J=2.1 Hz), 10.96 (1H, brs), 13.98 (1H, s).

Example 21

N-(3-((2-aminopyrimidin-5-yl)ethynyl)-2,4-difluorophenyl)-5-chloro-2-(difluoromethoxy)benzenesulfonamide To a solution of 5-((3-amino-2,6-difluorophenyl)ethynyl)-N-(4-methoxybenzyl)pyrimidin-2-amine (70 mg) in pyridine (2 mL) was added 5-chloro-2-(difluoromethoxy)benzene-1-sulfonyl chloride (52.9 mg) at 0° C. The mixture was stirred at room temperature for 2 hr. The reaction mixture was concentrated to give a residue. To the residue was added TFA (2 mL) and the mixture was stirred at 70° C. for 2 hr. The reaction mixture was neutralized with a saturated aqueous sodium hydrogen carbonate solution at 0° C., and the mixture was extracted with ethyl acetate. The obtained organic layer was washed with saturated brine, dried over magnesium sulfate and concentrated to give a residue. The residue was purified by silica gel column chromatography (ethyl acetate/hexane) and washed with ethanol to give the title compound (22 mg).

$^1$H NMR (300 MHz, DMSO-$d_6$) δ 7.00-7.53 (6H, m), 7.72-7.86 (2H, m), 8.43 (2H, s), 10.51 (1H, s).

Example 22

2,5-dichloro-N-(2,4-difluoro-3-((2-(((2R)-1-hydroxypropan-2-yl)amino)pyrimidin-5-yl)ethynyl)phenyl)benzenesulfonamide TFA Salt A mixture of 2,5-dichloro-N-(3-((2-chloropyrimidin-5-yl)ethynyl)-2,4-difluorophenyl)benzenesulfonamide (28 mg), D-alaninol (9 mg), DIPEA (0.031 mL) and DMSO (0.5 mL) was stirred at room temperature overnight. The reaction mixture was purified by HPLC (C18, mobile phase: water/acetonitrile (0.1% TFA-containing system)). Fractions containing the object product were collected and concentrated by blowing air at 60° C. to give the title compound (21.4 mg).

Example 23

2,3,5,6-tetrachloro-N-(2,4-difluoro-3-(1H-pyrazolo[3,4-b]pyridin-5-ylethynyl)phenyl)benzenesulfonamide a) 2,3,5,6-tetrachlorobenzene-1-sulfonyl Chloride Thionyl chloride (1 mL) was added dropwise to water (5 mL) at 0° C. The mixture was stirred overnight while allowing to warm to room temperature. Copper(I) chloride (9.9 mg) was added and the mixture was cooled to 0° C. to give solution A. A solution of sodium nitrite (76 mg) in water (1 mL) was added dropwise to a mixture of 2,3,5,6-tetrachloroaniline (231 mg) and concentrated hydrochloric acid (2 mL) at 0° C. The mixture was stirred at 0° C. for 10 min to give mixture B. The supernatant of mixture B was added to solution A at 0° C. The mixture was stirred at 0° C. for 1 hr, and the precipitate was collected by filtration and washed with water to give a crude purified product of the title compound (196 mg). The product was used for the reaction of the next step without further purification.

b) 2,3,5,6-tetrachloro-N-(2,4-difluoro-3-(1H-pyrazolo[3,4-b]pyridin-5-ylethynyl)phenyl)benzenesulfonamide To a solution of 3-((1H-pyrazolo[3,4-b]pyridin-5-yl)ethynyl)-2,4-difluoroaniline (20 mg) in pyridine (0.30 mL) was added 2,3,5,6-tetrachlorobenzene-1-sulfonyl chloride (46.5 mg) at room temperature. The mixture was stirred at room temperature for 1 hr. To the reaction mixture were added 2,3,5,6-tetrachlorobenzene-1-sulfonyl chloride (46.5 mg). The mixture was stirred at room temperature for 1 hr. Methanol (1 mL) was added and the mixture was stirred at room temperature for 10 min and concentrated to give a residue. The same reaction using the same amounts was performed 2 times in total. The residue was purified by silica gel column chromatography (ethyl acetate/hexane) and washed with ethyl acetate/hexane to give the title compound (21.1 mg).

$^1$H NMR (300 MHz, DMSO-$d_6$) δ 7.16-7.41 (2H, m), 8.22 (1H, d, J=1.3 Hz), 8.43 (1H, s), 8.54 (1H, d, J=1.9 Hz), 8.67 (1H, d, J=1.9 Hz), 11.10 (1H, brs), 13.97 (1H, s).

Example 24

5-bromo-N-(2,4-difluoro-3-(1H-pyrazolo[3,4-b]pyridin-5-ylethynyl)phenyl)-2-fluorobenzenesulfonamide TFA Salt A solution of 3-((1H-pyrazolo[3,4-b]pyridin-5-yl)ethynyl)-2,4-difluoroaniline (22 mg) in pyridine (0.6 mL) was added to a solution of 5-bromo-2-fluorobenzene-1-sulfonyl chloride (24 mg) in THF (0.2 mL) at −15° C. The mixture was stirred at −15° C. to 0° C. for 1 hr. The reaction mixture was diluted with ethyl acetate, water was added and the mixture was stirred for 2 min. The organic layer was collected and further extracted with ethyl acetate from the aqueous layer. The combined organic layer was concentrated by blowing air at 60° C. to give a residue. The residue was purified by HPLC (C18, mobile phase: water/acetonitrile (0.1% TFA-containing system)). Fractions containing the object product were collected and concentrated by blowing air at 60° C. to give the title compound (11.2 mg).

Example 25

3,5-dichloro-N-(2,4-difluoro-3-(1H-pyrazolo[3,4-b]pyridin-5-ylethynyl)phenyl)benzenesulfonamide 3,5-Dichlorobenzene-1-sulfonyl chloride (72 mg) was added to a solution of 3-((1H-pyrazolo[3,4-b]pyridin-5-yl)ethynyl)-2,4-difluoroaniline (80 mg) in pyridine (2 mL) at 0° C. The mixture was stirred at 0° C. for 30 min. To the reaction mixture was added methanol, and the mixture was concentrated under reduced pressure. The residue was purified by silica gel column chromatography (ethyl acetate/hexane) and washed with ethyl acetate to give the title compound (73 mg).

$^1$H NMR (300 MHz, DMSO-$d_6$) δ 7.01-7.42 (2H, m), 7.71 (2H, d, J=1.8 Hz), 8.03 (1H, t, J=1.9 Hz), 8.22 (1H, d,

J=1.3 Hz), 8.54 (1H, d, J=2.0 Hz), 8.67 (1H, d, J=2.0 Hz), 10.64 (1H, s), 13.98 (1H, brs).

Example 26

5-chloro-N-(2,4-difluoro-3-(1H-pyrazolo[3,4-b]pyridin-5-ylethynyl)phenyl)-2-fluorobenzenesulfonamide TFA Salt A solution of 3-((1H-pyrazolo[3,4-b]pyridin-5-yl)ethynyl)-2,4-difluoroaniline (22 mg) in pyridine (0.6 mL) was added to a solution of 5-chloro-2-fluorobenzene-1-sulfonyl chloride (20 mg) in THF (0.2 mL) at −15° C. The mixture was stirred at −15° C. to 0° C. for 1 hr. The reaction mixture was diluted with ethyl acetate, water was added and the mixture was stirred for 2 min. The organic layer was collected and further extracted with ethyl acetate from the aqueous layer. The combined organic layer was concentrated by blowing air at 60° C. to give a residue. The residue was purified by HPLC (C18, mobile phase: water/acetonitrile (0.1% TFA-containing system)). Fractions containing the object product were collected and concentrated by blowing air at 60° C. to give the title compound (11.4 mg).

Example 27

N-(3-((2-aminopyrimidin-5-yl)ethynyl)-2,4-difluorophenyl)-3,5-dichlorobenzenesulfonamide 3,5-Dichlorobenzenesulfonyl chloride (68 mg) was added to a solution of 5-((3-amino-2,6-difluorophenyl)ethynyl)-N-(4-methoxybenzyl)pyrimidin-2-amine (50 mg) in pyridine (1 mL) at 0° C. The mixture was stirred at room temperature for 1 hr. The reaction mixture was diluted with toluene and concentrated to give a residue. To the residue was added TFA (2 mL) at room temperature, and the mixture was stirred at 70° C. for 2 hr. The reaction mixture was poured into a saturated aqueous sodium hydrogen carbonate solution and extracted 2 times with ethyl acetate. The obtained organic layer was washed with saturated brine, dried over magnesium sulfate and concentrated to give a residue. The residue was purified by HPLC (C18, mobile phase: water/acetonitrile (0.1% TFA-containing system)). Fractions containing the object product were collected, neutralized with a saturated aqueous sodium hydrogen carbonate solution, and extracted 2 times with ethyl acetate. The collected organic layer was washed with saturated brine, dried over magnesium sulfate and concentrated to give a residue. The residue was washed with ethyl acetate/IPE to give the title compound (39 mg).

$^1$H NMR (300 MHz, DMSO-$d_6$) δ 7.06-7.16 (1H, m), 7.17-7.34 (3H, m), 7.66 (2H, d, J=1.9 Hz), 7.93 (1H, d, J=1.8 Hz), 8.43 (2H, s), 10.60 (1H, brs).

Example 28

2,5-dichloro-N-(2,4-difluoro-3-((2-((3-hydroxypropyl)amino)pyrimidin-5-yl)ethynyl)phenyl)benzenesulfonamide TFA Salt A mixture of 2,5-dichloro-N-(3-((2-chloropyrimidin-5-yl)ethynyl)-2,4-difluorophenyl)benzenesulfonamide (28 mg), 3-amino-1-propanol (9 mg), DIPEA (0.031 mL) and DMSO (0.5 mL) was stirred at room temperature overnight. The reaction mixture was purified by HPLC (C18, mobile phase: water/acetonitrile (0.1% TFA-containing system)). Fractions containing the object product were collected and concentrated by blowing air at 60° C. to give the title compound (20.7 mg).

Example 29

N-(3-((2-aminopyrimidin-5-yl)ethynyl)-2,4-difluorophenyl)-5-chloro-2-cyanobenzenesulfonamide a) 5-chloro-2-cyanobenzene-1-sulfonyl Chloride To ice-cooled water (60 mL) was added dropwise thionyl chloride (10 mL) over 1.5 hr and the mixture was stirred at 0° C. for 30 min. To this solution was added copper(I) chloride (0.13 g) to give solution A. To the ice-cooled concentrated hydrochloric acid (12 mL) was added 2-amino-4-chlorobenzonitrile (2.0 g) and the mixture was stirred at 0° C. for 10 min. To the obtained mixture was added dropwise a solution of sodium nitrite (1.10 g) in water (4.4 mL) at 0° C. and the mixture was stirred at 00° C. for 10 min. The obtained mixture was added dropwise to solution A at 0° C. and the mixture was stirred at 0° C. for 1 hr. The precipitate was collected by filtration and washed with water to give the title compound as a crude purified product. The obtained crude purified product was purified by silica gel column chromatography (ethyl acetate/hexane) to give the title compound (2.24 g).

$^1$H NMR (300 MHz, DMSO-$d_6$) δ 7.61 (1H, dd, J=8.2, 2.3 Hz), 7.81 (1H, d, J=2.1 Hz), 7.85 (1H, d, J=8.2 Hz).

b) N-(3-((2-aminopyrimidin-5-yl)ethynyl)-2,4-difluorophenyl)-5-chloro-2-cyanobenzenesulfonamide 5-Chloro-2-cyanobenzene-1-sulfonyl chloride (65 mg) was added to a solution of 5-((3-amino-2,6-difluorophenyl)ethynyl)-N-(4-methoxybenzyl)pyrimidin-2-amine (50 mg) in pyridine (1 mL) at 00° C. The mixture was stirred at room temperature for 1 hr. 5-Chloro-2-cyanobenzene-1-sulfonyl chloride (35 mg) was added and the mixture was stirred at room temperature overnight. The reaction mixture was diluted with toluene and concentrated to give a residue. To the residue was added TFA (2 mL) at room temperature and the mixture was stirred at 70° C. for 2 hr. The reaction mixture was diluted with saturated aqueous sodium hydrogen carbonate solution and extracted 2 times with ethyl acetate. The obtained organic layer was washed with saturated brine, dried over magnesium sulfate and concentrated to give a residue. The residue was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The obtained organic layer was dried over magnesium sulfate and concentrated. The residue was purified by silica gel column chromatography (ethyl acetate/hexane) and washed with ethyl acetate/IPE to give the title compound (10 mg).

$^1$H NMR (300 MHz, DMSO-$d_6$) δ 7.12-7.39 (4H, m), 7.93-8.05 (2H, m), 8.15 (1H, d, J=8.2 Hz), 8.43 (2H, s), 10.87 (1H, brs).

Example 30

2,5-dichloro-N-(3-((2-(ethylamino)pyrimidin-5-yl)ethynyl)-2,4-difluorophenyl)benzenesulfonamide TFA Salt A mixture of 2,5-dichloro-N-(3-((2-chloropyrimidin-5-yl)ethynyl)-2,4-difluorophenyl)benzenesulfonamide (28 mg), ethylamine (5 mg), DIPEA (0.031 mL) and DMSO (0.5 mL) was stirred at room temperature overnight. The reaction mixture was purified by HPLC (C18, mobile phase: water/acetonitrile (0.1% TFA-containing system)). Fractions containing the object product were collected and concentrated by blowing air at 60° C. to give the title compound (19.6 mg).

Example 31

N-(3-((5-amino-6-methylpyrazin-2-yl)ethynyl)-2,4-difluorophenyl)-5-chloro-2-methylbenzenesulfonamide A mixture of 5-chloro-N-(3-ethynyl-2,4-difluorophenyl)-2-methylbenzenesulfonamide (100 mg), 5-bromo-3-methylpyrazin-2-amine (55 mg), dichlorobis(tricyclohexylphosphine)palladium(II) (14 mg), cesium carbonate (381 mg) and DMSO (2 mL) was stirred under microwave irradiation at 120° C. for 2 hr. After cooling to room temperature, the reaction mixture was filtered through celite, and the filtrate was diluted with water and extracted with ethyl acetate. The obtained organic layer was washed with saturated brine, dried over magnesium sulfate and concentrated to give a residue. The residue was purified by silica gel column chromatography (ethyl acetate/hexane) and further purified by HPLC (C18, mobile phase: water/acetonitrile (0.1% TFA-containing system)). Fractions containing the object product were collected, neutralized with a saturated aqueous sodium hydrogen carbonate solution, and extracted with ethyl acetate. The obtained organic layer was dried over magnesium sulfate and concentrated to give a residue. The residue was washed with ethyl acetate/IPE/hexane to give the title compound (32 mg).

$^1$H NMR (300 MHz, DMSO-$d_6$) δ 2.29 (3H, s), 2.57 (3H, s), 6.87 (2H, s), 7.13-7.33 (2H, m), 7.47 (1H, d, J=8.1 Hz), 7.58-7.68 (2H, m), 8.04 (1H, s), 10.56 (1H, s).

Example 32

2,5-dichloro-N-(2,4-difluoro-3-((2-((trans-4-hydroxycyclohexyl)amino)pyrimidin-5-yl)ethynyl)phenyl)benzenesulfonamide TFA Salt A mixture of 2,5-dichloro-N-(3-((2-chloropyrimidin-5-yl)ethynyl)-2,4-difluorophenyl)benzenesulfonamide (28 mg), trans-4-aminocyclohexanol (14 mg), DIPEA (0.031 mL) and DMSO (0.5 mL) was stirred at room temperature overnight. The reaction mixture was purified by HPLC (C18, mobile phase: water/acetonitrile (0.1% TFA-containing system)). Fractions containing the object product were collected and concentrated by blowing air at 60° C. to give the title compound (5.5 mg).

Example 33

3,5-dichloro-N-(2,4-difluoro-3-(1H-pyrazolo[3,4-b]pyridin-5-ylethynyl)phenyl)-2-methoxybenzenesulfonamide a) 3,5-dichloro-2-methoxybenzene-1-sulfonyl Chloride To a mixture of 3,5-dichloro-2-hydroxybenzene-1-sulfonyl chloride (300 mg), 42% trifluoroborane hydrofluoride aqueous solution (0.183 mL) and diethyl ether (2 mL) was added 0.6 M (diazomethyl)trimethylsilane/hexane solution (2 mL) at 0° C. The mixture was stirred at 0° C. for 1 hr and 0.6M (diazomethyl)trimethylsilane/hexane solution (1 mL) was further added. The mixture was stirred at 0° C. for 1.5 hr and 0.6M (diazomethyl)trimethylsilane/hexane solution (1 mL) was further added. The mixture was stirred at 0° C. for 2 hr, diluted with water and extracted with ethyl acetate. The obtained organic layer was washed with saturated brine, dried over magnesium sulfate and concentrated to give a crude purified product of the title compound (390 mg). The product was used without further purification for the next step.

b) 3,5-dichloro-N-(2,4-difluoro-3-(1H-pyrazolo[3,4-b]pyridin-5-ylethynyl)phenyl)-2-methoxybenzenesulfonamide To a solution of 3-((1H-pyrazolo[3,4-b]pyridin-5-yl)ethynyl)-2,4-difluoroaniline (355 mg) in pyridine (5 mL) was added 3,5-dichloro-2-methoxybenzene-1-sulfonyl chloride (317 mg) at 0° C. The mixture was stirred at room temperature for 16 hr. To the reaction mixture was added methanol, and the mixture was concentrated. The residue was purified by silica gel column chromatography (ethyl acetate/hexane) and further purified by HPLC (C18, mobile phase: water/acetonitrile (0.1% TFA-containing system)). Fractions containing the object product were collected, neutralized with a saturated aqueous sodium hydrogen carbonate solution and extracted with ethyl acetate. The obtained organic layer was washed with saturated brine, dried over magnesium sulfate and concentrated. The residue was washed with ethyl acetate/IPE/hexane to give the title compound (17 mg).

$^1$H NMR (300 MHz, DMSO-$d_6$) δ 3.89 (3H, s), 7.13-7.26 (1H, m), 7.26-7.42 (1H, m), 7.66 (1H, d, J=2.5 Hz), 8.06 (1H, d, J=2.5 Hz), 8.22 (1H, d, J=1.3 Hz), 8.54 (1H, d, J=1.3 Hz), 8.68 (1H, d, J=2.0 Hz), 10.52 (1H, s), 13.98 (1H, s).

Example 34

2,5-dichloro-N-(3-((2,4-diaminopyrimidin-5-yl)ethynyl)-2,4-difluorophenyl)benzenesulfonamide a) 5-iodopyrimidine-2,4-diamine NIS (2.30 g) was added to a mixture of pyrimidine-2,4-diamine (1.12 g), acetic acid (20 mL) and methanol (20 mL) at 0° C. The mixture was stirred at room temperature for 2 hr. The reaction mixture was quenched with a saturated aqueous sodium thiosulfate solution at 0° C., and neutralized with 8N aqueous sodium hydroxide solution. The precipitate was collected by filtration and washed with water to give the title compound (1.85 g).

$^1$H NMR (300 MHz, DMSO-$d_6$) δ 6.07 (2H, s), 6.35 (2H, brs), 7.92 (1H, s).

b) 2,5-dichloro-N-(3-((2,4-diaminopyrimidin-5-yl)ethynyl)-2,4-difluorophenyl)benzenesulfonamide A mixture of 2,5-dichloro-N-(3-ethynyl-2,4-difluorophenyl)benzenesulfonamide (100 mg), 5-iodopyrimidine-2,4-diamine (98 mg), triethylamine (1 mL), bis(triphenylphosphine)palladium(II) dichloride (14 mg), copper(I) iodide (3.7 mg) and DMF (1 mL) was stirred under microwave irradiation at 100° C. for 2 hr. The reaction mixture was filtered through celite, water was added and the mixture was extracted with ethyl acetate. The organic layer was washed with saturated brine, dried over magnesium sulfate and concentrated to give a residue. The residue was purified by silica gel column chromatography (ethyl acetate/hexane and methanol/ethyl acetate). The obtained crude purified product of the title compound was washed with ethyl acetate/heptane to give the title compound (64 mg).

$^1$H NMR (300 MHz, DMSO-d$_6$) δ 6.38-6.62 (4H, m), 7.05-7.32 (2H, m), 7.70-7.77 (2H, m), 7.85 (1H, dd, J=1.8, 1.1 Hz), 7.92-7.96 (1H, m), 10.83 (1H, brs).

Example 35

N-(3-((2-aminopyrimidin-5-yl)ethynyl)-2,4-difluorophenyl)-2-chloro-5-(trifluoromethyl)benzenesulfonamide a) 2-chloro-5-(trifluoromethyl)benzene-1-sulfonyl Chloride Thionyl chloride (4.48 mL) was added dropwise to water (25.8 mL) at 0° C. over 30 min. The mixture was stirred for 16 hr while allowing to warm to room temperature. Copper (I) chloride (51 mg) was added and the mixture was cooled to 0° C. to give solution A. A solution of sodium nitrite (388 mg) in water (1.57 mL) was added dropwise to a mixture of 2-chloro-5-(trifluoromethyl)aniline (1 g) and concentrated hydrochloric acid (5.11 mL) at 0° C. over 30 min. The mixture was stirred at 0° C. for 30 min to give mixture B. The supernatant of mixture B was added to solution A at 0° C. over 10 min. The mixture was stirred at 0° C. for 30 min and extracted with ethyl acetate. The obtained organic layer was washed with saturated brine, dried over magnesium sulfate and concentrated to give a residue. The residue was purified by silica gel column chromatography (ethyl acetate/hexane) to give the title compound (944 mg).

$^1$H NMR (300 MHz, DMSO-d$_6$) δ 7.61-7.73 (2H, m), 8.13 (1H, d, J=2.3 Hz).

b) 2-chloro-N-(3-ethynyl-2,4-difluorophenyl)-5-(trifluoromethyl)benzenesulfonamide 2-Chloro-5-(trifluoromethyl)benzene-1-sulfonyl chloride (167 mg) was added to a solution of 3-ethynyl-2,4-difluoroaniline (77 mg) in pyridine (1.01 mL) at room temperature. The mixture was stirred at room temperature for 3 days. The reaction mixture was concentrated and the residue was purified by silica gel column chromatography (ethyl acetate/hexane) to give the title compound as a crude purified product. To the obtained crude purified product of the title compound were added methanol (2.02 mL), THF (3.6 g) and 2M aqueous sodium hydroxide solution (1.25 mL). The mixture was stirred at room temperature for 30 min. The reaction mixture was diluted with saturated aqueous sodium hydrogen carbonate solution and extracted with ethyl acetate. The obtained organic layer was washed with saturated brine, dried over magnesium sulfate and concentrated to give the title compound (229 mg).

MS: [M−H]⁻ 394.0.

c) N-(3-((2-aminopyrimidin-5-yl)ethynyl)-2,4-difluorophenyl)-2-chloro-5-(trifluoromethyl)benzenesulfonamide A mixture of 2-chloro-N-(3-ethynyl-2,4-difluorophenyl)-5-(trifluoromethyl)benzenesulfonamide (198 mg), 5-iodopyrimidin-2-amine (166 mg), dichlorobis(tricyclohexylphosphine)palladium(II) (24.6 mg), DMSO (3.16 mL) and cesium carbonate (652 mg) was stirred under microwave irradiation at 120° C. for 1.5 hr. The reaction mixture was diluted with ethyl acetate, and an insoluble material was removed by filtration. The filtrate was concentrated to give a residue. The residue was purified by silica gel column chromatography (ethyl acetate/hexane) and subjected to ethyl acetate. The precipitate was collected by filtration and washed with ethyl acetate to give the title compound (60 mg).

$^1$H NMR (300 MHz, DMSO-d$_6$) δ 7.13-7.23 (1H, m), 7.25-7.36 (3H, m), 7.96-8.01 (1H, m), 8.06-8.11 (2H, m), 8.42 (2H, s), 10.86 (1H, s).

Example 36

2,5-dichloro-N-(2,4-difluoro-3-((2-((2-hydroxyethyl)amino)pyrimidin-5-yl)ethynyl)phenyl)benzenesulfonamide TFA Salt A mixture of 2,5-dichloro-N-(3-((2-chloropyrimidin-5-yl)ethynyl)-2,4-difluorophenyl)benzenesulfonamide (28 mg), ethanolamine (7 mg), DIPEA (0.031 mL) and DMSO (0.5 mL) was stirred at room temperature overnight. The reaction mixture was purified by HPLC (C18, mobile phase: water/acetonitrile (0.1% TFA-containing system)). Fractions containing the object product were collected and concentrated by blowing air at 60° C. to give the title compound (20.5 mg).

Example 37

2,5-dichloro-N-(2,4-difluoro-3-((2-(methylamino)pyrimidin-5-yl)ethynyl)phenyl)benzenesulfonamide TFA Salt A mixture of 2,5-dichloro-N-(3-ethynyl-2,4-difluorophenyl)benzenesulfonamide (29 mg), 5-iodo-N-methylpyrimidin-2-amine (38 mg), cesium carbonate (104 mg), bis(tricyclohexylphosphine)palladium(II) dichloride (5.6 mg) and DMSO (0.5 mL) was stirred under microwave irradiation at 120° C. for 2 hr. After cooling to room temperature, the precipitate was removed by filtration, and the filtrate was purified by HPLC (C18, mobile phase: water/acetonitrile (0.1% TFA-containing system)). Fractions containing the object product were collected and concentrated by blowing air at 60° C. to give the title compound (11.5 mg).

Example 38

2,3-dichloro-N-(2,4-difluoro-3-(1H-pyrazolo[3,4-b]pyridin-5-ylethynyl)phenyl)benzenesulfonamide TFA Salt To a solution of 2,3-dichlorobenzenesulfonyl chloride (22 mg) in THF (0.2 mL) was added a solution of 3-((1H-pyrazolo[3,4-b]pyridin-5-yl)ethynyl)-2,4-difluoroaniline (22 mg) in pyridine (0.6 mL) at −15° C. The mixture was stirred at −15° C. to 0° C. for 1 hr. The reaction mixture was diluted with ethyl acetate, water was added, and the mixture was stirred for 2 min. The organic layer was collected and further extracted with ethyl acetate from the aqueous layer. The combined organic layer was concentrated by blowing air at 60° C. to give a residue. The residue was purified by HPLC (C18, mobile phase: water/acetonitrile (0.1% TFA-containing system)). Fractions containing the object product were collected and concentrated by blowing air at 60° C. to give the title compound (11.7 mg).

Example 105

5-chloro-N-(2,4-difluoro-3-((2-(isopropylamino)pyrimidin-5-yl)ethynyl)phenyl)-2-methylpyridine-3-sulfonamide a) 5-iodo-N-isopropylpyrimidin-2-amine

Propan-2-amine (0.713 mL) was added to a solution of 2-chloro-5-iodopyrimidine (1.0 g), DIPEA (1.49 mL) in DMSO (10 mL) at room temperature. The mixture was stirred at 70° C. for 2 hr. The reaction mixture was diluted with water at room temperature and extracted with ethyl acetate. The obtained organic layer was washed with saturated brine, dried over magnesium sulfate and concentrated to give a residue. The residue was purified by silica gel column chromatography (ethyl acetate/hexane) to give the title compound (815 mg).

$^1$H NMR (300 MHz, DMSO-$d_6$) δ 1.12 (6H, d, J=6.6 Hz), 3.94 (1H, dt, J=7.9, 6.6 Hz), 7.24 (1H, d, J=7.9 Hz), 8.39 (2H, s).

b) 5-chloro-N-(3-ethynyl-2,4-difluorophenyl)-2-methylpyridine-3-sulfonamide A mixture of 3-ethynyl-2,4-difluoroaniline (289 mg), 5-chloro-2-methylpyridine-3-sulfonyl chloride (427 mg) and pyridine (4.48 g) was stirred at room temperature overnight. To the reaction mixture was added methanol (5 mL), and the mixture was stirred at room temperature for 10 min. The reaction mixture was concentrated under reduced pressure. The residue was purified by silica gel column chromatography (ethyl acetate/hexane) to give the title compound (420 mg).

$^1$H NMR (300 MHz, DMSO-$d_6$) δ 2.72-2.77 (3H, m), 4.85 (1H, s), 7.19 (1H, td, J=8.9, 1.6 Hz), 7.35 (1H, dt, J=9.0, 5.9 Hz), 8.03 (1H, d, J=2.4 Hz), 8.78 (1H, d, J=2.4 Hz), 10.79 (1H, s).

c) 5-chloro-N-(2,4-difluoro-3-((2-(isopropylamino)pyrimidin-5-yl)ethynyl)phenyl)-2-methylpyridine-3-sulfonamide A mixture of 5-chloro-N-(3-ethynyl-2,4-difluorophenyl)-2-methylpyridine-3-sulfonamide (86 mg), 5-iodo-N-isopropylpyrimidin-2-amine (99 mg), dichlorobis(tricyclohexylphosphine)palladium(II) (12 mg), cesium carbonate (326 mg) and DMSO (2.13 mL) was stirred under a nitrogen atmosphere at 120° C. for 1.5 hr. After cooling to room temperature, the mixture was diluted with water/saturated brine and extracted with ethyl acetate. The obtained organic layer was washed with saturated brine, dried over magnesium sulfate and concentrated to give a residue. The residue was purified by silica gel column chromatography (ethyl acetate/hexane) to give the title compound as a crude purified product. The obtained crude purified product of the title compound was dissolved in DMF/toluene and subjected to silica gel column chromatography (NH, methanol/ethyl acetate) to elute a byproduct. Silica gel supporting the title compound was added to ethyl acetate (10 mL), acetic acid (2 mL) and water (10 mL), and the mixture was stirred at room temperature for 10 min. The mixture was filtered and silica gel on the filter was treated 4 times with ethyl acetate/acetic acid (3 mL/0.6 mL) to elute the object product. The organic layer was collected from the filtrate, and the organic layer was washed with water and saturated brine, dried over magnesium sulfate and concentrated to give the title compound (44.9 mg).

$^1$H NMR (300 MHz, DMSO-$d_6$) δ 1.15 (6H, d, J=6.4 Hz), 2.76 (3H, s), 3.94-4.15 (1H, m), 7.14-7.36 (2H, m), 7.75 (1H, d, J=7.9 Hz), 8.05 (1H, d, J=2.4 Hz), 8.46 (2H, brs), 8.78 (1H, d, J=2.4 Hz), 10.82 (1H, s).

Example 106

5-chloro-N-(2,4-difluoro-3-((2-(isopropylamino)pyrimidin-5-yl)ethynyl)phenyl)-2-methoxypyridine-3-sulfonamide A mixture of 5-chloro-N-(3-ethynyl-2,4-difluorophenyl)-2-methoxypyridine-3-sulfonamide (100 mg), 5-iodo-N-isopropylpyrimidin-2-amine (95 mg), dichlorobis(tricyclohexylphosphine)palladium(II) (14 mg), cesium carbonate (363 mg) and DMSO (2 mL) was stirred under microwave irradiation 120° C. for 2 hr was stirred. After cooling to room temperature, the reaction mixture was filtered through celite. The filtrate was diluted with water, and the mixture was extracted with ethyl acetate. The obtained organic layer was washed with saturated brine, dried over magnesium sulfate and concentrated to give a residue. The residue was purified by silica gel column chromatography (ethyl acetate/hexane) and washed with ethanol to give the title compound (40 mg).

$^1$H NMR (300 MHz, DMSO-$d_6$) δ 1.16 (6H, d, J=6.5 Hz), 3.94 (3H, s), 4.00-4.15 (1H, m), 7.09-7.24 (1H, m), 7.31 (1H, td, J=8.9, 6.0 Hz), 7.74 (1H, d, J=7.9 Hz), 8.07 (1H, d, J=2.6 Hz), 8.47 (2H, brs), 8.52 (1H, d, J=2.5 Hz), 10.45 (1H, s).

Example 107

5-chloro-N-(2,4-difluoro-3-((2-((2-hydroxy-2-methylpropyl)amino)pyrimidin-5-yl)ethynyl)phenyl)-2-methoxypyridine-3-sulfonamide a) 1-((5-iodopyrimidin-2-yl)amino)-2-methylpropan-2-ol

1-Amino-2-methylpropan-2-ol (0.39 mL) was added to a solution of 2-chloro-5-iodopyrimidine (1.0 g), DIPEA (1.49 mL) in DMSO (10 mL) at room temperature. The mixture was stirred at 70° C. for 16 hr. The reaction mixture was diluted with water at room temperature, and the mixture was extracted with ethyl acetate. The obtained organic layer was washed with saturated brine, dried over magnesium sulfate and concentrated to give a residue. The residue was purified by silica gel column chromatography (ethyl acetate/hexane) to give the title compound (1.13 g).

$^1$H NMR (300 MHz, DMSO-$d_6$) δ 1.08 (6H, s), 3.25 (2H, d, J=6.2 Hz), 4.48 (1H, s), 7.03 (1H, t, J=6.2 Hz), 8.39 (2H, s).

b) 5-chloro-N-(2,4-difluoro-3-((2-((2-hydroxy-2-methylpropyl)amino)pyrimidin-5-yl)ethynyl)phenyl)-2-methoxypyridine-3-sulfonamide A mixture of 5-chloro-N-(3-ethynyl-2,4-difluorophenyl)-2-methoxypyridine-3-sulfonamide (100 mg), 1-((5-iodopyrimidin-2-yl)amino)-2-methylpropan-2-ol (106 mg), dichlorobis(tricyclohexylphosphine)palladium(II) (14 mg), cesium carbonate (363 mg) and DMSO (2 mL) was stirred under microwave irradiation at 120° C. for 2 hr. After cooling to room temperature, the reaction mixture was filtered through celite. The filtrate was diluted with water, and the mixture was extracted with ethyl acetate. The obtained organic layer was washed with saturated brine, dried over magnesium sulfate and concentrated to give a residue. The residue was purified by silica gel column chromatography (ethyl acetate/hexane) and washed with ethanol/ethyl acetate to give the title compound (9.3 mg).

$^1$H NMR (300 MHz, DMSO-$d_6$) δ 1.10 (6H, s), 3.34 (2H, d, J=6.2 Hz), 3.93 (3H, s), 4.51 (1H, s), 7.11-7.24 (1H, m), 7.31 (1H, td, J=8.9, 6.0 Hz), 7.52 (1H, t, J=6.2 Hz), 8.06 (1H, d, J=2.6 Hz), 8.40-8.63 (3H, m), 10.45 (1H, s).

Example 108

5-chloro-N-(2,4-difluoro-3-((2-((1-hydroxy-2-methylpropan-2-yl)amino)pyrimidin-5-yl)ethynyl)phenyl)-2-methoxypyridine-3-sulfonamide a) 2-((5-iodopyrimidin-2-yl)amino)-2-methylpropan-1-ol DIPEA (1.49 mL) was added to a solution of 2-amino-2-methylpropan-1-ol (0.80 mL) and 2-chloro-5-iodopyrimidine (1.0 g) in DMSO (10 mL) at room temperature. The mixture was stirred at 70° C. for 16 hr. The reaction mixture was diluted with water at room temperature, and the mixture was extracted with ethyl acetate. The obtained organic layer was washed with saturated brine, dried over magnesium sulfate and concentrated to give a residue. The residue was purified by silica gel column chromatography (ethyl acetate/hexane) to give the title compound (215 mg).

$^1$H NMR (300 MHz, DMSO-$d_6$) δ 1.27 (6H, s), 3.46 (2H, d, J=5.9 Hz), 4.84 (1H, t, J=5.9 Hz), 6.63 (1H, s), 8.40 (2H, s).

b) 5-chloro-N-(2,4-difluoro-3-((2-((1-hydroxy-2-methylpropan-2-yl)amino)pyrimidin-5-yl)ethynyl) phenyl)-2-methoxypyridine-3-sulfonamide A mixture of 5-chloro-N-(3-ethynyl-2,4-difluorophenyl)-2-methoxypyridine-3-sulfonamide (100 mg), 2-((5-iodopyrimidin-2-yl)amino)-2-methylpropan-1-ol (106 mg), dichlorobis(tricyclohexylphosphine)palladium(II) (14 mg), cesium carbonate (363 mg) and DMSO (2 mL) was stirred under microwave irradiation at 120° C. for 2 hr. After cooling to room temperature, the reaction mixture was filtered through celite. The filtrate was diluted with water, and the mixture was extracted with ethyl acetate. The obtained organic layer was washed with saturated brine, dried over magnesium sulfate and concentrated to give a residue. The residue was purified by silica gel column chromatography (ethyl acetate/hexane) and further purified by HPLC (C18, mobile phase: water/acetonitrile (0.1% TFA-containing system)). Fractions containing the object product were collected, neutralized with a saturated aqueous sodium hydrogen carbonate solution, and the mixture was extracted with ethyl acetate. The obtained organic layer was washed with saturated brine, dried over magnesium sulfate and concentrated to give the title compound (15 mg).

$^1$H NMR (300 MHz, DMSO-$d_6$) δ 1.31 (6H, s), 3.51 (2H, s), 3.94 (3H, s), 4.87 (1H, brs), 7.12 (1H, s), 7.14-7.25 (1H, m), 7.32 (1H, td, J=8.8, 6.0 Hz), 8.07 (1H, d, J=2.5 Hz), 8.47 (2H, s), 8.52 (1H, d, J=2.5 Hz), 10.45 (1H, s).

Example 109

N-(3-((3-amino-1,2,4-triazin-6-yl)ethynyl)-2,4-difluorophenyl)-5-chloro-2-methoxypyridine-3-sulfonamide a) 6-bromo-1,2,4-triazin-3-amine Water (15 mL) was added to a suspension of 3-amino-1,2,4-triazine (1.0 g) in acetonitrile (10 mL) at room temperature and the mixture was stirred until it became a solution. To the obtained solution was added NBS (2.0 g) at 0° C., and the mixture was stirred for 1 hr. The mixture was allowed to warm to room temperature and further stirred for 1 hr. The reaction mixture was poured into 10% aqueous sodium carbonate solution and extracted 2 times with ethyl acetate. The obtained organic layer was washed with saturated brine, dried over magnesium sulfate and concentrated. The obtained residue was washed with ethanol/IPE to give the title compound (816 mg).

$^1$H NMR (300 MHz, DMSO-$d_6$) δ 7.47 (2H, brs), 8.40 (1H, s).

b) N-(3-((3-amino-1,2,4-triazin-6-yl)ethynyl)-2,4-difluorophenyl)-5-chloro-2-methoxypyridine-3-sulfonamide A mixture of 5-chloro-N-(3-ethynyl-2,4-difluorophenyl)-2-methoxypyridine-3-sulfonamide (100 mg), 6-bromo-1,2,4-triazin-3-amine (50 mg), bis(di-tert-butyl(4-dimethylaminophenyl)phosphine)dichloropalladium(II) (10 mg), copper (I) iodide (5 mg), triethylamine (0.12 mL) and acetonitrile (2 mL) was stirred under microwave irradiation at 100° C. for 1 hr. After cooling to room temperature, the reaction mixture was poured into saturated aqueous sodium hydrogen carbonate solution and the mixture was extracted 2 times with ethyl acetate. The obtained organic layer was washed with saturated brine, dried over magnesium sulfate and concentrated to give a residue. The residue was purified by silica gel column chromatography (ethyl acetate/hexane) to give the title compound as a crude purified product. The obtained crude purified product of the title compound was subjected to silica gel column chromatography (NH, methanol/ethyl acetate) to elute a byproduct. Silica gel supporting the title compound was added to ethyl acetate (10 mL), acetic acid (2 mL) and water (10 mL), and the mixture was stirred at room temperature for 10 min. The mixture was filtered and silica gel on the filter was treated 4 times with ethyl acetate/acetic acid (4 mL/1 mL) to elute the object product. The filtrate was diluted with water and extracted 2 times with ethyl acetate. The obtained organic layer was washed with water, saturated aqueous sodium hydrogen carbonate solution and saturated brine, dried over magnesium sulfate and concentrated. The obtained residue was washed with ethyl acetate/IPE to give the title compound (53 mg).

$^1$H NMR (300 MHz, DMSO-$d_6$) δ 3.93 (3H, s), 7.24 (1H, td, J=8.9, 1.4 Hz), 7.40 (1H, td, J=8.9, 6.0 Hz), 7.86 (2H, brs), 8.08 (1H, d, J=2.5 Hz), 8.45 (1H, s), 8.51 (1H, d, J=2.5 Hz), 10.52 (1H, s).

Example 110

N-(3-((5-amino-6-methylpyrazin-2-yl)ethynyl)-2,4-difluorophenyl)-5-chloro-2-methoxypyridine-3-sulfonamide A mixture of 5-chloro-N-(3-ethynyl-2,4-difluorophenyl)-2-methoxypyridine-3-sulfonamide (108 mg), 2-amino-5- bromo-3-methylpyrazine (54 mg), dichlorobis(tricyclohexylphosphine)palladium(II) (11 mg), cesium carbonate (290 mg) and DMSO (2 mL) was stirred under microwave irradiation at 120° C. for 2 hr. After cooling to room temperature, the reaction mixture was purified by silica gel column chromatography (ethyl acetate/hexane) and further purified by HPLC (C18, mobile phase: water/acetonitrile (0.1% TFA-containing system)). Fractions containing the object product were collected, neutralized with a saturated aqueous sodium hydrogen carbonate solution and extracted 2 times with ethyl acetate. The obtained organic layer was washed with saturated brine, dried over magnesium sulfate and concentrated to give a residue. The residue was washed with ethyl acetate/IPE and dried under reduced pressure to give the title compound (63 mg).

$^1$H NMR (300 MHz, DMSO-$d_6$) δ 2.30 (3H, s), 3.93 (3H, s), 6.86 (2H, s), 7.10-7.23 (1H, m), 7.32 (1H, td, J=8.9, 6.0 Hz), 8.04 (1H, s), 8.06 (1H, d, J=2.5 Hz), 8.49 (1H, d, J=2.6 Hz), 10.46 (1H, s).

Example 111

N-(2,4-difluoro-3-(1H-pyrazolo[3,4-b]pyridin-5-ylethynyl)phenyl)-3,5-dimethylbenzenesulfonamide TFA Salt To a solution of 3,5-dimethylbenzenesulfonyl chloride (18 mg) in THF (0.2 mL) was added a solution of 3-((1H-pyrazolo[3,4-b]pyridin-5-yl)ethynyl)-2,4-difluoroaniline (22 mg) in pyridine (0.6 mL) at −15° C. The mixture was stirred at −15° C. to 0° C. for 1 hr. The reaction mixture was diluted with ethyl acetate, water was added, and the mixture was stirred for 2 min. The organic layer was collected and further extracted with ethyl acetate from the aqueous layer. The combined organic layer was concentrated by blowing air at 60° C. to give a residue. The residue was purified by HPLC (C18, mobile phase: water/acetonitrile (0.1% TFA-containing system)). Fractions containing the object product were collected and concentrated by blowing air at 60° C. to give the title compound (15.2 mg).

Example 112

N-(2,4-difluoro-3-(1H-pyrazolo[3,4-b]pyridin-5-ylethynyl)phenyl)-2,5-dimethylbenzenesulfonamide TFA Salt To a solution of 2,5-dimethylbenzenesulfonyl chloride (18 mg) in THF (0.2 mL) was added a solution of 3-((1H-pyrazolo[3,4-b]pyridin-5-yl)ethynyl)-2,4-difluoroaniline (22 mg) in pyridine (0.6 mL) at −15° C. The mixture was stirred at −15° C. to 0° C. for 1 hr. The reaction mixture was diluted with ethyl acetate, water was added, and the mixture was stirred for 2 min. The organic layer was collected and further extracted with ethyl acetate from the aqueous layer. The combined organic layer was concentrated by blowing air at 60° C. to give a residue. The residue was purified by HPLC (C18, mobile phase: water/acetonitrile (0.1% TFA-containing system)). Fractions containing the object product were collected and concentrated by blowing air at 60° C. to give the title compound (12.3 mg).

Example 123

N-(3-((2-aminopyrimidin-5-yl)ethynyl)-2-fluorophenyl)-5-chloro-2-methoxypyridine-3-sulfonamide a) 2-fluoro-3-[2-(trimethylsilyl)ethynyl]aniline Copper(I) iodide (3.0 g), triphenylphosphine (8.3 g) and diisopropylethylamine (111 mL) were added to a solution of 3-bromo-2-fluoroaniline (60.0 g) in toluene (300 mL) at room temperature. To the mixture were added under an argon atmosphere trimethylsilylacetylene (65.5 mL) and bis(triphenylphosphine)palladium(II) dichloride (11.5 g). The mixture was heated in a sealed tube for 5 hr at 80° C. After cooling, the reaction mixture was diluted with ethyl acetate (600 mL) and filtered through celite. The filtrate was washed with water and saturated brine, and the obtained organic layer was dried over sodium sulfate and concentrated. The residue was purified by silica gel column chromatography (ethyl acetate/hexane) to give the title compound (55.0 g).

$^1$H NMR (400 MHz, DMSO-$d_6$) δ 0.22 (9H, s), 5.27 (2H, brs), 6.57-6.61 (1H, m), 6.76-8.86 (2H, m).

b) 3-ethynyl-2-fluoroaniline

1% Aqueous potassium hydroxide solution (29.8 g) was added to a solution of 2-fluoro-3-[2-(trimethylsilyl)ethynyl]aniline (55.0 g) in methanol (300 mL) at 0-5° C. The mixture was stirred for 4 hr while allowing to warm to room temperature. The reaction mixture was concentrated under reduced pressure and diluted with water (400 mL). The organic substance was extracted two times with ethyl acetate (400 mL). The combined organic layer was washed two times with water (300 mL) and once with saturated brine (300 mL). The obtained organic layer was dried over sodium sulfate and concentrated to give the title compound (35.0 g).

$^1$H NMR (400 MHz, DMSO-$d_6$) δ 4.32 (1H, s), 5.29 (2H, brs), 6.61-6.64 (1H, m), 6.77-8.87 (2H, m).

c) 5-chloro-N-(3-ethynyl-2-fluorophenyl)-2-methoxypyridine-3-sulfonamide

A mixture of 3-ethynyl-2-fluoroaniline (135 mg), 5-chloro-2-methoxypyridine-3-sulfonyl chloride (290 mg) and pyridine (2.41 mL) was stirred at room temperature overnight. To the reaction mixture was added methanol (5 mL), and the mixture was stirred at room temperature for 10 min and concentrated. The residue was purified by silica gel column chromatography (ethyl acetate/hexane) to give the title compound (225 mg).

$^1$H NMR (300 MHz, DMSO-$d_6$) δ 3.91 (3H, s), 4.52 (1H, s), 7.11-7.19 (1H, m), 7.28-7.42 (2H, m), 8.06 (1H, d, J=2.6 Hz), 8.51 (1H, d, J=2.4 Hz), 10.46 (1H, s).

d) N-(3-((2-aminopyrimidin-5-yl)ethynyl)-2-fluorophenyl)-5-chloro-2-methoxypyridine-3-sulfonamide A mixture of 5-chloro-N-(3-ethynyl-2-fluorophenyl)-2-methoxypyridine-3-sulfonamide (225 mg), 5-iodopyrimidin-2-amine (190 mg), bis(di-tert-butyl(4-dimethylaminophenyl)phosphine)dichloropalladium(II) (22.2 mg), copper (I) iodide (12.6 mg), triethylamine (0.92 mL) and DMSO (2.34 mL) was stirred under microwave irradiation at 100° C. for 1 hr. After cooling to room temperature, the mixture was diluted with water/saturated brine and extracted with ethyl acetate. The obtained organic layer was washed with saturated brine, dried over magnesium sulfate and concentrated to give a residue. The residue was purified by silica gel column chromatography (ethyl acetate/hexane) and subjected to ethyl acetate. The precipitate was collected by filtration and dried under reduced pressure to give the title compound (121 mg).

$^1$H NMR (300 MHz, DMSO-$d_6$) δ 3.93 (3H, s), 7.12-7.32 (4H, m), 7.39 (1H, t, J=6.9 Hz), 8.08 (1H, d, J=2.4 Hz), 8.42 (2H, s), 8.51 (1H, d, J=2.4 Hz), 10.48 (1H, s).

Example 124

N-(3-((2-aminopyrimidin-5-yl)ethynyl)-4-chloro-2-fluorophenyl)-5-chloro-2-methoxypyridine-3-sulfonamide a) N-(4-chloro-2-fluorophenyl)acetamide

A mixture of 4-chloro-2-fluoroaniline (50.0 g), acetic anhydride (52.6 g) and acetic acid (500 mL) was stirred at room temperature for 2 hr. After confirmation of completion of the reaction by TLC, the reaction mixture was poured into ice water. The precipitate was collected by filtration, washed with water and dried under reduced pressure to give the title compound as a crude purified product. The obtained crude purified product of the title compound was dissolved in ethyl acetate, washed with saturated aqueous sodium hydrogen carbonate solution, water and saturated brine, dried over sodium sulfate and concentrated to give the title compound (62.5 g).

$^1$H NMR (500 MHz, CDCl$_3$) δ 2.22 (3H, s), 7.11-7.13 (2H, m), 7.35 (1H, brs), 8.27 (1H, t, J=8.5 Hz).

b) N-(4-chloro-2-fluoro-3-iodophenyl)acetamide

To a solution of N-(4-chloro-2-fluorophenyl)acetamide (20.0 g) in THF (100 mL) was added 2.5M n-butyllithium/hexane solution (85.2 mL) at −70° C., and the mixture was stirred at the same temperature for 2 hr. To the reaction mixture was added 2-iodo-1,1,1-trifluoroethane (21.0 mL) at the same temperature, and the mixture was stirred at room temperature for 3 hr. After confirmation of completion of the reaction by TLC, the reaction mixture was quenched with 3N hydrochloric acid and extracted 2 times with ethyl acetate. The combined organic layer was washed with saturated brine, dried over sodium sulfate and concentrated under reduced pressure to give a crude purified product of the title compound (20.0 g). The product was used without further purification for the next step.

c) 4-chloro-2-fluoro-3-iodoaniline

To a solution of N-(4-chloro-2-fluoro-3-iodophenyl)acetamide (20.0 g) in methanol (200 mL) was added concentrated hydrochloric acid (25 mL) at room temperature, and the mixture was heated and refluxed for 2 hr. After confirmation of completion of the reaction by TLC, the reaction mixture was concentrated under reduced pressure. The residue was poured into cooled water, and the mixture was adjusted to pH~9-10 with 3N aqueous sodium hydroxide solution and extracted with ethyl acetate. The obtained organic layer was dried over sodium sulfate and dried under reduced pressure. The residue was purified by silica gel column chromatography (ethyl acetate/petroleum ether) to give the title compound (12.0 g).

$^1$H NMR (400 MHz, CDCl$_3$) δ 3.80 (2H, brs), 6.70 (1H, t, J=8.8 Hz), 7.05 (1H, dd, J=8.4, 1.6 Hz).

d) 4-chloro-3-ethynyl-2-fluoroaniline

To a solution of 4-chloro-2-fluoro-3-iodoaniline (5.0 g) in DMF (7.6 mL) were added bis(triphenylphosphine)palladium(II) dichloride (0.258 g), copper(I) iodide (0.140 g), triethylamine (12.9 mL), and trimethylsilylacetylene (3.9 mL) at room temperature, and the mixture was stirred under microwave irradiation at 120° C. for 20 min. After confirmation of completion of the reaction by TLC, the reaction mixture was filtered through celite. The filtrate was concentrated to give the title compound as a crude purified product. To a solution of the obtained crude purified product of the title compound in THF (75 mL) was added 1M TBAF/THF solution (25 mL) at room temperature, and the mixture was stirred at the same temperature for 30 min. After confirmation of completion of the reaction by TLC, the reaction mixture was concentrated under reduced pressure. The residue was purified by silica gel column chromatography (ethyl acetate/petroleum ether) to give the title compound as a crude purified product. The same reaction was performed 6 times in total and the combined crude purified products of the title compound were washed with n-pentane to give the title compound (10.0 g).

$^1$H NMR (400 MHz, CDCl$_3$) δ 3.57 (1H, s), 3.76 (2H, brs), 6.70 (1H, t, J=8.8 Hz), 6.99 (1H, dd, J=8.8, 1.5 Hz).

e) 5-chloro-N-(4-chloro-3-ethynyl-2-fluorophenyl)-2-methoxypyridine-3-sulfonamide To a solution of 4-chloro-3-ethynyl-2-fluoroaniline (100 mg) in pyridine (1 mL) was added a solution of 5-chloro-2-methoxypyridine-3-sulfonyl chloride (185 mg) in THF (0.1 mL) at 0° C. The mixture was stirred at room temperature for 1 hr. The reaction mixture was concentrated and the residue was purified by silica gel column chromatography (ethyl acetate/hexane) to give a crude purified product of the title compound (164 mg).

$^1$H NMR (300 MHz, DMSO-d$_6$) δ 3.90 (3H, s), 4.93 (1H, d, J=0.7 Hz), 7.29-7.44 (2H, m), 8.09 (1H, d, J=2.6 Hz), 8.52 (1H, d, J=2.5 Hz), 10.59 (1H, s).

f) N-(3-((2-aminopyrimidin-5-yl)ethynyl)-4-chloro-2-fluorophenyl)-5-chloro-2-methoxypyridine-3-sulfonamide A mixture of 5-chloro-N-(4-chloro-3-ethynyl-2-fluorophenyl)-2-methoxypyridine-3-sulfonamide (88 mg), 5-iodopyrimidin-2-amine (67 mg), dichlorobis(tricyclohexylphosphine)palladium(II) (12 mg), cesium carbonate (233 mg) and DMSO (2 mL) was stirred under microwave irradiation at 130° C. for 30 min. After cooling to room temperature, the reaction mixture was purified by silica gel column chromatography (ethyl acetate/hexane) to give the title compound as a crude purified product. The obtained crude purified product of the title compound was subjected to silica gel column chromatography (NH, methanol/ethyl acetate) to elute a byproduct. Silica gel supporting the title compound was added to ethyl acetate (10 mL), acetic acid (2 mL) and water (10 mL), and the mixture was stirred at room temperature for 10 min. The mixture was filtered and silica gel on the filter was treated 4 times with ethyl acetate/acetic acid (4 mL/1 mL) to elute the object product. The filtrate was diluted with water and extracted 2 times with ethyl acetate. To the obtained residue was added saturated aqueous sodium hydrogen carbonate solution, and the mixture was extracted 2 times with ethyl acetate. The obtained organic layer was washed with saturated brine, dried over magnesium sulfate and concentrated. The obtained residue was washed with ethyl acetate to give the title compound (55 mg).

$^1$H NMR (300 MHz, DMSO-d$_6$) δ 3.92 (3H, s), 7.26-7.36 (3H, m), 7.37-7.44 (1H, m), 8.10 (1H, d, J=2.6 Hz), 8.44 (2H, s), 8.52 (1H, d, J=2.5 Hz), 10.61 (1H, s).

Example 125

N-(3-((2-aminopyrimidin-5-yl)ethynyl)-2-chloro-4-fluorophenyl)-5-chloro-2-methoxypyridine-3-sulfonamide a) 1-chloro-3-fluoro-2-iodobenzene

To a solution of 1-chloro-3-fluorobenzene (20.0 g) in THF (100 mL) was added 2.5 M n-butyllithium/hexane solution (79.7 mL) at −78° C., and the mixture was stirred at the same temperature for 1 hr. To the reaction mixture was added a solution of iodine (46.6 g) in THF (100 mL) at the same temperature, and the mixture was stirred at room temperature for 2 hr. After confirmation of completion of the reaction by TLC, the reaction mixture was quenched with water and extracted 2 times with ethyl acetate. The combined organic layer was washed with water and saturated brine, dried over sodium sulfate and concentrated to give a crude purified product of the title compound (20.0 g). The product was used without further purification for the next step.

b) 2-chloro-4-fluoro-3-iodo-1-nitrobenzene

To a solution of 1-chloro-3-fluoro-2-iodobenzene (15.0 g) in concentrated sulfuric acid (75 mL) was added concentrated nitric acid (5.1 mL) at 0° C., and the mixture was stirred at room temperature for 2 hr. After confirmation of completion of the reaction by TLC, the reaction mixture was poured into ice-cooled water and extracted 3 times with ethyl acetate. The combined organic layer was washed with saturated brine, dried over sodium sulfate and concentrated to give a crude purified product of the title compound (15.0 g). The product was used without further purification for the next step.

c) 2-chloro-4-fluoro-3-iodoaniline

To a stirred solution of 2-chloro-4-fluoro-3-iodo-1-nitrobenzene (15.0 g) in concentrated hydrochloric acid/ethanol (120 mL, 1:7) was added iron (8.33 g) at 50° C., and the mixture was refluxed for 2 hr. After confirmation of completion of the reaction by TLC, the reaction mixture was concentrated under reduced pressure. The residue was dissolved in water, adjusted to pH~8-9 with 1N aqueous sodium hydroxide solution and extracted 2 times with ethyl acetate. The combined organic layer was dried over sodium sulfate and concentrated under reduced pressure. The residue was purified by silica gel column chromatography (ethyl acetate/petroleum ether) to give the title compound (5.0 g).
$^1$H NMR (400 MHz, CDCl$_3$) δ 4.07 (2H, brs), 6.73 (1H, dd, J=9.0, 5.0 Hz), 6.84 (1H, dd, J=9.0, 7.0 Hz).

d) 2-chloro-3-ethynyl-4-fluoroaniline

To a solution of 2-chloro-4-fluoro-3-iodoaniline (5.0 g) in DMF (7.6 mL) were added bis(triphenylphosphine)palladium(II) dichloride (0.258 g), copper(I) iodide (0.140 g), triethylamine (12.8 mL), and trimethylsilylacetylene (3.9 mL) at room temperature, and the mixture was stirred under microwave irradiation at 120° C. for 20 min. After confirmation of completion of the reaction by TLC, the reaction mixture was filtered through celite. The filtrate was concentrated to give the title compound as a crude purified product. To a solution of the obtained crude purified product of the title compound in THF (75 mL) was added 1M TBAF/THF solution (25 mL) at room temperature and the mixture was stirred at the same temperature for 30 min. After confirmation of completion of the reaction by TLC, the reaction mixture was concentrated under reduced pressure. The residue was purified by silica gel column chromatography (ethyl acetate/petroleum ether) to give the title compound (0.690 g).
$^1$H NMR (400 MHz, CDCl$_3$) δ 3.58 (1H, s), 3.98 (2H, brs), 6.72 (1H, dd, J=9.1, 5.1 Hz), 6.86 (1H, t, J=8.8 Hz).

e) 5-chloro-N-(2-chloro-3-ethynyl-4-fluorophenyl)-2-methoxypyridine-3-sulfonamide To a solution of 2-chloro-3-ethynyl-4-fluoroaniline (50 mg) in pyridine (1 mL) was added a solution of 5-chloro-2-methoxypyridine-3-sulfonyl chloride (98 mg) in THF (0.1 mL) at 0° C. The mixture was stirred at room temperature for 1 hr. The reaction mixture was concentrated. To a solution of 2-chloro-3-ethynyl-4-fluoroaniline (50 mg) in pyridine (1 mL) was added a solution of 5-chloro-2-methoxypyridine-3-sulfonyl chloride (98 mg) in THF (0.1 mL) at room temperature. The mixture was stirred at room temperature for 1 hr. The reaction mixture was concentrated. These residues were combined and purified by silica gel column chromatography (ethyl acetate/hexane) to give a crude purified product of the title compound (150 mg).
$^1$H NMR (300 MHz, DMSO-d$_6$) δ 3.86 (3H, s), 4.92 (1H, d, J=0.6 Hz), 7.28-7.46 (2H, m), 8.02 (1H, d, J=2.4 Hz), 8.51 (1H, d, J=2.6 Hz), 10.44 (1H, brs).

f) N-(3-((2-aminopyrimidin-5-yl)ethynyl)-2-chloro-4-fluorophenyl)-5-chloro-2-methoxypyridine-3-sulfonamide A mixture of 5-chloro-N-(2-chloro-3-ethynyl-4-fluorophenyl)-2-methoxypyridine-3-sulfonamide (146 mg), 5-iodopyrimidin-2-amine (140 mg), dichlorobis(tricyclohexylphosphine)palladium(II) (21 mg), cesium carbonate (546 mg) and DMSO (4 mL) was stirred under microwave irradiation at 130° C. for 30 min. After cooling to room temperature, the reaction mixture was purified by silica gel column chromatography (ethyl acetate/hexane) to give the title compound as a crude purified product. The obtained crude purified product of the title compound was subjected to silica gel column chromatography (NH, methanol/ethyl acetate) to elute a byproduct. Silica gel supporting the title compound was added to ethyl acetate (10 mL), acetic acid (2 mL) and water (10 mL), and the mixture was stirred at room temperature for 10 min. The mixture was filtered and silica gel on the filter was treated 4 times with ethyl acetate/acetic acid (4 mL/1 mL) to elute the object product. The filtrate was diluted with water and extracted 2 times with ethyl acetate. To the obtained residue was added saturated aqueous sodium hydrogen carbonate solution, and the mixture was extracted 2 times with ethyl acetate. The obtained organic layer was washed with saturated brine, dried over magnesium sulfate and concentrated. The obtained residue was washed with ethyl acetate to give the title compound (60 mg).
$^1$H NMR (300 MHz, DMSO-d$_6$) δ 3.90 (3H, s), 7.25-7.44 (4H, m), 8.03 (1H, d, J=2.6 Hz), 8.43 (2H, s), 8.52 (1H, d, J=2.5 Hz), 10.44 (1H, brs).

Example 126

N-(3-((2-aminopyrimidin-5-yl)ethynyl)-2-chlorophenyl)-5-chloro-2-methoxypyridine-3-sulfonamide a) 2-chloro-3-iodobenzoic Acid

A solution of 3-amino-2-chloro-benzoic acid (20.0 g) in 20% aqueous sulfuric acid (130 mL) was cooled to 0° C., and a solution of sodium nitrite (10.4 g) in water (20 mL) was added dropwise at 0° C. The mixture was stirred at 0° C. for 1 hr and a solution of potassium iodide (25.6 g) in water (20 mL) was added dropwise while keeping at 0-5° C. The reaction mixture was stirred overnight, and the precipitate was collected by filtration. The obtained solid was washed 5 times with water (60 mL) and dried. The obtained crude purified product was purified by silica gel column chromatography (ethyl acetate/hexane) to give the title compound (20.0 g).
$^1$H NMR (400 MHz, DMSO-$d_6$) δ 7.17 (1H, t, J=7.7 Hz), 7.69 (1H, d, J=7.3 Hz), 8.10 (1H, d, J=7.2 Hz), 13.60 (1H, brs).

b) tert-butyl N-(2-chloro-3-iodophenyl)carbamate

DIPEA (76.3 mL) and diphenylphosphoryl azide (66.3 mL) were added to a solution of 2-chloro-3-iodobenzoic acid (60.0 g) in tert-butanol (1.2 L) at room temperature. The mixture was stirred at room temperature for 1 hr, heated to 110° C. and stirred for 18 hr. To the reaction mixture was added water (50 mL) and the mixture was concentrated under reduced pressure. The residue was diluted with water (400 mL) and the organic substance was extracted 2 times with ethyl acetate (500 mL). The obtained organic layer was washed twice with water (500 mL) and once with saturated brine, dried over sodium sulfate and concentrated. The residue was purified by silica gel column chromatography (ethyl acetate/hexane) to give the title compound (55.0 g).
$^1$H NMR (400 MHz, DMSO-$d_6$) δ 1.45 (9H, s), 7.06 (1H, t, J=8.0 Hz), 7.56 (1H, d, J=8.0 Hz), 7.72 (1H, d, J=7.8 Hz), 8.78 (1H, brs).

c) tert-butyl N-{2-chloro-3-[2-(trimethylsilyl)ethynyl]phenyl}carbamate

Copper(I) iodide (3.0 g), triphenylphosphine (8.3 g), and diisopropylethylamine (113 g) were added to a solution of tert-butyl N-(2-chloro-3-iodophenyl)carbamate (112 g) in toluene (338 mL) at room temperature. To the mixture was added under an argon atmosphere bis(triphenylphosphine)palladium(II) dichloride (11.6 g). Trimethylsilylacetylene (77.8 mL) was added and the mixture was heated in a sealed tube for 20 hr at 80° C. After cooling, the reaction mixture was diluted with ethyl acetate (1 L) and filtered through celite. The filtrate was washed with water and saturated brine, and the obtained organic layer was dried over sodium sulfate and concentrated. The residue was purified by silica gel column chromatography (ethyl acetate/hexane) to give the title compound (72.4 g).
$^1$H NMR (400 MHz, DMSO-$d_6$) δ 0.25 (9H, s), 1.46 (9H, s), 7.28 (1H, t, J=7.9 Hz), 7.33-7.35 (1H, dd, J=1.6, 7.7 Hz), 7.61 (1H, d, J=8.0 Hz), 8.75 (1H, s).

d) tert-butyl N-(2-chloro-3-ethynylphenyl)carbamate

To a solution of potassium hydroxide (39.5 g) and tert-butyl N-{2-chloro-3-[2-(trimethylsilyl)ethynyl]phenyl}carbamate (76.0 g) in methanol (750 mL) was added little by little under ice-cooling. The mixture was stirred at room temperature for 3 hr and concentrated under reduced pressure. The residue was diluted with water (400 mL). The organic substance was extracted two times with ethyl acetate (500 mL) and the combined organic layer was washed 3 times with water (500 mL) and once with saturated brine (400 mL). The obtained organic layer was dried over sodium sulfate and concentrated to give the title compound (55.0 g).
$^1$H NMR (400 MHz, DMSO-$d_6$) δ 1.46 (9H, s), 4.57 (1H, s), 7.30 (1H, t, J=7.8 Hz), 7.38 (1H, d, J=7.4 Hz), 7.61 (1H, d, J=7.9 Hz), 8.76 (1H, brs).

e) 2-chloro-3-ethynylaniline Hydrochloride

A mixture of tert-butyl N-(2-chloro-3-ethynylphenyl)carbamate (56.5 g) and 4N hydrochloric acid/1,4-dioxane solution (1 L) was stirred at room temperature overnight. The reaction mixture was concentrated under reduced pressure and diethyl ether (500 mL) was added to the residue. The mixture was stirred for 20 min, and the precipitate was collected by filtration and dried under an argon atmosphere to give the title compound (40.5 g).
$^1$H NMR (400 MHz, DMSO-$d_6$) δ 4.41 (1H, s), 6.81 (1H, d, J=7.4 Hz), 6.88 (1H, d, J=8.1 Hz), 7.04 (1H, t, J=7.7 Hz).

f) 5-chloro-N-(2-chloro-3-ethynylphenyl)-2-methoxypyridine-3-sulfonamide

A mixture of 2-chloro-3-ethynylaniline hydrochloride (188 mg), 5-chloro-2-methoxypyridine-3-sulfonyl chloride (242 mg) and pyridine (2.41 mL) was stirred at room temperature overnight. To the reaction mixture was added methanol (5 mL), and the mixture was stirred at room temperature for 10 min and concentrated. The residue was purified by silica gel column chromatography (ethyl acetate/hexane) to give a crude purified product of the title compound (185 mg). The product was used without further purification for the next step.
MS: [M+H]$^+$ 357.0.

g) N-(3-((2-aminopyrimidin-5-yl)ethynyl)-2-chlorophenyl)-5-chloro-2-methoxypyridine-3-sulfonamide A mixture of 5-chloro-N-(2-chloro-3-ethynylphenyl)-2-methoxypyridine-3-sulfonamide (185 mg), 5-iodopyrimidin-2-amine (149 mg), bis(di-tert-butyl(4-dimethylaminophenyl)phosphine)dichloropalladium(II) (17.4 mg), copper (I) iodide (9.9 mg), triethylamine (0.72 mL) and DMSO (1.83 mL) was stirred under microwave irradiation at 100° C. for 1 hr. After cooling to room temperature, the mixture was diluted with water/saturated brine and extracted with ethyl acetate. The obtained organic layer was washed with saturated brine, dried over magnesium sulfate and concentrated to give a residue. The residue was purified by silica gel column chromatography (ethyl acetate/hexane) to give the title compound as a crude purified product. The obtained crude purified product of the title compound was subjected to silica gel column chromatography (NH, methanol/ethyl acetate) to elute a byproduct. Silica gel supporting the title compound was added to ethyl acetate (20 mL), acetic acid (4 mL) and water (20 mL), and the mixture was stirred at room temperature for 10 min. The mixture was filtered and silica gel on the filter was treated 4 times with ethyl acetate/acetic acid (6 mL/1.2 mL) to elute the object product. The organic layer was collected from the filtrate, and the organic layer was washed with water and saturated aqueous sodium hydrogen carbonate solution and saturated brine, dried over magnesium sulfate and concentrated to give a residue. The residue was purified by silica gel column chromatography (ethyl acetate/hexane) and subjected to ethyl acetate/hexane and the precipitate was collected by filtration to give the title compound (31 mg).
$^1$H NMR (300 MHz, DMSO-$d_6$) δ 3.88 (3H, s), 7.24 (2H, brs), 7.31-7.38 (2H, m), 7.44-7.52 (1H, m), 8.03 (1H, d, J=2.6 Hz), 8.42 (2H, s), 8.48-8.52 (1H, m), 10.37 (1H, s).

Example 127

3-((3-((2-aminopyrimidin-5-yl)ethynyl)-2,4-difluorophenyl)sulfamoyl)-5-chloro-2-methoxybenzyl Acetate a) methyl 3-bromo-5-chloro-2-methoxybenzoate A mixture of methyl 5-chloro-2-methoxybenzoate (30.0 g), NBS (32.0 g) and acetic acid (160 mL) was stirred at 80° C. for 4 hr. The reaction mixture was concentrated under reduced pressure and the residue was neutralized with a saturated aqueous sodium hydrogen carbonate solution at room temperature and extracted with ethyl acetate. The obtained organic layer was washed with saturated brine, dried over magnesium sulfate and concentrated to give a residue. The residue was purified by silica gel column chromatography (NH, ethyl acetate/hexane) to give the title compound (27.5 g).

$^1$H NMR (300 MHz, DMSO-$d_6$) δ 3.81 (3H, s), 3.87 (3H, s), 7.76 (1H, d, J=2.6 Hz), 8.05 (1H, d, J=2.6 Hz).

b) methyl 3-(benzylthio)-5-chloro-2-methoxybenzoate

A mixture of methyl 3-bromo-5-chloro-2-methoxybenzoate (26.4 g), benzylmercaptan (12.2 mL), tris(dibenzylideneacetone)dipalladium(0) (4.32 g), 4,5-bis(diphenylphosphino)-9,9-dimethylxanthene (5.47 g), DIPEA (41.2 mL) and toluene (220 mL) was stirred under a nitrogen atmosphere at 100° C. for 4 hr. After cooling to room temperature, the reaction mixture was diluted with water and an insoluble material was removed by filtration. The filtrate was extracted with ethyl acetate. The obtained organic layer was washed with saturated brine, dried over magnesium sulfate and concentrated to give a residue. The residue was purified by silica gel column chromatography (NH, ethyl acetate/hexane) to give the title compound (29.1 g).

$^1$H NMR (300 MHz, DMSO-$d_6$) δ 3.75 (3H, s), 3.84 (3H, s), 4.31 (2H, s), 7.23-7.38 (3H, m), 7.39-7.45 (2H, m), 7.48 (1H, d, J=2.5 Hz), 7.56 (1H, d, J=2.5 Hz).

c) (3-(benzylthio)-5-chloro-2-methoxyphenyl)methanol

Calcium chloride (14.2 g) was dissolved in ethanol (170 mL) at room temperature. To the obtained solution was added sodium borohydride (9.70 g) at 0° C., and the mixture was stirred at the same temperature for 20 min. To the reaction mixture was added a solution of methyl 3-(benzylthio)-5-chloro-2-methoxybenzoate (23.0 g) in THF (170 mL), and the mixture was stirred under a water bath for 2 hr while paying attention to prevent the inside temperature from exceeding 30° C. The reaction mixture was quenched at 0° C. with saturated aqueous ammonium chloride solution and extracted with ethyl acetate. The obtained organic layer was washed with saturated brine, dried over magnesium sulfate and concentrated to give a crude purified product of the title compound (20.3 g). The product was used without further purification for the next step.

$^1$H NMR (300 MHz, DMSO-$d_6$) δ 3.67 (3H, s), 4.26 (2H, s), 4.50 (2H, d, J=5.0 Hz), 5.29 (1H, t, J=5.6 Hz), 7.20-7.28 (3H, m), 7.29-7.36 (2H, m), 7.38-7.42 (2H, m).

d) 3-(benzylthio)-5-chloro-2-methoxybenzyl acetate

To a solution of (3-(benzylthio)-5-chloro-2-methoxyphenyl)methanol (20.3 g), DMAP (1.68 g) and triethylamine (19.2 mL) in THF (160 mL) was added dropwise acetic anhydride (7.8 mL) at room temperature. The mixture was stirred at 50° C. for 2 hr. The reaction mixture was diluted with water at room temperature and extracted with ethyl acetate. The obtained organic layer was washed with saturated brine, dried over magnesium sulfate and concentrated to give a residue. The residue was purified by silica gel column chromatography (ethyl acetate/hexane) to give the title compound (23.0 g).

$^1$H NMR (300 MHz, DMSO-$d_6$) δ 2.07 (3H, s), 3.72 (3H, s), 4.29 (2H, s), 5.04 (2H, s), 7.19-7.44 (7H, m).

e) 5-chloro-3-(chlorosulfonyl)-2-methoxybenzyl acetate

To a solution of 3-(benzylthio)-5-chloro-2-methoxybenzyl acetate (8.18 g) in acetic acid (45 mL)-water (15 mL) was added NCS (13.0 g) at 0° C. The mixture was stirred at room temperature for 1 hr and concentrated under reduced pressure. The residue was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give the title compound (5.18 g).

$^1$H NMR (300 MHz, DMSO-$d_6$) δ 2.09 (3H, s), 3.83 (3H, s), 5.06 (2H, s), 7.39 (1H, d, J=2.9 Hz), 7.67 (1H, d, J=2.8 Hz).

f) 5-chloro-3-(N-(3-ethynyl-2,4-difluorophenyl)sulfamoyl)-2-methoxybenzyl acetate To a solution of 3-ethynyl-2,4-difluoroaniline (2.20 g) in pyridine (20 mL) was added a solution of 5-chloro-3-(chlorosulfonyl)-2-methoxybenzyl acetate (4.95 g) in THF (10 mL) at 70° C. The mixture was stirred at the same temperature for 1 hr and concentrated under reduced pressure. The residue was diluted with 1N hydrochloric acid at room temperature and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with IPE to give the title compound (5.38 g).

$^1$H NMR (300 MHz, DMSO-$d_6$) δ 2.11 (3H, s), 3.82 (3H, s), 4.84 (1H, s), 5.14 (2H, s), 7.11-7.20 (1H, m), 7.29 (1H, td, J=8.9, 6.0 Hz), 7.64 (1H, d, J=2.7 Hz), 7.78 (1H, d, J=2.7 Hz), 10.34 (1H, s).

g) 3-((3-((2-aminopyrimidin-5-yl)ethynyl)-2,4-difluorophenyl)sulfamoyl)-5-chloro-2-methoxybenzyl acetate A mixture of 5-chloro-3-(N-(3-ethynyl-2,4-difluorophenyl)sulfamoyl)-2-methoxybenzyl acetate (300 mg), dichlorobis(tricyclohexylphosphine)palladium(II) (51.5 mg), DIPEA (2 mL), copper(I) iodide (26.6 mg), 5-iodopyrimidin-2-amine (201 mg) and DMSO (3 mL) was stirred under microwave irradiation at 100° C. for 1 hr. After cooling to room temperature, the reaction mixture was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (258 mg).

¹H NMR (300 MHz, DMSO-d₆) δ 2.09 (3H, s), 3.83 (3H, s), 5.15 (2H, s), 7.12-7.28 (2H, m), 7.30 (2H, s), 7.66 (1H, d, J=2.7 Hz), 7.78 (1H, d, J=2.7 Hz), 8.43 (2H, s), 10.34 (1H, s).

Example 128

3-((3-((3-amino-1,2,4-triazin-6-yl)ethynyl)-2,4-difluorophenyl)sulfamoyl)-5-chloro-2-methoxybenzyl Acetate A mixture of 5-chloro-3-(N-(3-ethynyl-2,4-difluorophenyl)sulfamoyl)-2-methoxybenzyl acetate (300 mg), dichlorobis(tricyclohexylphosphine)palladium(II) (51.5 mg), DIPEA (2 mL), copper(I) iodide (26.6 mg), 6-bromo-1,2,4-triazin-3-amine (159 mg) and DMSO (3 mL) was stirred under microwave irradiation at 100° C. for 1 hr. After cooling to room temperature, the reaction mixture was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (227 mg).

¹H NMR (300 MHz, DMSO-d₆) δ 2.09 (3H, s), 3.83 (3H, s), 5.15 (2H, s), 7.18-7.27 (1H, m), 7.34 (1H, td, J=8.9, 5.9 Hz), 7.67 (1H, d, J=2.7 Hz), 7.71-8.03 (3H, m), 8.45 (1H, s), 10.41 (1H, s).

Example 129

N-(3-((2-aminopyrimidin-5-yl)ethynyl)-2,4-difluorophenyl)-5-chloro-3-(hydroxymethyl)-2-methoxybenzenesulfonamide To a solution of 3-((3-((2-aminopyrimidin-5-yl)ethynyl)-2,4-difluorophenyl) sulfamoyl)-5-chloro-2-methoxybenzyl acetate (230 mg) in methanol (3 mL) was added 2N aqueous sodium hydroxide solution (1.5 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate to give the title compound (150 mg).

¹H NMR (300 MHz, DMSO-d₆) δ 3.79 (3H, s), 4.60 (2H, d, J=5.8 Hz), 5.53 (1H, t, J=5.7 Hz), 7.13-7.27 (2H, m), 7.30 (2H, s), 7.56 (1H, d, J=2.7 Hz), 7.74 (1H, d, J=2.7 Hz), 8.44 (2H, s), 10.27 (1H, s).

Example 130

N-(3-((3-amino-1,2,4-triazin-6-yl)ethynyl)-2,4-difluorophenyl)-5-chloro-3-(hydroxymethyl)-2-methoxybenzenesulfonamide To a solution of 3-((3-((3-amino-1,2,4-triazin-6-yl)ethynyl)-2,4-difluorophenyl)sulfamoyl)-5-chloro-2-methoxybenzyl acetate (205 mg) in methanol (3 mL) was added 2N aqueous sodium hydroxide solution (1.5 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate to give the title compound (93 mg).

¹H NMR (300 MHz, DMSO-d₆) δ 3.79 (3H, s), 4.60 (2H, d, J=5.8 Hz), 5.53 (1H, t, J=5.8 Hz), 7.18-7.27 (1H, m), 7.34 (1H, td, J=8.9, 6.0 Hz), 7.58 (1H, d, J=2.7 Hz), 7.66-8.09 (3H, m), 8.45 (1H, s), 10.34 (1H, s).

Example 131

N-(3-((5-amino-6-methylpyrazin-2-yl)ethynyl)-2,4-difluorophenyl)-5-chloro-3-(hydroxymethyl)-2-methoxybenzenesulfonamide a) 3-(N-(3-((5-amino-6-methylpyrazin-2-yl)ethynyl)-2,4-difluorophenyl)sulfamoyl)-5-chloro-2-methoxybenzyl Acetate A mixture of 5-chloro-3-(N-(3-ethynyl-2,4-difluorophenyl)sulfamoyl)-2-methoxybenzyl acetate (200 mg), dichlorobis(tricyclohexylphosphine)palladium(II) (34.3 mg), DIPEA (2 mL), copper(I) iodide (17.7 mg), 5-bromo-3-methylpyrazin-2-amine (114 mg) and DMSO (2 mL) was stirred under microwave irradiation at 100° C. for 1 hr. After cooling to room temperature, the reaction mixture was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give the title compound (216 mg).

MS: [M+H]⁺ 537.0.

b) N-(3-((5-amino-6-methylpyrazin-2-yl)ethynyl)-2,4-difluorophenyl)-5-chloro-3-(hydroxymethyl)-2-methoxybenzenesulfonamide To a solution of 3-(N-(3-((5-amino-6-methylpyrazin-2-yl)ethynyl)-2,4-difluorophenyl)sulfamoyl)-5-chloro-2-methoxybenzyl acetate (215 mg) in methanol (3 mL) was added 2N aqueous sodium hydroxide solution (1.5 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate to give the title compound (45.6 mg).

¹H NMR (300 MHz, DMSO-d₆) δ 2.30 (3H, s), 3.79 (3H, s), 4.60 (2H, d, J=5.5 Hz), 5.53 (1H, t, J=5.5 Hz), 6.87 (2H, brs), 7.11-7.35 (2H, m), 7.57 (1H, brs), 7.73 (1H, brs), 8.05 (1H, s), 10.28 (1H, s).

Example 136

N-(3-((2-aminopyrimidin-5-yl)ethynyl)-2,4-difluorophenyl)-5-chloro-2-(trifluoromethyl)pyridine-3-sulfonamide a) 3-(benzylthio)-5-chloro-2-(trifluoromethyl)pyridine A mixture of 3-bromo-5-chloro-2-(trifluoromethyl)pyridine (804 mg), benzylmercaptan (0.40 mL), tris(dibenzylideneacetone)dipalladium(0) (142 mg), 1,1'-bis(diphenylphosphino)ferrocene (172 mg), DIPEA (1.10 mL) and toluene (10 mL) was stirred under a nitrogen atmosphere at 100° C. for 2 hr. The reaction mixture was filtered to remove an insoluble material, and concentrated under reduced pressure. The residue was purified by silica gel column chromatography (ethyl acetate/hexane) and further purified by silica gel column chromatography (NH, hexane) to give the title compound (810 mg).

$^1$H NMR (300 MHz, DMSO-d$_6$) δ 4.50 (2H, s), 7.21-7.46 (5H, m), 8.29 (1H, d, J=1.6 Hz), 8.55 (1H, d, J=1.8 Hz).

b) 5-chloro-2-(trifluoromethyl)pyridine-3-sulfonyl chloride

NCS (1.41 g) was added to a solution of 3-(benzylthio)-5-chloro-2-(trifluoromethyl)pyridine (802 mg) in acetic acid (10 mL)-water (2 mL) little by little at 0° C. The mixture was stirred at room temperature for 1 hr, and the reaction mixture was diluted with water and extracted with ethyl acetate. The obtained organic layer was washed with water and saturated brine, dried over magnesium sulfate and concentrated to give a residue. The residue was purified by silica gel column chromatography (ethyl acetate/hexane) to give the title compound (893 mg).

$^1$H NMR (300 MHz, DMSO-d$_6$) δ 8.39 (1H, dd, J=2.4, 0.6 Hz), 8.76 (1H, dd, J=2.4, 0.6 Hz).

c) N-(3-((2-aminopyrimidin-5-yl)ethynyl)-2,4-difluorophenyl)-5-chloro-2-(trifluoromethyl)pyridine-3-sulfonamide 5-Chloro-2-(trifluoromethyl)pyridine-3-sulfonyl chloride (128 mg) was added to a solution of 5-((3-amino-2,6-difluorophenyl)ethynyl)-N-(4-methoxybenzyl)pyrimidin-2-amine (80 mg) in pyridine (1 mL) at room temperature. The mixture was stirred at room temperature for 1 hr and 5-chloro-2-(trifluoromethyl)pyridine-3-sulfonyl chloride (90 mg) was further added. The mixture was stirred at room temperature for 1 hr, and the reaction mixture was diluted with toluene and concentrated under reduced pressure. To the residue was added TFA (2 mL) at room temperature, and the mixture was stirred at 70° C. for 2 hr. The reaction mixture was concentrated under reduced pressure, poured into saturated aqueous sodium hydrogen carbonate solution, and the mixture was extracted with ethyl acetate. The obtained organic layer was washed with saturated brine, dried over magnesium sulfate and concentrated to give a residue. The residue was purified by silica gel column chromatography (ethyl acetate/hexane) to give the title compound as a crude purified product. To a solution of the obtained crude purified product of the title compound in methanol (3 mL)-THF (3 mL) was added 2N aqueous sodium hydroxide solution (0.1 mL), and the mixture was stirred at room temperature for 30 min. The reaction mixture was poured into water, and the mixture was extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (52 mg).

$^1$H NMR (300 MHz, DMSO-d$_6$) δ 7.16-7.26 (1H, m), 7.27-7.41 (3H, m), 8.43 (2H, s), 8.49 (1H, d, J=2.0 Hz), 9.10 (1H, d, J=2.1 Hz), 10.92 (1H, brs).

Example 137

5-chloro-N-(3-((2-(ethylamino)pyrimidin-5-yl)ethynyl)-2,4-difluorophenyl)-3-(hydroxymethyl)-2-methoxybenzenesulfonamide a) 5-chloro-3-(N-(3-((2-chloropyrimidin-5-yl)ethynyl)-2,4-difluorophenyl)sulfamoyl)-2-methoxybenzyl Acetate A mixture of 5-chloro-3-(N-(3-ethynyl-2,4-difluorophenyl)sulfamoyl)-2-methoxybenzyl acetate (3.00 g), dichlorobis(tricyclohexylphosphine)palladium(II) (515 mg), DIPEA (20 mL), copper(I) iodide (266 mg), 2-chloro-5-iodopyrimidine (2.18 g) and DMSO (18 mL) was stirred under microwave irradiation at 60° C. for 1 hr. After cooling to room temperature, the reaction mixture was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (3.37 g).

$^1$H NMR (300 MHz, DMSO-d$_6$) δ 2.09 (3H, s), 3.82 (3H, s), 5.15 (2H, s), 7.19-7.30 (1H, m), 7.37 (1H, td, J=8.9, 6.0 Hz), 7.67 (1H, d, J=2.7 Hz), 7.78 (1H, d, J=2.7 Hz), 9.03 (2H, s), 10.43 (1H, s).

b) 5-chloro-N-(3-((2-chloropyrimidin-5-yl)ethynyl)-2,4-difluorophenyl)-3-(hydroxymethyl)-2-methoxybenzenesulfonamide To a solution of 5-chloro-3-(N-(3-((2-chloropyrimidin-5-yl)ethynyl)-2,4-difluorophenyl)sulfamoyl)-2-methoxybenzyl acetate (100 mg) in THF (3 mL) was added 2N aqueous sodium hydroxide solution (0.8 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give the title compound (89 mg).

MS: [M−H]$^−$ 498.1.

c) 5-chloro-N-(3-((2-(ethylamino)pyrimidin-5-yl)ethynyl)-2,4-difluorophenyl)-3-(hydroxymethyl)-2-methoxybenzenesulfonamide A mixture of 5-chloro-N-(3-((2-chloropyrimidin-5-yl)ethynyl)-2,4-difluorophenyl)-3-(hydroxymethyl)-2-methoxybenzenesulfonamide (15 mg), ethylamine (4 mg), DIEPA (0.016 mL) and acetonitrile (0.5 mL) was stirred at 70° C. for 4 hr. The reaction mixture was diluted with DMSO (0.5 mL) and separated by HPLC (C18, mobile phase: 10 mM aqueous ammonium hydrogen carbonate solution/acetonitrile), and the obtained fraction was concentrated to give the title compound (5.2 mg).

Example 138

5-chloro-N-(3-((2-(cyclopropylamino)pyrimidin-5-yl)ethynyl)-2,4-difluorophenyl)-3-(hydroxymethyl)-2-methoxybenzenesulfonamide A mixture of 5-chloro-N-(3-((2-chloropyrimidin-5-yl)ethynyl)-2,4-difluorophenyl)-3-(hydroxymethyl)-2-methoxybenzenesulfonamide (15 mg), cyclopropylamine (5 mg), DIEPA (0.016 mL) and acetonitrile (0.5 mL) was stirred at 70° C. for 4 hr. The reaction mixture was diluted with DMSO (0.5 mL) and separated by HPLC (C18, mobile phase: 10 mM aqueous ammonium hydrogen carbonate solution/acetonitrile), and the obtained fraction was concentrated to give the title compound (10.3 mg).

Example 140

5-chloro-N-(2,4-difluoro-3-((2-(oxetan-3-ylamino) pyrimidin-5-yl)ethynyl)phenyl)-3-(hydroxymethyl)-2-methoxybenzenesulfonamide A mixture of 5-chloro-N-(3-((2-chloropyrimidin-5-yl)ethynyl)-2,4-difluorophenyl)-3-(hydroxymethyl)-2-methoxybenzenesulfonamide (15 mg), 3-oxetanamine (7 mg), DIEPA (0.016 mL) and acetonitrile (0.5 mL) was stirred at 70° C. for 4 hr. The reaction mixture was diluted with DMSO (0.5 mL) and separated by HPLC (C18, mobile phase: 10 mM aqueous ammonium hydrogen carbonate solution/acetonitrile), and the obtained fraction was concentrated to give the title compound (10.2 mg).

Example 141

5-chloro-N-(2,4-difluoro-3-((2-(tetrahydrofuran-3-ylamino)pyrimidin-5-yl)ethynyl)phenyl)-3-(hydroxymethyl)-2-methoxybenzenesulfonamide A mixture of 5-chloro-N-(3-((2-chloropyrimidin-5-yl)ethynyl)-2,4-difluorophenyl)-3-(hydroxymethyl)-2-methoxybenzenesulfonamide (15 mg), 3-aminotetrahydrofuran (8 mg), DIEPA (0.016 mL) and acetonitrile (0.5 mL) was stirred at 70° C. for 4 hr. The reaction mixture was diluted with DMSO (0.5 mL) and separated by HPLC (C18, mobile phase: 10 mM aqueous ammonium hydrogen carbonate solution/acetonitrile), and the obtained fraction was concentrated to give the title compound (9.9 mg).

Example 145

5-chloro-N-(2,4-difluoro-3-((2-(((tetrahydrofuran-3-yl)methyl)amino)pyrimidin-5-yl)ethynyl)phenyl)-3-(hydroxymethyl)-2-methoxybenzenesulfonamide A mixture of 5-chloro-N-(3-((2-chloropyrimidin-5-yl)ethynyl)-2,4-difluorophenyl)-3-(hydroxymethyl)-2-methoxybenzenesulfonamide (15 mg), (tetrahydrofuran-3-yl)methanamine (9 mg), DIEPA (0.016 mL) and acetonitrile (0.5 mL) was stirred at 70° C. for 4 hr. The reaction mixture was diluted with DMSO (0.5 mL) and separated by HPLC (C18, mobile phase: 10 mM aqueous ammonium hydrogen carbonate solution/acetonitrile), and the obtained fraction was concentrated to give the title compound (12.3 mg).

Example 149

5-chloro-N-(2,4-difluoro-3-((2-((2-hydroxyethyl) amino)pyrimidin-5-yl)ethynyl)phenyl)-3-(hydroxymethyl)-2-methoxybenzenesulfonamide A mixture of 5-chloro-N-(3-((2-chloropyrimidin-5-yl)ethynyl)-2,4-difluorophenyl)-3-(hydroxymethyl)-2-methoxybenzenesulfonamide (15 mg), ethanolamine (5 mg), DIEPA (0.016 mL) and acetonitrile (0.5 mL) was stirred at 70° C. for 4 hr. The reaction mixture was diluted with DMSO (0.5 mL) and separated by HPLC (C18, mobile phase: 10 mM aqueous ammonium hydrogen carbonate solution/acetonitrile), and the obtained fraction was concentrated to give the title compound (6.6 mg).

Example 150

5-chloro-N-(2,4-difluoro-3-((2-(((2R)-1-hydroxypropan-2-yl)amino)pyrimidin-5-yl)ethynyl)phenyl)-3-(hydroxymethyl)-2-methoxybenzenesulfonamide A mixture of 5-chloro-N-(3-((2-chloropyrimidin-5-yl)ethynyl)-2,4-difluorophenyl)-3-(hydroxymethyl)-2-methoxybenzenesulfonamide (15 mg), D-alaninol (7 mg), DIEPA (0.016 mL) and acetonitrile (0.5 mL) was stirred at 70° C. for 4 hr. The reaction mixture was diluted with DMSO (0.5 mL) and separated by HPLC (C18, mobile phase: 10 mM aqueous ammonium hydrogen carbonate solution/acetonitrile), and the obtained fraction was concentrated to give the title compound (10.6 mg).

Example 153

5-chloro-N-(2,4-difluoro-3-((2-((trans-4-hydroxycyclohexyl)amino)pyrimidin-5-yl)ethynyl)phenyl)-3-(hydroxymethyl)-2-methoxybenzenesulfonamide A mixture of 5-chloro-N-(3-((2-chloropyrimidin-5-yl)ethynyl)-2,4-difluorophenyl)-3-(hydroxymethyl)-2-methoxybenzenesulfonamide (15 mg), trans-4-aminocyclohexanol (10 mg), DIEPA (0.016 mL) and acetonitrile (0.5 mL) was stirred at 70° C. for 4 hr. The reaction mixture was diluted with DMSO (0.5 mL) and separated by HPLC (C18, mobile phase: 10 mM aqueous ammonium hydrogen carbonate solution/acetonitrile), and the obtained fraction was concentrated to give the title compound (1.2 mg).

Example 158

N-(3-((3-amino-1,2,4-triazin-6-yl)ethynyl)-2,4-difluorophenyl)-5-chloro-2-methylpyridine-3-sulfonamide A mixture of 5-chloro-N-(3-ethynyl-2,4-difluorophenyl)-2-methylpyridine-3-sulfonamide (103 mg), dichlorobis(tricyclohexylphosphine)palladium(II) (22 mg), DIPEA (0.84 mL), copper(I) iodide (11 mg), 6-bromo-1,2,4-triazin-3-amine (68 mg) and DMSO (1.3 mL) was stirred under microwave irradiation at 100° C. for 1 hr. After cooling to room temperature, the reaction mixture was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give the title compound as a crude purified product. The obtained crude purified product of the title compound was subjected to silica gel column chromatography (NH, methanol/ethyl acetate) to elute a byproduct. Silica gel supporting the title compound was added to ethyl acetate (20 mL), acetic acid (4 mL) and water (20 mL), and the mixture was stirred at room temperature for 10 min. The mixture was filtered and silica gel on the filter was treated 4 times with ethyl acetate/acetic acid (6 mL/1.2 mL) to elute the object product. The filtrate was diluted with ethyl acetate and washed with saturated aqueous sodium hydrogen carbonate solution. The obtained organic layer was washed with saturated brine, dried over magnesium sulfate and concentrated. The obtained residue was washed with ethyl acetate/hexane to give the title compound (39.9 mg).

$^1$H NMR (300 MHz, DMSO-$d_6$) δ 2.77 (3H, s), 7.20-7.46 (2H, m), 7.87 (2H, brs), 8.07 (1H, d, J=2.4 Hz), 8.44 (1H, s), 8.77 (1H, d, J=2.4 Hz), 10.88 (1H, s).

Example 159

N-(3-((2-aminopyrimidin-5-yl)ethynyl)-2,4-difluorophenyl)-5-chloro-3-hydroxy-2,3-dihydro-1-benzofuran-7-sulfonamide a) 2-bromo-1-(3-bromo-5-chloro-2-hydroxyphenyl)ethanone To a solution of 1-(3-bromo-5-chloro-2-hydroxyphenyl)ethanone (7.93 g) in acetic acid (50 mL) was added bromine (2 mL) at room temperature. The mixture was stirred at 70° C. for 3 hr. The reaction mixture was concentrated under reduced pressure and the obtained residue was washed with IPE to give the title compound (6.90 g).

$^1$H NMR (300 MHz, DMSO-$d_6$) δ 5.03 (2H, s), 8.03-8.07 (2H, m), 11.89 (1H, brs).

b) 7-bromo-5-chlorobenzofuran-3(2H)-one

To a solution of 2-bromo-1-(3-bromo-5-chloro-2-hydroxyphenyl)ethanone (6.70 g) in acetonitrile (130 mL) was added potassium carbonate (4.23 g) at 0° C. The mixture was stirred under a nitrogen atmosphere at room temperature for 40 min. The reaction mixture was acidified with 1N hydrochloric acid at 0° C. and extracted with ethyl acetate. The obtained organic layer was washed with saturated brine, dried over magnesium sulfate and concentrated to give a residue. The residue was washed with IPE to give the title compound (3.41 g).

$^1$H NMR (300 MHz, DMSO-$d_6$) δ 4.99 (2H, s), 7.74 (1H, d, J=2.2 Hz), 8.14 (1H, d, J=2.2 Hz).

c) 7-bromo-5-chloro-2,3-dihydrobenzofuran-3-ol

To a solution of 7-bromo-5-chlorobenzofuran-3(2H)-one (3.40 g) in THF (50 mL)-methanol (5 mL) was added sodium borohydride (0.78 g) at 0° C. The mixture was stirred at the same temperature for 1 hr, and the reaction mixture was quenched with saturated aqueous ammonium chloride solution at the same temperature and extracted with ethyl acetate. The obtained organic layer was washed with saturated brine, dried over magnesium sulfate and concentrated to give a residue. The residue was purified by silica gel column chromatography (ethyl acetate/hexane) to give the title compound (3.30 g).

$^1$H NMR (300 MHz, DMSO-$d_6$) δ 4.35 (1H, dd, J=10.3, 3.2 Hz), 4.65 (1H, dd, J=10.3, 7.0 Hz), 5.36 (1H, td, J=6.3, 3.2 Hz), 5.87 (1H, d, J=5.9 Hz), 7.40 (1H, dd, J=2.1, 0.7 Hz), 7.57 (1H, d, J=2.1 Hz).

d) 7-bromo-5-chloro-2,3-dihydrobenzofuran-3-yl Acetate

To a solution of 7-bromo-5-chloro-2,3-dihydrobenzofuran-3-ol (3.29 g), DMAP (322 mg) and triethylamine (4.6 mL) in THF (35 mL) was added dropwise acetic anhydride (1.5 mL) at room temperature. The mixture was stirred at 60° C. for 1 hr. The reaction mixture was diluted with water at 0° C. and extracted with ethyl acetate. The obtained organic layer was washed with saturated brine, dried over magnesium sulfate and concentrated to give a residue. The residue was purified by silica gel column chromatography (ethyl acetate/hexane) to give the title compound (3.18 g).

$^1$H NMR (300 MHz, DMSO-$d_6$) δ 2.04 (3H, s), 4.64 (1H, dd, J=11.4, 2.5 Hz), 4.74-4.83 (1H, m), 6.28 (1H, dd, J=6.7, 2.4 Hz), 7.48-7.51 (1H, m), 7.70 (1H, d, J=2.2 Hz).

e) 7-(benzylthio)-5-chloro-2,3-dihydrobenzofuran-3-yl Acetate

A mixture of 7-bromo-5-chloro-2,3-dihydrobenzofuran-3-yl acetate (3.17 g), benzylmercaptan (1.7 mL), tris(dibenzylideneacetone)dipalladium(0) (498 mg), 4,5-bis(diphenylphosphino)-9,9-dimethylxanthene (629 mg), DIPEA (4.7 mL) and toluene (30 mL) was stirred under a nitrogen atmosphere at 90° C. for 3 hr. After cooling to room temperature, the reaction mixture was diluted with water and extracted with ethyl acetate. The obtained organic layer was washed with saturated brine, dried over magnesium sulfate and concentrated to give a residue. The residue was purified by silica gel column chromatography (NH, ethyl acetate/hexane) to give the title compound (2.95 g).

$^1$H NMR (300 MHz, DMSO-$d_6$) δ 2.03 (3H, s), 4.28 (2H, s), 4.55-4.63 (1H, m), 4.68-4.77 (1H, m), 6.19 (1H, dd, J=6.6, 2.3 Hz), 7.23-7.37 (7H, m).

f) 5-chloro-7-(chlorosulfonyl)-2,3-dihydrobenzofuran-3-yl acetate

NCS (4.69 g) was added to a solution of 7-(benzylthio)-5-chloro-2,3-dihydrobenzofuran-3-yl acetate (2.94 g) in acetic acid (27 mL)-water (9 mL) at 0° C. The mixture was stirred at room temperature for 1 hr and the reaction mixture was concentrated under reduced pressure. The residue was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give the title compound (2.53 g).

$^1$H NMR (300 MHz, DMSO-$d_6$) δ 2.03 (3H, s), 4.50-4.59 (1H, m), 4.62-4.71 (1H, m), 6.17 (1H, dd, J=6.6, 2.1 Hz), 7.41-7.43 (1H, m), 7.50 (1H, d, J=2.5 Hz).

g) 5-chloro-7-(N-(3-ethynyl-2,4-difluorophenyl)sulfamoyl)-2,3-dihydrobenzofuran-3-yl Acetate To a solution of 3-ethynyl-2,4-difluoroaniline (1.13 g) in pyridine (15 mL) was added a solution of 5-chloro-7-(chlorosulfonyl)-2,3-dihydrobenzofuran-3-yl acetate (2.52 g) in THF (5 mL) at 70° C. The mixture was stirred at the same temperature for 1 hr and concentrated under reduced pressure. The residue was diluted with 1N hydrochloric acid at room temperature and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with IPE to give the title compound (2.46 g).

$^1$H NMR (300 MHz, DMSO-$d_6$) δ 2.05 (3H, s), 4.62 (1H, dd, J=11.4, 2.4 Hz), 4.70-4.79 (1H, m), 4.86 (1H, s), 6.24 (1H, dd, J=6.5, 2.3 Hz), 7.13-7.21 (1H, m), 7.30 (1H, td, J=8.9, 6.0 Hz), 7.55 (1H, d, J=2.4 Hz), 7.77-7.80 (1H, m), 10.46 (1H, s).

h) 7-(N-(3-((2-aminopyrimidin-5-yl)ethynyl)-2,4-difluorophenyl) sulfamoyl)-5-chloro-2,3-dihydrobenzofuran-3-yl Acetate A mixture of 5-chloro-7-(N-(3-ethynyl-2,4-difluorophenyl)sulfamoyl)-2,3-dihydrobenzofuran-3-yl acetate (290 mg), dichlorobis(tricyclohexylphosphine)palladium(II) (50.0 mg), DIPEA (2 mL), copper(I) iodide (25.8 mg), 5-iodopyrimidin-2-amine (195 mg) and DMSO (3 mL) was stirred under microwave irradiation at 100° C. for 1 hr. After cooling to room temperature, the reaction mixture was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give the title compound (254 mg).

MS: [M−H]⁻ 519.1.

i) N-(3-((2-aminopyrimidin-5-yl)ethynyl)-2,4-difluorophenyl)-5-chloro-3-hydroxy-2,3-dihydro-1-benzofuran-7-sulfonamide To a solution of 7-(N-(3-((2-aminopyrimidin-5-yl)ethynyl)-2,4-difluorophenyl)sulfamoyl)-5-chloro-2,3-dihydrobenzofuran-3-yl acetate (253 mg) in methanol (3 mL) was added 2N aqueous sodium hydroxide solution (1.5 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (137 mg).

¹H NMR (300 MHz, DMSO-d₆) δ 4.36 (1H, dd, J=10.3, 3.1 Hz), 4.62 (1H, dd, J=10.3, 6.9 Hz), 5.28-5.38 (1H, m), 5.94 (1H, d, J=5.6 Hz), 7.13-7.27 (2H, m), 7.30 (2H, s), 7.47 (1H, d, J=2.2 Hz), 7.68 (1H, d, J=1.9 Hz), 8.44 (2H, s), 10.37 (1H, s).

Example 162

N-(3-((2-aminopyrimidin-5-yl)ethynyl)-2,4-difluorophenyl)-5-chloro-2-(difluoromethoxy)pyridine-3-sulfonamide a) 3-amino-5-chloropyridin-2-ol

A mixture of 5-chloro-3-nitropyridin-2-ol (30.0 g), iron (14.5 g), ammonium chloride (46.5 g) and ethanol/water (300 mL, 3/1, v/v) was stirred at 90° C. for 2 hr. The reaction mixture was filtered, and the filtrate was concentrated under reduced pressure. The residue was purified by silica gel column chromatography (ethyl acetate/petroleum ether) to give the title compound (20.0 g).

MS: [M+H]⁺ 145.3.

b) tert-butyl 5-chloro-2-hydroxypyridin-3-ylcarbamate

A mixture of 3-amino-5-chloropyridin-2-ol (20.0 g), di-tert-butyl dicarbonate (33.4 g), DMAP (848 mg), triethylamine (14.0 g) and DCM (200 mL) was stirred at room temperature for 4 hr. The reaction mixture was concentrated under reduced pressure, and the residue was purified by silica gel column chromatography (ethyl acetate/petroleum ether) to give the title compound (9.50 g).

MS: [M+Na]⁺267.1.

c) tert-butyl 5-chloro-2-(difluoromethoxy)pyridin-3-ylcarbamate

A mixture of tert-butyl 5-chloro-2-hydroxypyridin-3-ylcarbamate (22.0 g), 2-chloro-2,2-difluoroacetic acid (16.4 g), potassium carbonate (37.3 g) and DMF (200 mL) was stirred at 50° C. overnight. The reaction mixture was quenched with water and extracted with ethyl acetate. The obtained organic layer was washed with saturated brine, dried over sodium sulfate and concentrated to give a crude purified product of the title compound (18.0 g). The product was used without further purification for the next step.

MS: [M+H]⁺ 295.2.

d) 5-chloro-2-(difluoromethoxy)pyridin-3-amine

A mixture of tert-butyl 5-chloro-2-(difluoromethoxy)pyridin-3-ylcarbamate (18.0 g), TFA (20 mL) and DCM (200 mL) was stirred at room temperature overnight. The reaction mixture was concentrated under reduced pressure, and the residue was separated by HPLC (C18, mobile phase: water/acetonitrile) and concentrated under reduced pressure to give the title compound (2.61 g).

MS: [M+H]⁺ 194.6.

¹H NMR (400 MHz, DMSO-d₆) δ 5.66 (2H, brs), 7.09 (1H, d, J=2.4 Hz), 7.39 (1H, d, J=2.4 Hz), 7.60 (1H, t, J=51.2 Hz).

¹³C NMR (400 MHz, DMSO-d₆) δ 114.90 (t, J=253.0 Hz), 120.27, 127.15, 129.18, 134.09, 144.70.

e) 3-(benzylthio)-5-chloro-2-(difluoromethoxy)pyridine

Pentyl nitrite (0.293 mL) was added dropwise to a solution of 5-chloro-2-(difluoromethoxy)pyridin-3-amine (195 mg) and 1,2-dibenzyl disulfide (296 mg) in acetonitrile (2.1 mL) at 80° C. The mixture was concentrated under reduced pressure, and the residue was purified by silica gel column chromatography (ethyl acetate/hexane) to give a crude purified product of the title compound (109 mg). The product was used without further purification for the next step.

MS: [M+H]⁺ 302.0.

f) 5-chloro-2-(difluoromethoxy)pyridine-3-sulfonyl chloride

NCS (289 mg) was added to a solution of 3-(benzylthio)-5-chloro-2-(difluoromethoxy)pyridine (109 mg) in acetic acid (0.62 mL)-water (0.20 mL) at room temperature. The mixture was stirred at room temperature overnight, and the reaction mixture was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give a crude purified product of the title compound (58 mg). The product was used without further purification for the next step.

g) 5-chloro-2-(difluoromethoxy)-N-(3-ethynyl-2,4-difluorophenyl)pyridine-3-sulfonamide 5-Chloro-2-(difluoromethoxy)pyridine-3-sulfonyl chloride (58 mg) was added to a solution of 3-ethynyl-2,4-difluoroaniline (32 mg) in pyridine (0.50 mL) at room temperature. The mixture was stirred at room temperature over the weekend. To the reaction mixture was added methanol (2 mL) and the mixture was concentrated under reduced pressure. The residue was purified by silica gel column chromatography (ethyl acetate/hexane) to give a crude purified product of the title compound (52 mg). The product was used without further purification for the next step.

MS: [M−H]⁻ 393.1.

h) N-(3-((2-aminopyrimidin-5-yl)ethynyl)-2,4-difluorophenyl)-5-chloro-2-(difluoromethoxy)pyridine-3-sulfonamide A mixture of bis(di-tert-butyl(4-dimethylaminophenyl)phosphine)dichloropalladium(II) (4.5 mg), 5-chloro-2-(difluoromethoxy)-N-(3-ethynyl-2,4-difluorophenyl)pyridine-3-sulfonamide (53 mg), 5-iodopyrimidin-2-amine (39 mg), triethylamine (0.19 mL) and copper(I) iodide (2.6 mg) in DMSO (0.48 mL) was stirred under microwave irradiation at 100° C. for 1 hr. The reaction mixture was diluted with ethyl acetate and washed with water, saturated aqueous sodium hydrogen carbonate solution and saturated brine. The obtained organic layer was dried over magnesium sulfate and concentrated to give a residue. The residue was purified by silica gel column chromatography (ethyl acetate/hexane) to give the title compound as a crude purified product. The obtained crude purified product of the title compound was subjected to silica gel column chromatography (NH, methanol/ethyl acetate) to elute a byproduct. Silica gel supporting the title compound was added to ethyl acetate (20 mL), acetic acid (4 mL) and water (20 mL), and the mixture was stirred at room temperature for 10 min. The mixture was filtered and silica gel on the filter was treated 4 times with ethyl acetate/acetic acid (6 mL/1.2 mL) to elute the object product. The filtrate was diluted with ethyl acetate and washed with saturated aqueous sodium hydrogen carbonate solution. The obtained organic layer was washed with saturated brine, dried over magnesium sulfate and concentrated. The obtained crude purified product of the title compound was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The extract was dried over anhydrous magnesium sulfate and concentrated under reduced pressure to give the title compound (26.8 mg).

¹H NMR (300 MHz, DMSO-d₆) δ 7.13-7.22 (1H, m), 7.26-7.40 (3H, m), 7.49-8.00 (1H, m), 8.29 (1H, d, J=2.4 Hz), 8.43 (2H, s), 8.62 (1H, d, J=2.1 Hz), 10.75 (1H, s).

Example 163

5-chloro-N-(2,4-difluoro-3-((2-((1-methyl-1H-pyrazol-4-yl)amino)pyrimidin-5-yl)ethynyl)phenyl)-2-methylpyridine-3-sulfonamide a) 5-iodo-N-(1-methyl-1H-pyrazol-4-yl)pyrimidin-2-amine

To a solution of 2-chloro-5-iodopyrimidine (100 mg) in 2-methoxyethanol (3 mL) were added 1-methyl-1H-pyrazol-4-amine (53 mg) and TFA (0.064 mL) at room temperature. The mixture was stirred at 100° C. for 16 hr. The reaction mixture was neutralized with saturated aqueous sodium hydrogen carbonate solution at room temperature and extracted with ethyl acetate. The obtained organic layer was washed with saturated brine, dried over magnesium sulfate and concentrated to give a residue. The residue was purified by silica gel column chromatography (ethyl acetate/hexane) to give the title compound (74 mg).

¹H NMR (300 MHz, DMSO-d₆) δ 3.79 (3H, s), 7.44 (1H, s), 7.83 (1H, s), 8.55 (2H, s), 9.61 (1H, s).

b) 5-chloro-N-(2,4-difluoro-3-((2-((1-methyl-1H-pyrazol-4-yl)amino)pyrimidin-5-yl)ethynyl)phenyl)-2-methylpyridine-3-sulfonamide A mixture of 5-chloro-N-(3-ethynyl-2,4-difluorophenyl)-2-methylpyridine-3-sulfonamide (77 mg), 5-iodo-N-(1-methyl-1H-pyrazol-4-yl)pyrimidin-2-amine (74 mg), bis(tricyclohexylphosphine)palladium(II) dichloride (11 mg), cesium carbonate (291 mg) and DMSO (2 mL) was stirred at 120° C. for 16 hr. After cooling to room temperature, the reaction mixture was filtered through celite, and the filtrate was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/heptane to give the title compound (28 mg).

¹H NMR (300 MHz, DMSO-d₆) δ 2.77 (3H, s), 3.82 (3H, s), 7.15-7.27 (1H, m), 7.33 (1H, td, J=8.9, 5.9 Hz), 7.51 (1H, d, J=0.7 Hz), 7.91 (1H, s), 8.06 (1H, d, J=2.4 Hz), 8.60 (2H, s), 8.78 (1H, d, J=2.4 Hz), 10.02 (1H, s), 10.84 (1H, brs).

Example 165

N-(3-((2-aminopyrimidin-5-yl)ethynyl)-2,4-difluorophenyl)-3,6-dichloroimidazo[1,2-a]pyridine-8-sulfonamide a) 8-bromo-6-chloroimidazo[1,2-a]pyridine A mixture of 3-bromo-5-chloro-2-pyridinamine (5.0 g), bromoacetoaldehyde diethyl acetal (7.3 mL), p-toluenesulfonic acid monohydrate (498 mg) and ethanol (20 mL) was stirred at 80° C. overnight. The reaction mixture was concentrated under reduced pressure, and the residue was diluted with saturated aqueous sodium hydrogen carbonate solution and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (4.71 g).

¹H NMR (300 MHz, DMSO-d₆) δ 7.68 (1H, d, J=1.2 Hz), 7.75 (1H, d, J=1.8 Hz), 8.06 (1H, d, J=1.2 Hz), 8.91 (1H, d, J=1.8 Hz).

b) 8-(benzylthio)-6-chloroimidazo[1,2-a]pyridine

A mixture of 8-bromo-6-chloroimidazo[1,2-a]pyridine (2.50 g), benzylmercaptan (1.40 mL), tris(dibenzylideneacetone)dipalladium(0) (248 mg), 1,1'-bis(diphenylphosphino)ferrocene (298 mg), DIPEA (3.8 mL) and toluene (20 mL) was stirred under a nitrogen atmosphere at 100° C. for 2 hr. The reaction mixture was filtered to remove an insoluble material and concentrated under reduced pressure. The residue was purified by silica gel column chromatography (ethyl acetate/hexane) to give the title compound (3.01 g).

¹H NMR (300 MHz, DMSO-d₆) δ 4.47 (2H, s), 7.13 (1H, d, J=1.8 Hz), 7.22-7.39 (3H, m), 7.39-7.47 (2H, m), 7.59 (1H, d, J=1.1 Hz), 7.93 (1H, d, J=1.2 Hz), 8.64 (1H, d, J=1.9 Hz).

c) 3,6-dichloroimidazo[1,2-a]pyridine-8-sulfonic acid

To a mixture of 8-(benzylthio)-6-chloroimidazo[1,2-a]pyridine (1.50 g), acetic acid (15 mL) and water (5 mL) was added NCS (3.0 g) little by little at room temperature. The mixture was stirred at room temperature overnight. The reaction mixture was concentrated under reduced pressure, and the residue was diluted with water/ethyl acetate. The precipitate was collected by filtration, washed with water and ethyl acetate, and dried under reduced pressure to give the title compound (438 mg).

MS: [M+H]$^+$ 266.9.

$^1$H NMR (300 MHz, DMSO-d$_6$) δ 8.01 (1H, d, J=1.8 Hz), 8.40 (1H, s), 9.08 (1H, d, J=1.9 Hz).

d) 3,6-dichloroimidazo[1,2-a]pyridine-8-sulfonyl chloride

A mixture of 3,6-dichloroimidazo[1,2-a]pyridine-8-sulfonic acid (250 mg), DMF (0.3 mL) and thionyl chloride (3 mL) was heated under reflux for 4 hr. The reaction mixture was concentrated under reduced pressure, the residue was poured into saturated aqueous sodium hydrogen carbonate solution, and the mixture was extracted with ethyl acetate. The obtained organic layer was washed with saturated brine, dried over magnesium sulfate and concentrated to give a residue. The residue was purified by silica gel column chromatography (ethyl acetate/hexane) to give the title compound (135 mg).

MS: [M+H]$^+$ 284.9.

$^1$H NMR (300 MHz, DMSO-d$_6$) δ 8.05 (1H, d, J=1.9 Hz), 8.47 (1H, s), 9.13 (1H, d, J=1.9 Hz).

e) N-(3-((2-aminopyrimidin-5-yl)ethynyl)-2,4-difluorophenyl)-3,6-dichloroimidazo[1,2-a]pyridine-8-sulfonamide To a solution of 5-((3-amino-2,6-difluorophenyl)ethynyl)-N-(4-methoxybenzyl)pyrimidin-2-amine (98 mg) in pyridine (3 mL) was added a solution of 3,6-dichloroimidazo[1,2-a]pyridine-8-sulfonyl chloride (124 mg) in THF (0.5 mL) at room temperature, and the mixture was stirred at room temperature for 3 days. The reaction mixture was diluted with toluene and concentrated under reduced pressure. To the residue was added TFA (2 mL) at room temperature and the mixture was stirred at 70° C. for 2 hr. The reaction mixture was concentrated under reduced pressure, and the residue was diluted with saturated aqueous sodium hydrogen carbonate solution. The precipitate was collected by filtration and washed with water to give the title compound as a crude purified product. The obtained crude purified product of the title compound was purified by silica gel column chromatography (ethyl acetate/hexane) to give a residue. The obtained residue was washed with ethyl acetate/IPE, and dried under reduced pressure to give the title compound (64 mg).

$^1$H NMR (300 MHz, DMSO-d$_6$) δ 7.06-7.16 (1H, m), 7.22 (1H, td, J=8.8, 6.0 Hz), 7.29 (2H, s), 7.74 (1H, d, J=1.9 Hz), 7.93 (1H, s), 8.42 (2H, s), 8.95 (1H, d, J=1.9 Hz), 10.66 (1H, brs).

Example 168

5-chloro-N-(3-((3-(cyclopropylamino)-1,2,4-triazin-6-yl)ethynyl)-2,4-difluorophenyl)-3-(hydroxymethyl)-2-methoxybenzenesulfonamide a) 5-chloro-3-(N-(3-((3-chloro-1,2,4-triazin-6-yl)ethynyl)-2,4-difluorophenyl) sulfamoyl)-2-methoxybenzyl Acetate To a solution of 3-((3-((3-amino-1,2,4-triazin-6-yl)ethynyl)-2,4-difluorophenyl)sulfamoyl)-5-chloro-2-methoxybenzyl acetate (1.80 g) and copper(II) chloride (0.92 g) in DMF (5 mL)-acetonitrile (20 mL) was added dropwise amyl nitrite (1.5 mL) at room temperature. The mixture was stirred at 50° C. for 3 hr. The reaction mixture was concentrated under reduced pressure, and the residue was diluted with saturated aqueous sodium hydrogen carbonate solution at room temperature, and the mixture was extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (1.01 g).

$^1$H NMR (300 MHz, DMSO-d$_6$) δ 2.10 (3H, s), 3.82 (3H, s), 5.15 (2H, s), 7.25-7.35 (1H, m), 7.45 (1H, td, J=8.9, 6.0 Hz), 7.69 (1H, d, J=2.7 Hz), 7.79 (1H, d, J=2.7 Hz), 9.11 (1H, s), 10.50 (1H, s).

b) 5-chloro-N-(3-((3-(cyclopropylamino)-1,2,4-triazin-6-yl)ethynyl)-2,4-difluorophenyl)-3-(hydroxymethyl)-2-methoxybenzenesulfonamide A mixture of 5-chloro-3-(N-(3-((3-chloro-1,2,4-triazin-6-yl)ethynyl)-2,4-difluorophenyl)sulfamoyl)-2-methoxybenzyl acetate (250 mg), cyclopropylamine (53 mg), DIEPA (0.16 mL) and acetonitrile (3 mL) was stirred at room temperature for 1 hr. The reaction mixture was concentrated under reduced pressure to give a residue. The residue was dissolved in methanol (3 mL) and 2N aqueous sodium hydroxide solution (1 mL) was added to the obtained solution at room temperature. The mixture was stirred at the same temperature for 30 min, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (207 mg).

$^1$H NMR (300 MHz, DMSO-d$_6$) δ 0.52-0.63 (2H, m), 0.77 (2H, d, J=5.1 Hz), 2.69-3.00 (1H, m), 3.79 (3H, s), 4.60 (2H, d, J=5.7 Hz), 5.54 (1H, t, J=5.7 Hz), 7.18-7.27 (1H, m), 7.34 (1H, td, J=8.9, 6.0 Hz), 7.58 (1H, d, J=2.8 Hz), 7.74 (1H, d, J=2.8 Hz), 8.22-9.03 (2H, m), 10.35 (1H, s).

Example 171

N-(3-((2-aminopyrimidin-5-yl)ethynyl)-2,4-difluorophenyl)-5-chloro-2-(methylamino)pyridine-3-sulfonamide a) 2,5-dichloropyridine-3-sulfonyl Chloride

Thionyl chloride (8.75 mL) was added dropwise to water (50.4 mL) at 0° C. over 30 min. The mixture was stirred at room temperature for 5 hr. To the reaction mixture was added copper(I) chloride (99 mg) at room temperature, and the mixture was cooled to 0° C. to give reaction mixture A. A solution of sodium nitrite (759 mg) in water (3.06 mL) was added dropwise to a mixture of 2,5-dichloropyridin-3-amine (1.63 g) and concentrated hydrochloric acid (10 mL) at 0° C. over 30 min. The mixture was stirred at the same temperature for 10 min to give mixture B. Mixture B was added dropwise to the aforementioned reaction mixture A at 0° C. for 30 min. The obtained mixture was further stirred at the same temperature for 30 min and the precipitate was collected by filtration, washed with water and dried under reduced pressure to give the title compound (1.85 g).

$^1$H NMR (300 MHz, DMSO-$d_6$) δ 8.18 (1H, d, J=2.6 Hz), 8.46 (1H, d, J=2.6 Hz).

b) 2,5-dichloro-N-(3-ethynyl-2,4-difluorophenyl)pyridine-3-sulfonamide

A mixture of 2,5-dichloropyridine-3-sulfonyl chloride (271 mg), 3-ethynyl-2,4-difluoroaniline (153 mg) and pyridine (2.42 mL) was stirred at room temperature for 30 min. To the reaction mixture was added toluene (3 mL) and the mixture was concentrated under reduced pressure. The residue was purified by silica gel column chromatography (ethyl acetate/hexane) to give the title compound (292 mg).

$^1$H NMR (300 MHz, DMSO-$d_6$) δ 4.85 (1H, s), 7.17 (1H, td, J=9.0, 1.2 Hz), 7.36 (1H, td, J=9.0, 6.0 Hz), 8.31 (1H, d, J=2.6 Hz), 8.79 (1H, d, J=2.4 Hz), 10.98 (1H, brs).

c) 5-chloro-N-(3-ethynyl-2,4-difluorophenyl)-2-(methylamino)pyridine-3-sulfonamide A mixture of 2,5-dichloro-N-(3-ethynyl-2,4-difluorophenyl)pyridine-3-sulfonamide (116 mg), 40% aqueous methylamine solution (0.276 mL) and THF (2.59 mL) was stirred under microwave irradiation at 100° C. for 3 hr. The reaction mixture was poured into saturated aqueous sodium hydrogen carbonate solution, and the mixture was extracted with ethyl acetate. The obtained organic layer was dried over magnesium sulfate and concentrated to give a crude purified product of the title compound (116 mg). The product was used without further purification for the next step.

MS: [M+H]$^+$ 358.0.

d) N-(3-((2-aminopyrimidin-5-yl)ethynyl)-2,4-difluorophenyl)-5-chloro-2-(methylamino)pyridine-3-sulfonamide A mixture of 5-chloro-N-(3-ethynyl-2,4-difluorophenyl)-2-(methylamino)pyridine-3-sulfonamide (114 mg), 5-iodopyrimidin-2-amine (92 mg), bis(di-tert-butyl(4-dimethylaminophenyl)phosphine)dichloropalladium(II) (11 mg), copper(I) iodide (6.0 mg), triethylamine (0.45 mL) and DMSO (1.14 mL) was stirred at 100° C. for 1 hr. After cooling to room temperature, the mixture was diluted with ethyl acetate, washed with water, saturated aqueous sodium hydrogen carbonate solution and saturated brine, dried over magnesium sulfate and concentrated to give a residue. The residue was purified by silica gel column chromatography (ethyl acetate/hexane) and subjected to DMSO/methanol. The precipitate was collected by filtration and washed with methanol to give the title compound (46.9 mg).

$^1$H NMR (300 MHz, DMSO-$d_6$) δ 2.91 (3H, d, J=4.7 Hz), 6.61-6.69 (1H, m), 7.16-7.35 (4H, m), 7.70 (1H, d, J=2.6 Hz), 8.34 (1H, d, J=2.4 Hz), 8.44 (2H, s), 10.54 (1H, s).

Example 173

N-(3-((2-aminopyrimidin-5-yl)ethynyl)-2,4-difluorophenyl)-5-chloro-1-benzofuran-7-sulfonamide a) 5-chloro-2,3-dihydrobenzofuran A mixture of 2,3-dihydrobenzofuran (2.00 g), NCS (2.70 g), acetic acid (2.0 mL) and acetonitrile (20 mL) was stirred at room temperature for 2 days. The reaction mixture was diluted with a saturated aqueous sodium hydrogen carbonate solution and extracted with ethyl acetate. The obtained organic layer was washed with saturated brine, dried over magnesium sulfate and concentrated to give a residue. The residue was purified by silica gel column chromatography (ethyl acetate/hexane) to give the title compound (2.28 g).

$^1$H NMR (300 MHz, DMSO-$d_6$) δ 3.18 (2H, t, J=8.8 Hz), 4.54 (2H, t, J=8.7 Hz), 6.76 (1H, dd, J=8.5, 0.3 Hz), 7.10 (1H, ddt, J=8.4, 2.3, 0.8 Hz), 7.27 (1H, dt, J=2.1, 1.1 Hz).

b) 5-chloro-2,3-dihydrobenzofuran-7-sulfonyl chloride

5-Chloro-2,3-dihydrobenzofuran (2.22 g) was added to chlorosulfonic acid (4 mL) at 0° C., and the mixture was stirred at the same temperature for 1 hr. The reaction mixture was poured into ice water, and the mixture was extracted with ethyl acetate. The obtained organic layer was washed with saturated brine, dried over magnesium sulfate and concentrated to give a residue. The residue was purified by silica gel column chromatography (ethyl acetate/hexane) to give the title compound (2.17 g).

$^1$H NMR (300 MHz, DMSO-$d_6$) δ 3.15 (2H, t, J=8.9 Hz), 4.55 (2H, t, J=8.8 Hz), 7.23 (1H, dt, J=2.3, 1.1 Hz), 7.27-7.32 (1H, m).

c) 5-chlorobenzofuran-7-sulfonyl Chloride

A mixture of 5-chloro-2,3-dihydrobenzofuran-7-sulfonyl chloride (1.00 g), NBS (842 mg), benzoyl peroxide (96 mg) and chlorobenzene (15 mL) was stirred at 1000° C. for 1 hr. The reaction mixture was purified by silica gel column chromatography (ethyl acetate/hexane) to give the title compound (656 mg).

$^1$H NMR (300 MHz, DMSO-$d_6$) δ 6.95 (1H, d, J=2.2 Hz), 7.46 (1H, dd, J=2.2, 0.4 Hz), 7.71 (1H, d, J=2.3 Hz), 8.09 (1H, d, J=2.2 Hz).

d) N-(3-((2-aminopyrimidin-5-yl)ethynyl)-2,4-difluorophenyl)-5-chloro-1-benzofuran-7-sulfonamide To a solution of 5-((3-amino-2,6-difluorophenyl)ethynyl)-N-(4-methoxybenzyl)pyrimidin-2-amine (102 mg) in pyridine (3 mL) was added a solution of 5-chlorobenzofuran-7-sulfonyl chloride (100 mg) in THF (0.5 mL) at room temperature, and the mixture was stirred at room temperature for 1 hr. The reaction mixture was diluted with toluene and concentrated under reduced pressure. To the residue was added TFA (2 mL) at room temperature, and mixture was stirred at 70° C. for 2 hr. The reaction mixture was poured into saturated aqueous sodium hydrogen carbonate solution and extracted with ethyl acetate. The obtained organic layer was washed with saturated brine, dried over magnesium sulfate and concentrated to give a residue. The residue was purified by silica gel column chromatography (ethyl acetate/hexane) to give a residue. The residue was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The extract was dried over anhydrous magnesium sulfate and concentrated under reduced pressure to give a residue. The residue was washed with ethyl acetate/IPE and dried under reduced pressure to give the title compound (39 mg).

$^1$H NMR (300 MHz, DMSO-$d_6$) δ 7.11 (1H, d, J=2.3 Hz), 7.13-7.26 (2H, m), 7.30 (2H, s), 7.56 (1H, d, J=2.1 Hz), 8.09 (1H, d, J=2.1 Hz), 8.19 (1H, d, J=2.3 Hz), 8.41 (2H, s), 10.72 (1H, s).

Example 174

5-chloro-N-(2,4-difluoro-3-((2-((trans-4-hydroxycyclohexyl)amino)pyrimidin-5-yl)ethynyl)phenyl)-2-methoxypyridine-3-sulfonamide a) 5-chloro-N-(3-((2-chloropyrimidin-5-yl)ethynyl)-2,4-difluorophenyl)-2-methoxypyridine-3-sulfonamide A mixture of 5-chloro-N-(3-ethynyl-2,4-difluorophenyl)-2-methoxypyridine-3-sulfonamide (359 mg), dichlorobis(tricyclohexylphosphine)palladium(II) (74 mg), DIPEA (2.62 mL), copper(I) iodide (38 mg), 2-chloro-5-iodopyrimidine (313 mg) and DMSO (2.84 mL) was stirred at 60° C. for 1 hr. After cooling to room temperature, the reaction mixture was diluted with water and extracted with ethyl acetate. The obtained organic layer was washed with saturated aqueous sodium hydrogen carbonate solution and saturated brine, dried over magnesium sulfate and concentrated to give a residue. The residue was purified by silica gel column chromatography (ethyl acetate/hexane) to give a crude purified product of the title compound (393 mg). The product was used without further purification for the next step.

MS: [M+H]$^+$ 471.0.

b) 5-chloro-N-(2,4-difluoro-3-((2-((trans-4-hydroxycyclohexyl)amino)pyrimidin-5-yl)ethynyl)phenyl)-2-methoxypyridine-3-sulfonamide A mixture of 5-chloro-N-(3-((2-chloropyrimidin-5-yl)ethynyl)-2,4-difluorophenyl)-2-methoxypyridine-3-sulfonamide (100 mg), trans-4-aminocyclohexanol (48.9 mg), DIPEA (0.074 mL) and acetonitrile (1.12 mL) was stirred at 60° C. for 5 hr. The reaction mixture was concentrated under reduced pressure, and the residue was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The extract was dried over anhydrous magnesium sulfate and concentrated under reduced pressure to give a residue. The residue was washed with ethyl acetate/hexane to give the title compound (64.6 mg).

$^1$H NMR (300 MHz, DMSO-$d_6$) δ 1.18-1.38 (4H, m), 1.77-1.92 (4H, m), 3.34-3.45 (1H, m), 3.62-3.75 (1H, m), 3.92 (3H, s), 4.55 (1H, d, J=4.3 Hz), 7.10-7.20 (1H, m), 7.24-7.36 (1H, m), 7.73 (1H, d, J=8.1 Hz), 8.05 (1H, d, J=2.4 Hz), 8.40-8.53 (3H, m), 10.45 (1H, s).

Example 175

5-chloro-N-(2,4-difluoro-3-((2-(((2R)-1-hydroxypropan-2-yl)amino)pyrimidin-5-yl)ethynyl)phenyl)-2-methoxypyridine-3-sulfonamide A mixture of 5-chloro-N-(3-((2-chloropyrimidin-5-yl)ethynyl)-2,4-difluorophenyl)-2-methoxypyridine-3-sulfonamide (100 mg), (R)-2-aminopropan-1-ol (31.9 mg), DIPEA (0.074 mL) and acetonitrile (1.11 mL) was stirred at 60° C. for 3 hr. The reaction mixture was concentrated under reduced pressure, and the residue was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The extract was dried over anhydrous magnesium sulfate and concentrated under reduced pressure to give a residue. The residue was washed with ethyl acetate/hexane to give the title compound (64.6 mg).

$^1$H NMR (300 MHz, DMSO-$d_6$) δ 1.12 (3H, d, J=6.6 Hz), 3.46 (1H, dt, J=10.7, 5.6 Hz), 3.89-4.08 (5H, m), 4.71 (1H, t, J=5.7 Hz), 7.12-7.21 (1H, m), 7.31 (1H, td, J=8.9, 6.0 Hz), 7.55 (1H, d, J=8.1 Hz), 8.06 (1H, d, J=2.6 Hz), 8.44-8.52 (3H, m), 10.45 (1H, s).

Example 176

2,5-dichloro-N-(2,4-difluoro-3-((2-((trans-4-hydroxycyclohexyl)amino)pyrimidin-5-yl)ethynyl)phenyl)-3-(hydroxymethyl)benzenesulfonamide a) ethyl 3-(benzylthio)-2,5-dichlorobenzoate Amyl nitrite (8 mL) was added dropwise to a solution of ethyl 3-amino-2,5-dichlorobenzoate (5.0 g) and 1,2-dibenzyl disulfide (6.32 g) in acetonitrile (60 mL) at 70° C. The mixture was stirred at 70° C. for 1 hr. The same reaction was repeated 4 times in total, and the reaction mixtures were combined and concentrated under reduced pressure. The residue was purified by silica gel column chromatography (NH, ethyl acetate/hexane) to give a residue. The obtained residue was washed with hexane to give the title compound (9.81 g).

$^1$H NMR (300 MHz, DMSO-$d_6$) δ 1.31 (3H, t, J=7.1 Hz), 4.32 (2H, q, J=7.1 Hz), 4.42 (2H, s), 7.25-7.39 (3H, m), 7.42-7.48 (2H, m), 7.57 (1H, d, J=2.4 Hz), 7.63 (1H, d, J=2.4 Hz).

b) (3-(benzylthio)-2,5-dichlorophenyl)methanol

To a solution of calcium chloride (6.37 g) in ethanol (70 mL) was added sodium borohydride (4.35 g) at 0° C., and the mixture was stirred at the same temperature for 20 min. To the reaction mixture were added a solution of ethyl 3-(benzylthio)-2,5-dichlorobenzoate (9.80 g) in THF (70 mL), and the mixture was stirred at 0° C. for 10 min and at room temperature for 2 hr. The reaction mixture was quenched with saturated aqueous ammonium chloride solution at 0° C. and extracted with ethyl acetate. The obtained organic layer was washed with saturated brine, dried over magnesium sulfate and concentrated to give a crude purified product of the title compound (8.42 g). The product was used without further purification for the next step.

$^1$H NMR (300 MHz, DMSO-$d_6$) δ 4.37 (2H, s), 4.52 (2H, d, J=5.8 Hz), 5.57 (1H, t, J=5.8 Hz), 7.26-7.38 (5H, m), 7.41-7.46 (2H, m).

c) 3-(benzylthio)-2,5-dichlorobenzyl acetate

To a solution of (3-(benzylthio)-2,5-dichlorophenyl)methanol (8.41 g), DMAP (0.687 g) and triethylamine (8 mL) in THF (70 mL) was added dropwise acetic anhydride (3.2 mL) at room temperature. The reaction mixture was stirred at 50° C. for 2 hr. The reaction mixture was diluted with water at room temperature and extracted with ethyl acetate. The obtained organic layer was washed with saturated brine, dried over magnesium sulfate and concentrated to give a residue. The residue was purified by silica gel column chromatography (ethyl acetate/hexane) to give the title compound (8.15 g).

$^1$H NMR (300 MHz, DMSO-$d_6$) δ 2.10 (3H, s), 4.39 (2H, s), 5.11 (2H, s), 7.24-7.40 (4H, m), 7.41-7.49 (3H, m).

d) 2,5-dichloro-3-(chlorosulfonyl)benzyl acetate

NCS (12.7 g) was added to a solution of 3-(benzylthio)-2,5-dichlorobenzyl acetate (8.13 g) in acetic acid (40 mL)-THF (10 mL)-water (10 mL) at 0° C. The mixture was stirred at room temperature for 1 hr, and the reaction mixture was concentrated under reduced pressure. The residue was diluted with water and extracted with ethyl acetate. The obtained organic layer was washed with saturated brine, dried over magnesium sulfate and concentrated to give a residue. The residue was purified by silica gel column chromatography (ethyl acetate/hexane) to give the title compound (7.50 g).

$^1$H NMR (300 MHz, DMSO-$d_6$) δ 2.12 (3H, s), 5.14 (2H, s), 7.52 (1H, d, J=2.6 Hz), 7.85 (1H, d, J=2.8 Hz).

e) 2,5-dichloro-3-(N-(3-ethynyl-2,4-difluorophenyl)sulfamoyl)benzyl Acetate To a solution of 3-ethynyl-2,4-difluoroaniline (3.30 g) in pyridine (30 mL) was added a solution of 2,5-dichloro-3-(chlorosulfonyl)benzyl acetate (7.50 g) in THF (10 mL) at 70° C. The mixture was stirred at the same temperature for 1 hr and concentrated under reduced pressure. The residue was diluted with 1N hydrochloric acid at room temperature and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with IPE to give the title compound (7.46 g).

$^1$H NMR (300 MHz, DMSO-$d_6$) δ 2.13 (3H, s), 4.86 (1H, s), 5.22 (2H, s), 7.13-7.22 (1H, m), 7.32 (1H, td, J=8.9, 5.9 Hz), 7.84-7.87 (1H, m), 7.88-7.91 (1H, m), 10.78 (1H, s).

f) 2,5-dichloro-3-(N-(3-((2-chloropyrimidin-5-yl)ethynyl)-2,4-difluorophenyl)sulfamoyl)benzyl acetate A mixture of 2,5-dichloro-3-(N-(3-ethynyl-2,4-difluorophenyl)sulfamoyl)benzyl acetate (1.45 g), dichlorobis(tricyclohexylphosphine)palladium(II) (246 mg), DIPEA (9 mL), copper(I) iodide (127 mg), 2-chloro-5-iodopyrimidin-2-amine (1.04 g) and DMSO (10 mL) was stirred under microwave irradiation at 60° C. for 1 hr. The same reaction was repeated twice in total, the reaction mixtures were combined, cooled to room temperature, diluted with water and ethyl acetate and an insoluble material was removed by filtration. The filtrate was extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (2.60 g).

$^1$H NMR (300 MHz, DMSO-$d_6$) δ 2.12 (3H, s), 5.23 (2H, s), 7.21-7.31 (1H, m), 7.41 (1H, td, J=8.9, 5.9 Hz), 7.86-7.93 (2H, m), 9.03 (2H, s), 10.89 (1H, s).

g) 2,5-dichloro-3-(N-(2,4-difluoro-3-((2-(trans-4-hydroxycyclohexyl)amino)pyrimidin-5-yl)ethynyl)phenyl)sulfamoyl)benzyl Acetate A mixture of 2,5-dichloro-3-(N-(3-((2-chloropyrimidin-5-yl)ethynyl)-2,4-difluorophenyl)sulfamoyl)benzyl acetate (300 mg), trans-4-aminocyclohexanol hydrochloride (125 mg), DIPEA (0.20 mL) and THF (4 mL) was stirred at 700° C. for 2 hr. The reaction mixture was diluted with saturated aqueous sodium hydrogen carbonate solution at room temperature and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) to give the title compound (243 mg).

MS: [M+H]$^+$ 625.1.

h) 2,5-dichloro-N-(2,4-difluoro-3-((2-((trans-4-hydroxycyclohexyl)amino)pyrimidin-5-yl)ethynyl)phenyl)-3-(hydroxymethyl)benzenesulfonamide To a solution of 2,5-dichloro-3-(N-(2,4-difluoro-3-((2-(trans-4-hydroxycyclohexyl)amino)pyrimidin-5-yl)ethynyl)phenyl)sulfamoyl)benzyl acetate (243 mg) in methanol (4 mL) was added 2N aqueous sodium hydroxide solution (1 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (103 mg).

$^1$H NMR (300 MHz, DMSO-$d_6$) δ 1.14-1.40 (4H, m), 1.78-1.92 (4H, m), 3.35-3.47 (1H, m), 3.61-3.78 (1H, m), 4.51-4.59 (1H, m), 4.63 (2H, d, J=5.4 Hz), 5.75 (1H, t, J=5.6 Hz), 7.13-7.22 (1H, m), 7.22-7.32 (1H, m), 7.73 (1H, d, J=8.0 Hz), 7.77-7.83 (2H, m), 8.40-8.54 (2H, m), 10.72 (1H, s).

Example 177

2,5-dichloro-N-(2,4-difluoro-3-((3-((trans-4-hydroxycyclohexyl)amino)-1,2,4-triazin-6-yl)ethynyl)phenyl)-3-(hydroxymethyl)benzenesulfonamide a) 3-(N-(3-((3-amino-1,2,4-triazin-6-yl)ethynyl)-2,4-difluorophenyl)sulfamoyl)-2,5-dichlorobenzyl Acetate A mixture of 2,5-dichloro-3-(N-(3-ethynyl-2,4-difluorophenyl)sulfamoyl)benzyl acetate (4.50 g), dichlorobis(tricyclohexylphosphine)palladium(II) (765 mg), DIPEA (27 mL), copper(I) iodide (395 mg), 6-bromo-1,2,4-triazin-3-amine (2.36 g) and DMSO (30 mL) was stirred under microwave irradiation at 100° C. for 1 hr. After cooling to room temperature, the reaction mixture was diluted with water and ethyl acetate, and an insoluble material was removed by filtration. The filtrate was extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (2.78 g).

$^1$H NMR (300 MHz, DMSO-$d_6$) δ 2.12 (3H, s), 5.22 (2H, s), 7.18-7.30 (1H, m), 7.37 (1H, td, J=8.9, 5.9 Hz), 7.69-8.04 (4H, m), 8.44 (1H, s), 10.86 (1H, s).

b) 2,5-dichloro-3-(N-(3-((3-chloro-1,2,4-triazin-6-yl)ethynyl)-2,4-difluorophenyl)sulfamoyl)benzyl Acetate To a solution of 3-(N-(3-((3-amino-1,2,4-triazin-6-yl)ethynyl)-2,4-difluorophenyl)sulfamoyl)-2,5-dichlorobenzyl acetate (2.45 g) and copper(II) chloride (1.25 g) in DMF (5 mL)-acetonitrile (20 mL) was added dropwise amyl nitrite (1.9 mL) at room temperature. The mixture was stirred at 50° C. for 3 hr. The reaction mixture was concentrated under reduced pressure, and the residue was diluted with saturated aqueous sodium hydrogen carbonate solution at room temperature and extracted with ethyl acetate. The obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (1.28 g).

$^1$H NMR (300 MHz, DMSO-$d_6$) δ 2.13 (3H, s), 5.22 (2H, s), 7.31 (1H, td, J=8.9, 1.5 Hz), 7.48 (1H, td, J=9.0, 5.9 Hz), 7.88-7.93 (2H, m), 9.11 (1H, s), 10.95 (1H, brs).

c) 2,5-dichloro-3-(N-(2,4-difluoro-3-((3-(trans-4-hydroxycyclohexyl)amino)-1,2,4-triazin-6-yl)ethynyl)phenyl)sulfamoyl)benzyl Acetate A mixture of 2,5-dichloro-3-(N-(3-((3-chloro-1,2,4-triazin-6-yl)ethynyl)-2,4-difluorophenyl)sulfamoyl)benzyl acetate (300 mg), DIPEA (0.2 mL), trans-4-aminocyclohexanol hydrochloride (125 mg) and THF (4 mL) was stirred at 60° C. for 1 hr. The reaction mixture was diluted with saturated aqueous sodium hydrogen carbonate solution at room temperature and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) to give the title compound (207 mg).

MS: [M+H]$^+$ 626.0.

d) 2,5-dichloro-N-(2,4-difluoro-3-((3-((trans-4-hydroxycyclohexyl)amino)-1,2,4-triazin-6-yl)ethynyl)phenyl)-3-(hydroxymethyl)benzenesulfonamide To a solution of 2,5-dichloro-3-(N-(2,4-difluoro-3-((3-(trans-4-hydroxycyclohexyl)amino)-1,2,4-triazin-6-yl)ethynyl)phenyl)sulfamoyl)benzyl acetate (275 mg) in methanol (4 mL) was added 2N aqueous sodium hydroxide solution (1.5 mL) at room temperature. The mixture was stirred at the same temperature for 1 hr and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (172 mg).

$^1$H NMR (300 MHz, DMSO-$d_6$) δ 1.25-1.44 (4H, m), 1.79-1.96 (4H, m), 3.37-3.48 (1H, m), 3.63-3.96 (1H, m), 4.57 (1H, brs), 4.63 (2H, d, J=4.9 Hz), 5.75 (1H, t, J=5.6 Hz), 7.20-7.28 (1H, m), 7.36 (1H, td, J=8.9, 6.0 Hz), 7.78-7.84 (2H, m), 8.04-8.67 (2H, m), 10.79 (1H, s).

Example 178

2,5-dichloro-N-(2,4-difluoro-3-((3-(((2R)-1-hydroxypropan-2-yl)amino)-1,2,4-triazin-6-yl)ethynyl)phenyl)-3-(hydroxymethyl)benzenesulfonamide a) (R)-2,5-dichloro-3-(N-(2,4-difluoro-3-((3-((1-hydroxypropan-2-yl)amino)-1,2,4-triazin-6-yl)ethynyl)phenyl)sulfamoyl)benzyl Acetate A mixture of 2,5-dichloro-3-(N-(3-((3-chloro-1,2,4-triazin-6-yl)ethynyl)-2,4-difluorophenyl)sulfamoyl)benzyl acetate (300 mg), (R)-2-aminopropan-1-ol (62 mg), DIPEA (0.2 mL) and THF (4 mL) was stirred at room temperature for 2 hr. The reaction mixture was diluted with water at room temperature and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) to give the title compound (279 mg).

MS: [M+H]$^+$ 586.1.

b) 2,5-dichloro-N-(2,4-difluoro-3-((3-(((2R)-1-hydroxypropan-2-yl)amino)-1,2,4-triazin-6-yl)ethynyl)phenyl)-3-(hydroxymethyl)benzenesulfonamide To a solution of (R)-2,5-dichloro-3-(N-(2,4-difluoro-3-((3-((1-hydroxypropan-2-yl)amino)-1,2,4-triazin-6-yl)ethynyl)phenyl)sulfamoyl)benzyl acetate (279 mg) in methanol (4 mL) was added 2N aqueous sodium hydroxide solution (1.5 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (139 mg).

$^1$H NMR (300 MHz, DMSO-$d_6$) δ 1.15-1.19 (3H, m), 3.35-3.43 (1H, m), 3.44-3.55 (1H, m), 3.87-4.31 (1H, m), 4.63 (2H, d, J=5.2 Hz), 4.77 (1H, brs), 5.75 (1H, t, J=5.6 Hz), 7.19-7.28 (1H, m), 7.36 (1H, td, J=8.9, 5.9 Hz), 7.78-7.83 (2H, m), 7.83-8.45 (1H, m), 8.47 (1H, s), 10.79 (1H, s).

Example 179

2,5-dichloro-N-(2,4-difluoro-3-((3-(oxetan-3-ylamino)-1,2,4-triazin-6-yl)ethynyl)phenyl)-3-(hydroxymethyl)benzenesulfonamide a) 2,5-dichloro-3-(N-(2,4-difluoro-3-((3-(oxetan-3-ylamino)-1,2,4-triazin-6-yl)ethynyl)phenyl)sulfamoyl)benzyl Acetate A mixture of 2,5-dichloro-3-(N-(3-((3-chloro-1,2,4-triazin-6-yl)ethynyl)-2,4-difluorophenyl)sulfamoyl)benzyl acetate (300 mg), oxetan-3-amine (60 mg), DIPEA (0.2 mL) and THF (4 mL) was stirred at room temperature for 2 hr. The reaction mixture was diluted with water at room temperature and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) to give the title compound (277 mg).

MS: [M+H]⁺ 584.0.

b) 2,5-dichloro-N-(2,4-difluoro-3-((3-(oxetan-3-ylamino)-1,2,4-triazin-6-yl)ethynyl)phenyl)-3-(hydroxymethyl)benzenesulfonamide To a solution of 2,5-dichloro-3-(N-(2,4-difluoro-3-((3-(oxetan-3-ylamino)-1,2,4-triazin-6-yl)ethynyl)phenyl)sulfamoyl)benzyl acetate (277 mg) in methanol (4 mL) was added 2N aqueous sodium hydroxide solution (1.5 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (175 mg).

¹H NMR (300 MHz, DMSO-d₆) δ 4.58 (2H, t, J=6.4 Hz), 4.63 (2H, d, J=4.3 Hz), 4.81 (2H, t, J=6.0 Hz), 4.89-5.17 (1H, m), 5.75 (1H, t, J=5.3 Hz), 7.18-7.30 (1H, m), 7.38 (1H, td, J=8.9, 6.0 Hz), 7.75-7.87 (2H, m), 8.53 (1H, s), 8.80-9.52 (1H, m), 10.80 (1H, s).

Example 180

2,5-dichloro-N-(2,4-difluoro-3-((2-(((2R)-1-hydroxypropan-2-yl)amino)pyrimidin-5-yl)ethynyl)phenyl)-3-(hydroxymethyl)benzenesulfonamide A mixture of 2,5-dichloro-3-(N-(3-((2-chloropyrimidin-5-yl)ethynyl)-2,4-difluorophenyl)sulfamoyl)benzyl acetate (300 mg), (R)-2-aminopropan-1-ol (62 mg), DIPEA (0.2 mL) and THF (4 mL) was stirred at 60° C. overnight. The reaction mixture was diluted with water at room temperature and extracted with ethyl acetate. The obtained organic layer was washed with saturated brine, dried over anhydrous magnesium sulfate and concentrated under reduced pressure to give a residue. The residue was dissolved in methanol (4 mL), and 2N aqueous sodium hydroxide solution (1.5 mL) was added to the obtained solution at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (209 mg).

¹H NMR (300 MHz, DMSO-d₆) δ 1.13 (3H, d, J=6.8 Hz), 3.26-3.37 (1H, m), 3.46 (1H, dt, J=10.6, 5.3 Hz), 3.95-4.08 (1H, m), 4.63 (2H, d, J=5.5 Hz), 4.72 (1H, t, J=5.6 Hz), 5.76 (1H, t, J=5.7 Hz), 7.13-7.22 (1H, m), 7.27 (1H, td, J=8.8, 5.9 Hz), 7.56 (1H, d, J=8.1 Hz), 7.77-7.83 (2H, m), 8.47 (2H, brs), 10.73 (1H, brs).

By stirring a mixture of 2,5-dichloro-3-(N-(3-((2-chloropyrimidin-5-yl)ethynyl)-2,4-difluorophenyl)sulfamoyl)benzyl acetate (300 mg), (S)-2-aminopropan-1-ol (82 mg), DIPEA (0.2 mL) and THF (3 mL) at 60° C. for 6 hr and treating the obtained reaction mixture in the same manner as above, an isomer of Example 180, 2,5-dichloro-N-(2,4-difluoro-3-((2-(((2S)-1-hydroxypropan-2-yl)amino)pyrimidin-5-yl)ethynyl)phenyl)-3-(hydroxymethyl)benzenesulfonamide (Example 180a; 235 mg), was obtained.

¹H NMR (300 MHz, DMSO-d₆) δ 1.13 (3H, d, J=6.6 Hz), 3.26-3.38 (1H, m), 3.41-3.51 (1H, m), 3.96-4.05 (1H, m), 4.63 (2H, d, J=5.2 Hz), 4.72 (1H, brs), 5.76 (1H, t, J=5.7 Hz), 7.13-7.33 (2H, m), 7.57 (1H, d, J=8.2 Hz), 7.76-7.85 (2H, m), 8.47 (2H, brs), 10.74 (1H, brs).

Example 181

2,5-dichloro-N-(2,4-difluoro-3-((2-(oxetan-3-ylamino)pyrimidin-5-yl)ethynyl)phenyl)-3-(hydroxymethyl)benzenesulfonamide A mixture of 2,5-dichloro-3-(N-(3-((2-chloropyrimidin-5-yl)ethynyl)-2,4-difluorophenyl)sulfamoyl)benzyl acetate (300 mg), oxetan-3-amine (60 mg), DIPEA (0.2 mL) and THF (4 mL) was stirred at 60° C. overnight. The reaction mixture was diluted with water at room temperature and extracted with ethyl acetate. The obtained organic layer was washed with saturated brine, dried over anhydrous magnesium sulfate and concentrated under reduced pressure to give a residue. The residue was dissolved in methanol (4 mL), and 2N aqueous sodium hydroxide solution (1.5 mL) was added to the obtained solution at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (243 mg).

¹H NMR (300 MHz, DMSO-d₆) δ 4.53 (2H, t, J=6.4 Hz), 4.63 (2H, d, J=5.0 Hz), 4.77 (2H, t, J=6.8 Hz), 4.88-5.03 (1H, m), 5.75 (1H, t, J=5.6 Hz), 7.14-7.23 (1H, m), 7.29 (1H, td, J=8.8, 5.9 Hz), 7.77-7.80 (1H, m), 7.80-7.83 (1H, m), 8.51 (2H, s), 8.58 (1H, d, J=6.0 Hz), 10.73 (1H, s).

Example 182

5-chloro-N-(2,4-difluoro-3-((2-((trans-4-hydroxycyclohexyl)amino)pyrimidin-5-yl)ethynyl)phenyl)-2-(methylamino)pyridine-3-sulfonamide a) 5-chloro-N-(3-((2-chloropyrimidin-5-yl)ethynyl)-2,4-difluorophenyl)-2-(methylamino)pyridine-3-sulfonamide A mixture of 5-chloro-N-(3-ethynyl-2,4-difluorophenyl)-2-(methylamino)pyridine-3-sulfonamide (321 mg), dichlorobis(tricyclohexylphosphine)palladium(II) (66 mg), DIPEA (2.35 mL), copper(I) iodide (34 mg), 2-chloro-5-iodopyrimidine (280 mg) and DMSO (2.55 mL) was stirred at 60° C. for 1 hr. After cooling to room temperature, the reaction mixture was diluted with ethyl acetate, washed with saturated aqueous sodium hydrogen carbonate solution and saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (256 mg).

¹H NMR (300 MHz, DMSO-d₆) δ 2.91 (3H, d, J=4.5 Hz), 6.62-6.70 (1H, m), 7.23-7.31 (1H, m), 7.41 (1H, td, J=8.9, 6.0 Hz), 7.72 (1H, d, J=2.6 Hz), 8.34 (1H, d, J=2.4 Hz), 9.03 (2H, s), 10.62 (1H, brs).

b) 5-chloro-N-(2,4-difluoro-3-((2-((trans-4-hydroxycyclohexyl)amino)pyrimidin-5-yl)ethynyl)phenyl)-2-(methylamino)pyridine-3-sulfonamide A mixture of 5-chloro-N-(3-((2-chloropyrimidin-5-yl)ethynyl)-2,4-difluorophenyl)-2-(methylamino)pyridine-3- sulfonamide (128 mg), trans-4-aminocyclohexanol (62.7 mg), DIPEA (0.095 mL) and acetonitrile (1.4 mL) was stirred at 60° C. for 8 hr. The reaction mixture was concentrated under reduced pressure, and the residue was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The extract was dried over anhydrous magnesium sulfate and concentrated under reduced pressure to give a residue. The residue was washed with ethyl acetate/hexane to give the title compound (49.5 mg).

$^1$H NMR (300 MHz, DMSO-d$_6$) δ 1.14-1.39 (4H, m), 1.75-1.93 (4H, m), 2.87 (3H, d, J=4.9 Hz), 3.28-3.46 (2H, m), 3.60-3.76 (1H, m), 4.56 (1H, d, J=4.3 Hz), 6.85 (1H, t, J=8.0 Hz), 7.10-7.23 (2H, m, J=6.2 Hz), 7.63-7.68 (2H, m), 8.07 (1H, d, J=2.6 Hz), 8.43 (2H, brs).

Example 183

5-chloro-N-(2,4-difluoro-3-((2-(((2R)-1-hydroxypropan-2-yl)amino)pyrimidin-5-yl)ethynyl)phenyl)-2-(methylamino)pyridine-3-sulfonamide A mixture of 5-chloro-N-(3-((2-chloropyrimidin-5-yl)ethynyl)-2,4-difluorophenyl)-2-(methylamino)pyridine-3-sulfonamide (128 mg), (R)-2-aminopropan-1-ol (40.9 mg), DIPEA (0.095 mL) and acetonitrile (1.4 mL) was stirred at 60° C. for 6 hr. The reaction mixture was concentrated under reduced pressure, and the residue was separated by HPLC (C18, mobile phase: water/acetonitrile (0.1% TFA-containing system)). To the obtained fraction was added a saturated aqueous sodium hydrogen carbonate solution, and the mixture was extracted with ethyl acetate. The extract was dried over anhydrous magnesium sulfate and concentrated under reduced pressure to give a residue. The residue was washed with ethyl acetate/hexane to give the title compound (86.7 mg).

$^1$H NMR (300 MHz, DMSO-d$_6$) δ 1.12 (3H, d, J=6.6 Hz), 2.90 (3H, d, J=4.7 Hz), 3.25-3.35 (1H, m), 3.46 (1H, dt, J=10.6, 5.5 Hz), 3.94-4.07 (1H, m), 4.72 (1H, t, J=5.7 Hz), 6.82-6.91 (1H, m), 7.00-7.11 (1H, m), 7.24 (1H, td, J=9.0, 6.0 Hz), 7.53 (1H, d, J=8.1 Hz), 7.69 (1H, d, J=2.4 Hz), 8.23 (1H, d, J=2.4 Hz), 8.46 (2H, brs), 10.55 (1H, brs).

Example 184

5-chloro-N-(2,4-difluoro-3-((2-(((2R)-1-hydroxypropan-2-yl)amino)pyrimidin-5-yl)ethynyl)phenyl)-3-hydroxy-2,3-dihydro-1-benzofuran-7-sulfonamide a) 5-chloro-7-(N-(3-((2-chloropyrimidin-5-yl)ethynyl)-2,4-difluorophenyl)sulfamoyl)-2,3-dihydrobenzofuran-3-yl Acetate A mixture of 5-chloro-7-(N-(3-ethynyl-2,4-difluorophenyl)sulfamoyl)-2,3-dihydrobenzofuran-3-yl acetate (2.44 g), dichlorobis(tricyclohexylphosphine)palladium(II) (421 mg), DIPEA (16 mL), copper(I) iodide (217 mg), 2-chloro-5-iodopyrimidine (1.65 g) and DMSO (16 mL) was stirred under microwave irradiation at 60° C. for 1 hr. After cooling to room temperature, the reaction mixture was diluted with water and ethyl acetate and an insoluble material was removed by filtration. The filtrate was extracted with ethyl acetate, and the obtained organic layer was washed with saturated brine, dried over magnesium sulfate and concentrated to give a residue. The residue was purified by silica gel column chromatography (ethyl acetate/hexane) to give a residue. The obtained residue was washed with ethyl acetate/IPE to give the title compound (2.33 g).

$^1$H NMR (300 MHz, DMSO-d$_6$) δ 2.03 (3H, s), 4.60-4.69 (1H, m), 4.71-4.81 (1H, m), 6.25 (1H, dd, J=6.4, 2.3 Hz), 7.21-7.31 (1H, m), 7.37 (1H, td, J=8.9, 6.0 Hz), 7.58 (1H, d, J=2.3 Hz), 7.80 (1H, d, J=2.1 Hz), 9.04 (2H, s), 10.56 (1H, s).

b) 5-chloro-7-(N-(2,4-difluoro-3-((2-(((R)-1-hydroxypropan-2-yl)amino)pyrimidin-5-yl)ethynyl)phenyl)sulfamoyl)-2,3-dihydrobenzofuran-3-yl Acetate A mixture of 5-chloro-7-(N-(3-((2-chloropyrimidin-5-yl)ethynyl)-2,4-difluorophenyl)sulfamoyl)-2,3-dihydrobenzofuran-3-yl acetate (600 mg), (R)-2-aminopropan-1-ol (125 mg), DIPEA (0.4 mL) and THF (6 mL) was stirred at 70° C. for 2 hr. The reaction mixture was diluted with water at room temperature and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) to give the title compound (628 mg).

MS: [M+H]$^+$ 579.1.

c) 5-chloro-N-(2,4-difluoro-3-((2-(((2R)-1-hydroxypropan-2-yl)amino)pyrimidin-5-yl)ethynyl)phenyl)-3-hydroxy-2,3-dihydro-1-benzofuran-7-sulfonamide To a solution of 5-chloro-7-(N-(2,4-difluoro-3-((2-(((R)-1-hydroxypropan-2-yl)amino)pyrimidin-5-yl)ethynyl)phenyl)sulfamoyl)-2,3-dihydrobenzofuran-3-yl acetate (628 mg) in methanol (5 mL) was added 2N aqueous sodium hydroxide solution (2.5 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (417 mg).

$^1$H NMR (300 MHz, DMSO-d$_6$) δ 1.13 (3H, d, J=6.7 Hz), 3.26-3.38 (1H, m), 3.46 (1H, dt, J=10.7, 5.5 Hz), 3.94-4.09 (1H, m), 4.36 (1H, dd, J=10.3, 3.1 Hz), 4.61 (1H, dd, J=10.3, 6.8 Hz), 4.72 (1H, t, J=5.7 Hz), 5.28-5.39 (1H, m), 5.94 (1H, d, J=5.5 Hz), 7.11-7.29 (2H, m), 7.47 (1H, d, J=2.3 Hz), 7.56 (1H, d, J=8.2 Hz), 7.68 (1H, d, J=2.0 Hz), 8.47 (2H, brs), 10.37 (1H, s).

Example 185

5-chloro-N-(2,4-difluoro-3-((2-((trans-4-hydroxycyclohexyl)amino)pyrimidin-5-yl)ethynyl)phenyl)-3-hydroxy-2,3-dihydro-1-benzofuran-7-sulfonamide a) 5-chloro-7-(N-(2,4-difluoro-3-(2-((trans-4-hydroxycyclohexyl)amino)pyrimidin-5-yl)ethynyl)phenyl)sulfamoyl)-2,3-dihydrobenzofuran-3-yl Acetate A mixture of 5-chloro-7-(N-(3-((2-chloropyrimidin-5-yl)ethynyl)-2,4-difluorophenyl)sulfamoyl)-2,3-dihydrobenzofuran-3-yl acetate (600 mg), trans-4-aminocyclohexanol (192 mg), DIPEA (0.4 mL) and THF (6 mL) was stirred at 60° C. for 1 hr. The reaction mixture was diluted with saturated aqueous sodium hydrogen carbonate solution at room temperature and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) to give the title compound (538 mg).

MS: [M+H]$^+$ 619.1.

b) 5-chloro-N-(2,4-difluoro-3-((2-((trans-4-hydroxycyclohexyl)amino)pyrimidin-5-yl)ethynyl)phenyl)-3-hydroxy-2,3-dihydro-1-benzofuran-7-sulfonamide To a solution of 5-chloro-7-(N-(2,4-difluoro-3-((2-((trans-4-hydroxycyclohexyl)amino)pyrimidin-5-yl)ethynyl)phenyl)sulfamoyl)-2,3-dihydrobenzofuran-3-yl acetate (538 mg) in methanol (5 mL) was added 2N aqueous sodium hydroxide solution (2 mL) at room temperature. The mixture was stirred at the same temperature for 1 hr, and the reaction mixture was neutralized with 1N hydrochloric acid and extracted with ethyl acetate. The obtained organic layer was washed with saturated brine, dried over magnesium sulfate and concentrated to give a residue. The obtained residue was washed with ethyl acetate/IPE to give the title compound (363 mg).

$^1$H NMR (300 MHz, DMSO-d$_6$) δ 1.17-1.37 (4H, m), 1.77-1.94 (4H, m), 3.34-3.46 (1H, m), 3.64-3.77 (1H, m), 4.36 (1H, dd, J=10.2, 3.2 Hz), 4.56 (1H, d, J=4.3 Hz), 4.61 (1H, dd, J=10.3, 6.9 Hz), 5.28-5.37 (1H, m), 5.94 (1H, d, J=5.6 Hz), 7.12-7.29 (2H, m), 7.47 (1H, d, J=2.3 Hz), 7.68 (1H, d, J=2.0 Hz), 7.74 (1H, d, J=8.0 Hz), 8.46 (2H, d, J=12.2 Hz), 10.37 (1H, s).

Example 186

5-chloro-N-(2,4-difluoro-3-((2-(((2R)-1-hydroxypropan-2-yl)amino)pyrimidin-5-yl)ethynyl)phenyl)-3-hydroxy-2,3-dihydro-1-benzofuran-7-sulfonamide (Optical Isomer not Having Absolute Configuration of the Dihydrobenzofuran Ring Moiety)

5-chloro-N-(2,4-difluoro-3-((2-(((2R)-1-hydroxypropan-2-yl)amino)pyrimidin-5-yl)ethynyl)phenyl)-3-hydroxy-2,3-dihydro-1-benzofuran-7-sulfonamide (150 mg) was optically resolved by HPLC (CHIRALPAC AD, mobile phase: hexane/2-propanol (450/550, v/v)), the fraction of the peak eluted earlier was concentrated under reduced pressure to give a residue. The residue was washed with ethyl acetate/IPE and dried under reduced pressure to give the title compound (43.5 mg).

$^1$H NMR (300 MHz, DMSO-d$_6$) δ 1.13 (3H, d, J=6.7 Hz), 3.26-3.37 (1H, m), 3.42-3.52 (1H, m), 3.94-4.09 (1H, m), 4.36 (1H, dd, J=10.3, 3.1 Hz), 4.62 (1H, dd, J=10.3, 6.9 Hz), 4.72 (1H, t, J=5.7 Hz), 5.28-5.37 (1H, m), 5.94 (1H, d, J=5.5 Hz), 7.11-7.31 (2H, m), 7.47 (1H, d, J=2.3 Hz), 7.56 (1H, d, J=8.1 Hz), 7.68 (1H, d, J=2.1 Hz), 8.47 (2H, brs), 10.37 (1H, s).

Example 187

5-chloro-N-(2,4-difluoro-3-((2-(((2R)-1-hydroxypropan-2-yl)amino)pyrimidin-5-yl) ethynyl)phenyl)-3-hydroxy-2,3-dihydro-1-benzofuran-7-sulfonamide (Optical Isomer not Having Absolute Configuration of the Dihydrobenzofuran Ring Moiety)

In the optical resolution step shown in Example 186, the fraction of the peak eluted later was concentrated under reduced pressure to give a residue. The residue was washed with ethyl acetate/IPE and dried under reduced pressure to give the title compound (60.3 mg).

$^1$H NMR (300 MHz, DMSO-d$_6$) δ 1.13 (3H, d, J=6.6 Hz), 3.26-3.37 (1H, m), 3.42-3.52 (1H, m), 3.97-4.06 (1H, m), 4.36 (1H, dd, J=10.3, 3.1 Hz), 4.62 (1H, dd, J=10.3, 6.9 Hz), 4.72 (1H, t, J=5.7 Hz), 5.28-5.37 (1H, m), 5.94 (1H, d, J=5.5 Hz), 7.12-7.29 (2H, m), 7.47 (1H, d, J=2.3 Hz), 7.56 (1H, d, J=8.1 Hz), 7.68 (1H, d, J=2.2 Hz), 8.47 (2H, brs), 10.37 (1H, s).

Example 188

5-chloro-N-(2,4-difluoro-3-((2-((trans-4-hydroxycyclohexyl)amino)pyrimidin-5-yl)ethynyl)phenyl)-2-methylpyridine-3-sulfonamide a) 5-chloro-N-(3-((2-chloropyrimidin-5-yl)ethynyl)-2,4-difluorophenyl)-2-methylpyridine-3-sulfonamide A mixture of 2-chloro-5-iodopyrimidine (225 mg), 5-chloro-N-(3-ethynyl-2,4-difluorophenyl)-2-methylpyridine-3-sulfonamide (265 mg), dichlorobis(tricyclohexylphosphine)palladium(II) (58 mg), copper(I) iodide (30 mg), DIPEA (2.1 mL) and DMSO (2.1 mL) was stirred under microwave irradiation at 60° C. for 1 hr. The reaction mixture was diluted with ethyl acetate and water, and an insoluble material was removed by filtration. The filtrate was extracted with ethyl acetate. The obtained organic layer was washed with saturated brine, dried over magnesium sulfate and concentrated to give a residue. The residue was purified by silica gel column chromatography (ethyl acetate/hexane) to give the title compound (307 mg).

$^1$H NMR (300 MHz, DMSO-d) δ 2.77 (3H, s), 7.23 (1H, td, J=8.9, 1.4 Hz), 7.41 (1H, td, J=9.0, 6.0 Hz), 8.06 (1H, d, J=2.2 Hz), 8.75 (1H, d, J=2.4 Hz), 9.02 (2H, s), 10.91 (1H, brs).

b) 5-chloro-N-(2,4-difluoro-3-((2-((trans-4-hydroxycyclohexyl)amino)pyrimidin-5-yl)ethynyl)phenyl)-2-methylpyridine-3-sulfonamide A mixture of 5-chloro-N-(3-((2-chloropyrimidin-5-yl)ethynyl)-2,4-difluorophenyl)-2-methylpyridine-3-sulfonamide (70 mg), trans-4-aminocyclohexanol (32 mg), DIPEA (0.08 mL), acetonitrile (3 mL) and THF (3 mL) was stirred at 80° C. overnight. The reaction mixture was diluted with saturated aqueous sodium hydrogen carbonate solution and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) and washed with ethyl acetate/IPE to give the title compound (63 mg).

$^1$H NMR (300 MHz, DMSO-d$_6$) δ 1.11-1.41 (4H, m), 1.73-1.95 (4H, m), 2.76 (3H, s), 3.31-3.47 (1H, m), 3.58-3.79 (1H, m), 4.56 (1H, brs), 7.15-7.26 (1H, m), 7.31 (1H, td, J=8.9, 6.0 Hz), 7.75 (1H, d, J=8.0 Hz), 8.06 (1H, d, J=2.4 Hz), 8.35-8.56 (2H, m), 8.78 (1H, d, J=2.4 Hz), 10.82 (1H, s).

Example 189

5-chloro-N-(2,4-difluoro-3-((2-(((2R)-1-hydroxypropan-2-yl)amino)pyrimidin-5-yl)ethynyl)phenyl)-2-methylpyridine-3-sulfonamide A mixture of 5-chloro-N-(3-((2-chloropyrimidin-5-yl)ethynyl)-2,4-difluorophenyl)-2-methylpyridine-3-sulfonamide (70 mg), (R)-2-aminopropan-1-ol (24 mg), DIPEA (0.08 mL), acetonitrile (3 mL) and THF (3 mL) was stirred at 80° C. overnight. The reaction mixture was diluted with saturated aqueous sodium hydrogen carbonate solution and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) and washed with ethyl acetate/IPE to give the title compound (60 mg).

$^1$H NMR (300 MHz, DMSO-$d_6$) δ 1.12 (3H, d, J=6.6 Hz), 2.76 (3H, s), 3.23-3.54 (2H, m), 3.91-4.10 (1H, m), 4.72 (1H, brs), 7.15-7.26 (1H, m), 7.31 (1H, td, J=8.9, 6.0 Hz), 7.57 (1H, d, J=8.2 Hz), 8.06 (1H, d, J=2.4 Hz), 8.46 (2H, brs), 8.78 (1H, d, J=2.4 Hz), 10.82 (1H, s).

Example 190

5-chloro-N-(2,4-difluoro-3-((2-((trans-4-hydroxycyclohexyl)amino)pyrimidin-5-yl)ethynyl)phenyl)-3-hydroxy-2,3-dihydro-1-benzofuran-7-sulfonamide (Optical Isomer)

5-Chloro-N-(2,4-difluoro-3-((2-((trans-4-hydroxycyclohexyl)amino)pyrimidin-5-yl)ethynyl)phenyl)-3-hydroxy-2,3-dihydro-1-benzofuran-7-sulfonamide (150 mg) was optically resolved by SFC (CHIRALCEL AD-H, mobile phase: $CO_2$/methanol (600/400, v/v)), and the fraction of the peak eluted earlier was concentrated under reduced pressure to give a residue. The residue was washed with ethyl acetate/IPE and dried under reduced pressure to give the title compound (44.5 mg).

$^1$H NMR (300 MHz, DMSO-$d_6$) 1.13-1.39 (4H, m), 1.77-1.92 (4H, m), 3.34-3.46 (1H, m), 3.63-3.78 (1H, m), 4.36 (1H, dd, J=10.3, 3.1 Hz), 4.56 (1H, d, J=4.2 Hz), 4.61 (1H, dd, J=10.3, 6.9 Hz), 5.27-5.38 (1H, m), 5.94 (1H, d, J=5.5 Hz), 7.10-7.30 (2H, m), 7.47 (1H, d, J=2.3 Hz), 7.67 (1H, d, J=2.1 Hz), 7.74 (1H, d, J=8.0 Hz), 8.46 (2H, d, J=11.6 Hz), 10.37 (1H, s).

Example 191

5-chloro-N-(2,4-difluoro-3-((2-((trans-4-hydroxycyclohexyl)amino)pyrimidin-5-yl)ethynyl)phenyl)-3-hydroxy-2,3-dihydro-1-benzofuran-7-sulfonamide (Optical Isomer)

In the optical resolution step shown in Example 190, the fraction of the peak eluted later was concentrated under reduced pressure to give a residue. The residue was washed with ethyl acetate/IPE and dried under reduced pressure to give the title compound (50.8 mg).

$^1$H NMR (300 MHz, DMSO-$d_6$) δ 1.13-1.40 (4H, m), 1.78-1.92 (4H, m), 3.35-3.46 (1H, m), 3.64-3.78 (1H, m), 4.36 (1H, dd, J=10.3, 3.1 Hz), 4.56 (1H, d, J=4.3 Hz), 4.61 (1H, dd, J=10.3, 6.9 Hz), 5.27-5.38 (1H, m), 5.94 (1H, d, J=5.5 Hz), 7.10-7.30 (2H, m), 7.47 (1H, d, J=2.3 Hz), 7.68 (1H, d, J=2.1 Hz), 7.74 (1H, d, J=7.9 Hz), 8.47 (2H, d, J=11.2 Hz), 10.37 (1H, s).

Example 192

N-(3-((2-aminopyrimidin-5-yl) ethynyl)-2,4-difluorophenyl)-6-chloro-1-methyl-1H-indazole-4-sulfonamide a) 4-(benzylthio)-6-chloro-1-methyl-1H-indazole A mixture of 4-bromo-6-chloro-1H-indazole (740 mg), iodomethane (0.23 mL), cesium carbonate (1.34 g), THF (12 mL) and DMF (3 mL) was stirred at room temperature for 1 hr. The reaction mixture was filtered to remove an insoluble material and concentrated under reduced pressure. The residue was purified by silica gel column chromatography (ethyl acetate/hexane) to give a mixture (735 mg) of 4-bromo-6-chloro-1-methyl-1H-indazole and 4-bromo-6-chloro-2-methyl-2H-indazole. A mixture of this mixture (730 mg), benzylmercaptan (0.40 mL), tris(dibenzylideneacetone)dipalladium(0) (68 mg), 1,1'-bis(diphenylphosphino)ferrocene (83 mg), DIPEA (1.10 mL) and toluene (10 mL) was stirred under a nitrogen atmosphere at 100° C. for 1 hr. The reaction mixture was filtered to remove an insoluble material and concentrated under reduced pressure. The residue was purified by silica gel column chromatography (ethyl acetate/hexane) to give the title compound (592 mg).

$^1$H NMR (300 MHz, DMSO-$d_6$) δ 4.01 (3H, s), 4.44 (2H, s), 7.08 (1H, d, J=1.5 Hz), 7.21-7.37 (3H, m), 7.37-7.46 (2H, m), 7.63-7.68 (1H, m), 8.03 (1H, d, J=1.0 Hz).

b) 6-chloro-1-methyl-1H-indazole-4-sulfonyl chloride

To a suspension of 4-(benzylthio)-6-chloro-1-methyl-1H-indazole (205 mg), acetic acid (6 mL) and water (1.5 mL) was added NCS (410 mg) at room temperature. The mixture was stirred at room temperature for 1 hr, and the reaction mixture was diluted with water and extracted with ethyl acetate. The obtained organic layer was washed with water and saturated brine, dried over magnesium sulfate and concentrated to give a residue. The residue was purified by silica gel column chromatography (ethyl acetate/hexane) to give the title compound (176 mg).

$^1$H NMR (300 MHz, DMSO-$d_6$) δ 4.03 (3H, s), 7.27 (1H, d, J=1.7 Hz), 7.81 (1H, dd, J=1.7, 0.9 Hz), 8.13 (1H, d, J=0.9 Hz).

c) N-(3-((2-aminopyrimidin-5-yl)ethynyl)-2,4-difluorophenyl)-6-chloro-1-methyl-1H-indazole-4-sulfonamide To a solution of 5-((3-amino-2,6-difluorophenyl)ethynyl)-N-(4-methoxybenzyl)pyrimidin-2-amine (90 mg) in pyridine (3 mL) was added 6-chloro-1-methyl-1H-indazole-4-sulfonyl chloride (78 mg) at room temperature. The mixture was stirred at room temperature for 1 hr. The reaction mixture was diluted with toluene and concentrated to give a residue. To the residue was added TFA (2 mL) at room temperature and the mixture was stirred at 70° C. for 2 hr. The reaction mixture was diluted with saturated aqueous sodium hydrogen carbonate solution and extracted with ethyl acetate. The obtained organic layer was washed with saturated brine, dried over magnesium sulfate and concentrated to give a residue. The residue was purified by silica gel column chromatography (ethyl acetate/hexane) and washed with ethyl acetate/IPE to give the title compound (91 mg).

$^1$H NMR (300 MHz, DMSO-$d_6$) δ 4.10 (3H, s), 7.11-7.28 (2H, m), 7.30 (2H, s), 7.45 (1H, d, J=1.6 Hz), 8.06 (1H, d, J=0.9 Hz), 8.27 (1H, dd, J=1.6, 1.0 Hz), 8.40 (2H, s), 10.70 (1H, s).

Example 193

5-chloro-N-(2,4-difluoro-3-((2-(((2S)-1-hydroxypropan-2-yl)amino)pyrimidin-5-yl)ethynyl)phenyl)-2-methylpyridine-3-sulfonamide A mixture of 5-chloro-N-(3-((2-chloropyrimidin-5-yl) ethynyl)-2,4-difluorophenyl)-2-methylpyridine-3-sulfonamide (70 mg), (S)-2-aminopropan-1-ol (26 mg), DIPEA (0.08 mL), acetonitrile (3 mL) and THF (3 mL) was stirred at 80° C. overnight. The reaction mixture was diluted with saturated aqueous sodium hydrogen carbonate solution and extracted with ethyl acetate. The obtained organic layer was washed with saturated brine, dried over anhydrous magnesium sulfate and concentrated under reduced pressure to give a residue. The residue was purified by silica gel column chromatography (ethyl acetate/hexane) and washed with ethyl acetate/IPE to give the title compound (56 mg).

$^1$H NMR (300 MHz, DMSO-$d_6$) δ 1.12 (3H, d, J=6.6 Hz), 2.77 (3H, s), 3.24-3.54 (2H, m), 3.91-4.11 (1H, m), 4.72 (1H, brs), 7.15-7.26 (1H, m), 7.32 (1H, td, J=8.9, 5.9 Hz), 7.57 (1H, d, J=8.2 Hz), 8.06 (1H, d, J=2.3 Hz), 8.46 (2H, brs), 8.78 (1H, d, J=2.4 Hz), 10.82 (1H, s).

The compounds of Examples 39-104, 113-122, 132-135, 139, 142-144, 146-148, 151-152, 154-157, 160-161, 164, 166-167, 169-170, 172, 194-196 in the following Tables were produced according to the methods shown in the above-mentioned Examples, or a method analogous thereto. The Example compounds are shown in the following Tables. In the Tables, MS shows measured value.

TABLE 1-1

| Ex. No. | IUPAC name | structural formula | salt | MS |
|---|---|---|---|---|
| 1 | 2,5-dichloro-N-(2,4-difluoro-3-(1H-pyrazolo[3,4-b]pyridin-5-ylethynyl)phenyl)-3-(hydroxymethyl)benzenesulfonamide | | free base/ acid | 509.1 |
| 2 | 5-chloro-N-(2,4-difluoro-3-(1H-pyrazolo[3,4-b]pyridin-5-ylethynyl)phenyl)-2-methylpyridine-3-sulfonamide | | free base/ acid | 457.9 / 460.0 |
| 3 | N-(3-((2-aminopyrimidin-5-yl)ethynyl)-2,4-difluorophenyl)-5-chloro-2-methylpyridine-3-sulfonamide | | free base/ acid | 433.8 |
| 4 | N-(3-((2-aminopyrimidin-5-yl)ethynyl)-2,4-difluorophenyl)-2,5-dichloro-3-(hydroxymethyl)benzenesulfonamide | | free base/ acid | 485.0 / 485.0 / 485.1 |
| 5 | 5-chloro-N-(2,4-difluoro-3-(1H-pyrazolo[3,4-b]pyridin-5-ylethynyl)phenyl)-2-methoxypyridine-3-sulfonamide | | free base/ acid | 476.1 |

TABLE 1-1-continued

| Ex. No. | IUPAC name | structural formula | salt | MS |
|---|---|---|---|---|
| 6 | N-(3-((2-aminopyrimidin-5-yl)ethynyl)-2,4-difluorophenyl)-5-chloro-2-(trifluoromethyl)-benzenesulfonamide | | free base/acid | 489.0 |

TABLE 1-2

| Ex. No. | IUPAC name | structural formula | salt | MS |
|---|---|---|---|---|
| 7 | N-(3-((2-aminopyrimidin-5-yl)ethynyl)-2,4-difluorophenyl)-5-chloro-2-methoxypyridine-3-sulfonamide | | AcOH | 452.0<br>449.9<br>452.1<br>452.0 |
| 8 | 5-chloro-N-(2,4-difluoro-3-(1H-pyrazolo[3,4-b]pyridin-5-ylethynyl)phenyl)-2,3-dihydro-1-benzofuran-7-sulfonamide | | free base/acid | 487.1 |
| 9 | N-(3-((2-aminopyrimidin-5-yl)ethynyl)-2,4-difluorophenyl)-5-chloro-2,3-dihydro-1-benzofuran-7-sulfonamide | | free base/acid | 463.1 |
| 10 | 2,5-dichloro-N-(2,4-difluoro-3-(1H-pyrazolo[3,4-b]pyridin-5-ylethynyl)phenyl)-benzenesulfonamide | | CF$_3$COOH | 479.1 |

TABLE 1-2-continued

| Ex. No. | IUPAC name | structural formula | salt | MS |
|---|---|---|---|---|
| 11 | 2,5-dichloro-N-(3-((2-(cyclopropylamino)-pyrimidin-5-yl)ethynyl)-2,4-difluorophenyl)-benzenesulfonamide | | CF$_3$COOH | 495.1 |
| 12 | N-(3-((2-aminopyrimidin-5-yl)ethynyl)-2,4-difluorophenyl)-5-chloro-2-(trifluoromethoxy)-benzenesulfonamide | | free base/ acid | 505.0 |

TABLE 1-3

| Ex. No. | IUPAC name | structural formula | salt | MS |
|---|---|---|---|---|
| 13 | N-(3-((2-aminopyrimidin-5-yl)ethynyl)-2,4-difluorophenyl)-2,5-dichlorobenzene-sulfonamide | | CF$_3$COOH | 455.0 |
| 14 | 2,5-dichloro-N-(2,4-difluoro-3-(1H-pyrazolo[3,4-b]pyridin-5-ylethynyl)phenyl)-benzenesulfonaraide | | free base/ acid | 479.0 477.0 477.0 |
| 15 | 5-chloro-N-(2,4-difluoro-3-(1H-pyrazolo[3,4-b]pyridin-5-ylethynyl)phenyl)-2-methylbenzene-sulfonamide | | free base/ acid | 456.8 |

TABLE 1-3-continued

| Ex. No. | IUPAC name | structural formula | salt | MS |
|---|---|---|---|---|
| 16 | 2,5-dichloro-N-(2,4-difluoro-3-((2-(tetrahydrofuran-3-ylamino)pyrimidin-5-yl)ethynyl)phenyl)-benzenesulfonamide | | CF$_3$COOH | 525.2 |
| 17 | N-(3-((2-aminopyrimidin-5-yl)ethynyl)-2,4-difluorophenyl)-2,5-dichlorobenzene-sulfonamide | | free base/ acid | 455.0 452.9 |
| 18 | 3-bromo-N-(2,4-difluoro-3-(1H-pyrazolo[3,4-b]pyridin-5-ylethynyl)phenyl)-5-methylbenzene-sulfonamide | | free base/ acid | 503.0 501.1 |

TABLE 1-4

| Ex. No. | IUPAC name | structural formula | salt | MS |
|---|---|---|---|---|
| 19 | N-(3-((2-aminopyrimidin-5-yl)ethynyl)-2,4-difluorophenyl)-5-chloro-2-methylbenzene-sulfonamide | | free base/ acid | 435.0 |
| 20 | 2,3,5-trichloro-N-(2,4-difluoro-3-(1H-pyrazolo[3,4-b]pyridin-5-ylethynyl)phenyl)-benzenesulfonamide | | free base/ acid | 510.9 |

TABLE 1-4-continued

| Ex. No. | IUPAC name | structural formula | salt | MS |
|---|---|---|---|---|
| 21 | N-(3-((2-aminopyrimidin-5-yl)ethynyl)-2,4-difluorophenyl)-5-chloro-2-(difluoromethoxy)-benzenesulfonamide | | free base/acid | 487.0 |
| 22 | 2,5-dichloro-N-(2,4-difluoro-3-((2-(((2R)-1-hydroxypropan-2-yl)amino)pyrimidin-5-yl)ethynyl)phenyl)-benzenesulfonamide | | CF₃COOH | 513.1 |
| 23 | 2,3,5,6-tetrachloro-N-(2,4-difluoro-3-(1H-pyrazolo[3,4-b]pyridin-5-ylethynyl)phenyl)-benzenesulfonamide | | free base/acid | 547.0 |
| 24 | 5-bromo-N-(2,4-difluoro-3-(1H-pyrazolo[3,4-b]pyridin-5-ylethynyl)phenyl)-2-fluorobenzene-sulfonamide | | CF₃COOH | 505.0 |

TABLE 1-5

| Ex. No. | IUPAC name | structural formula | salt | MS |
|---|---|---|---|---|
| 25 | 3,5-dichloro-N-(2,4-difluoro-3-(1H-pyrazolo[3,4-b]pyridin-5-ylethynyl)phenyl)-benzenesulfonamide | | 2CF₃COOH | 351.2 |
| 26 | 5-chloro-N-(2,4-difluoro-3-(1H-pyrazolo[3,4-b]pyridin-5-ylethynyl)phenyl)-2-fluorobenzene-sulfonamide | | free base/acid | 477.1 477.1 |
| 27 | N-(3-((2-aminopyrimidin-5-yl)ethynyl)-2,4-difluorophenyl)-3,5-dichlorobenzene-sulfonamide | | CF₃COOH | 463.0 |
| 28 | 2,5-dichloro-N-(2,4-difluoro-3-((2-((3-hydroxypropyl)amino)-pyrimidin-5-yl)ethynyl)phenyl)-benzenesulfonamide | | free base/acid | 452.9 |
| 29 | N-(3-((2-aminopyrimidin-5-yl)ethynyl)-2,4-difluorophenyl)-5-chloro-2-cyanobenzene-sulfonamide | | CF₃COOH | 513.1 |

TABLE 1-5-continued

| Ex. No. | IUPAC name | structural formula | salt | MS |
|---|---|---|---|---|
| 30 | 2,5-dichloro-N-(3-((2-(ethylamino)pyrimidin-5-yl)ethynyl)-2,4-difluorophenyl)-benzenesulfonamide | | free base/ acid | 444.0 |

TABLE 1-6

| Ex. No. | IUPAC name | structural formula | salt | MS |
|---|---|---|---|---|
| 31 | N-(3-((5-amino-6-methylpyrazin-2-yl)ethynyl)-2,4-difluorophenyl)-5-chloro-2-methylbenzene-sulfonamide | | free base/ acid | 449.1 |
| 32 | 2,5-dichloro-N-(2,4-difluoro-3-((2-((trans-4-hydroxycyclohexyl)-amino)pyrimidin-5-yl)ethynyl)phenyl)-benzenesulfonamide | | $CF_3COOH$ | 553.1 |
| 33 | 3,5-dichloro-N-(2,4-difluoro-3-(1H-pyrazolo[3,4-b]pyridin-5-ylethynyl)phenyl)-2-methoxybenzene-sulfonamide | | free base/ acid | 507.0 |
| 34 | 2,5-dichloro-N-(3-((2,4-diaminopyrimidin-5-yl)ethynyl)-2,4-difluorophenyl)-benzenesulfonamide | | free base/ acid | 470.0 |

TABLE 1-6-continued

| Ex. No. | IUPAC name | structural formula | salt | MS |
|---|---|---|---|---|
| 35 | N-(3-((2-aminopyrimidin-5-yl)ethynyl)-2,4-difluorophenyl)-2-chloro-5-(trifluoromethyl)-benzenesulfonamide | | free base/ acid | 489.1 |
| 36 | 2,5-dichloro-N-(2,4-difluoro-3-((2-((2-hydroxyethyl)amino)-pyrimidin-5-yl)ethynyl)phenyl)-benzenesulfonamide | | CF₃COOH | 499.1 |

TABLE 1-7

| Ex. No. | IUPAC name | structural formula | salt | MS |
|---|---|---|---|---|
| 37 | 2,5-dichloro-N-(2,4-difluoro-3-((2-(methylamino)pyrimidin-5-yl)ethynyl)phenyl)-benzenesulfonamide | | CF₃COOH | 469.0 |
| 38 | 2,3-dichloro-N-(2,4-difluoro-3-(1H-pyrazolo[3,4-b]pyridin-5-ylethynyl)phenyl)-benzenesulfonamide | | CF₃COOH | 479.1 |
| 39 | N-(3-((5-amino-6-methylpyrazin-2-yl)ethynyl)-2,4-difluorophenyl)-2,5-dichlorobenzene-sulfonamide | | CF₃COOH | 469.0 |

TABLE 1-7-continued

| Ex. No. | IUPAC name | structural formula | salt | MS |
|---|---|---|---|---|
| 40 | 2-chloro-N-(2,4-difluoro-3-(1H-pyrazolo[3,4-b]pyridin-5-ylethynyl)phenyl)-5-methylbenzenesulfonamide | | free base/acid | 459.1 |
| 41 | 2,5-dichloro-N-(2,4-difluoro-3-((2-(((3S,4R)-4-hydroxytetrahydrofuran-3-yl)amino)pyrimidin-5-yl)ethynyl)phenyl)-benzenesulfonamide | | CF$_3$COOH | 541.2 |
| 42 | 3-bromo-N-(2,4-difluoro-3-(1H-pyrazolo[3,4-b]pyridin-5-ylethynyl)phenyl)-5-(trifluoromethyl)-benzenesulfonamide | | CF$_3$COOH | 557.1 |

TABLE 1-8

| Ex. No. | IUPAC name | structural formula | salt | MS |
|---|---|---|---|---|
| 43 | 2,5-dichloro-N-(2,4-difluoro-3-((2-(isopropylamino)-pyrimidin-5-yl)ethynyl)phenyl)-benzenesulfonamide | | CF$_3$COOH | 497.1 |

TABLE 1-8-continued

| Ex. No. | IUPAC name | structural formula | salt | MS |
|---|---|---|---|---|
| 44 | 2,5-dichloro-N-(2,4-difluoro-3-((2-((3-methoxypropyl)amino)-pyrimidin-5-yl)ethynyl)phenyl)-benzenesulfonamide | | CF$_3$COOH | 527.2 |
| 45 | 2,6-dichloro-N-(2,4-difluoro-3-(1H-pyrazolo[3,4-b]pyridin-5-ylethynyl)phenyl)-benzenesulfonamide | | CF$_3$COOH | 479.0 |
| 46 | 5-chloro-N-(2,4-difluoro-3-(1H-pyrazolo[3,4-b]pyridin-5-ylethynyl)phenyl)-2-methoxybenzene-sulfonamide | | free base/acid | 472.9 |
| 47 | 2,5-dichloro-N-(2,4-difluoro-3-((2-(tetrahydro-2H-pyran-4-ylamino)pyrimidin-5-yl)ethynyl)phenyl)-benzenesulfonamide | | CF$_3$COOH | 539.2 |
| 48 | 5-chloro-N-(2,4-difluoro-3-(1H-pyrazolo[3,4-b]pyridin-5-ylethynyl)phenyl)-2-(hydroxymethyl)-benzenesulfonamide | | free base/acid | 475.0 |

TABLE 1-9

| Ex. No. | IUPAC name | structural formula | salt | MS |
|---|---|---|---|---|
| 49 | 5-bromo-N-(2,4-difluoro-3-(1H-pyrazolo[3,4-b]pyridin-5-ylethynyl)phenyl)-2-methoxybenzenesulfonamide | | free base/ acid | 519.1 519.0 |
| 50 | 2,5-dichloro-N-(2,4-difluoro-3-((2-(((2R)-2-hydroxypropyl)amino)pyrimidin-5-yl)ethynyl)phenyl)-benzenesulfonamide | | $CF_3COOH$ | 513.1 |
| 51 | 2,5-dichloro-N-(2,4-difluoro-3-((2-(((2S)-1-hydroxypropan-2-yl)amino)pyrimidin-5-yl)ethynyl)phenyl)-benzenesulfonamide | | $CF_3COOH$ | 513.1 |
| 52 | 2,5-dichloro-N-(2,4-difluoro-3-((2-(propylamino)pyrimidin-5-yl)ethynyl)phenyl)-benzenesulfonamide | | $CF_3COOH$ | 497.1 |
| 53 | 3-bromo-N-(2,4-difluoro-3-(1H-pyrazolo[3,4-b]pyridin-5-ylethynyl)phenyl)-5-fluorobenzenesulfonamide | | $CF_3COOH$ | 505.1 |

TABLE 1-9-continued

| Ex. No. | IUPAC name | structural formula | salt | MS |
|---|---|---|---|---|
| 54 | 2,5-dichloro-N-(2,4-difluoro-3-((2-((1-methylcyclopropyl)amino)pyrimidin-5-yl)ethynyl)phenyl)benzenesulfonamide | | CF$_3$COOH | 509.1 |

TABLE 1-10

| Ex. No. | IUPAC name | structural formula | salt | MS |
|---|---|---|---|---|
| 55 | N-(2,4-difluoro-3-(1H-pyrazolo[3,4-b]pyridin-5-ylethynyl)phenyl)-2-fluoro-5-methylbenzenesulfonamide | | CF$_3$COOH | 443.2 |
| 56 | 2,5-dichloro-N-(2,4-difluoro-3-((2-(((2S)-2-hydroxypropyl)amino)pyrimidin-5-yl)ethynyl)phenyl)benzenesulfonamide | | CF$_3$COOH | 513.1 |
| 57 | 2,5-dichloro-N-(2,4-difluoro-3-((2-(trans-4-hydroxypyrrolidin-3-yl)amino)pyrimidin-5-yl)ethynyl)phenyl)benzenesulfonamide | | 2CF$_3$COOH | 540.2 |

TABLE 1-10-continued

| Ex. No. | IUPAC name | structural formula | salt | MS |
|---|---|---|---|---|
| 58 | 2,5-dichloro-N-(2,4-difluoro-3-((2-((1-hydroxy-2-methylpropan-2-yl)amino)pyrimidin-5-yl)ethynyl)phenyl)-benzenesulfonamide | | CF$_3$COOH | 527.2 |
| 59 | N-(2,4-difluoro-3-(1H-pyrazolo[3,4-b]pyridin-5-ylethynyl)phenyl)-2,5-difluorobenzene-sulfonamide | | CF$_3$COOH | 447.1 |
| 60 | 2,5-dichloro-N-(2,4-difluoro-3-((2-((1-(hydroxymethyl)-cyclopropyl)amino)-pyrimidin-5-yl)ethynyl)phenyl)-benzenesulfonamide | | CF$_3$COOH | 525.1 |

TABLE 1-11

| Ex. No. | IUPAC name | structural formula | salt | MS |
|---|---|---|---|---|
| 61 | N-(3-((5-aminopyrazin-2-yl)ethynyl)-2,4-difluorophenyl)-2,5-dichlorobenzene-sulfonamide | | CF$_3$COOH | 455.0 |
| 62 | N-(3-((2-aminopyrimidin-5-yl)ethynyl)-2,4-difluorophenyl)-5-chloro-2-methoxybenzene-sulfonamide | | free base/ acid | 448.8 |

TABLE 1-11-continued

| Ex. No. | IUPAC name | structural formula | salt | MS |
|---|---|---|---|---|
| 63 | 2,5-dichloro-N-(3-((2-((cyclopropylmethyl)-amino)pyrimidin-5-yl)ethynyl)-2,4-difluorophenyl)-benzenesulfonamide | | free base/acid | 509.1 |
| 64 | 2,5-dichloro-N-(2,4-difluoro-3-((2-((cis-4-hydroxypyrrolidin-3-yl)amino)pyrimidin-5-yl)ethynyl)phenyl)-benzenesulfonamide | | 2CF₃COOH | 540.2 |
| 65 | 2-chloro-N-(2,4-difluoro-3-(1H-pyrazolo[3,4-b]pyridin-5-ylethynyl)phenyl)-6-methylbenzene-sulfonamide | | CF₃COOH | 459.2 |
| 66 | 2,5-dichloro-N-(2,4-difluoro-3-((2-((2-hydroxy-2-methylpropyl)amino)-pyrimidin-5-yl)ethynyl)-phenyl)benzene-sulfonamide | | CF₃COOH | 527.2 |

TABLE 1-12

| Ex. No. | IUPAC name | structural formula | salt | MS |
|---|---|---|---|---|
| 67 | 2,5-dichloro-N-(3-((2-(cyclopentylamino)-pyrimidin-5-yl)ethynyl)-2,4-difluorophenyl)-benzenesulfonamide | | free base/acid | 523.2 |
| 68 | N-(5-((3-(((2,5-dichlorophenyl)-sulfonyl)amino)-2,6-difluorophenyl)-ethynyl)pyridin-2-yl)acetamide | | $CF_3COOH$ | 495.9 |
| 69 | N-(2,4-difluoro-3-(1H-pyrazolo[3,4-b]pyridin-5-ylethynyl)phenyl)-2,6-difluorobenzene-sulfonamide | | $CF_3COOH$ | 447.1 |
| 70 | 2,5-dichloro-N-(2,4-difluoro-3-((7-oxo-5,6,7,8-tetrahydro-1,8-naphthyridin-3-yl)ethynyl)phenyl)-benzenesulfonamide | | $CF_3COOH$ | 506.0 |
| 71 | N-(3-((2-aminopyrimidin-5-yl)ethynyl)-2,4-difluorophenyl)-2-methoxy-5-(trifluoromethyl)-benzenesulfonamide | | $CF_3COOH$ | 485.2 |

TABLE 1-12-continued

| Ex. No. | IUPAC name | structural formula | salt | MS |
|---|---|---|---|---|
| 72 | 3-bromo-N-(2,4-difluoro-3-(1H-pyrazolo[3,4-b]pyridin-5-ylethynyl)phenyl)-4-methoxybenzenesulfonamide | | free base/acid | 519.0 |

TABLE 1-13

| Ex. No. | IUPAC name | structural formula | salt | MS |
|---|---|---|---|---|
| 73 | N-(3-((6-amino-5-fluoropyridin-3-yl)ethynyl)-2,4-difluorophenyl)-2,5-dichlorobenzenesulfonamide | | $CF_3COOH$ | 472.0 |
| 74 | 2,5-dichloro-N-(2,4-difluoro-3-((2-(isobutylamino)-pyrimidin-5-yl)ethynyl)phenyl)-benzenesulfonamide | | $CF_3COOH$ | 511.1 |
| 75 | 2,5-dichloro-N-(2,4-difluoro-3-((3-oxo-3,4-dihydro-2H-pyrido[3,2-b][1,4]oxazin-7-yl)ethynyl)phenyl)-benzenesulfonamide | | $CF_3COOH$ | 510.0 |

TABLE 1-13-continued

| Ex. No. | IUPAC name | structural formula | salt | MS |
|---|---|---|---|---|
| 76 | 2,5-dichloro-N-(2,4-difluoro-3-((4-methoxypyridin-3-yl)ethynyl)phenyl)-benzenesulfonamide | | CF$_3$COOH | 469.0 |
| 77 | 5-bromo-6-chloro-N-(2,4-difluoro-3-(1H-pyrazolo[3,4-b]pyridin-5-ylethynyl)phenyl)-pyridine-3-sulfonamide | | free base/acid | 522.0 |
| 78 | ethyl 2,5-dichloro-3-((2,4-difluoro-3-(1H-pyrazolo[3,4-b]pyridin-5-ylethynyl)phenyl)-sulfamoyl)benzoate | | free base/acid | 551.0 |

TABLE 1-14

| Ex. No. | IUPAC name | structural formula | salt | MS |
|---|---|---|---|---|
| 79 | N-(2,4-difluoro-3-(1H-pyrazolo[3,4-b]pyridin-5-ylethynyl)phenyl)-3,5-difluorobenzene-sulfonamide | | free base/acid | 447.1 |
| 80 | N-(3-((6-amino-5-methylpyridin-3-yl)ethynyl)-2,4-difluorophenyl)-2,5-dichlorobenzene-sulfonamide | | CF$_3$COOH | 468.0 |

TABLE 1-14-continued

| Ex. No. | IUPAC name | structural formula | salt | MS |
|---|---|---|---|---|
| 81 | 4-bromo-N-(2,4-difluoro-3-(1H-pyrazolo[3,4-b]pyridin-5-ylethynyl)phenyl)-3-fluorobenzene-sulfonamide | | free base/acid | 505.1 |
| 82 | 2,5-dichloro-N-(2,4-difluoro-3-((5-methoxypyridin-3-yl)ethynyl)phenyl)-benzenesulfonamide | | CF$_3$COOH | 469.1 |
| 83 | 3-chloro-N-(2,4-difluoro-3-(1H-pyrazolo[3,4-b]pyridin-5-ylethynyl)phenyl)-4-fluorobenzene-sulfonamide | | free base/acid | 463.0 |
| 84 | 3-bromo-N-(2,4-difluoro-3-(1H-pyrazolo[3,4-b]pyridin-5-ylethynyl)phenyl)-4-fluorobenzene-sulfonamide | | CF$_3$COOH | 505.0 |

TABLE 1-15

| Ex. No. | IUPAC name | structural formula | salt | MS |
|---|---|---|---|---|
| 85 | N-(5-((3-(((2,5-dichlorophenyl)sulfonyl)-amino)-2,6-difluorophenyl)ethynyl)-pyridin-2-yl)-cyclopropanecarboxamide | | CF₃COOH | 520.0 |
| 86 | 3,4-dichloro-N-(2,4-difluoro-3-(1H-pyrazolo[3,4-b]pyridin-5-ylethynyl)phenyl)-benzenesulfonamide | | free base/acid | 477.1 |
| 87 | 5-chloro-N-(2,4-difluoro-3-(1H-pyrazolo[3,4-b]pyridin-5-ylethynyl)-phenyl)naphthalene-1-sulfonamide | | free base/acid | 495.1 |
| 88 | 2,5-dichloro-N-(2,4-difluoro-3-((2-((2-methoxy-2-methylpropyl)-amino)pyrimidin-5-yl)ethynyl)phenyl)-benzenesulfonamide | | CF₃COOH | 541.2 |

TABLE 1-15-continued

| Ex. No. | IUPAC name | structural formula | salt | MS |
|---|---|---|---|---|
| 89 | 4-bromo-3-chloro-N-(2,4-difluoro-3-(1H-pyrazolo[3,4-b]pyridin-5-ylethynyl)phenyl)-benzenesulfonamide | | free base/acid | 523.0 |
| 90 | N-(3-((2-aminopyrimidin-5-yl)ethynyl)-2,4-difluorophenyl)-5-chloro-2-ethoxybenzene-sulfonamide | | free base/acid | 465.2 |

TABLE 1-16

| Ex. No. | IUPAC name | structural formula | salt | MS |
|---|---|---|---|---|
| 91 | N-(3-((6-aminopyridin-3-yl)ethynyl)-2,4-difluorophenyl)-2,5-dichlorobenzene-sulfonamide | | CF$_3$COOH | 454.0 |
| 92 | N-(2,4-difluoro-3-(1H-pyrazolo[3,4-b]pyridin-5-ylethynyl)phenyl)-3,4-difluorobenzene-sulfonamide | | free base/acid | 447.1 |

TABLE 1-16-continued

| Ex. No. | IUPAC name | structural formula | salt | MS |
|---|---|---|---|---|
| 93 | 3-chloro-N-(2,4-difluoro-3-(1H-pyrazolo[3,4-b]pyridin-5-ylethynyl)phenyl)-4-methylbenzenesulfonamide | | free acid/base | 459.2 |
| 94 | 2,5-dichloro-N-(3-((2-(cyclohexylamino)-pyrimidin-5-yl)ethynyl)-2,4-difluorophenyl)-benzenesulfonamide | | CF$_3$COOH | 537.1 |
| 95 | 2,5-dichloro-N-(2,4-difluoro-3-((2-(((1-hydroxycyclopentyl)methyl)amino)pyrimidin-5-yl)ethynyl)phenyl)-benzenesulfonamide | | CF$_3$COOH | 553.1 |
| 96 | methyl 4-chloro-2-((2,4-difluoro-3-(1H-pyrazolo[3,4-b]pyridin-5-ylethynyl)phenyl)-sulfamoyl)benzoate | | free base/acid | 503.1 |

TABLE 1-17

| Ex. No. | IUPAC name | structural formula | salt | MS |
|---|---|---|---|---|
| 97 | N-(3-((6-amino-4-methylpyridin-3-yl)ethynyl)-2,4-difluorophenyl)-2,5-dichlorobenzene-sulfonamide | | CF$_3$COOH | 468.0 |
| 98 | N-(2,4-difluoro-3-(1H-pyrazolo[3,4-b]pyridin-5-ylethynyl)phenyl)-quinoline-8-sulfonamide | | free base/acid | 462.2 |
| 99 | 2,5-dichloro-3-((2,4-difluoro-3-(1H-pyrazolo[3,4-b]pyridin-5-ylethynyl)phenyl)-sulfamoyl)benzamide | | free base/acid | 522.0 |
| 100 | 2,5-dichloro-N-(2,4-difluoro-3-((2-((1-methylcyclopentyl)-amino)pyrimidin-5-yl)ethynyl)phenyl)-benzenesulfonamide | | CF$_3$COOH | 537.2 |
| 101 | 3-chloro-4-cyano-N-(2,4-difluoro-3-(1H-pyrazolo[3,4-b]pyridin-5-ylethynyl)phenyl)-benzenesulfonamide | | free base/acid | 470.1 |

TABLE 1-17-continued

| Ex. No. | IUPAC name | structural formula | salt | MS |
|---|---|---|---|---|
| 102 | 2,5-dichloro-N-(2,4-difluoro-3-(1,8-naphthyridin-3-ylethynyl)phenyl)-benzenesulfonamide | | CF₃COOH | 490.0 |

TABLE 1-18

| Ex. No. | IUPAC name | structural formula | salt | MS |
|---|---|---|---|---|
| 103 | 2,5-dichloro-3-((2,4-difluoro-3-(1H-pyrazolo[3,4-b]pyridin-5-ylethynyl)phenyl)-sulfamoyl)benzoic acid | | free base/acid | 523.0 |
| 104 | 2,5-dichloro-N-(2,4-difluoro-3-((2-((2-methylbutan-2-yl)-amino)pyrimidin-5-yl)ethynyl)phenyl)-benzenesulfonamide | | CF₃COOH | 522.9 |
| 105 | 5-chloro-N-(2,4-difluoro-3-((2-(isopropylamino)-pyrimidin-5-yl)ethynyl)phenyl)-2-methylpyridine-3-sulfonamide | | free base/acid | 478.2 |

TABLE 1-18-continued

| Ex. No. | IUPAC name | structural formula | salt | MS |
|---|---|---|---|---|
| 106 | 5-chloro-N-(2,4-difluoro-3-((2-(isopropylamino)-pyrimidin-5-yl)ethynyl)phenyl)-2-methoxypyridine-3-sulfonamide | | free base/acid | 494.2 |
| 107 | 5-chloro-N-(2,4-difluoro-3-((2-((2-hydroxy-2-methylpropyl)amino)-pyrimidin-5-yl)ethynyl)phenyl)-2-methoxypyridine-3-sulfonamide | | free base/acid | 524.2 |
| 108 | 5-chloro-N-(2,4-difluoro-3-((2-((1-hydroxy-2-methylpropan-2-yl)amino)pyrimidin-5-yl)ethynyl)phenyl)-2-methoxypyridine-3-sulfonamide | | free base/acid | 524.2 |

TABLE 1-19

| Ex. No. | IUPAC name | structural formula | salt | MS |
|---|---|---|---|---|
| 109 | N-(3-((3-amino-1,2,4-triazin-6-yl)ethynyl)-2,4-difluorophenyl)-5-chloro-2-methoxypyridine-3-sulfonamide | | free base/acid | 453.1 |

TABLE 1-19-continued

| Ex. No. | IUPAC name | structural formula | salt | MS |
|---|---|---|---|---|
| 110 | N-(3-((5-amino-6-methylpyrazin-2-yl)ethynyl)-2,4-difluorophenyl)-5-chloro-2-methoxypyridine-3-sulfonamide | | free base/acid | 466.0 |
| 111 | N-(2,4-difluoro-3-(1H-pyrazolo[3,4-b]pyridin-5-ylethynyl)phenyl)-3,5-dimethylbenzenesulfonamide | | CF$_3$COOH | 439.1 |
| 112 | N-(2,4-difluoro-3-(1H-pyrazolo[3,4-b]pyridin-5-ylethynyl)phenyl)-2,5-dimethylbenzenesulfonamide | | CF$_3$COOH | 439.1 |
| 113 | N-(2,4-difluoro-3-(1H-pyrazolo[3,4-b]pyridin-5-ylethynyl)phenyl)-3,4-dimethylbenzenesulfonamide | | free base/acid | 439.2 |
| 114 | N-(2,4-difluoro-3-(1H-pyrazolo[3,4-b]pyridin-5-ylethynyl)phenyl)-3,4-dimethoxybenzenesulfonamide | | free base/acid | 471.1 |

TABLE 1-20

| Ex. No. | IUPAC name | structural formula | salt | MS |
|---|---|---|---|---|
| 115 | methyl 3-((3-((2-aminopyrimidin-5-yl)ethynyl)-2,4-difluorophenyl)sulfamoyl)-4-methoxybenzoate | | free base/acid | 473.0 |
| 116 | N-(3-((2-aminopyrimidin-5-yl)ethynyl)-2,4-difluorophenyl)-5-(2-hydroxypropan-2-yl)-2-methoxybenzenesulfonamide | | free base/acid | 473.0 |
| 117 | N-(3-((2-aminopyrimidin-5-yl)ethynyl)-2,4-difluorophenyl)-5-(hydroxymethyl)-2-methoxybenzenesulfonamide | | free base/acid | 444.9 |
| 118 | 3-((3-((2-aminopyrimidin-5-yl)ethynyl)-2,4-difluorophenyl)sulfamoyl)-4-methoxy-N-methylbenzamide | | free base/acid | 474.2 |
| 119 | 3-((3-((2-aminopyrimidin-5-yl)ethynyl)-2,4-difluorophenyl)sulfamoyl)-4-methoxybenzamide | | free base/acid | 457.9 |
| 120 | N-(3-((6-amino-2-methylpyridin-3-yl)ethynyl)-2,4-difluorophenyl)-2,5-dichlorobenzenesulfonamide | | CF$_3$COOH | 468.0 |

TABLE 1-21

| Ex. No. | IUPAC name | structural formula | salt | MS |
|---|---|---|---|---|
| 121 | N-(3-((6-amino-2,4-dimethylpyridin-3-yl)ethynyl)-2,4-difluorophenyl)-2,5-dichlorobenzene-sulfonamide | | CF$_3$COOH | 482.0 |
| 122 | 3-((3-((2-aminopyrimidin-5-yl)ethynyl)-2,4-difluorophenyl)-sulfamoyl)-4-methoxybenzoic acid | | free base/acid | 459.0 |
| 123 | N-(3-((2-aminopyrimidin-5-yl)ethynyl)-2-fluorophenyl)-5-chloro-2-methoxypyridine-3-sulfonamide | | free base/acid | 434.0 |
| 124 | N-(3-((2-aminopyrimidin-5-yl)ethynyl)-4-chloro-2-fluorophenyl)-5-chloro-2-methoxypyridine-3-sulfonamide | | free base/acid | 467.9 |
| 125 | N-(3-((2-aminopyrimidin-5-yl)ethynyl)-2-chloro-4-fluorophenyl)-5-chloro-2-methoxypyridine-3-sulfonamide | | free base/acid | 465.9 |
| 126 | N-(3-((2-aminopyrimidin-5-yl)ethynyl)-2-chlorophenyl)-5-chloro-2-methoxypyridine-3-sulfonamide | | free base/acid | 450.1 |

TABLE 1-22

| Ex. No. | IUPAC name | structural formula | salt | MS |
|---|---|---|---|---|
| 127 | 3-((3-((2-aminopyrimidin-5-yl)ethynyl)-2,4-difluorophenyl)sulfamoyl)-5-chloro-2-methoxybenzyl acetate | 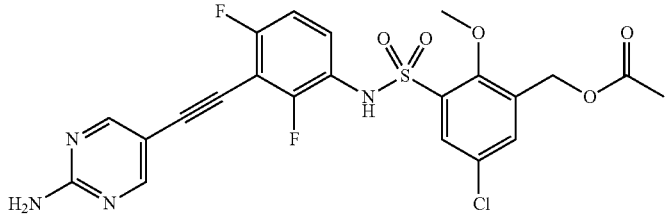 [SMILES: COc1c(COC(C)=O)cc(Cl)cc1S(=O)(=O)Nc1ccc(F)c(C#Cc2cnc(N)nc2)c1F] | free base/acid | 523.1 |
| 128 | 3-((3-((3-amino-1,2,4-triazin-6-yl)ethynyl)-2,4-difluorophenyl)sulfamoyl)-5-chloro-2-methoxybenzyl acetate | 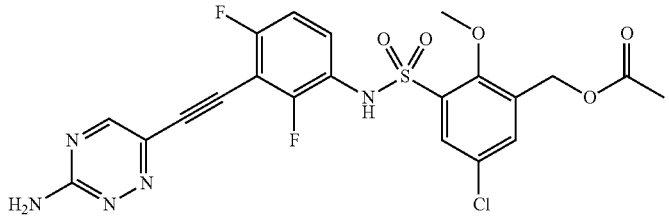 [SMILES: COc1c(COC(C)=O)cc(Cl)cc1S(=O)(=O)Nc1ccc(F)c(C#Cc2cnc(N)nn2)c1F] | free base/acid | 524.2 |
| 129 | N-(3-((2-aminopyrimidin-5-yl)ethynyl)-2,4-difluorophenyl)-5-chloro-3-(hydroxymethyl)-2-methoxybenzenesulfonamide | 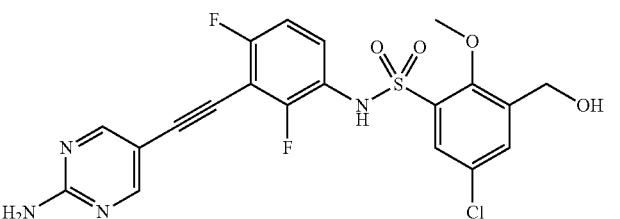 | free base/acid | 478.9 |
| 130 | N-(3-((3-amino-1,2,4-triazin-6-yl)ethynyl)-2,4-difluorophenyl)-5-chloro-3-(hydroxymethyl)-2-methoxybenzenesulfonamide | 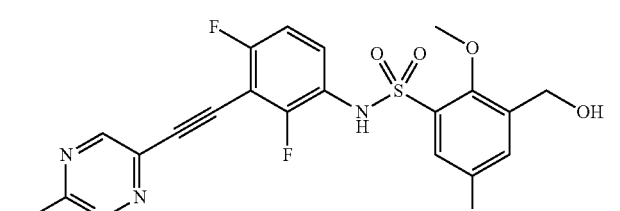 | free base/acid | 482.0 |
| 131 | N-(3-((5-amino-6-methylpyrazin-2-yl)ethynyl)-2,4-difluorophenyl)-5-chloro-3-(hydroxymethyl)-2-methoxybenzenesulfonamide | 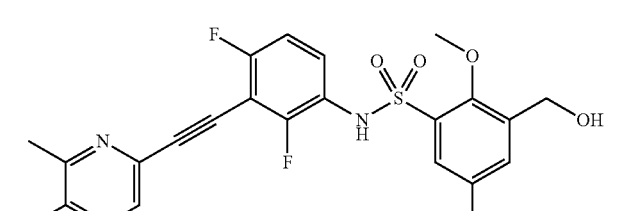 | free base/acid | 495.1 |
| 132 | 5-chloro-N-(3-((2-((2,2-difluoroethyl)amino)pyrimidin-5-yl)ethynyl)-2,4-difluorophenyl)-3-(hydroxymethyl)-2-methoxybenzenesulfonamide | 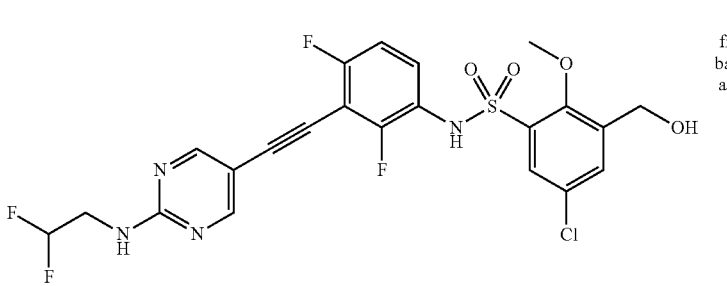 | free base/acid | 545.1 |

TABLE 1-23

| Ex. No. | IUPAC name | structural formula | salt | MS |
|---|---|---|---|---|
| 133 | 5-chloro-N-(3-(2,3-dihydro-1H-pyrrolo[2,3-b]pyridin-5-ylethynyl)-2,4-difluorophenyl)-3-(hydroxymethyl)-2-methoxybenzenesulfonamide | | free base/ acid | 506.1 |
| 134 | N-(3-((2-aminopyrimidin-5-yl)ethynyl)-2,4-difluorophenyl)-5-chloro-2-(hydroxymethyl)-pyridine-3-sulfonamide | | free base/ acid | 449.9 |
| 135 | N-(5-((3-(((2,5-dichlorophenyl)sulfonyl)-amino)-2,6-difluorophenyl)ethynyl)-pyrimidin-2-yl)acetamide | | free base/ acid | 497.0 |
| 136 | N-(3-((2-aminopyrimidin-5-yl)ethynyl)-2,4-difluorophenyl)-5-chloro-2-(trifluoromethyl)-pyridine-3-sulfonamide | | free base/ acid | 487.9 |
| 137 | 5-chloro-N-(3-((2-(ethylamino)pyrimidin-5-yl)ethynyl)-2,4-difluorophenyl)-3-(hydroxymethyl)-2-methoxybenzenesulfonamide | | free base/ acid | 509.2 |
| 138 | 5-chloro-N-(3-((2-(cyclopropylamino)-pyrimidin-5-yl)ethynyl)-2,4-difluorophenyl)-3-(hydroxymethyl)-2-methoxybenzenesulfonamide | | free base/ acid | 521.1 521.1 |

TABLE 1-24

| Ex. No. | IUPAC name | structural formula | salt | MS |
|---|---|---|---|---|
| 139 | 5-chloro-N-(3-((2-((cyclopropylmethyl)-amino)pyrimidin-5-yl)ethynyl)-2,4-difluorophenyl)-3-(hydroxymethyl)-2-methoxybenzene-sulfonamide | | free base/ acid | 535.2 |
| 140 | 5-chloro-N-(2,4-difluoro-3-((2-(oxetan-3-ylamino)pyrimidin-5-yl)ethynyl)phenyl)-3-(hydroxymethyl)-2-methoxybenzene-sulfonamide | | free base/ acid | 537.1 537.2 |
| 141 | 5-chloro-N-(2,4-difluoro-3-((2-(tetrahydrofuran-3-ylamino)pyrimidin-5-yl)ethynyl)phenyl)-3-(hydroxymethyl)-2-methoxybenzene-sulfonamide | | free base/ acid | 551.1 |
| 142 | 5-chloro-N-(2,4-difluoro-3-((2-(tetrahydro-2H-pyran-3-ylamino)pyrimidin-5-yl)ethynyl)phenyl)-3-(hydroxymethyl)-2-methoxybenzene-sulfonamide | | free base/ acid | 565.1 |

TABLE 1-24-continued

| Ex. No. | IUPAC name | structural formula | salt | MS |
|---|---|---|---|---|
| 143 | 5-chloro-N-(2,4-difluoro-3-((2-(tetrahydro-2H-pyran-4-ylamino)pyrimidin-5-yl)ethynyl)phenyl)-3-(hydroxymethyl)-2-methoxybenzene-sulfonamide | | free base/ acid | 565.1 |
| 144 | 5-chloro-N-(2,4-difluoro-3-((2-((tetrahydrofuran-2-ylmethyl)amino)pyrimidin-5-yl)ethynyl)phenyl)-3-(hydroxy-methyl)-2-methoxy-benzenesulfonamide | | free base/ acid | 565.1 |

TABLE 1-25

| Ex. No. | IUPAC name | structural formula | salt | MS |
|---|---|---|---|---|
| 145 | 5-chloro-N-(2,4-difluoro-3-((2-((tetrahydrofuran-3-ylmethyl)amino)pyrimidin-5-yl)ethynyl)phenyl)-3-(hydroxymethyl)-2-methoxybenzenesulfonamide | | free base/ acid | 565.1 |
| 146 | 5-chloro-N-(2,4-difluoro-3-((2-((tetrahydro-2H-pyran-2-ylmethyl)amino)pyrimidin-5-yl)ethynyl)phenyl)-3-(hydroxymethyl)-2-methoxybenzenesulfonamide | | free base/ acid | 579.1 |

TABLE 1-25-continued

| Ex. No. | IUPAC name | structural formula | salt | MS |
|---|---|---|---|---|
| 147 | 5-chloro-N-(2,4-difluoro-3-((2-((tetrahydro-2H-pyran-3-ylmethyl)amino)pyrimidin-5-yl)ethynyl)phenyl)-3-(hydroxymethyl)-2-methoxybenzenesulfonamide | | free base/acid | 579.1 |
| 148 | 5-chloro-N-(2,4-difluoro-3-((2-((tetrahydro-2H-pyran-4-ylmethyl)amino)pyrimidin-5-yl)ethynyl)phenyl)-3-(hydroxymethyl)-2-methoxybenzenesulfonamide | | free base/acid | 579.1 |
| 149 | 5-chloro-N-(2,4-difluoro-3-((2-((2-hydroxyethyl)-amino)pyrimidin-5-yl)ethynyl)phenyl)-3-(hydroxymethyl)-2-methoxybenzenesulfonamide | | free base/acid | 525.1 525.2 |
| 150 | 5-chloro-N-(2,4-difluoro-3-((2-(((2R)-1-hydroxypropan-2-yl)amino)pyrimidin-5-yl)ethynyl)phenyl)-3-(hydroxymethyl)-2-methoxybenzenesulfonamide | | free base/acid | 539.1 539.0 |

TABLE 1-26

| Ex. No. | IUPAC name | structural formula | salt | MS |
|---|---|---|---|---|
| 151 | 5-chloro-N-(2,4-difluoro-3-((2-((3-hydroxy-2,2-dimethylpropyl)amino)-pyrimidin-5-yl)ethynyl)phenyl)-3-(hydroxymethyl)-2-methoxybenzenesulfonamide | | free base/ acid | 567.1 |
| 152 | 5-chloro-N-(2,4-difluoro-3-((2-((cis-4-hydroxycyclohexyl)amino)-pyrimidin-5-yl)ethynyl)phenyl)-3-(hydroxymethyl)-2-methoxybenzenesulfonamide | | free base/ acid | 579.1 |
| 153 | 5-chloro-N-(2,4-difluoro-3-((2-((trans-4-hydroxycyclohexyl)amino)-pyrimidin-5-yl)ethynyl)phenyl)-3-(hydroxymethyl)-2-methoxybenzenesulfonamide | | free base/ acid | 579.1 579.1 |
| 154 | 5-chloro-N-(2,4-difluoro-3-((2-(((1-hydroxycyclopropyl)-methyl)amino)pyrimidin-5-yl)ethynyl)phenyl)-3-(hydroxymethyl)-2-methoxybenzenesulfonamide | | free base/ acid | 551.1 551.1 |

TABLE 1-26-continued

| Ex. No. | IUPAC name | structural formula | salt | MS |
|---|---|---|---|---|
| 155 | 5-chloro-N-(2,4-difluoro-3-((2-(((1-hydroxycyclobutyl)-methyl)amino)pyrimidin-5-yl)ethynyl)phenyl)-3-(hydroxymethyl)-2-methoxybenzenesulfonamide | | free base/acid | 565.1 |
| 156 | 5-chloro-N-(2,4-difluoro-3-((2-(((1-hydroxycyclopentyl)methyl)-amino)pyrimidin-5-yl)ethynyl)phenyl)-3-(hydroxymethyl)-2-methoxybenzenesulfonamide | | free base/acid | 579.1 |

TABLE 1-27

| Ex. No. | IUPAC name | structural formula | salt | MS |
|---|---|---|---|---|
| 157 | 5-chloro-N-(2,4-difluoro-3-((2-(((2-methyltetrahydrofuran-2-yl)methyl)amino)-pyrimidin-5-yl)ethynyl)phenyl)-3-(hydroxymethyl)-2-methoxybenzene-sulfonamide | | free base/acid | 579.1 |
| 158 | N-(3-((3-amino-1,2,4-triazin-6-yl)ethynyl)-2,4-difluorophenyl)-5-chloro-2-methylpyridiine-3-sulfonamide | | free base/acid | 437.0 |
| 159 | N-(3-((2-aminopyrimidin-5-yl)ethynyl)-2,4-difluorophenyl)-5-chloro-3-hydroxy-2,3-dihydro-1-benzofuran-7-sulfonamide | | free base/acid | 479.0 |

TABLE 1-27-continued

| Ex. No. | IUPAC name | structural formula | salt | MS |
|---|---|---|---|---|
| 160 | N-(3-((3-amino-1,2,4-triazin-6-yl)ethynyl)-2,4-difluorophenyl)-5-chloro-3-hydroxy-2,3-dihydro-1-benzofuran-7-sulfonamide | | free base/ acid | 480.0 |
| 161 | 5-chloro-N-(2,4-difluoro-3-((2-((1-hydroxy-2-methylpropan-2-yl)amino)pyrimidin-5-yl)ethynyl)phenyl)-2-methylpyridine-3-sulfonamide | | free base/ acid | 508.1 |
| 162 | N-(3-((2-aminopyrimidin-5-yl)ethynyl)-2,4-difluorophenyl)-5-chloro-2-(difluoromethoxy)-pyridine-3-sulfonamide | | free base/ acid | 485.9 |

TABLE 1-28

| Ex. No. | IUPAC name | structural formula | salt | MS |
|---|---|---|---|---|
| 163 | 5-chloro-N-(2,4-difluoro-3-((2-((1-methyl-1H-pyrazol-4-yl)amino)pyrimidin-5-yl)ethynyl)phenyl)-2-methylpyridine-3-sulfonamide | | free base/ acid | 514.0 |
| 164 | N-(3-((2-aminopyrimidin-5-yl)ethynyl)-2,4-difluorophenyl)-5-chloro-3-(2-hydroxypropan-2-yl)-2-methoxybenzenesulfonamide | | free base/ acid | 507.1 |

TABLE 1-28-continued

| Ex. No. | IUPAC name | structural formula | salt | MS |
|---|---|---|---|---|
| 165 | N-(3-((2-aminopyrimidin-5-yl)ethynyl)-2,4-difluorophenyl)-3,6-dichloroimidazo[1,2-a]pyridine-8-sulfonamide | | free base/acid | 494.9 |
| 166 | N-(3-((2-aminopyrimidin-5-yl)ethynyl)-2,4-difluorophenyl)-5-cyano-2-methylpyridine-3-sulfonamide | | free base/acid | 425.0 |
| 167 | N-(3-((2-aminopyrimidin-5-yl)ethynyl)-2,4-difluorophenyl)-5-cyano-2-methoxypyridine-3-sulfonamide | | free base/acid | 443.1 |
| 168 | 5-chloro-N-(3-((3-(cyclopropylamino)-1,2,4-triazin-6-yl)ethynyl)-2,4-difluorophenyl)-3-(hydroxymethyl)-2-methoxybenzenesulfonamide | | free base/acid | 522.1 |

TABLE 1-29

| Ex. No. | IUPAC name | structural formula | salt | MS |
|---|---|---|---|---|
| 169 | 5-chloro-N-(2,4-difluoro-3-((3-(oxetan-3-ylamino)-1,2,4-triazin-6-yl)ethynyl)phenyl)-3-(hydroxymethyl)-2-methoxybenzenesulfonamide | | free base/acid | 538.2 |

TABLE 1-29-continued

| Ex. No. | IUPAC name | structural formula | salt | MS |
|---|---|---|---|---|
| 170 | 5-chloro-N-(2,4-difluoro-3-((3-(((2R)-1-hydroxypropan-2-yl)amino)-1,2,4-triazin-6-yl)ethynyl)phenyl)-3-(hydroxymethyl)-2-methoxybenzenesulfonamide | | free base/acid | 540.2 |
| 171 | N-(3-((2-aminopyrimidin-5-yl)ethynyl)-2,4-difluorophenyl)-5-chloro-2-(methylamino)pyridine-3-sulfonamide | | free base/acid | 448.9 |
| 172 | N-(3-((2-aminopyrimidin-5-yl)ethynyl)-2,4-difluorophenyl)-5-chloro-2-hydroxypyridine-3-sulfonamide | | free base/acid | 438.0 |
| 173 | N-(3-((2-aminopyrimidin-5-yl)ethynyl)-2,4-difluorophenyl)-5-chloro-1-benzofuran-7-sulfonamide | | free base/acid | 461.0 |
| 174 | 5-chloro-N-(2,4-difluoro-3-((2-((trans-4-hydroxycyclohexyl)amino)-pyrimidin-5-yl)ethynyl)phenyl)-2-methoxypyridine-3-sulfonamide | | free base/acid | 550.1 |

TABLE 1-30

| Ex. No. | IUPAC name | structural formula | salt | MS |
|---|---|---|---|---|
| 175 | 5-chloro-N-(2,4-difluoro-3-((2-(((2R)-1-hydroxypropan-2-yl)amino)pyrimidin-5-yl)ethynyl)phenyl)-2-methoxypyridine-3-sulfonamide | | free base/acid | 510.1 |
| 176 | 2,5-dichloro-N-(2,4-difluoro-3-((2-((trans-4-hydroxycyclohexyl)-amino)pyrimidin-5-yl)ethynyl)phenyl)-3-(hydroxymethyl)-benzenesulfonamide | | free base/acid | 583.1 |
| 177 | 2,5-dichloro-N-(2,4-difluoro-3-((3-((trans-4-hydroxycyclohexyl)-amino)-1,2,4-triazin-6-yl)ethynyl)phenyl)-3-(hydroxymethyl)-benzenesulfonamide | | free base/acid | 584.1 |
| 178 | 2,5-dichloro-N-(2,4-difluoro-3-((3-(((2R)-1-hydroxypropan-2-yl)amino)-1,2,4-triazin-6-yl)ethynyl)phenyl)-3-(hydroxymethyl)-benzenesulfonamide | | free base/acid | 544.0 |
| 179 | 2,5-dichloro-N-(2,4-difluoro-3-((3-(oxetan-3-ylamino)-1,2,4-triazin-6-yl)ethynyl)phenyl)-3-(hydroxymethyl)-benzenesulfonamide | | free base/acid | 542.0 |
| 180 | 2,5-dichloro-N-(2,4-difluoro-3-((2-(((2R)-1-hydroxypropan-2-yl)amino)pyrimidin-5-yl)ethynyl)phenyl)-3-(hydroxymethyl)-benzenesulfonamide | | free base/acid | 543.0 |

TABLE 1-31

| Ex. No. | IUPAC name | structural formula | salt | MS |
|---|---|---|---|---|
| 181 | 2,5-dichloro-N-(2,4-difluoro-3-((2-(oxetan-3-ylamino)pyrimidin-5-yl)ethynyl)phenyl)-3-(hydroxymethyl)-benzenesulfonamide | | free base/acid | 541.1 |
| 182 | 5-chloro-N-(2,4-difluoro-3-((2-((trans-4-hydroxycyclohexyl)-amino)pyrimidin-5-yl)ethynyl)phenyl)-2-(methylamino)pyridine-3-sulfonamide | | free base/acid | 549.1 |
| 183 | 5-chloro-N-(2,4-difluoro-3-((2-(((2R)-1-hydroxypropan-2-yl)amino)pyrimidin-5-yl)ethynyl)phenyl)-2-(methylamino)pyridine-3-sulfonamide | | free base/acid | 509.2 |
| 184 | 5-chloro-N-(2,4-difluoro-3-((2-(((2R)-1-hydroxypropan-2-yl)amino)pyrimidin-5-yl)ethynyl)phenyl)-3-hydroxy-2,3-dihydro-1-benzofuran-7-sulfonamide | | free base/acid | 537.1 |
| 185 | 5-chloro-N-(2,4-difluoro-3-((2-((trans-4-hydroxycyclohexyl)-amino)pyrimidin-5-yl)ethynyl)phenyl)-3-hydroxy-2,3-dihydro-1-benzofuran-7-sulfonamide | | free base/acid | 577.1 |
| 186 | 5-chloro-N-(2,4-difluoro-3-((2-(((2R)-1-hydroxypropan-2-yl)amino)pyrimidin-5-y)ethynyl)phenyl)-3-hydroxy-2,3-dihydro-1-benzofuran-7-sulfonamide (optical isomer not having absolute configuration of benzofuran ring moiety) | | free base/acid | 537.1 |

TABLE 1-32

| Ex. No. | IUPAC name | structural formula | salt | MS |
|---|---|---|---|---|
| 187 | 5-chloro-N-(2,4-difluoro-3-((2-(((2R)-1-hydroxypropan-2-yl)amino)pyrimidin-5-yl)ethynyl)phenyl)-3-hydroxy-2,3-dihydro-1-benzofuran-7-sulfonamide (optical isomer not having absolute configuration of benzofuran ring moiety) | | free base/acid | 537.1 |
| 188 | 5-chloro-N-(2,4-difluoro-3-((2-((trans-4-hydroxycyclohexyl)-amino)pyrimidin-5-yl)ethynyl)phenyl)-2-methylpyridine-3-sulfonamide | | free base/acid | 534.1 |
| 189 | 5-chloro-N-(2,4-difluoro-3-((2-(((2R)-1-hydroxypropan-2-yl)amino)pyrimidin-5-yl)ethynyl)phenyl)-2-methylpyridine-3-sulfonamide | | free base/acid | 494.1 |
| 190 | 5-chloro-N-(2,4-difluoro-3-((2-((trans-4-hydroxycyclohexyl)-amino)pyrimidin-5-yl)ethynyl)phenyl)-3-hydroxy-2,3-dihydro-1-benzofuran-7-sulfonamide (optical isomer) | | free base/acid | 577.1 |
| 191 | 5-chloro-N-(2,4-difluoro-3-((2-((trans-4-hydroxycyclohexyl)-amino)pyrimidin-5-yl)ethynyl)phenyl)-3-hydroxy-2,3-dihydro-1-benzofuran-7-sulfonamide (optical isomer) | | free base/acid | 577.1 |
| 192 | N-(3-((2-aminopyrimidin-5-yl)ethynyl)-2,4-difluorophenyl)-6-chloro-1-methyl-1H-indazole-4-sulfonamide | | free base/acid | 472.9 |

TABLE 1-33

| Ex. No. | IUPAC name | salt | MS |
|---|---|---|---|
| 193 | 5-chloro-N-(2,4-difluoro-3-((2-(((2S)-1-hydroxypropan-2-yl)amino)pyrimidin-5-yl)ethynyl)phenyl)-2-methylpyridine-3-sulfonamide | free base/acid | 494.1 |
| 194 | 2,5-dichloro-N-(2,4-difluoro-3-(pyrimidin-5-ylethynyl)phenyl)-benzenesulfonamide | free base/acid | 437.9 |
| 195 | 2,5-dichloro-N-(2,4-difluoro-3-(pyrazin-2-ylethynyl)phenyl)-benzenesulfonamide | free base/acid | 437.9 |
| 196 | 2,5-dichloro-N-(2,4-difluoro-3-(pyridin-3-ylethynyl)phenyl)-benzenesulfonamide | free base/acid | 439.0 |
| 7a | N-(3-((2-aminopyrimidin-5-yl)ethynyl)-2,4-difluorophenyl)-5-chloro-2-methoxypyridine-3-sulfonamide | free base/acid | 452.0 |
| 180a | 2,5-dichloro-N-(2,4-difluoro-3-((2-(((2S)-1-hydroxypropan-2-yl)amino)pyrimidin-5-yl)ethynyl)phenyl)-3-(hydroxymethyl)-benzenesulfonamide | free base/acid | 543.0 |

The compounds of Reference Examples 1-105, 107-108, 110, 112-121 in the following Tables were produced according to the methods shown in the above-mentioned Examples, or a method analogous thereto. The Reference Example compounds are shown in the following Tables. In the Tables, MS shows measured value.

TABLE 2-1

| Ref. Ex. No. | IUPAC name | structural formula | salt | MS |
|---|---|---|---|---|
| 1 | N-(2,4-difluoro-3-(1H-pyrazolo[3,4-b]pyridin-5-ylethynyl)phenyl)-2-methylpyridine-3-sulfonamide | | free base/acid | 426.1 |
| 2 | N-(2,4-difluoro-3-((3-(pyridin-4-yl)-1H-pyrazolo[3,4-b]pyridin-5-yl)ethynyl)phenyl)-3-fluorobenzenesulfonamide | | free base/acid | 506.2 |
| 3 | 5-bromo-N-(2,-fluoro-3-(1H-pyrazolo[3,4-b]pyridin-5-ylethynyl)-phenyl)pyridine-3-sulfonamide | | free base/acid | 472.2 |
| 4 | 5-bromo-N-(2-chloro-3-(1H-pyrazolo[3,4-b]pyridin-5-ylethynyl)-phenyl)pyridine-3-sulfonamide | | free base/acid | 488.0 |
| 5 | 5-chloro-N-(2,4-difluoro-3-(1H-pyrazolo[3,4-b]pyridin-5-ylethynyl)-phenyl)pyridine-3-sulfonamide | | CF$_3$COOH | 446.1 |

TABLE 2-1-continued

| Ref. Ex. No. | IUPAC name | structural formula | salt | MS |
|---|---|---|---|---|
| 6 | N-(2,4-difluoro-3-(1H-pyrazolo[3,4-b]pyridin-5-ylethynyl)phenyl)-2-(trifluoromethoxy)-benzenesulfonamide | | CF$_3$COOH | 495.1 |

TABLE 2-2

| Ref. Ex. No. | IUPAC name | structural formula | salt | MS |
|---|---|---|---|---|
| 7 | N-(2,4-difluoro-3-(1H-pyrazolo[3,4-b]pyridin-5-ylethynyl)phenyl)-2-(trifluoromethyl)-benzenesulfonamide | | CF$_3$COOH | 479.2 |
| 8 | 5-bromo-N-(4-chloro-2-fluoro-3-(1H-pyrazolo[3,4-b]pyridin-5-ylethynyl)phenyl)-pyridine-3-sulfonamide | | free base/acid | 503.9 |
| 9 | N-(2,4-difluoro-3-(1H-pyrazolo[3,4-b]pyridin-5-ylethynyl)phenyl)-2-methylbenzenesulfonamide | | CF$_3$COOH | 425.1 |

TABLE 2-2-continued

| Ref. Ex. No. | IUPAC name | structural formula | salt | MS |
|---|---|---|---|---|
| 10 | 2-chloro-N-(2,4-difluoro-3-(1H-pyrazolo[3,4-b]pyridin-5-ylethynyl)phenyl)-benzenesulfonamide | | CF₃COOH | 445.1 |
| 11 | 5-bromo-N-(2,4-difluoro-3-(1H-pyrazolo[3,4-b]pyridin-5-ylethynyl)-phenyl)pyridine-3-sulfonamide | | free base/ acid | 490.0 |
| 12 | N-(3-((2-aminopyrimidin-5-yl)ethynyl)-2,4-difluorophenyl)-2-(trifluoromethoxy)-benzenesulfonamide | | free base/ acid | 468.9 |

TABLE 2-3

| Ref. Ex. No. | IUPAC name | structural formula | salt | MS |
|---|---|---|---|---|
| 13 | 2-chloro-N-(2,4-difluoro-3-(1H-pyrazolo[3,4-b]pyridin-5-ylethynyl)phenyl)-pyridine-3-sulfonamide | | free base/ acid | 446.1 |

TABLE 2-3-continued

| Ref. Ex. No. | IUPAC name | structural formula | salt | MS |
|---|---|---|---|---|
| 14 | 2-cyano-N-(2,4-difluoro-3-(1H-pyrazolo[3,4-b]pyridin-5-ylethynyl)-phenyl)benzene-sulfonamide | | CF₃COOH | 436.1 |
| 15 | 3-bromo-N-(2,4-difluoro-3-(1H-pyrazolo[3,4-b]pyridin-5-ylethynyl)phenyl)-benzenesulfonamide | | free base/acid | 487.0 |
| 16 | 4-chloro-N-(2,4-difluoro-3-(1H-pyrazolo[3,4-b]pyridin-5-ylethynyl)-phenyl)pyridine-3-sulfonamide | | CF₃COOH | 446.1 |
| 17 | N-(2,4-difluoro-3-(1H-pyrazolo[3,4-b]pyridin-5-ylethynyl)phenyl)-3-methylbenzenesulfonamide | | free base/acid | 425.1 |
| 18 | N-(2,4-difluoro-3-(1H-pyrazolo[3,4-b]pyridin-5-ylethynyl)phenyl)-2-fluorobenzenesulfonamide | | CF₃COOH | 429.1 |

TABLE 2-4

| Ref. Ex. No. | IUPAC name | structural formula | salt | MS |
|---|---|---|---|---|
| 19 | 3-chloro-N-(2,4-difluoro-3-(1H-pyrazolo[3,4-b]pyridin-5-ylethynyl)phenyl)-benzenesulfonamide | | free base/acid | 445.1 |
| 20 | N-(3-((2-aminopyrimidin-5-yl)ethynyl)-2,4-difluorophenyl)-2-methylbenzenesulfonamide | | free base/acid | 401.1 |
| 21 | 6-chloro-N-(2,4-difluoro-3-(1H-pyrazolo[3,4-b]pyridin-5-ylethynyl)phenyl)-pyridine-3-sulfonamide | | free base/acid | 446.0 |
| 22 | N-(3-((2-aminoopyrimidin-5-yl)ethynyl)-2,4-difluorophenyl)-3-chlorobenzenesulfonamide | | free base/acid | 421.1 |
| 23 | N-(3-((2-aminopyrimidin-5-yl)ethynyl)-2,4-difluorophenyl)-2-chlorobenzenesulfonamide | | free base/acid | 421.1 |
| 24 | N-(2,4-difluoro-3-(1H-pyrazolo[3,4-b]pyridin-5-ylethynyl)phenyl)-3-methoxybenzene-sulfonamide | | free base/acid | 441.1 |

TABLE 2-5

| Ref. Ex. No. | IUPAC name | structural formula | salt | MS |
|---|---|---|---|---|
| 25 | methyl 3-((2,4-difluoro-3-(1H-pyrazolo[3,4-b]pyridin-5-ylethynyl)-phenyl)sulfamoyl)-benzoate | | free base/acid | 469.2 |
| 26 | N-(3-((2-aminopyrimidin-5-yl)ethynyl)-2,4-difluorophenyl)-3-methylbenzene-sulfonamide | | free base/acid | |
| 27 | N-(2,4-difluoro-3-(1H-pyrazolo[3,4-b]pyridin-5-ylethynyl)phenyl)-2,3-dihydro-1-benzofuran-5-sulfonamide | | free base/acid | 453.1 |
| 28 | N-(3-((2-aminopyrimidin-5-yl)ethynyl)-2,4-difluorophenyl)-3-methoxybenzene-sulfonamide | | free base/acid | 417.1 |
| 29 | N-(3-((2-aminopyrimidin-5-yl)ethynyl)-2,4-difluorophenyl)-4-chlorobenzene-sulfonamide | | free base/acid | 421.1 |

TABLE 2-5-continued

| Ref. Ex. No. | IUPAC name | structural formula | salt | MS |
|---|---|---|---|---|
| 30 | 3-cyano-N-(2,4-difluoro-3-(1H-pyrazolo[3,4-b]pyridin-5-ylethynyl)phenyl)-benzenesulfonamide | | free base/ acid | 436.0 |

TABLE 2-6

| Ref. Ex. No. | IUPAC name | structural formula | salt | MS |
|---|---|---|---|---|
| 31 | 3-acetyl-N-(2,4-difluoro-3-(1H-pyrazolo[3,4-b]pyridin-5-ylethynyl)phenyl)-benzenesulfonamide | | free base/ acid | 453.1 |
| 32 | N-(2,4-difluoro-3-(1H-pyrazolo[3,4-b]pyridin-5-ylethynyl)phenyl)-2-methyl-1,3-benzothiazole-6-sulfonamide | | free base/ acid | 480.1 |
| 33 | 5-bromo-N-(2,6-difluoro-3-(1H-pyrazolo[3,4-b]pyridin-5-ylethynyl)phenyl)-pyridine-3-sulfonamide | | free base/ acid | 488.0 |

TABLE 2-6-continued

| Ref. Ex. No. | IUPAC name | structural formula | salt | MS |
|---|---|---|---|---|
| 34 | N-(3-((2-aminopyrimidin-5-yl)ethynyl)-2,4-difluorophenyl)-4-methylbenzenesulfonamide | | free base/acid | 401.1 |
| 35 | N-(2,4-difluoro-3-(1H-pyrazolo[3,4-b]pyridin-5-ylethynyl)phenyl)-3-(trifluoromethyl)-benzenesulfonamide | | free base/acid | 479.2 |
| 36 | N-(2,4-difluoro-3-(1H-pyrazolo[3,4-b]pyridin-5-ylethynyl)phenyl)-3-fluorobenzenesulfonamide | | free base/acid | 429.1 |

TABLE 2-7

| Ref. Ex. No. | IUPAC name | structural formula | salt | MS |
|---|---|---|---|---|
| 37 | 3-(difluoromethoxy)-N-(2,4-difluoro-3-(1H-pyrazolo[3,4-b]pyridin-5-ylethynyl)phenyl)-benzenesulfonamide | | free base/acid | 477.2 |

TABLE 2-7-continued

| Ref. Ex. No. | IUPAC name | structural formula | salt | MS |
|---|---|---|---|---|
| 38 | N-(2,4-difluoro-3-(1H-pyrazolo[3,4-b]pyridin-5-ylethynyl)phenyl)-3-(trifluoromethoxy)-benzenesulfonamide | | free base/acid | 495.1 |
| 39 | N-(2,4-difluoro-3-((3-(1-methylpiperidin-4-yl)-1H-pyrazolo[3,4-b]pyridin-5-yl)ethynyl)phenyl)-3-fluorobenzene-sulfonamide | | free base/acid | 526.2 |
| 40 | N-(2,4-difluoro-3-(1H-pyrazolo[3,4-b]pyridin-5-ylethynyl)phenyl)-6-methoxypyridine-3-sulfonamide | | free base/acid | 442.1 |
| 41 | N-(2,4-difluoro-3-(1H-pyrazolo[3,4-b]pyridin-5-ylethynyl)phenyl)-benzenesulfonamide | | CF$_3$COOH | 411.2 |
| 42 | N-(2,4-difluoro-3-((3-(4-fluorophenyl)-1H-pyrazolo[3,4-b]pyridin-5-yl)ethynyl)phenyl)-pyridine-3-sulfonamide | | free base/acid | 506.1 |

TABLE 2-8

| Ref. Ex. No. | IUPAC name | structural formula | salt | MS |
|---|---|---|---|---|
| 43 | 5-bromo-N-((5-bromopyridin-3-yl)sulfonyl)-N-(2,4-difluoro-3-(1H-pyrazolo[3,4-b]pyridin-5-ylethynyl)phenyl)-pyridine-3-sulfonamide | | free base/acid | |
| 44 | N-(3-((2-aminopyrimidin-5-yl)ethynyl)-2,4-difluorophenyl)-2-methoxybenzene-sulfonamide | | free base/acid | 417.1 |
| 45 | N-(2,4-difluoro-3-(1H-pyrazolo[3,4-b]pyridin-5-ylethynyl)phenyl)-pyridine-3-sulfonamide | | $CF_3COOH$ | 412.1 |
| 46 | N-(5-((2,6-difluoro-3-(((3-fluorophenyl)-sulfonyl)amino)phenyl)-ethynyl)pyridin-2-yl)acetamide | | free base/acid | 446.1 |
| 47 | 5-bromo-N-(2,4-difluoro-5-(1H-pyrazolo[3,4-b]pyridin-5-ylethynyl)-phenyl)pyridine-3-sulfonamide | | free base/acid | 490.0 |

TABLE 2-8-continued

| Ref. Ex. No. | IUPAC name | structural formula | salt | MS |
|---|---|---|---|---|
| 48 | 4-bromo-N-(2,4-difluoro-3-(1H-pyrazolo[3,4-b]pyridin-5-ylethynyl)phenyl)-benzenesulfonamide | | free base/acid | 487.1 |

TABLE 2-9

| Ref. Ex. No. | IUPAC name | structural formula | salt | MS |
|---|---|---|---|---|
| 49 | N-(2,4-difluoro-3-(1H-imidazo[4,5-b]pyridin-6-ylethynyl)-phenyl)pyridine-3-sulfonamide | | $CF_3COOH$ | 412.1 |
| 50 | N-(2,4-difluoro-3-(1H-pyrazolo[3,4-b]pyridin-5-ylethynyl)phenyl)-chromane-6-sulfonamide | | free base/acid | 467.2 |
| 51 | 2,5-dichloro-N-(2,4-difluoro-3-(1H-pyrazol-4-ylethynyl)-phenyl)benzene-sulfonamide | | free base/acid | 425.9 |

TABLE 2-9-continued

| Ref. Ex. No. | IUPAC name | structural formula | salt | MS |
|---|---|---|---|---|
| 52 | N-(2,4-difluoro-3-(1H-pyrazolo[3,4-b]pyridin-5-ylethynyl)phenyl)-3-oxo-3,4-dihydro-2H-1,4-benzoxazin-6-sulfonamide | | free base/acid | 482.1 |
| 53 | 2-((2,6-difluoro-3-((pyridin-3-ylsulfonyl)amino)-phenyl)ethynyl)-benzamide | | CF$_3$COOH | 414.1 |
| 54 | N-(2,4-difluoro-3-(1H-pyrazolo[3,4-b]pyridin-4-ylethynyl)phenyl)-pyridine-3-sulfonamide | | CF$_3$COOH | 412.1 |

TABLE 2-10

| Ref. Ex. No. | IUPAC name | structural formula | salt | MS |
|---|---|---|---|---|
| 55 | N-(3-((2-aminopyrimidin-5-yl)ethynyl)-2,4-difluorophenyl)-pyridine-3-sulfonamide | | CF$_3$COOH | 388.1 |
| 56 | N-(2,4-difluoro-3-((3-(4-fluorophenyl)-1H-pyrazolo[3,4-b]pyridin-5-yl)ethynyl)phenyl)-benzenesulfonamide | | free base/acid | 505.1 |

TABLE 2-10-continued

| Ref. Ex. No. | IUPAC name | structural formula | salt | MS |
|---|---|---|---|---|
| 57 | N-(3-((2-aminopyrimidin-5-yl)ethynyl)-2,4-difluorophenyl)-4-methoxybenzene-sulfonamide | | free base/acid | 417.1 |
| 58 | N-(2,4-difluoro-3-(1H-pyrazolo[3,4-b]pyridin-5-ylethynyl)phenyl)-2,3-dihydro-1,4-benzodioxine-6-sulfonamide | | free base/acid | 469.2 |
| 59 | N-(2,4-difluoro-3-(imidazo[1,2-b]pyridazin-3-ylethynyl)phenyl)-pyridine-3-sulfonamide | | CF$_3$COOH | 412.1 |
| 60 | N-(3-((6-aminopyridin-3-yl)ethynyl)-2,4-difluorophenyl)-pyridine-3-sulfonamide | | CF$_3$COOH | 387.1 |

TABLE 2-11

| Ref. Ex. No. | IUPAC name | structural formula | salt | MS |
|---|---|---|---|---|
| 61 | 5-((2,6-difluoro-3-((pyridin-3-ylsulfonyl)amino)-phenyl)ethynyl)-thiophene-2-carboxamide | | CF$_3$COOH | 420.0 |

TABLE 2-11-continued

| Ref. Ex. No. | IUPAC name | structural formula | salt | MS |
|---|---|---|---|---|
| 62 | 4-((2,6-difluoro-3-((pyridin-3-ylsulfonyl)amino)phenyl)ethynyl)benzamide | 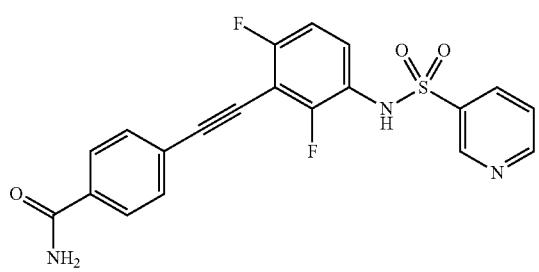 [SMILES: NC(=O)c1ccc(C#Cc2c(F)ccc(NS(=O)(=O)c3cccnc3)c2F)cc1] | CF₃COOH | 414.1 |
| 63 | N-(2,4-difluoro-3-((6-methylpyridin-3-yl)ethynyl)phenyl)pyridine-3-sulfonamide | 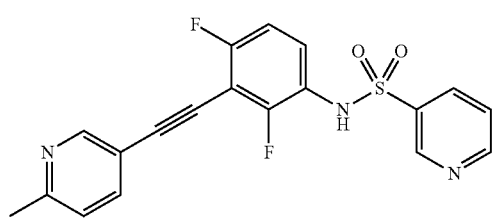 [SMILES: Cc1ccc(C#Cc2c(F)ccc(NS(=O)(=O)c3cccnc3)c2F)cn1] | CF₃COOH | 386.1 |
| 64 | N-(2,4-difluoro-3-(pyridin-3-ylethynyl)phenyl)pyridine-3-sulfonamide | 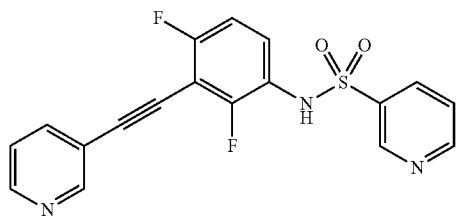 [SMILES: O=S(=O)(Nc1ccc(F)c(C#Cc2cccnc2)c1F)c1cccnc1] | CF₃COOH | 372.1 |
| 65 | N-(2,4-difluoro-3-(1H-[1,2,3]triazolo[4,5-b]pyridin-6-ylethynyl)phenyl)pyridine-3-sulfonamide | 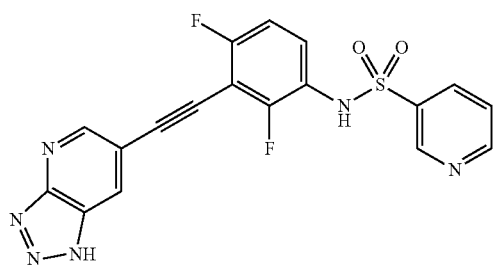 [SMILES: O=S(=O)(Nc1ccc(F)c(C#Cc2cnc3nn[nH]c3c2)c1F)c1cccnc1] | CF₃COOH | 413.1 |
| 66 | 3-((2,6-difluoro-3-((pyridin-3-ylsulfonyl)amino)phenyl)ethynyl)benzamide | 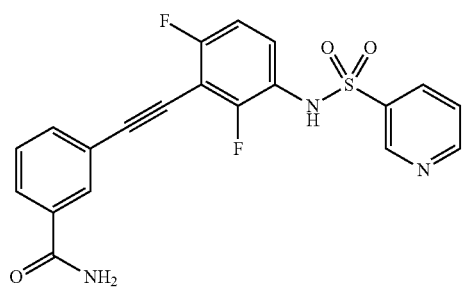 [SMILES: NC(=O)c1cccc(C#Cc2c(F)ccc(NS(=O)(=O)c3cccnc3)c2F)c1] | CF₃COOH | 414.1 |

TABLE 2-12

| Ref. Ex. No. | IUPAC name | structural formula | salt | MS |
|---|---|---|---|---|
| 67 | N-(3-((2-aminopyridin-3-yl)ethynyl)-2,4-difluorophenyl)-pyridine-3-sulfonamide | | CF$_3$COOH | 387.1 |
| 68 | N-(3-((3-cyclopropyl-1H-pyrazolo[3,4-b]pyridin-5-yl)ethynyl)-2,4-difluorophenyl)-3-fluorobenzene-sulfonamide | | free base/ acid | 469.1 |
| 69 | N-(3-((6-aminopyridin-2-yl)ethynyl)-2,4-difluorophenyl)-pyridine-3-sulfonamide | | CF$_3$COOH | 387.1 |
| 70 | 2,5-dichloro-N-(3-((1,5-dimethyl-1H-pyrazol-4-yl)ethynyl)-2,4-difluorophenyl)-benzenesulfonamide | | CF$_3$COOH | 456.0 |
| 71 | N-(3-((2-aminopyridin-4-yl)ethynyl)-2,4-difluorophenyl)-pyridine-3-sulfonamide | | CF$_3$COOH | 387.1 |
| 72 | N-(2,4-difluoro-3-(1H-pyrazolo[3,4-b]pyridin-5-ylethynyl)phenyl)-2-ethoxybenzene-sulfonamide | | CF$_3$COOH | 455.2 |

TABLE 2-13

| Ref. Ex. No. | IUPAC name | structural formula | salt | MS |
|---|---|---|---|---|
| 73 | N-(2,4-difluoro-3-((2-phenyl-1H-pyrrolo[2,3-b]pyridin-5-yl)ethynyl)phenyl)-3-fluorobenzene-sulfonamide | | free base/acid | 504.3 |
| 74 | 1-(2,4-dichlorophenyl)-N-(2,4-difluoro-3-(1H-pyrazolo[3,4-b]pyridin-5-ylethynyl)phenyl)-methanesulfonamide | | free base/acid | 490.9 |
| 75 | N-(2,4-difluoro-3-(1H-pyrazolo[3,4-b]pyridin-5-ylethynyl)phenyl)-5-phenylpyridine-3-sulfonamide | | free base/acid | 488.1 |
| 76 | N-(2,4-difluoro-3-(1H-pyrazolo[3,4-b]pyridin-5-ylethynyl)phenyl)-3-phenoxybenzene-sulfonamide | | free base/acid | 503.1 |

TABLE 2-13-continued

| Ref. Ex. No. | IUPAC name | structural formula | salt | MS |
|---|---|---|---|---|
| 77 | N-(2,4-difluoro-3-(1H-pyrazolo[3,4-b]pyridin-5-ylethynyl)phenyl)-6-(trifluoromethyl)-pyridine-3-sulfonamide | | free base/ acid | 478.0 |
| 78 | N-(2,4-difluoro-3-(1H-pyrazolo[3,4-b]pyridin-5-ylethynyl)phenyl)-pyridine-2-sulfonamide | | free base/ acid | 412.1 |

TABLE 2-14

| Ref. Ex. No. | IUPAC name | structural formula | salt | MS |
|---|---|---|---|---|
| 79 | N-(2,4-difluoro-3-(1H-pyrazolo[3,4-b]pyridin-5-ylethynyl)phenyl)-4'-methylbiphenyl-4-sulfonamide | | free base/ acid | 501.2 |
| 80 | N-(4-fluoro-3-((3-(4-fluorophenyl)-1H-pyrazolo[3,4-b]pyridin-5-yl)ethynyl)phenyl)-pyridine-3-sulfonamide | | free base/ acid | 486.1 |

| Ref. Ex. No. | IUPAC name | structural formula | salt | MS |
|---|---|---|---|---|
| 81 | N-(4-((3-(4-fluorophenyl)-1H-pyrazolo[3,4-b]pyridin-5-yl)ethynyl)phenyl)-pyridine-3-sulfonamide | 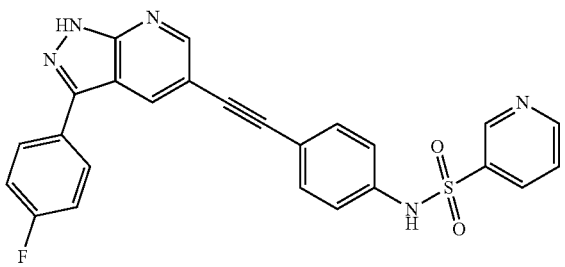 [SMILES: O=S(=O)(Nc1ccc(C#Cc2cnc3[nH]nc(-c4ccc(F)cc4)c3c2)cc1)c1cccnc1] | free base/acid | 470.1 |
| 82 | 5-bromo-N-(2-fluoro-5-(1H-pyrazolo[3,4-b]pyridin-5-ylethynyl)-phenyl)pyridine-3-sulfonamide | 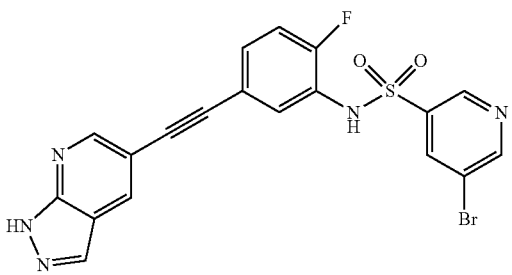 [SMILES: O=S(=O)(Nc1cc(C#Cc2cnc3[nH]ncc3c2)ccc1F)c1cncc(Br)c1] | free base/acid | 469.9 |
| 83 | N-(2-((3-(4-fluorophenyl)-1H-pyrazolo[3,4-b]pyridin-5-yl)ethynyl)phenyl)-pyridine-3-sulfonamide | 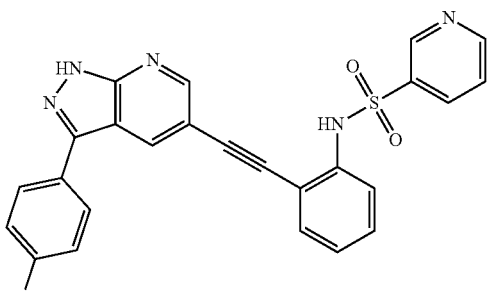 | free base/acid | 470.1 |
| 84 | N-(2,4-difluoro-3-(1H-pyrazolo[3,4-b]pyridin-5-ylethynyl)phenyl)-1H-indazole-5-sulfonamide | 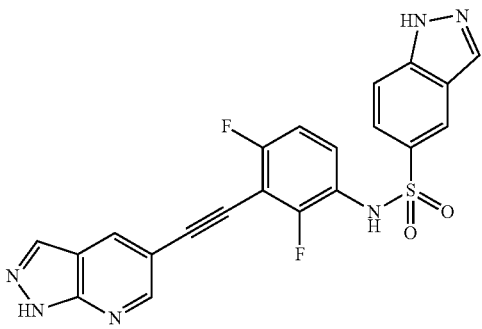 [SMILES: O=S(=O)(Nc1ccc(F)c(C#Cc2cnc3[nH]ncc3c2)c1F)c1ccc2[nH]ncc2c1] | free base/acid | 451.1 |

TABLE 2-15

| Ref. Ex. No. | IUPAC name | structural formula | salt | MS |
|---|---|---|---|---|
| 85 | 3-tert-butyl-N-(2,4-difluoro-3-(1H-pyrazolo[3,4-b]pyridin-5-ylethynyl)phenyl)-benzenesulfonamide | 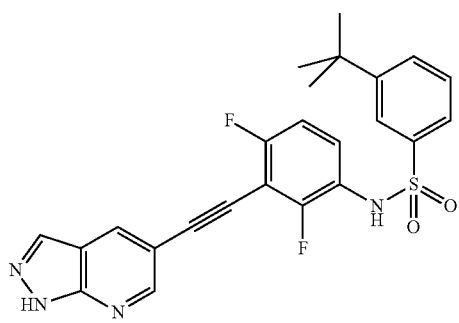 [SMILES: CC(C)(C)c1cccc(S(=O)(=O)Nc2ccc(F)c(C#Cc3cnc4[nH]ncc4c3)c2F)c1] | free base/ acid | 467.2 |
| 86 | 4'-chloro-N-(2,4-difluoro-3-(1H-pyrazolo[3,4-b]pyridin-5-ylethynyl)phenyl)-biphenyl-4-sulfonamide | 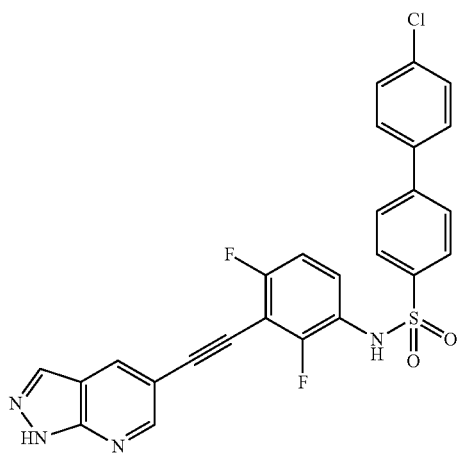 [SMILES: O=S(=O)(Nc1ccc(F)c(C#Cc2cnc3[nH]ncc3c2)c1F)c1ccc(-c2ccc(Cl)cc2)cc1] | free base/ acid | 521.1 |
| 87 | N-(2,4-difluoro-3-(1H-pyrazolo[3,4-b]pyridin-5-ylethynyl)phenyl)-biphenyl-3-sulfonamide | 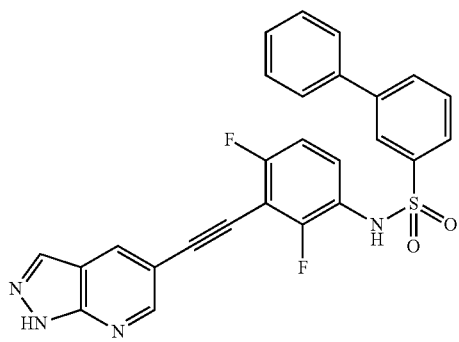 [SMILES: O=S(=O)(Nc1ccc(F)c(C#Cc2cnc3[nH]ncc3c2)c1F)c1cccc(-c2ccccc2)c1] | free base/ acid | 487.1 |
| 88 | N-(2,4-difluoro-3-(1H-pyrazolo[3,4-b]pyridin-5-ylethynyl)phenyl)-4'-methylbiphenyl-3-sulfonamide | 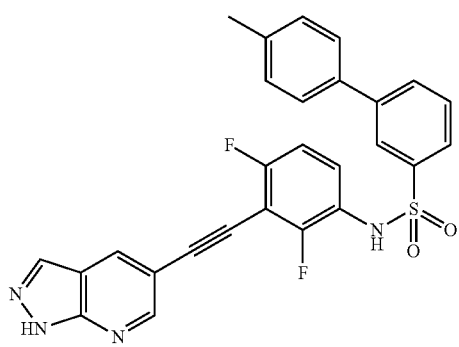 [SMILES: Cc1ccc(-c2cccc(S(=O)(=O)Nc3ccc(F)c(C#Cc4cnc5[nH]ncc5c4)c3F)c2)cc1] | free base/ acid | 501.2 |

TABLE 2-15-continued

| Ref. Ex. No. | IUPAC name | structural formula | salt | MS |
|---|---|---|---|---|
| 89 | N-(2,4-difluoro-3-(1H-pyrazolo[3,4-b]pyridin-5-ylethynyl)phenyl)-6-phenylpyridine-3-sulfonamide | | free base/acid | 487.9 |
| 90 | 4-acetyl-N-(2,4-difluoro-3-(1H-pyrazolo[3,4-b]pyridin-5-ylethynyl)phenyl)-3,4-dihydro-2H-1,4-benzoxazine-6-sulfonamide | | free base/acid | 510.1 |

TABLE 2-16

| Ref. Ex. No. | IUPAC name | structural formula | salt | MS |
|---|---|---|---|---|
| 91 | N-(3-((3-(4-fluorophenyl)-1H-pyrazolo[3,4-b]pyridin-5-yl)-ethynyl)phenyl)-pyridine-3-sulfonamide | | free base/acid | 470.1 |
| 92 | N-(2,4-difluoro-3-(1H-pyrazolo[3,4-b]pyridin-5-ylethynyl)phenyl)-4-methyl-3,4-dihydro-2H-1,4-benzoxazine-7-sulfonamide | | free base/acid | 482.1 |

TABLE 2-16-continued

| Ref. Ex. No. | IUPAC name | structural formula | salt | MS |
|---|---|---|---|---|
| 93 | 5-((3-amino-2,6-difluorophenyl)-ethynyl)-N-(4-methoxybenzyl)-pyrimidin-2-amine | | free base/ acid | 367.1 |
| 94 | 5-bromo-N-(2,4-difluoro-3-(1H-pyrazolo[3,4-b]pyridin-5-ylethynyl)phenyl)-N-methylpyridine-3-sulfonamide | | free base/ acid | 504.0 |
| 95 | 3,5-dichloro-N-(3-ethynyl-2,4-difluorophenyl)-benzenesulfonamide | | free base/ acid | 359.9 |
| 96 | N-(2,4-difluoro-3-(1H-pyrazolo[3,4-b]pyridin-5-ylethynyl)phenyl)-5,6,7,8-tetrahydronaphthalene-2-sulfonamide | | free base/ acid | 465.2 |

TABLE 2-17

| Ref. Ex. No. | IUPAC name | structural formula | salt | MS |
|---|---|---|---|---|
| 97 | N-(2,4-difluoro-3-(1H-pyrrolo[2,3-b]pyridin-5-ylethynyl)phenyl)-3-fluorobenzene-sulfonamide | | free base/ acid | 428.0 |

TABLE 2-17-continued

| Ref. Ex. No. | IUPAC name | structural formula | salt | MS |
|---|---|---|---|---|
| 98 | N-(2,4-difluoro-3-(1H-pyrazolo[3,4-b]pyridin-5-ylethynyl)phenyl)-3-(1,3-oxazol-5-yl)benzenesulfonamide | | free base/acid | 478.1 |
| 99 | N-(2,4-difluoro-3-(1H-pyrazolo[3,4-b]pyridin-5-ylethynyl)phenyl)-5-fluoropyridine-3-sulfonamide | | $CF_3COOH$ | 430.1 |
| 100 | 2,5-dichloro-N-(2,4-difluoro-3-(imidazo[1,2-a]pyrazin-5-ylethynyl)phenyl)-benzenesulfonamide | | $CF_3COOH$ | 479.0 |
| 101 | 2,5-dichloro-N-(2,4-difluoro-3-(imidazo[1,2-a]pyridin-3-ylethynyl)phenyl)-benzenesulfonamide | | $CF_3COOH$ | 478.0 |
| 102 | 2,5-dichloro-N-(2,4-difluoro-3-(pyrazolo[1,5-a]pyridin-3-ylethynyl)phenyl)-benzenesulfonamide | | $CF_3COOH$ | 476.0 |

TABLE 2-18

| Ref. Ex. No. | IUPAC name | structural formula | salt | MS |
|---|---|---|---|---|
| 103 | N-(3-((6-aminopyridazin-3-yl)ethynyl)-2,4-difluorophenyl)-2,5-dichlorobenzene-sulfonamide | | CF₃COOH | 455.0 |
| 104 | 2,5-dichloro-N-(3-((2-chloropyrimidin-5-yl)ethynyl)-2,4-difluorophenyl)-benzenesulfonamide | | free base/ acid | 471.8 |
| 105 | 2,5-dichloro-N-(2,4-difluoro-3-((6-methylpyridin-3-yl)ethynyl)phenyl)-benzenesulfonamide | | CF₃COOH | 453.0 |
| 107 | 2,5-dichloro-N-(2,4-difluoro-3-((2-methylpyrimidin-5-yl)ethynyl)phenyl)-benzenesulfonamide | | free base/ acid | 451.9 |
| 108 | 2,5-dichloro-N-(2,4-difluoro-3-((2-methoxypyrimidin-5-yl)ethynyl)phenyl)-benzenesulfonamide | | free base/ acid | 467.8 |

TABLE 2-19

| Ref. Ex. No. | IUPAC name | structural formula | salt | MS |
|---|---|---|---|---|
| 110 | 5-((3-(((2,5-dichlorophenyl)-sulfonyl)amino)-2,6-difluorophenyl)-ethynyl)pyrimidine-2-carboxamide | | free base/ acid | 480.9 |
| 112 | 2,5-dichloro-N-(2,4-difluoro-3-(pyridazin-4-ylethynyl)phenyl)-benzenesulfonamide | | free base/ acid | 440.0 |
| 113 | methyl 5-((3-(((2,5-dichlorophenyl)-sulfonyl)amino)-2,6-difluorophenyl)-ethynyl)pyrimidine-2-carboxylate | | free base/ acid | 495.9 |
| 114 | 2,5-dichloro-N-(3-((2-cyanopyrimidin-5-yl)ethynyl)-2,4-difluorophenyl)-benzenesulfonamide | | free base/ acid | 462.9 |

TABLE 2-20

| Ref. Ex. No. | IUPAC name | structural formula | salt | MS |
|---|---|---|---|---|
| 115 | 5-chloro-N-(2,4-difluoro-3-((2-(1H-pyrazol-5-yl)pyrimidin-5-yl)ethynyl)phenyl)-3-(hydroxymethyl)-2-methoxybenzene-sulfonamide | | free base/ acid | 532.1 |

TABLE 2-20-continued

| Ref. Ex. No. | IUPAC name | structural formula | salt | MS |
|---|---|---|---|---|
| 116 | 2,5-dichloro-N-(2,4-difluoro-3-((2-fluoropyrimidin-5-yl)ethynyl)phenyl)-benzenesulfonamide | 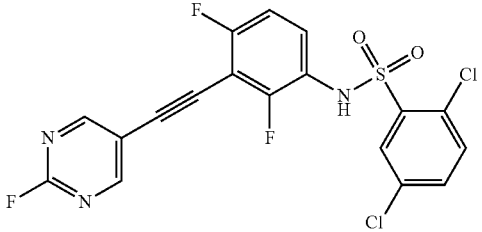 [SMILES: O=S(=O)(Nc1ccc(F)c(C#Cc2cnc(F)nc2)c1F)c1cc(Cl)ccc1Cl] | free base/acid | 455.9 |
| 117 | 2,5-dichloro-N-(2,4-difluoro-3-((6-methoxypyridin-3-yl)ethynyl)phenyl)-benzenesulfonamide | 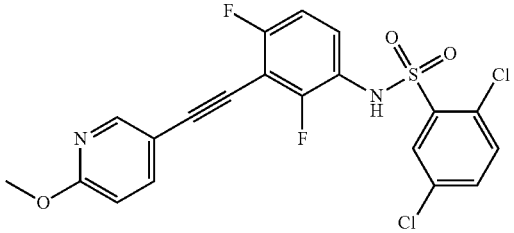 [SMILES: COc1ccc(C#Cc2c(F)ccc(NS(=O)(=O)c3cc(Cl)ccc3Cl)c2F)cn1] | free base/acid | 469.0 |
| 118 | 2,5-dichloro-N-(2,4-difluoro-3-((6-oxo-1,6-dihydropyridin-3-yl)ethynyl)phenyl)-benzenesulfonamide | 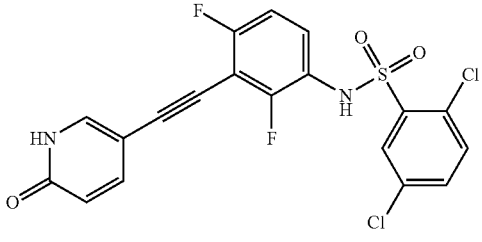 [SMILES: O=c1ccc(C#Cc2c(F)ccc(NS(=O)(=O)c3cc(Cl)ccc3Cl)c2F)c[nH]1] | free base/acid | 452.9 |
| 119 | 2,5-dichloro-N-(2,4-difluoro-3-((2-oxo-1,2-dihydropyridin-4-yl)ethynyl)phenyl)-benzenesulfonamide | 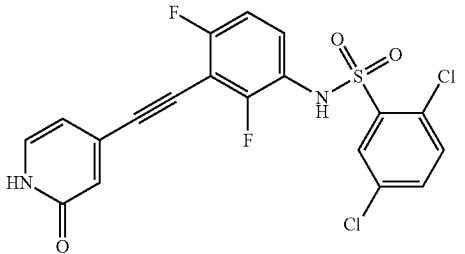 [SMILES: O=c1cc(C#Cc2c(F)ccc(NS(=O)(=O)c3cc(Cl)ccc3Cl)c2F)cc[nH]1] | free base/acid | 454.9 |
| 120 | N-(2-((2-aminopyrimidin-5-yl)ethynyl)-3-fluoropyridin-4-yl)-2,5-dichlorobenzene-sulfonamide | 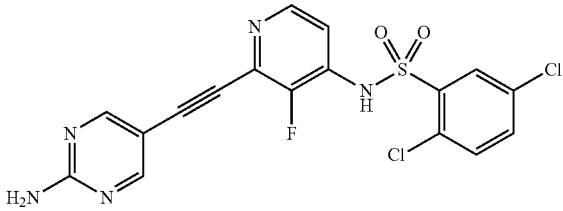 [SMILES: Nc1ncc(C#Cc2nccc(NS(=O)(=O)c3cc(Cl)ccc3Cl)c2F)cn1] | free base/acid | 438.0 |

TABLE 2-21

| Ref. Ex. No. | IUPAC name | structural formula | salt | MS |
|---|---|---|---|---|
| 121 | N-(3-((2-aminopyrimidin-5-yl)ethynyl)phenyl)-5-chloro-2-methoxypyridine-3-sulfonamide | | free base/ acid | 416.1 |

Experimental Example 1

GCN2 Enzyme Inhibition Assay

The GCN2 enzyme inhibitory activity of the compounds of Examples 1-38, 105-112, 123-126, 129-131, 136-138, 140, 141, 145, 149, 150, 153, 158, 159, 162, 163, 165, 168, 171, 173-186, 188-191, 193 was measured.

The GCN2 enzyme inhibitory activity of the compound of the present invention was evaluated using human GCN2 full-length protein (accession number Q9P2K8.3) purchased from Carna Biosciences, Inc. GCN2 enzyme was preserved at −70° C. and used.

The GCN2 enzyme inhibitory activity of the test compound was measured by the LanthaScreenTR-FRET (Time Resolved Fluorescence Resonance Energy Transfer) method (manufactured by ThermoFisher). A test compound (6 μM) diluted with an assay buffer (20 mM HEPES (pH 7.5), 10 mM $MgCl_2$, 2 mM DTT, 0.01% Tween-20, 1 mM EGTA) was added by 2 μL to each well of a 384 well plate (final concentration 3 μM). Then, GCN2 enzyme solution diluted with the assay buffer was added by 2 μL to each well. The enzyme solution was not added to a part of the wells to give a control group. After incubation at room temperature for 1 hr, 570 μM ATP solution containing 390 nM GFP-EIF2alpha physiological protein substrate (ThermoFisher) was added by 2 μL. After reaction at room temperature for 1 hr, TR-FRET Dilution Buffer (ThermoFisher) containing 4 nM Terbium-labeled anti-elF2alpha [pSer52] antibody (ThermoFisher) dissolved therein was added by 2 μL to each well. After standing at room temperature for 1 hr, time decomposition fluorescence measurement was performed on plate-reader Envision (manufactured by PerkinElmer). The inhibitory activity of each compound at a compound concentration of 3 μM was calculated as a relative activity value with the fluorescence intensity of the control group without addition of the enzyme solution as 100% inhibition. The results thereof are shown in Tables 3-1, 3-2.

TABLE 3-1

| Example No. | inhibitory rate |
|---|---|
| 1 | 100% |
| 2 | 100% |
| 3 | 99% |
| 4 | 100% |
| 5 | 99% |
| 6 | 99% |
| 7 | 100% |
| 8 | 100% |
| 9 | 99% |
| 10 | 99% |
| 11 | 99% |
| 12 | 99% |

TABLE 3-1-continued

| Example No. | inhibitory rate |
|---|---|
| 13 | 99% |
| 14 | 98% |
| 15 | 100% |
| 16 | 100% |
| 17 | 99% |
| 18 | 100% |
| 19 | 98% |
| 20 | 100% |
| 21 | 99% |
| 22 | 99% |
| 23 | 100% |
| 24 | 99% |
| 25 | 99% |
| 26 | 99% |
| 27 | 95% |
| 28 | 99% |
| 29 | 99% |
| 30 | 98% |
| 31 | 99% |
| 32 | 99% |
| 33 | 98% |
| 34 | 98% |
| 35 | 95% |
| 36 | 99% |
| 37 | 98% |
| 38 | 99% |
| 105 | 100% |
| 106 | 99% |
| 107 | 99% |
| 108 | 99% |
| 109 | 99% |
| 110 | 100% |
| 111 | 97% |
| 112 | 99% |
| 123 | 100% |
| 124 | 100% |
| 125 | 100% |
| 126 | 100% |

TABLE 3-2

| Example No. | inhibitory rate |
|---|---|
| 129 | 99% |
| 130 | 99% |
| 131 | 99% |
| 136 | 99% |
| 137 | 99% |
| 138 | 99% |
| 140 | 99% |
| 141 | 99% |
| 145 | 99% |
| 149 | 99% |
| 150 | 99% |
| 153 | 99% |
| 158 | 99% |
| 159 | 99% |

TABLE 3-2-continued

| Example No. | inhibitory rate |
|---|---|
| 162 | 99% |
| 163 | 100% |
| 165 | 96% |
| 168 | 99% |
| 171 | 100% |
| 173 | 99% |
| 174 | 99% |
| 175 | 99% |
| 176 | 100% |
| 177 | 100% |
| 178 | 100% |
| 179 | 102% |
| 180 | 103% |
| 181 | 102% |
| 182 | 102% |
| 183 | 103% |
| 184 | 99% |
| 185 | 100% |
| 186 | 100% |
| 188 | 100% |
| 189 | 99% |
| 190 | 99% |
| 191 | 99% |
| 193 | 98% |

From the results, it was clarified that the compound of the present invention has a GCN2 inhibitory activity.

Experimental Example 2

In Vitro Cell Proliferation Inhibition Assay

The cancer cell proliferation inhibitory activity of the compounds of Examples 1, 2, 4, 5, 7, 8, 10, 13-15, 17-20, 23-26, 31, 33, 37, 38, 129, 130, 137, 138, 140, 141, 145, 149, 150, 153, 154, 158, 159, 162, 163, 165, 168, 171, 173-193 was evaluated in vitro.

A cell suspension (40 µL) (1000 cells/well) of osteosarcoma cell line U-2-OS obtained from ATCC (American Type Culture Collection) was seeded on a 384 plate using McCoy's 5A low amino acid media (amino acid content 25%). The seeded cells were incubated (37° C., 5% $CO_2$) overnight to 24 hr at the longest. Each example compound was dissolved (10 mM) in DMSO, delivered to wells by using TECAN HP D300 (TECAN), and the plate was incubated for 72 hr (37° C., 5% $CO_2$). A well without addition of compound was treated similarly as a control group. Celltiter-Glo (registered trade mark) Luminescent Cell Viability Assay reagent (Promega KK) equilibrated at room temperature was added (40 µL/well) to cells in each well before compound treatment (untreated group) and 72 hours after compound treatment. After incubation for 10 min, cell proliferation inhibitory rate was measured by the amount of ATP which is a cell viability marker. Luminescence of cells showing ATP amount was measured using ARVO MX (PerkinElmer). Based on the luminescence values of the untreatment group, the control group without addition of Example compound solution, and the treatment group with addition of Example compound, the cell proliferation inhibitory rate (%) of the test compound at a compound concentration of 100 nM was calculated by the following formula and the results thereof are shown in Tables 4-1, 4-2.

Inhibitory rate (%)=(1−(luminescence value of treatment group−luminescence value of untreatment group)÷(luminescence value of control group−luminescence value of untreatment group))×100

TABLE 4-1

| Example No. | inhibitory rate |
|---|---|
| 1 | 66% |
| 2 | 92% |
| 4 | 90% |
| 5 | 91% |
| 7 | 96% |
| 8 | 78% |
| 10 | 63% |
| 13 | 70% |
| 14 | 42% |
| 15 | 75% |
| 17 | 73% |
| 18 | 63% |
| 19 | 87% |
| 20 | 63% |
| 23 | 72% |
| 24 | 37% |
| 25 | 44% |
| 26 | 41% |
| 31 | 53% |
| 33 | 40% |
| 37 | 45% |
| 38 | 22% |

TABLE 4-2

| Example No. | inhibitory rate |
|---|---|
| 129 | 70% |
| 130 | 68% |
| 137 | 75% |
| 138 | 87% |
| 140 | 76% |
| 141 | 75% |
| 145 | 69% |
| 149 | 70% |
| 150 | 77% |
| 153 | 78% |
| 154 | 70% |
| 158 | 43% |
| 159 | 60% |
| 162 | 35% |
| 163 | 88% |
| 165 | 27% |
| 168 | 57% |
| 171 | 82% |
| 173 | 76% |
| 174 | 83% |
| 175 | 75% |
| 176 | 77% |
| 177 | 72% |
| 178 | 74% |
| 179 | 75% |
| 180 | 76% |
| 181 | 80% |
| 182 | 71% |
| 183 | 77% |
| 184 | 59% |
| 185 | 56% |
| 186 | 43% |
| 187 | 64% |
| 188 | 77% |
| 189 | 79% |
| 190 | 65% |
| 191 | 74% |
| 192 | 43% |
| 193 | 64% |

From the results, it was clarified that the compound of the present invention has an activity to inhibit proliferation of osteosarcoma cell line U-2-OS.

Experimental Example 3

In Vitro ATF4 Expression Suppression Assay

A cell suspension (40 μL) (500000 cells/well) of human acute lymphoblastic leukemia cell line CCRF-CEM obtained from ATCC (American Type Culture Collection) was seeded on a 12 well plate using RPMI1640 medium. The seeded cells were incubated (37° C., 5% $CO_2$) overnight to 24 hr at the longest. L-asparaginase (Sigma-Aldrich Co. LLC.) was dissolved in PBS and treated in each well to a final concentration of 0.1 U/mL. Furthermore, each test compound was dissolved (10 mM) in DMSO, delivered to wells by using TECAN HP D300 (TECAN), and the plate was incubated for 4 hr (37° C., 5% $CO_2$). A well without addition of compound was treated similarly as a control group. Using a protein extract (10% glycerol, 1% sodium dodecyl sulfate, 62.5 mM Tris-HCl [pH 7.5], protease and phosphatase inhibitors [Complete mini and PhosSTOP, Sigma-Aldrich Co. LLC.]), protein was extracted and subjected to Western blot.

Protein extract solution was subjected to protein quantification with BCA Protein Assay Kit (Thermo Scientific), electrophoresed on 7.5-15% SDS-PAGE gel (DRC), and protein in the gel was transferred to PVDF membrane. The membrane was blocked with Starting Block T20 (PBS) Blocking Buffer (Thermo Scientific). ATF4 antibody (Cell signaling) was diluted 1000-fold with Can Get Signal (registered trade mark) Immunoreaction Enhancer Solution I (Toyobo) and reacted overnight at 4° C. The next day, HRP-conjugated anti-rabbit immunoglobulin (Cell signaling) was diluted 5000-fold with Can Get Signal (registered trade mark) Immunoreaction Enhancer Solution II (Toyobo) and reacted at room temperature for 1 hr. Thereafter, chemiluminescence was performed using ImmunoStar LD (Wako Pure Chemical Industries, Ltd.), and luminescence intensity was measured by LAS-3000 image analyzer (Fuji Film Co., Ltd.). Furthermore, the expression level of ATF4 was digitized by quantifying the luminescence intensity using Multi Gauge Ver. 3.1 (Fuji Film Co., Ltd.).

Based on the ATF4 expression level of the control group without addition of Example compound solution and the treatment group with addition of Example compound, the ATF4 expression inhibition ratio (%) of the test compound at a compound concentration of 400 nM was calculated by the following formula and the results thereof are shown in Table 5.

ATF4 expression inhibition ratio (%)=(1-(ATF4 expression level of treatment group)÷(ATF4 expression level of control group)×100

TABLE 5

| compound name | in vitro ATF4 expression inhibition ratio (%) |
|---|---|
| Example 7 | 97 |
| Example 4 | 97 |

From the results, it was clarified that the compound of the present invention has an activity to suppress ATF4 expression in the presence of L-asparaginase in vitro.

Experimental Example 4

In Vivo ATF4 Expression Suppression Assay

One million human acute lymphoblastic leukemia cell lines CCRF-CEM obtained from ATCC (American Type Culture Collection) were suspended in Matrigel solution (Corning) and implanted subcutaneously into 6-week-old female SCID mouse (CLEA Japan, Inc.) by injection. The mice in which the tumor engrafted to a size of about 200-1000 $mm^3$ tumor volume after transplantation were selected and 3 mice per group were used for the experiment. L-asparaginase (Kyowa Hakko Kogyo Co., Ltd.) was subcutaneously administered at a dose of 1000 U/kg 32 hr and 8 hr before tumor removal. A 0.5% methylcellulose suspension of the compound was orally administered at a dose of 10 mg/kg 8 hr before tumor removal. After tumor removal, protein was extracted using Lysing Matrix I tube (MP Biomedicals) containing a protein extract (10% glycerol, 1% sodium dodecyl sulfate, 62.5 mM Tris-HCl [pH 7.5], protease and phosphatase inhibitors [Complete mini and PhosS-TOP, Sigma-Aldrich Co. LLC.]) and subjected to Western blot.

Protein extract solution was subjected to protein quantification with BCA Protein Assay Kit (Thermo Scientific), electrophoresed on 7.5-15% SDS-PAGE gel (DRC), and protein in the gel was transferred to PVDF membrane. The membrane was blocked with Starting Block T20 (PBS) Blocking Buffer (Thermo Scientific). ATF4 antibody (Cell signaling) was diluted 1000-fold with Can Get Signal (registered trade mark) Immunoreaction Enhancer Solution I (Toyobo) and reacted overnight at 4° C. The next day, HRP-conjugated anti-rabbit immunoglobulin (Cell signaling) was diluted 5000-fold with Can Get Signal (registered trade mark) Immunoreaction Enhancer Solution II (Toyobo) and reacted at room temperature for 1 hr. Thereafter, chemiluminescence was performed using ImmunoStar LD (Wako Pure Chemical Industries, Ltd.), and luminescence intensity was measured by LAS-3000 image analyzer (Fuji Film Co., Ltd.). Furthermore, the expression level of ATF4 was digitized by quantifying the luminescence intensity using Multi Gauge Ver. 3.1 (Fuji Film Co., Ltd.).

Based on the ATF4 expression level of the control group orally administered with 0.5% methylcellulose suspension free of Example compound and the treatment group orally administered with Example compound suspension, the ATF4 expression inhibition ratio (%) of the test compound at a compound dose 10 mg/kg was calculated by the following formula and the results thereof are shown in Table 6.

ATF4 expression inhibition ratio (%)=(1-(ATF4 expression level of treatment group)÷(ATF4 expression level of control group))×100

TABLE 6

| compound name | in vivo ATF4 expression inhibition ratio (%) |
|---|---|
| Example 14 | 63 |
| Example 7 | 74 |
| Example 4 | 76 |

From the above results, it was clarified that the compound of the present invention has an activity to suppress ATF4 expression in the presence of L-asparaginase in vivo.

Experimental Example 5

In Vitro Tumor Proliferation Inhibitory Assay with Combined Use of Asparaginase A cell suspension (40 μL) (5000 cells/well) of human acute lymphoblastic leukemia cell line CCRF-CEM obtained from ATCC (American Type Culture Collection) was seeded on a 384 well plate using RPMI1640 medium.

The seeded cells were incubated (37° C., 5% $CO_2$) overnight to 24 hr at the longest. L-asparaginase (Sigma-Aldrich Co. LLC.) was dissolved in PBS and treated in each well to a final concentration of 0.1 U/mL. Furthermore, each test compound was dissolved (10 mM) in DMSO, delivered to wells by using TECAN HP D300 (TECAN), and the plate was incubated for 72 hr (37° C., 5% $CO_2$). A well without addition of compound was treated similarly as a control group. Celltiter-Glo (registered trade mark) Luminescent Cell Viability Assay reagent (Promega KK) equilibrated at room temperature was added to cells in each well 72 hours after compound treatment (40 μL/well). After incubation for 10 min, cell proliferation inhibitory rate was measured by the amount of ATP which is a cell viability marker.

Luminescence of cells showing ATP amount was measured using ARVO MX (PerkinElmer). Based on the luminescence value of the control group without addition of test compound solution and the treatment group with addition of test compound, the cell proliferation inhibitory rate (%) of the test compound at a compound concentration of 100 nM was calculated by the following formula and the results thereof are shown in Table 7.

Inhibitory rate (%)=(1−(luminescence value of treatment group)÷(luminescence value of control group))×100

TABLE 7

| compound name | in vitro cell proliferation inhibitory rate (%) |
| --- | --- |
| Example 7 | 90 |
| Example 4 | 89 |

From the above results, it was clarified that the combined use of the compound of the present invention and L-asparaginase has an activity to inhibit proliferation of human acute lymphoblastic leukemia cell line CCRF-CEM.

Experimental Example 6

In Vivo Tumor Proliferation Inhibitory Assay with Combined Use of Asparaginase

One million human acute lymphoblastic leukemia cells CCRF-CEM obtained from ATCC (American Type Culture Collection) were suspended in Matrigel solution (Corning) and implanted subcutaneously into 6-week-old female SCID mouse (CLEA Japan, Inc.) by injection. The mice in which the tumor engrafted to a size of about 200 $mm^3$ tumor volume after transplantation were selected and 5 mice per group were used for the experiment. A 0.5% methylcellulose suspension of the compound was orally administered twice per day for 9 days. Each compound was administered twice per day and the dose was 10 mg/kg for Example 14 and Example 7, and 6 mg/kg for Example 4. L-asparaginase (Kyowa Hakko Kogyo Co., Ltd.) was subcutaneously administered once per day at a dose of 1000 U/kg. Tumor diameter was measured one day before start of the administration and day 9 of the administration, and the tumor volume was calculated by the formula 1.

tumor volume=major axis×minor axis×minor axis× (½)   Formula 1

Tumor proliferation inhibitory rate (%) was calculated by the formula 2.

tumor proliferation inhibitory rate (%)=(1−(T9−T0)/ (C9−C0))×100   Formula 2

T9: average tumor volume of test drug administration group on day 9 of administration, T0: average tumor volume of test drug administration group one day before start of administration, C9: average tumor volume of control group on day 9 of administration, C0: average tumor volume of control group one day before start of administration The results of tumor proliferation inhibition rate of each test compound are shown in Table 8.

TABLE 8

| compound name | in vivo tumor proliferation inhibitory rate (%) GCN2 inhibitor, L-asparaginase, combined use |
| --- | --- |
| Example 14 | 1, 5, 64 |
| Example 7 | 7, 5, 65 |
| Example 4 | 2, 5, 60 |

From the above results, it was clarified that the combined use of the compound of the present invention and L-asparaginase has a superior antitumor effect in mouse xenograft model of acute lymphoblastic leukemia cells showing asparaginase resistance.

Formulation Example 1 (Production of Capsule)

1) compound of Example 1 30 mg 2) fine powder cellulose 10 mg 3) lactose 19 mg 4) magnesium stearate 1 mg total 60 mg 1), 2), 3) and 4) are mixed and filled in a gelatin capsule.

Formulation Example 2 (Production of Tablet)

1) compound of Example 1 30 g 2) lactose 50 g 3) cornstarch 15 g 4) calcium carboxymethylcellulose 44 g 5) magnesium stearate 1 g 1000 tablets 140 g total The total amount of 1), 2), 3) and 30 g of 4) are kneaded with water, vacuum dried and sieved. The sieved powder is mixed with 14 g of 4) and 1 g of 5), and the mixture is punched with a tableting machine. In this way, 1000 tablets containing mg of the compound of Example 1 per tablet are obtained.

INDUSTRIAL APPLICABILITY

The compound of the present invention may have a GCN2 inhibitory action, and is expected to be useful for the prophylaxis or treatment of GCN2 associated diseases including cancer and the like.

This application is based on patent application Nos. 2016-158038 and 2017-016275 filed in Japan, the contents of which are encompassed in full herein.

The invention claimed is:
1. A compound represented by the formula (I):

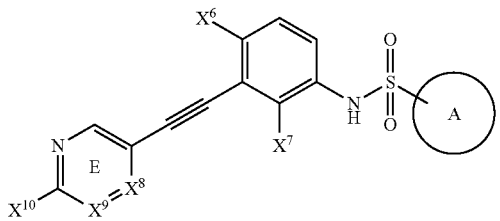

wherein
ring A is the formula:

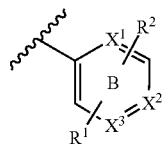

wherein ring B is an optionally further substituted 6-membered aromatic ring;
the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is a (1) a chlorine atom, (2) a bromine atom, (3) methyl, (4) trifluoromethyl, or (5) a hydroxy group substituted by methyl or trifluoromethyl;
$R^2$ is (1) a halogen atom, (2) a $C_{1-6}$ alkyl group optionally substituted by 1 to 3 substituents selected from the group consisting of a halogen atom and a hydroxy group, (3) a $C_{1-6}$ alkoxy group optionally substituted by 1 to 3 halogen atoms, or the formula:

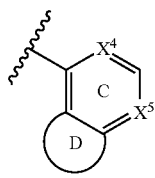

wherein ring C is a 6-membered aromatic ring optionally further substituted by 1 to 3 halogen atoms;
ring D is a 5- to 7-membered non-aromatic heterocycle;
one of $X^4$ and $X^5$ is a carbon atom, and the other one is a carbon atom or a nitrogen atom;
$X^6$ is a hydrogen atom, a fluorine atom, or a chlorine atom;
$X^7$ is a fluorine atom or a chlorine atom;
ring E is a nitrogen-containing 6-membered aromatic ring optionally further substituted by 1 to 3 $C_{1-6}$ alkyl groups;
the combination of $X^8$ and $X^9$ ($X^8$, $X^9$) is (carbon atom, nitrogen atom), (nitrogen atom, carbon atom) or (nitrogen atom, nitrogen atom); and
$X^{10}$ is an amino group optionally substituted by 1 to 2 substituents selected from the group consisting of (1) a $C_{1-6}$ alkyl group optionally substituted by 1 to 3 hydroxy groups, (2) a $C_{3-10}$ cycloalkyl group optionally substituted by 1 to 3 hydroxy groups and (3) a 3- to 14-membered non-aromatic heterocyclic group, or
$X^9$ and $X^{10}$ are bonded to each other to form an unsubstituted 5- to 14-membered aromatic heterocycle,
or a salt thereof.

2. The compound according to claim 1, wherein ring A is the formula

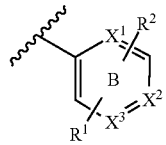

wherein the combination of $X^1$, $X^2$ and $X^3$ ($X^1$, $X^2$, $X^3$) is (carbon atom, carbon atom, carbon atom) or (carbon atom, carbon atom, nitrogen atom);
$R^1$ is (1) a chlorine atom, (2) a bromine atom, (3) methyl, (4) trifluoromethyl, or (5) a hydroxy group substituted by methyl or trifluoromethyl;
$R^2$ is (1) a halogen atom, (2) a $C_{1-6}$ alkyl group optionally substituted by 1 to 3 substituents selected from the group consisting of a halogen atom and a hydroxy group, or (3) a $C_{1-6}$ alkoxy group optionally substituted by 1 to 3 halogen atoms;
ring B is optionally further substituted by 1 to 3 substituents selected from the group consisting of (1) a halogen atom and (2) a $C_{1-6}$ alkyl group optionally substituted by 1 to 3 hydroxy groups;
$X^6$ is a hydrogen atom, a fluorine atom, or a chlorine atom;
$X^7$ is a fluorine atom or a chlorine atom;
the combination of $X^8$ and $X^9$ ($X^8$, $X^9$) is (carbon atom, nitrogen atom);
ring E is optionally further substituted by 1 to 3 $C_{1-6}$ alkyl groups; and
$X^{10}$ is an amino group optionally substituted by 1 to 2 substituents selected from the group consisting of (1) a $C_{1-6}$ alkyl group optionally substituted by 1 to 3 hydroxy groups, (2) a $C_{3-10}$ cycloalkyl group optionally substituted by 1 to 3 hydroxy groups and (3) a 3- to 14-membered non-aromatic heterocyclic group,
or a salt thereof.

3. N-(3-((2-Aminopyrimidin-5-yl)ethynyl)-2,4-difluorophenyl)-5-chloro-2-methoxypyridine-3-sulfonamide or a salt thereof.

4. 5-Chloro-N-(2,4-difluoro-3-((2-((trans-4-hydroxycyclohexyl)amino)pyrimidin-5-yl)ethynyl)phenyl)-2-methoxypyridine-3-sulfonamide or a salt thereof.

5. 2,5-Dichloro-N-(2,4-difluoro-3-((2-(((2R)-1-hydroxypropan-2-yl)amino)pyrimidin-5-yl)ethynyl)phenyl)-3-(hydroxymethyl)benzenesulfonamide or a salt thereof.

6. A medicament comprising the compound according to claim 1 or a salt thereof, and a pharmacologically acceptable carrier.

7. A method for the treatment of a cancer selected from the group consisting of osteosarcoma, acute lymphocytic leukemia, acute myeloid leukemia, pancreatic cancer, colorectal cancer, melanoma, lung cancer, ovarian cancer, hepatoma, malignant lymphoma and multiple myeloma in a mammal, comprising administering an effective amount of the compound according to claim 1 or a salt thereof to the mammal.

8. The compound according to claim 1, wherein ring A is the formula

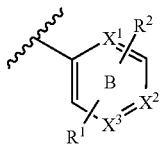

wherein the combination of $X^1$, $X^2$ and $X^3$ ($X^1$, $X^2$, $X^3$) is (carbon atom, carbon atom, carbon atom);
- $R^1$ is (1) a chlorine atom, (2) a bromine atom, (3) methyl, (4) trifluoromethyl, or (5) a hydroxy group substituted by methyl or trifluoromethyl;
- $R^2$ is (1) a halogen atom, (2) a $C_{1-6}$ alkyl group optionally substituted by 1 to 3 substituents selected from the group consisting of a halogen atom and a hydroxy group, or (3) a $C_{1-6}$ alkoxy group optionally substituted by 1 to 3 halogen atoms;
- ring B is further substituted by a substituent selected from the group consisting of (1) a halogen atom and (2) a $C_{1-6}$ alkyl group optionally substituted by 1 to 3 hydroxy groups;
- $X^6$ is a hydrogen atom, a fluorine atom, or a chlorine atom;
- $X^7$ is a fluorine atom or a chlorine atom;
- the combination of $X^8$ and $X^9$ ($X^8$, $X^9$) is (carbon atom, nitrogen atom);
- ring E is optionally further substituted by 1 to 3 $C_{1-6}$ alkyl groups; and
- $X^{10}$ is an amino group optionally substituted by 1 to 2 substituents selected from the group consisting of (1) a $C_{1-6}$ alkyl group optionally substituted by 1 to 3 hydroxy groups, (2) a $C_{3-10}$ cycloalkyl group optionally substituted by 1 to 3 hydroxy groups and (3) a 3- to 14-membered non-aromatic heterocyclic group, or a salt thereof.

9. The compound according to claim 1, wherein ring A is the formula

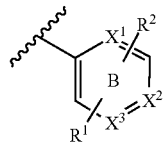

wherein the combination of $X^1$, $X^2$ and $X^3$ ($X^1$, $X^2$, $X^3$) is (carbon atom, carbon atom, nitrogen atom);
- $R^1$ is (1) a chlorine atom, (2) a bromine atom, (3) methyl, (4) trifluoromethyl, or (5) a hydroxy group substituted by methyl or trifluoromethyl;
- $R^2$ is (1) a halogen atom, (2) a $C_{1-6}$ alkyl group optionally substituted by 1 to 3 substituents selected from the group consisting of a halogen atom and a hydroxy group, or (3) a $C_{1-6}$ alkoxy group optionally substituted by 1 to 3 halogen atoms;
- $X^6$ is a hydrogen atom, a fluorine atom, or a chlorine atom;
- $X^7$ is a fluorine atom or a chlorine atom;
- the combination of $X^8$ and $X^9$ ($X^8$, $X^9$) is (carbon atom, nitrogen atom);
- ring E is optionally further substituted by 1 to 3 $C_{1-6}$ alkyl groups; and
- $X^{10}$ is an amino group optionally substituted by 1 to 2 substituents selected from the group consisting of (1) a $C_{1-6}$ alkyl group optionally substituted by 1 to 3 hydroxy groups, (2) a $C_{3-10}$ cycloalkyl group optionally substituted by 1 to 3 hydroxy groups and (3) a 3- to 14-membered non-aromatic heterocyclic group, or a salt thereof.

* * * * *